(12) United States Patent
Sapieha et al.

(10) Patent No.: US 10,766,964 B2
(45) Date of Patent: *Sep. 8, 2020

(54) COMPOSITIONS AND METHODS FOR TREATING AND PREVENTING INFLAMMATION

(71) Applicant: RSEM, LIMITED PARTNERSHIP, Montréal (CA)

(72) Inventors: Przemyslaw Sapieha, Montréal (CA); Normand Beaulieu, Montréal (CA)

(73) Assignee: RSEM, LIMITED PARTNERSHIP, Montreal (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/422,273

(22) Filed: May 24, 2019

(65) Prior Publication Data

US 2019/0359718 A1 Nov. 28, 2019

Related U.S. Application Data

(62) Division of application No. 15/507,407, filed as application No. PCT/CA2015/050862 on Sep. 8, 2015.

(Continued)

(51) Int. Cl.
| | |
|---|---|
| A61K 47/68 | (2017.01) |
| C12N 15/62 | (2006.01) |
| C07K 16/28 | (2006.01) |
| A61K 31/713 | (2006.01) |
| A61K 31/7105 | (2006.01) |
| C07K 14/71 | (2006.01) |
| C07K 16/22 | (2006.01) |

(Continued)

(52) U.S. Cl.
CPC ........ *C07K 16/2863* (2013.01); *A61K 31/713* (2013.01); *A61K 31/7105* (2013.01); *A61K 39/395* (2013.01); *C07K 14/71* (2013.01); *C07K 16/22* (2013.01); *C12N 15/113* (2013.01); *A61K 38/00* (2013.01); *A61K 2039/505* (2013.01); *C07K 2319/30* (2013.01); *C12N 2310/14* (2013.01)

(58) Field of Classification Search
None
See application file for complete search history.

(56) References Cited

U.S. PATENT DOCUMENTS

2015/0368327 A1    12/2015    Goshima et al.

FOREIGN PATENT DOCUMENTS

| CA | 2629028 | 5/2007 |
|---|---|---|
| CA | 2901946 | 8/2014 |

(Continued)

OTHER PUBLICATIONS

Gu et al., "Characterization of Neuropilin-1 Structural Features That Confer Binding to Semaphorin 3A and Vascular Endothelial Growth Factor 165*," *J Biol Chem* 277(20): 18069-18076, 2002.

(Continued)

*Primary Examiner* — Aurora M Fontainhas
(74) *Attorney, Agent, or Firm* — Klarquist Sparkman, LLP

(57) ABSTRACT

The present invention provides novel compounds compositions and methods for (i) treating or preventing inflammation; and (ii) preventing or reducing hyperactivation of innate immune response, by inhibiting NRP1-dependent cell-signaling. Also provided are compounds, composition, and methods of specifically inhibiting SEMA3A-mediated cell signaling.

19 Claims, 86 Drawing Sheets

Specification includes a Sequence Listing.

Related U.S. Application Data

(60) Provisional application No. 62/046,459, filed on Sep. 5, 2014.

(51) Int. Cl.
    *A61K 39/395*     (2006.01)
    *C12N 15/113*     (2010.01)
    *A61K 39/00*     (2006.01)
    *A61K 38/00*     (2006.01)

(56) References Cited

FOREIGN PATENT DOCUMENTS

| EP | 2497498 | 9/2012 |
|---|---|---|
| JP | 2009-501521 | 1/2009 |
| WO | WO 03/007803 | 1/2003 |
| WO | WO 03/035100 | 5/2003 |
| WO | WO 2007/009071 | 1/2007 |
| WO | WO 2009/060159 | 5/2009 |

OTHER PUBLICATIONS

Office Action dated Aug. 27, 2019 in connection with corresponding Japanese Application No. 2017-531928 (in Japanese accompanied by an English translation, 7 pages total).

Communication pursuant to Article 94(3) EPC, dated May 9, 2019, from European Application No. 15838150.9, 5 pages.

Mamluk et al., "Soluble Neuropilin Targeted to the Skin Inhibits Vascular Permeability," *Angiogenesis*, vol. 8:217-227, 2005.

Adamis et al., "Immunological mechanisms in the pathogenesis of diabetic retinopathy," *Semin Immunopathol*, vol. 30:65-84, 2008.

Ambati et al., "Mechanisms of age-related macular degeneration," *Neuron*, vol. 75:26-39, 2012.

Antonetti et al., "Diabetic retinopathy," *N Engl J Med*, vol. 366:1227-1239, 2012.

Appleton et al., "Structural studies of neuropilin/antibody complexes provide insights into semaphorin and VEGF binding," *EMBO J*, vol. 26:4902-4912, 2007.

Binet et al., "Neuronal ER Stress Impedes Myeloid-Cell-Induced Vascular Regeneration through IRE1α Degradation of Netrin-1," *Cell Metab*, vol. 17:353-371, 2013.

Bruder et al., "Neuropilin-1: a surface marker of regulatory T cells," *Eur J Immunol*, vol. 34:623-630, 2004.

Bussolino, et al., "Semaphoring vascular morphogenesis," *Endothelium*, vol. 13:81-91, 2006.

Carrer, et al., "Neuropilin-1 identifies a subset of bone marrow Gr1-monocytes that can induce tumor vessel normalization and inhibit tumor growth," *Cancer Res*, vol. 72:6371-6381, 2012.

Casazza, et al., "Impeding Macrophage Entry into Hypoxic Tumor Areas by SEMA3A/Nrp1 Signaling Blockade Inhibits Angiogenesis and Restores Antitumor Immunity," *Cancer Cell*, vol. 24:695-709, 2013.

Cerani, et al., "Neuron-Derived Semaphorin 3A is an Early Inducer of Vascular Permeability in Diabetic Retinopathy via Neuropilin-1," *Cell Metabolism*, vol. 18(4): 505-518, 2013.

Checchin, et al., "Potential role of microglia in retinal blood vessel formation," *Invest Ophthalmol Vis Sci*, vol. 47:3595-3602, 2006.

Clausen, et al., "Conditional gene targeting in macrophages and granulocytes using LysMcre mice," *Transgenic Res*, vol. 8:265-277, 1999.

Combadiere et al., "CX3CR1-dependent subretinal microglia cell accumulation is associated with cardinal features of age-related macular degeneration," *J Clin Invest* 117:2920-2928, 2007.

Connor, et al., "Increased dietary intake of omega-3-polyunsaturated fatty acids reduces pathological retinal angiogenesis," *Nat Med*, vol. 13:868-873, 2007.

Dammann, "Inflammation and retinopathy of prematurity," *Acta Paediatr*, vol. 99:975-977, 2010.

Dammann, et al., "Immaturity, perinatal inflammation, and retinopathy of prematurity: a multi-hit hypothesis," *Early Hum Dev*, vol. 85:325-329, 2009.

Deutschman, et al., "Sepsis: current dogma and new perspectives," *Immunity*, vol. 40:463-475, 2014.

Fantin, et al., "Tissue macrophages act as cellular chaperones for vascular anastomosis downstream of VEGF-mediated endothelial tip cell induction," *Blood*, vol. 116:829-840, 2010.

George et al., "Novel Stroke Therapeutics: Unraveling Stroke Pathophysiology and its Impact on Clinical Treatments," *Neuron*, vol. 87:297-309, 2015.

Geretti et al., "Neuropilin structure governs VEGF and semaphorin binding and regulates angiogenesis," *Angiogenesis*, vol. 11:31-39, 2008.

Gluzman-Poltorak, et al., "Vascular endothelial growth factor receptor-1 and neuropilin-2 form complexes," *J Biol Chem*, vol. 276:18688-18694, 2001.

Guttmann-Raviv, et al., "Semaphorin-3A and semaphorin-3F work together to repel endothelial cells and to inhibit their survival by induction of apoptosis," *J Biol Chem*, vol. 282:26294-26305, 2007.

Hartnett et al., "Mechanisms and management of retinopathy of prematurity," *N Engl J Med*, vol. 367:2515-2526, 2012.

Hellström et al., "Retinopathy of prematurity," *Lancet*, vol. 382:1445-1457, 2013.

Jiang et al., "Neuropilin 1 Directly Interacts with Fer Kinase to Mediate Semaphorin 3A-induced Death of Cortical Neurons," *J. Biol. Chem.*, vol. 285:9908-9918, 2010.

Joussen et al., "A central role for inflammation in the pathogenesis of diabetic retinopathy," *FASEB J*, vol. 18:1450-1452, 2004.

Joyal et al., "Ischemic neurons prevent vascular regeneration of neural tissue by secreting semaphorin 3A," *Blood*, vol. 117:6024-6035, 2011.

Kaštelan et al., "Inflammation and pharmacological treatment in diabetic retinopathy," *Mediators Inflamm*, vol. 2013:1-8, 2013.

Kempen et al., "The prevalence of diabetic retinopathy among adults in the United States," *Arch Ophthalmol*, vol. 122:552-563, 2004.

Kern et al., "Retinal ganglion cells in diabetes," *J Physiol*, vol. 586:4401-4408, 2008.

Klagsbrun et al., "A role for axon guidance receptors and ligands in blood vessel development and tumor angiogenesis," *Cytokine Growth Factor Rev*, vol. 16:535-548, 2005.

Klagsbrun et al., "The role of neuropilin in vascular and tumor biology," *Adv Exp Med Biol*, vol. 515:33-48, 2002.

Klebanov et al., "Upregulation of Semaphorin 3A and the associated biochemical and cellular events in a rat model of retinal detachment," *Graefes Arch Clin Exp Ophthalmol*, vol. 247:73-86, 2009.

Koppel et al., "Collapsin-1 covalently dimerizes, and dimerization is necessary for collapsing activity," *J Biol Chem*, vol. 273:15708-15713, 1998.

Lampron et al., "Innate immunity in the CNS: redefining the relationship between the CNS and Its environment," *Neuron*, vol. 78:214-232, 2013.

Lee et al., "Neuropilin-1 is required for vascular development and is a mediator of VEGF-dependent angiogenesis in zebrafish," *Proc Natl Acad Sci USA*, vol. 99:10470-10475, 2002.

Mamluk et al., "Neuropilin-1 binds vascular endothelial growth factor 165, placenta growth factor-2, and heparin via its b1b2 domain," *J Biol Chem*, vol. 277:24818-24825, 2002.

Mattapallil et al., "The Rd8 mutation of the Crb1 gene is present in vendor lines of C57BL/6N mice and embryonic stem cells, and confounds ocular induced mutant phenotypes," *Invest Ophthalmol Vis Sci*, vol. 53:2921-2927, 2012.

Miao et al., "Neuropilin-1 mediates collapsin-1/semaphorin III inhibition of endothelial cell motility: functional competition of collapsin-1 and vascular endothelial growth factor-165," *J Cell Biol*, vol. 146:233-242, 1999.

Miloudi et al., "Assessment of vascular regeneration in the CNS using the mouse retina," *J Vis Exp.*, vol. 88: e51351, 2014.

Neufeld et al., "The semaphorins: versatile regulators of tumour progression and tumour angiogenesis," *Nat Rev Cancer*, vol. 8:632-645, 2008.

Neufeld et al., "Semaphorins in angiogenesis and tumor progression," *Cold Spring Harb Perspect Med*, vol. 2:a006718, 2012.

(56) References Cited

OTHER PUBLICATIONS

Ousman et al., "Immune surveillance in the central nervous system," *Nat Neurosci*, vol. 15:1096-1101, 2012.

Ritter et al., "Myeloid progenitors differentiate into microglia and promote vascular repair in a model of ischemic retinopathy," *J Clin Invest*, vol. 116:3266-3276, 2006.

Robinson et al., "Nonvascular role for VEGF: VEGFR-1, 2 activity is critical for neural retinal development," *FASEB J*, vol. 15:1215-1217, 2001.

Rousselet et al., "Mouse model of intraluminal MCAO: cerebral infarct evaluation by cresyl violet staining," *J Vis Exp*. 69:e4038, doi:10.3791/4038, 2012.

Saint-Geniez et al., "Endogenous VEGF is required for visual function: evidence for a survival role on muller cells and photoreceptors," PLoS One, vol. 3:e3554, 2008.

Sapieha et al., "Proliferative retinopathies: angiogenesis that blinds," *Int J Biochem Cell Biol*, vol. 42:5-12, 2010.

Sapieha et al., "Retinopathy of prematurity: understanding ischemic retinal vasculopathies at an extreme of life," *J Clin Invest*, vol. 120:3022-3032, 2010.

Sapieha et al., "5-Lipoxygenase Metabolite 4-HDHA Is a Mediator of the Antiangiogenic Effect of {omega}-3 Polyunsaturated Fatty Acids," *Sci Transl Med*, 3:69ra12, 2011.

Sapieha, "Eyeing central neurons in vascular growth and reparative angiogenesis," *Blood*, vol. 120:2182-2194, 2012.

Sennlaub et al., "CCR2+ monocytes infiltrate atrophic lesions in age-related macular disease and mediate photoreceptor degeneration in experimental subretinal inflammation in Cx3cr1 deficient mice," *EMBO Mol Med*, vol. 5:1775-1793, 2013.

Shao et al., "Choroid Sprouting Assay: An Ex Vivo Model of Microvascular Angiogenesis," *PLoS One*, vol. 8:e69552, 2013.

Silva et al., "Effect of systemic medications on onset and progression of diabetic retinopathy," *Nat Rev Endocrinol*, vol. 6:494-508, 2010.

Smith et al., "Oxygen-induced retinopathy in the mouse," *Invest Ophthalmol Vis Sci*, vol. 35:101-111, 1994.

Soker et al., "Neuropilin-1 is Expressed by Endothelial and Tumor Cells as an Isoform-Specific Receptor for Vascular Endothelial Growth Factor," *Cell*, vol. 92:735-745, 1998.

Soker et al., "$VEGF_{165}$ Mediates Formation of Complexes Containing VEGFR-2 and Neuropilin-1 that Enhance $VEGF_{165}$-Receptor Binding," *J Cell Biochem*, vol. 85:357-368, 2002.

Stahl et al., "Computer-aided quantification of retinal neovascularization," *Angiogenesis*, vol. 12:297-301, 2009.

Stahl et al., "Postnatal Weight Gain Modifies Severity and Functional Outcome of Oxygen-Induced Proliferative Retinopathy," *Am J Pathol*, vol. 177(6):2715-2733, 2010.

Stahl et al., "PPARγ mediates a direct antiangiogenic effect of omega 3-PUFAs in proliferative retinopathy," *Circ Res*, vol. 107(4):495-500, 2010.

Stahl et al., "The mouse retina as an angiogenesis model," *Invest Ophthalmol Vis Sci*, vol. 51:2813-2826, 2010.

Supplementary European Search Report, dated Apr. 30, 2018, issued in connection with corresponding European Application No. EP15838150 (7 pages).

Takahashi et al., "Plexin-Neuropilin-1 Complexes Form Functional Semaphorin-3A Receptors," *Cell*, vol. 99:59-69, 1999.

Takamatsu et al., "Diverse Roles for Semaphorin-Plexin Signaling in the Immune System," *Trends Immunol.*, vol. 33:127-135, 2012.

Takeda et al., "CCR3 is a target for age-related macular degeneration diagnosis and therapy," *Nature*, vol. 460:225-230, 2009.

Tremblay et al., "Systemic inflammation perturbs developmental retinal angiogenesis and neuroretinal function," *Invest Ophthalmol Vis Sci*, vol. 54:8125-8139, 2013.

Van Rooijen et al., ""In vivo" depletion of macrophages by liposome-mediated "suicide"," *Methods Enzymol*, vol. 373:3-16, 2003.

Vieira et al., "Role of the neuropilin ligands VEGF164 and SEMA3A in neuronal and vascular patterning in the mouse," *Novartis Found Symp*, vol. 283:230-241, 2007.

Worthylake et al., "RhoA and ROCK Promote Migration by Limiting Membrane Protrusions," *J Biol Chem*, vol. 278:13578-13584, 2003.

Yancopoulos, "Clinical Application of Therapies Targeting VEGF," *Cell*, vol. 143:13-16, 2010.

International Search Report and Written Opinion of PCT/CA2015/050862, dated Nov. 5, 2015.

International Preliminary Report on Patentability of PCT/CA2015/050862, dated Mar. 7, 2017.

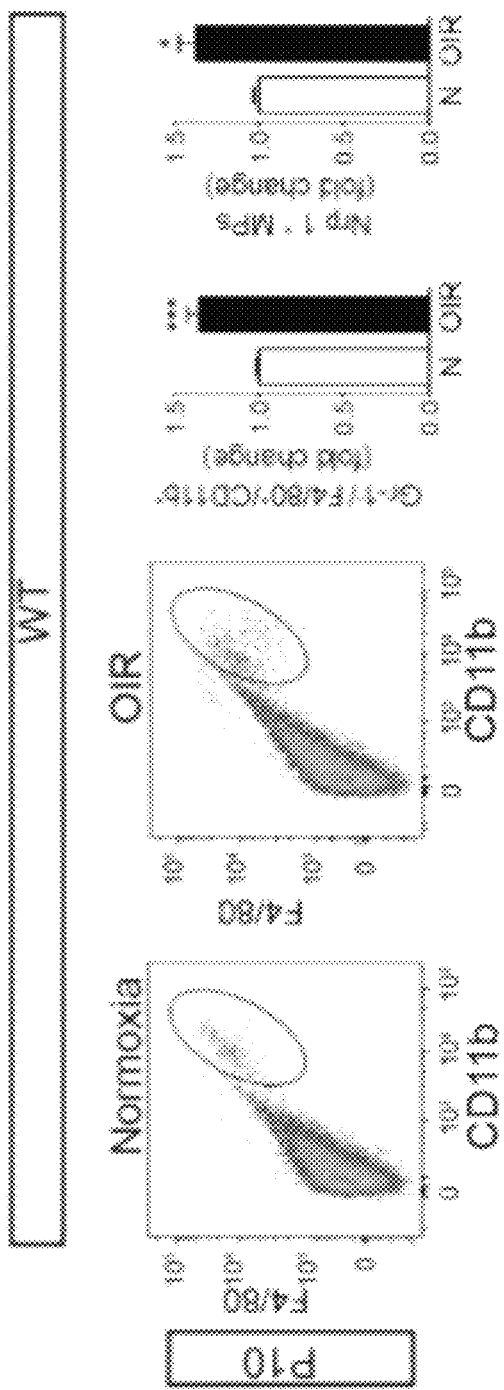

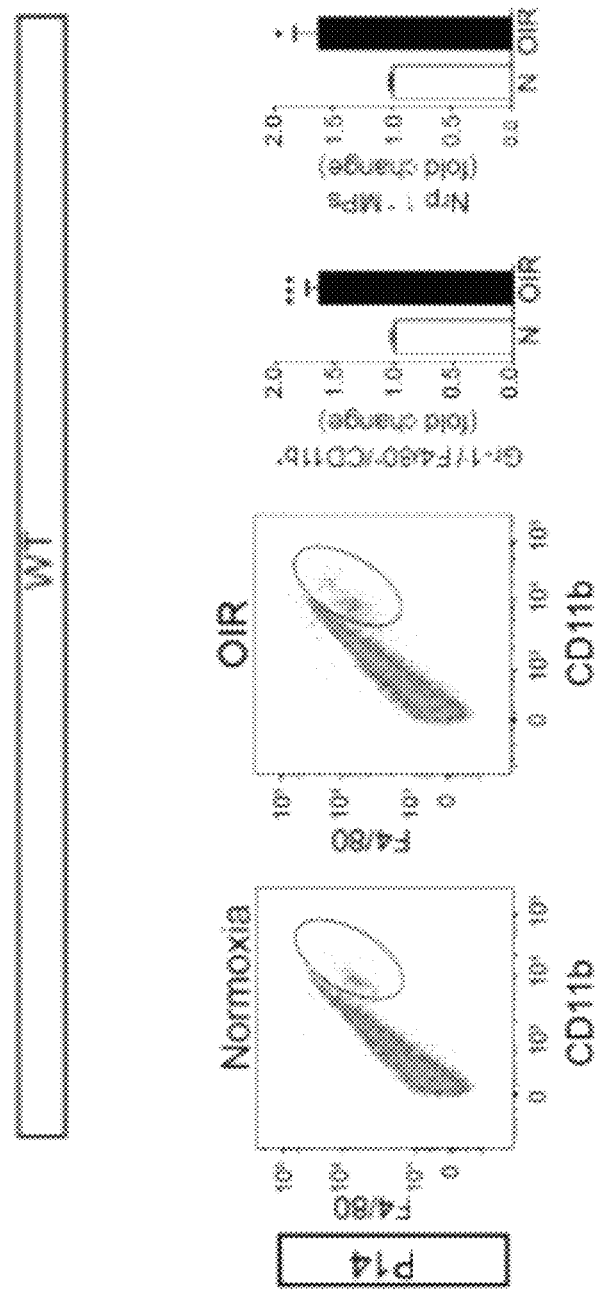

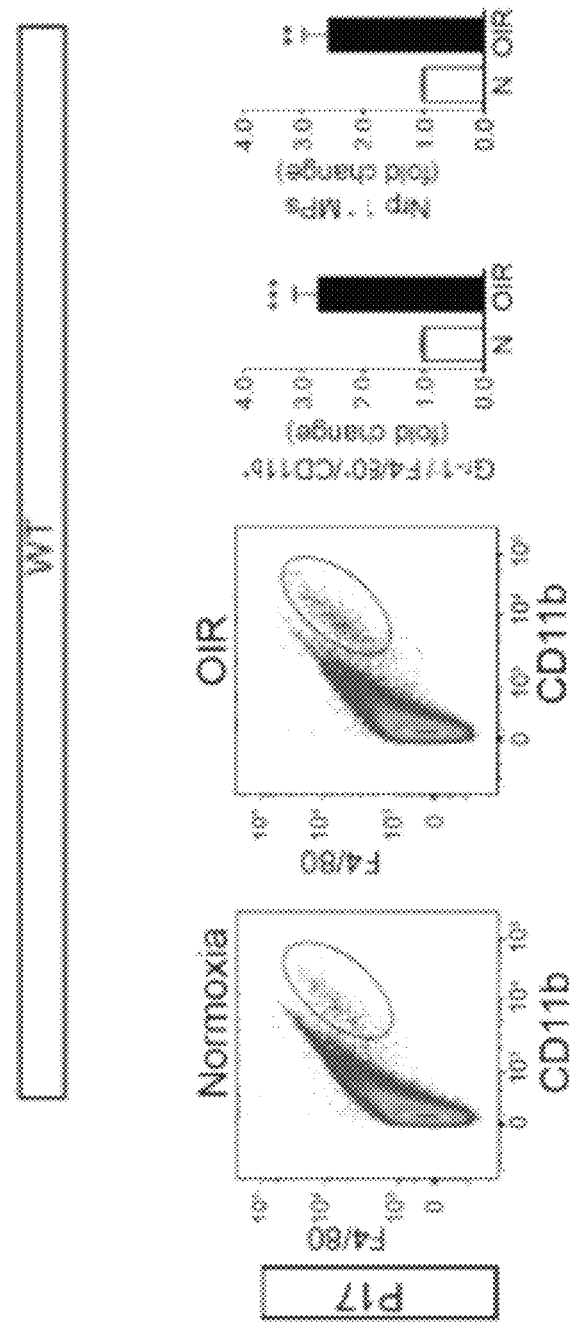

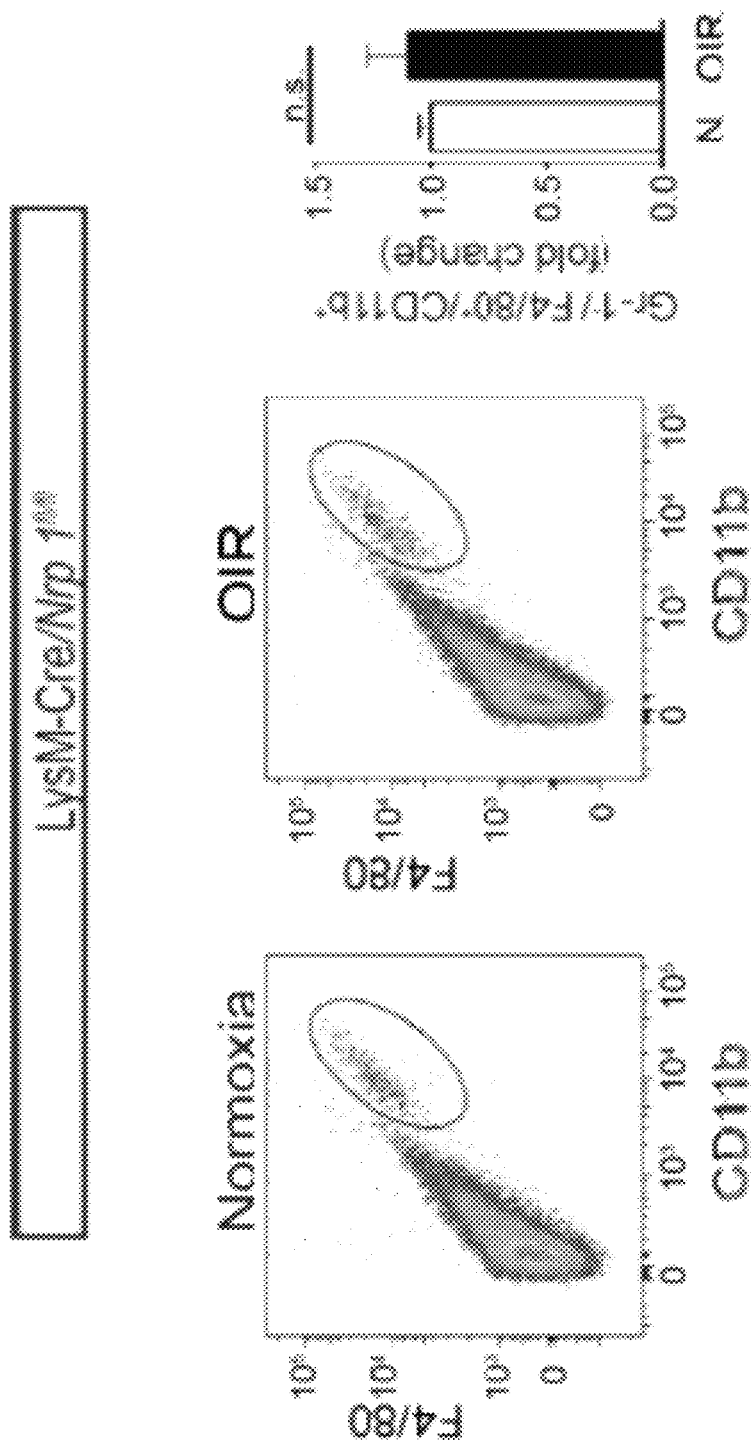

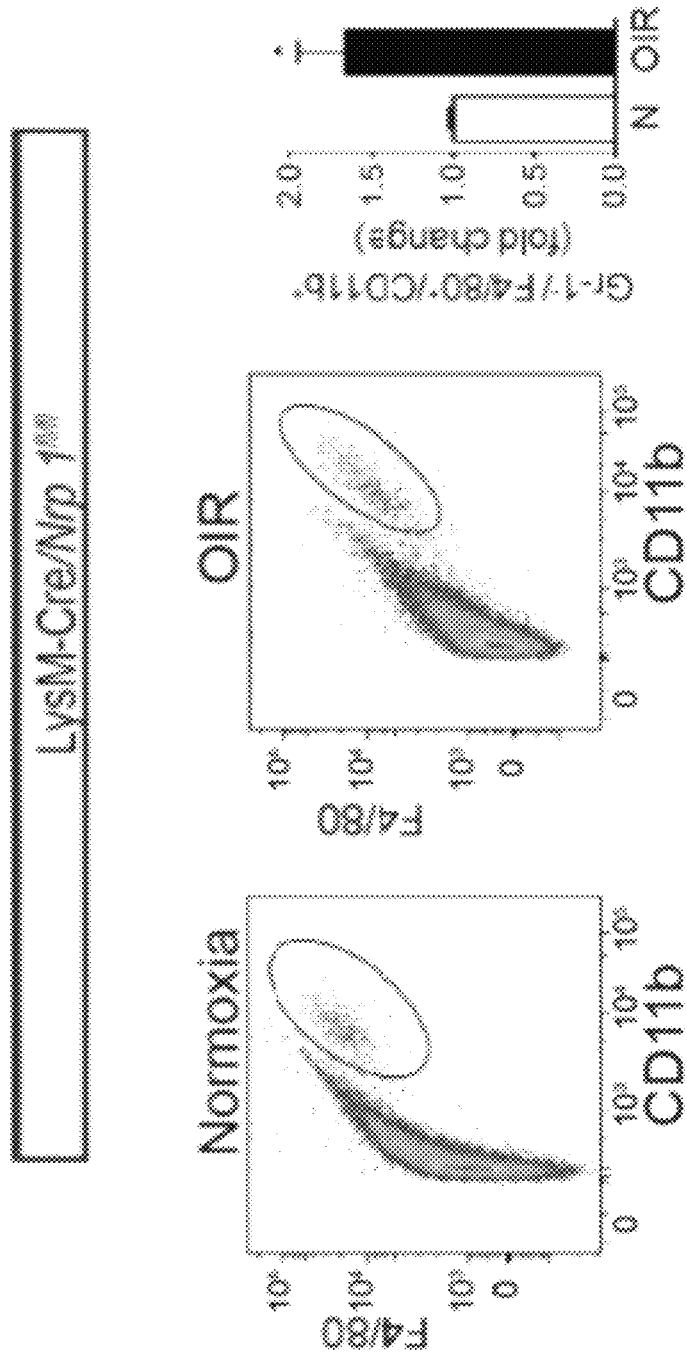

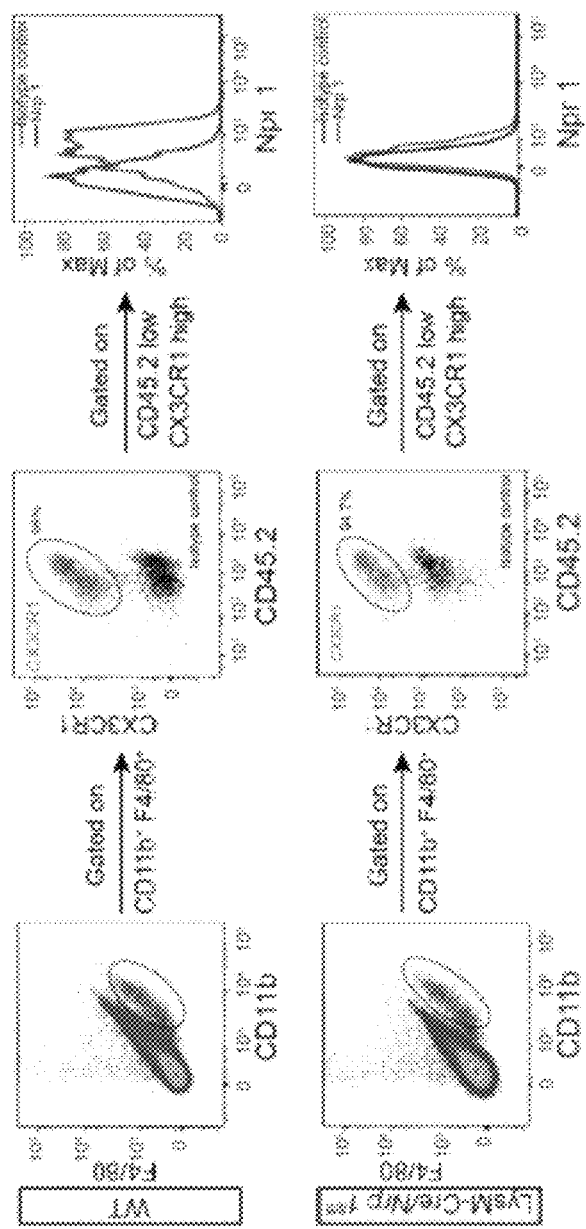
FIG. 1S
FIG. 1T
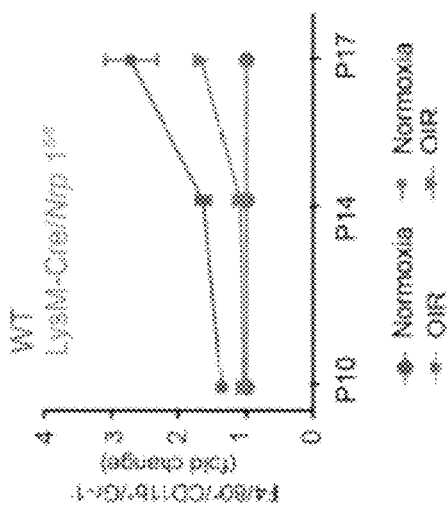
FIG. 1R

FIG. 2A
FIG. 2B
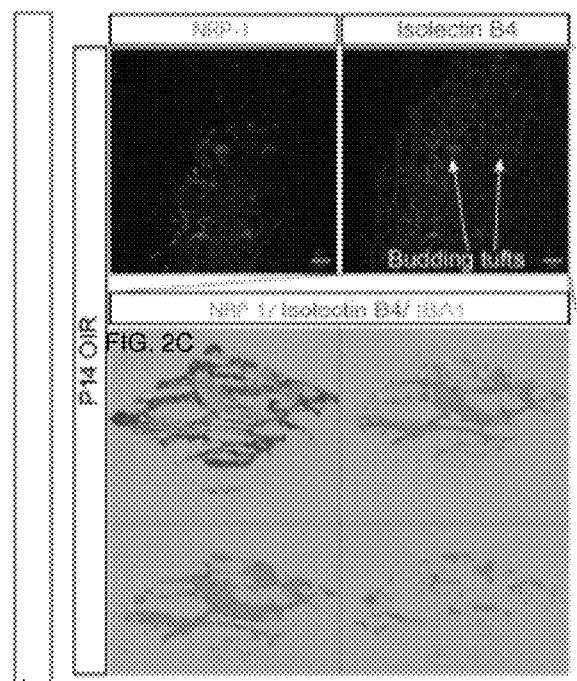
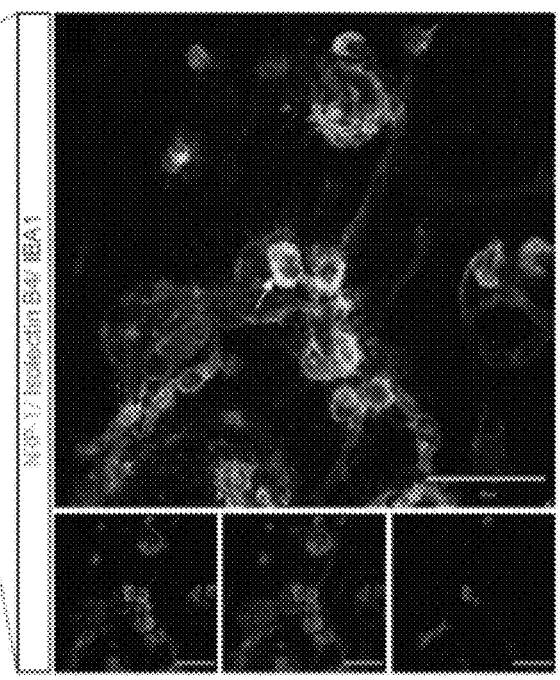
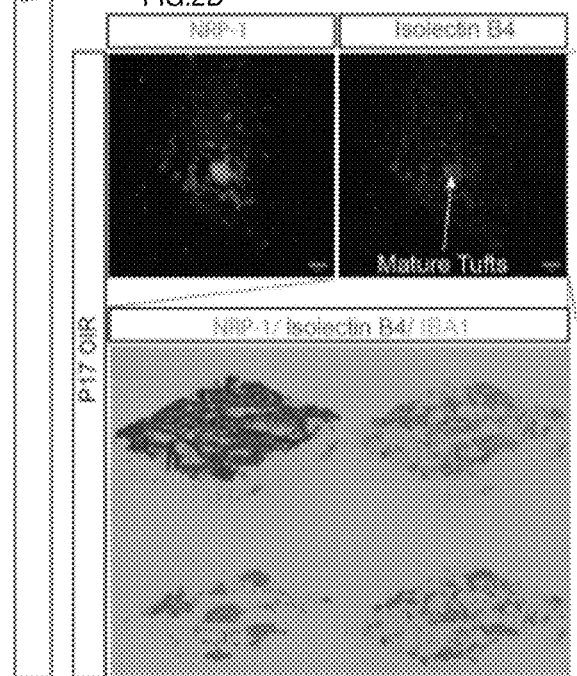
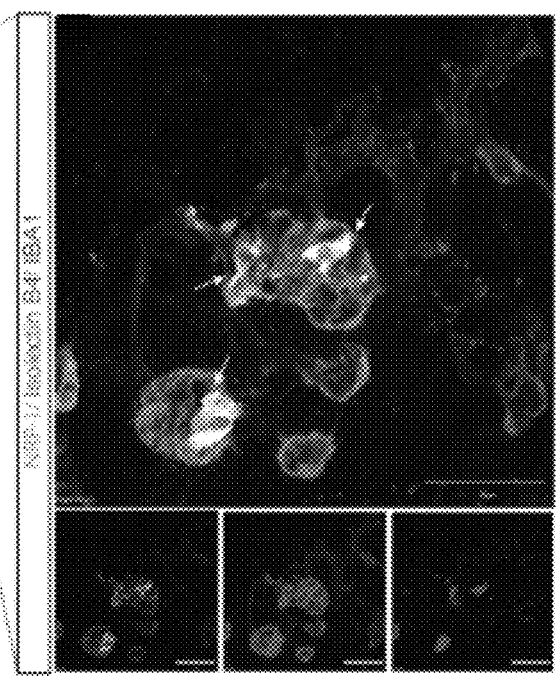
FIG. 2F
FIG. 2E

FIG. 2G
FIG. 2H
FIG. 2I
FIG. 2J
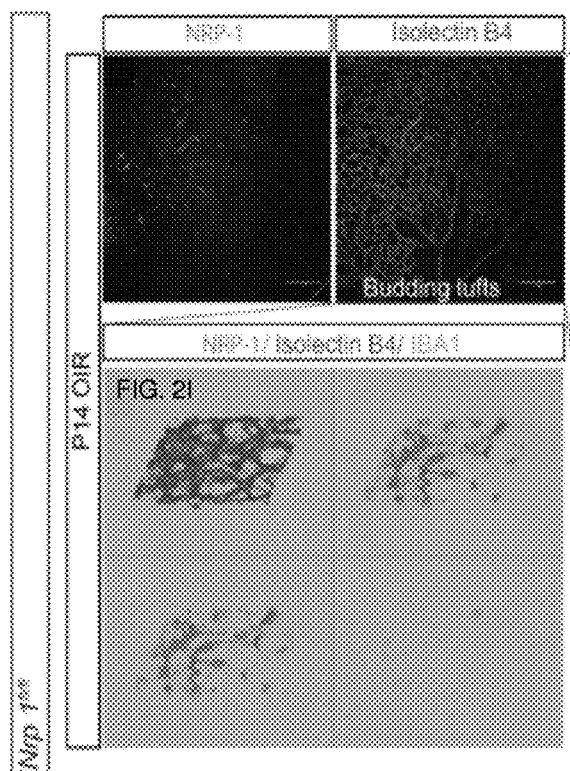
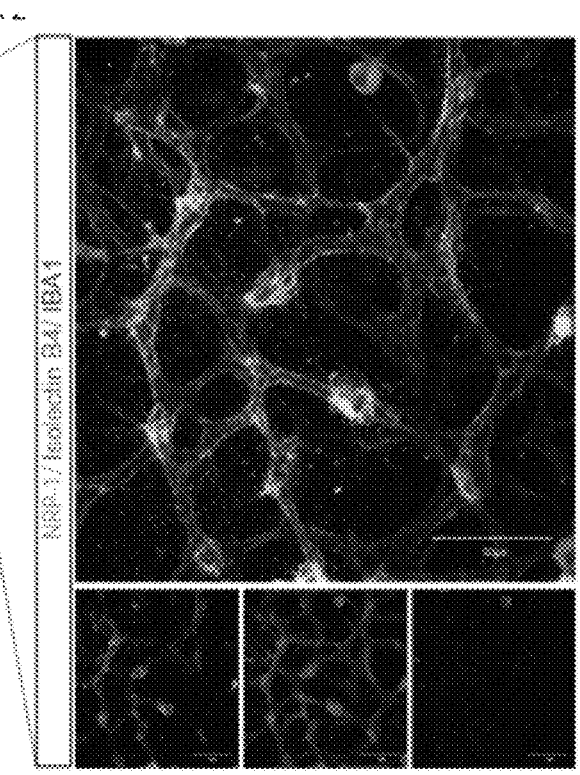
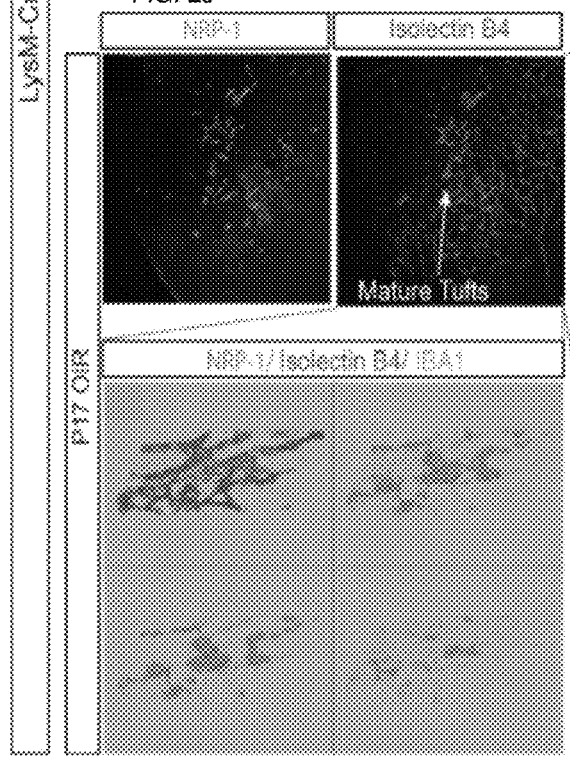
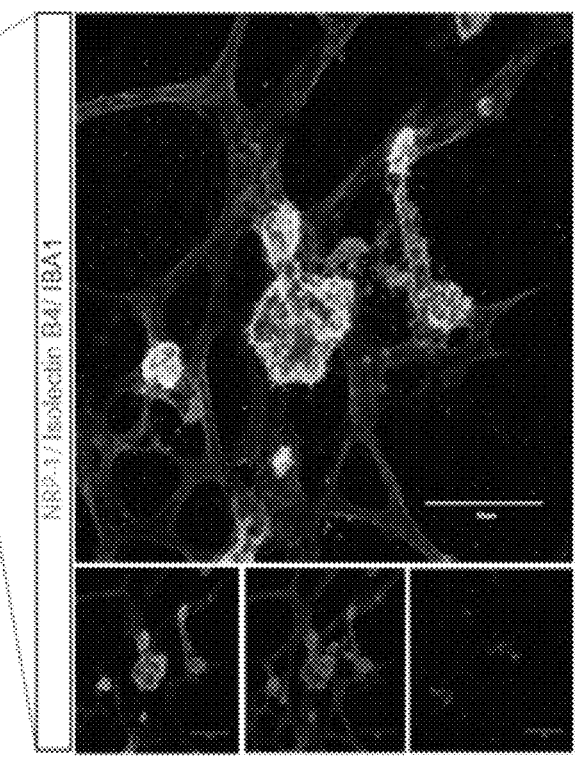
FIG. 2L
FIG. 2K FIG. 3A
FIG. 3B
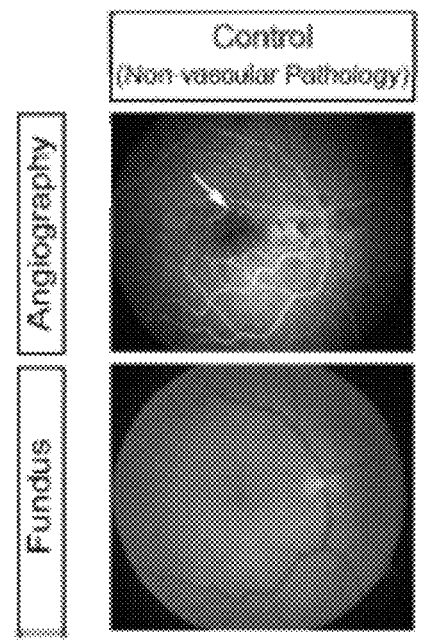
FIG. 3C
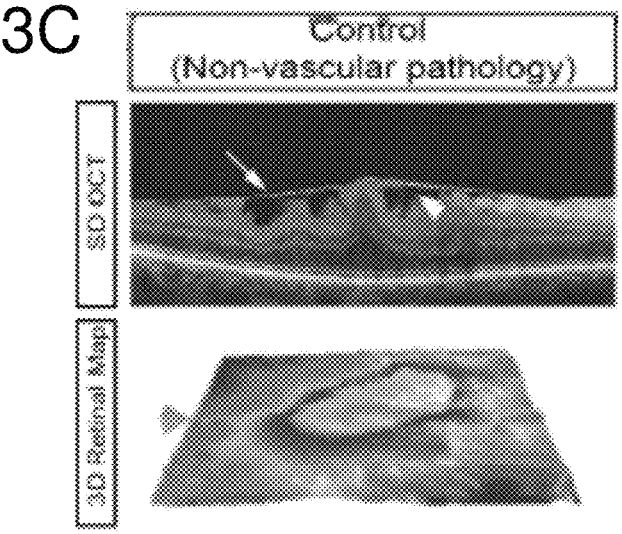

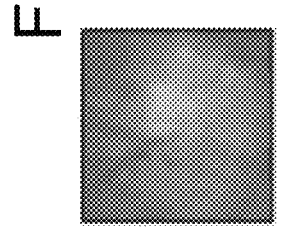
FIG. 3F
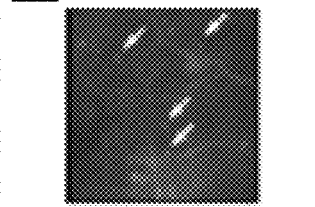
FIG. 3G
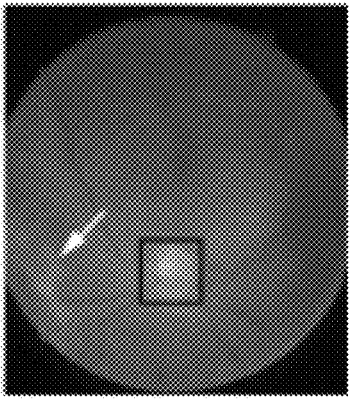
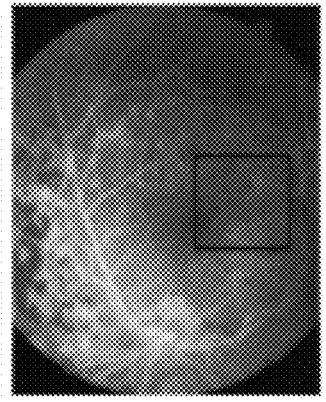
Proliferative Diabetic Retinopathy (PDR)
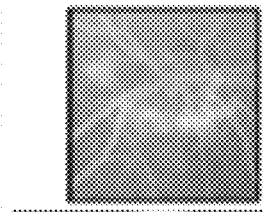
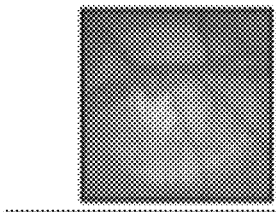
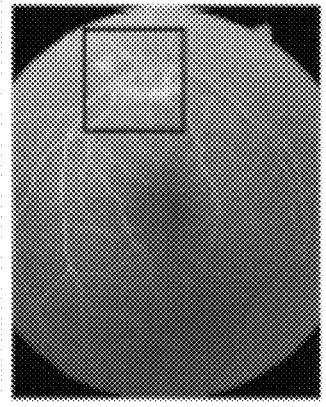
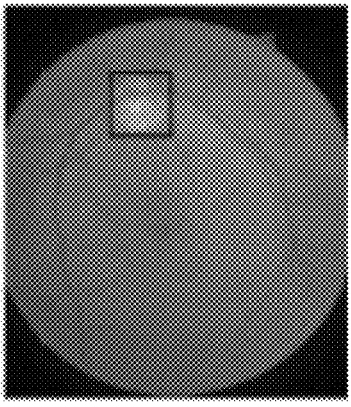
FIG. 3D
FIG. 3E

P17

Vehicle  NRP-1-Trap

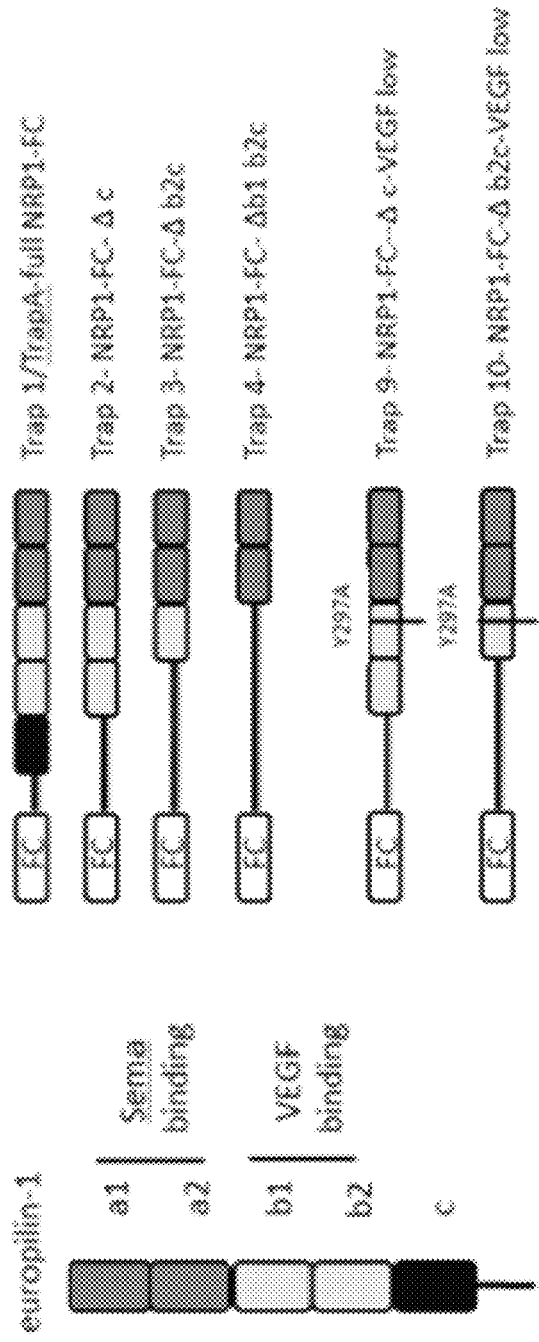
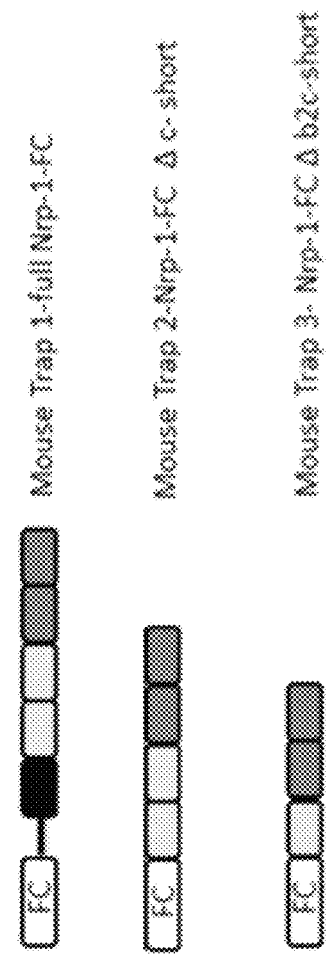
FIG. 19A
FIG. 19B
FIG. 19C

```
gaggcaacaacaactatgatacacctgagctgcggacttttccagctctctccacgcga
 E  G  N  N  Y  D  T  P  E  L  R  T  F  P  A  L  S  T  R
ttcatcaggatctacccgagagagcactcatgggggactggggtcagaatggagctg
 F  I  R  I  Y  P  E  R  A  T  H  G  G  L  G  L  R  M  E  L
ctgggctgtgaagtggaagccctacagctggaccgaccactcccaacgggaacttggtg
 L  G  C  E  V  E  A  P  T  A  G  P  T  T  P  N  G  N  L  V
gatgaatgtgatgacgaccaggccaactgccacagtggaacaggtgatgacttccagctc
 D  E  C  D  D  D  Q  A  N  C  H  S  G  T  G  D  D  F  Q  L
acaggtggaaccactgtgctggcacagaaaagccacggtcatagacagcaccatacaa
 T  G  G  T  T  V  L  A  T  E  K  P  T  V  I  D  S  T  I  Q
tcagagtttccaacatatggttttaactgtgaatttggctgggctctcacaagaccttc
 S  E  F  P  T  Y  G  F  N  C  E  F  G  W  G  S  H  K  T  F
tgccactggaacatgacaatcacgtgcagctcaagtggagtgtgttgaccagcaagacg
 C  H  W  N  M  T  I  T  C  S  S  S  G  V  C  D  Q  Q  D
ggacccattcaggatcacacaggagatggcaacttcatctattccaagctgacgaaat
 G  P  I  Q  D  H  T  G  D  G  N  F  I  Y  S  Q  A  D  E  N
cagaagggcaaagtggctcgcctggtgagccctgtggtttattcccagaactctgccac
 Q  K  G  K  V  A  R  L  V  S  P  V  V  Y  S  Q  N  S  A  H
tgcatgaccttctggtatcacatgtctgggtccacgtggcacactcagggtcaaactg
 C  M  T  F  W  Y  H  M  S  G  S  H  V  G  T  L  R  V  K  L
cggtaccagaagccagaggagtacgatcagctggtctggatggccattggacacaaggt
 R  Y  Q  K  P  E  E  Y  D  Q  L  V  W  M  A  I  G  H  Q  G
gaccactggaaggaaggcgtgtcttgctccacaagtctctgaaactttatcaggtgatt
 D  H  W  K  E  G  R  V  L  L  H  K  S  L  K  L  Y  Q  V  I
ttcgagggcgaaatcggaaaaggaaaccttggtgggattgctgtggatgacattagtatt
 F  E  G  E  I  G  K  G  N  L  G  G  I  A  V  D  D  I  S  I
aataaccacattcacaagaagattgtgcaaaacagcagactggataaaagaaccca
 N  N  H  I  S  Q  E  D  C  A  K  P  A  D  L  D  K  N  P
gaaattaaatgatgaaacagggagcacgccaggatacgaaggtgaaggagaaggtgac
 E  I  K  D  E  T  G  S  T  P  G  Y  E  G  E  G  D
aagaacatctccaggaagccaggcaatgtgttgaagaccctagaccccagatctgacaaa
 K  N  I  S  R  K  P  G  N  V  L  K  T  L  D  P  R  S  D  K
actcacacatgcccaccgtgcccagcacctgaactcctgggggaccgtcagtcttcctc
 T  H  T  C  P  P  C  P  A  P  E  L  L  G  G  P  S  V  F  L
ttccccccaaaacccaaggacaccctcatgatctcccggacccctgaggtcacatgcgtg
 F  P  P  K  P  K  D  T  L  M  I  S  R  T  P  E  V  T  C  V
gtggtggacgtgagccacgaagaccctgaggtcaagttcaactggtacgtggacggcgtg
 V  V  D  V  S  H  E  D  P  E  V  K  F  N  W  Y  V  D  G  V
gaggtgcataatgccaagacaaagccgcgggaggagcagtacaacagcacgtaccgtgtg
 E  V  H  N  A  K  T  K  P  R  E  E  Q  Y  N  S  T  Y  R  V
gtcagcgtcctcaccgtcctgcaccaggactggctgaatggcaaggagtacaagtgcaag
 V  S  V  L  T  V  L  H  Q  D  W  L  N  G  K  E  Y  K  C  K
gtctccaacaaagccctcccagcccccatcgagaaaaccatctccaaagccaaagggcag
 V  S  N  K  A  L  P  A  P  I  E  K  T  I  S  K  A  K  G  Q
ccccgagaaccacaggtgtacaccctgcccccatcccgggaggagatgaccaagaaccag
 P  R  E  P  Q  V  Y  T  L  P  P  S  R  E  E  M  T  K  N  Q
gtcagcctgacctgcctggtcaaaggcttctatcccagcgacatcgccgtggagtgggag
 V  S  L  T  C  L  V  K  G  F  Y  P  S  D  I  A  V  E  W  E
agcaatgggcagccggagaacaactacaagaccacgcctcccgtgctggactccgacggc
 S  N  G  Q  P  E  N  N  Y  K  T  T  P  P  V  L  D  S  D  G
tccttcttcctctacagcaagctcaccgtggacaagagcaggtggcagcaggggaacgtc
 S  F  F  L  Y  S  K  L  T  V  D  K  S  R  W  Q  Q  G  N  V
ttctcatgctccgtgatgcatgaggctctgcacaaccactacacgcagaagagcctctcc
 F  S  C  S  V  M  H  E  A  L  H  N  H  Y  T  Q  K  S  L  S
ctgtctccgggtaaa
 L  S  P  G  K
```

FIG. 20C

MERGLPLLCAVLALVLAPAGAFRNDKCGDTIKIESPGYLTSPGYPHSYHPSERCEWLIQA
PDPYQRIMINFNPHFDLEDRDCKYDYVEVFDGENENGHFRGKFCGKIAPPPVVSSGPFLF
IKFVSDYETHGAGFSIRYELFKRGPECSQNYTTFSGVIKSPGFPEKYPNSLECTYIVFAP
KMSEIILEFESFDLEPDSNPPGGMFCRYDRLEINDGFPDVGPHIGRYCGQKTPGRIRSSS
GILSMVFYTDSAIAKEGFSANYSVLQSSVSEDFKCMEALGMESGEIHSDQITASSQYSTN
WSAERSRLNYPENGWTPGEDSYREWIQVDLGLLRFVTAVGTQGAISKETKKKYYVKTYKI
DVSSNGEDWITIKEGNKPVLFQGNTNPTDVVVAVFPKPLITRFVRIKPATWETGISMRFE
VYGCKITDYPCSGMLGMVSGLISDSQITSSNQGDRNWMPENIRLVTSRSGWALPPAPHSY
INEWLQIDLGEEKIVRGIIIQGGKHRENKVFMRKFKIGYSNNGSDWKMIMDDSKRKAKSF
EGNNYDTPELRTFPALSTRFIRIYPERATHGGLGLRMELLGCZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLS
LSPGK

FIG. 20D

```
ATGGAGAGGGGGCTGCCGGCTCCTCTGCGCCGTGCTCGCCCTCGTCCTCGCCCCGGCCGGCTTTTC
GCAACGATAAATGTGGCGATACTATAAAAATTGAAAGCCCCGGGTACCTTACATCTCCTGGTTATCC
TCATTCTTATCACCCAAGTGAAAATGCGAATGGCTGATTCAGGCTCCGGACCCATACCAGAGAATT
ATGATCAACTTCAACCCTCACTTCGATTTGGAGGACAGAGACTGCAAGTATGACTACGTGGAAGTCT
TCGATGGAGAAAATGAAAATGGACATTTTAGGGGAAAGTTCTGTGGAAAGATAGCCCTCCTCCTGT
TGTGTCTTCACGGCCATTTCTTTTTATCAAATTGTCTCTGACTACGAAACACATGGTGCAGGATTT
TCCATACGTTATCAACTTTTCAACACAGGTCCTGAATGTTCCCAGAACTACACAACACCTAGTGGAG
TGATAAAGTCCGGCGGATTCCCTGAAAAATATCCGAACAGCCTTGAATGCACTTATATTGTCTTTGC
GCCAAAGATGTCAGACATTATCCTGGAATTTGAAAGCTTTGACCTGGAGCCTCACTCAAATCCTCCA
GGGGGGATGTTCTGTCCCTACGACCGGCTAGAAATCTGGGATGGATTCCCTGATGTTGGCCCTCACA
TTGGGCGTTACTGTGGACAGAAAACACCCAGGTCGAATCCGATCCTCATCGGGCATTCTCTCCATGGT
TTTTTACACCGACAGCCCGATAGCAAAGAAGGTTTCTCAGCAAACTACAGTGTCTTGCACAGCAGT
GTCTCAGAAGATTTCAAATGTATGGAAGCTCTGGGCATGGAATCAGGAGAAATTCATTCTGACCAGA
TCACAGCTTCTTCCCAGTATAGCACCAACTGGTCTGCAGAGCGCTCCCCGCCTGAACTACCCTGAGAA
TGGGTGCACTCCCGGAGAGGATTCCTACCGAGAGTGGATACAGGTAGACTTGGGCCTTCTGCCCTTT
GTCACGGCTGTCGGACACAGGGGCGCCCATTTCAAAAGAAACCAAGAAGAAATATTATGTCAACACTT
ACAAGATCGACGTAGCTCCAACGGGGAACACTGGATCACCATAAAGAAGGAAACAAACCTGTTCT
CTTTCAGGGAAACACCAACCCTACACATGTTGTGGTTGCAGTATTCCCCAAACCACTGATAACTCGA
TTTGTCCGAATCAAGCCTGCAACTTGGGAAACTGGCATATCTATGAGATTTGAAGTATATGGTTGCA
AGATAACACATTATCCTTCCTCTGGAATGTTGGGTATGGTGTCTGGACTTATTCTGACTCCCACAT
CACATCATCCAACCAAGGGGACAGAAACTGGATGCCTGAAAACATCGCCTGGTAACAGTCCTCT
GGCTGGGCACTTCCACCCCGCACCTCATTCCTACATCAATCAGTGGCTCCAAATAGACCTGGGGCAGG
ACAAGATCGTGAGGGGCATCATCATTCAGGGCTGGGAAGCACCGACACAACAAGCTGTTCATGAGGAA
GTTCAAGATCGGGTACAGCAACAACGGCTCGGACTGGAAGATGATCATGGATGACAGCAAACGCAAG
GCGAAGTCTTTTCAGGGCAACAACAACTATGATACACCTGAGCTGCCGGACTTTTCCAGCTCTCTCCA
CGGGATTCATCAGGATCTACCCCGAGAGAGCCCACTCATGGGCGACTGGGGCTCAGAATGGAGCTGCT
GGGCTCGTNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNN
NNNNNNNNNNNNNNNNNNNNNGACAAAACTCACACATGCCTCACCCGTGCCCAGCACCTGAA
CTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCACGAGGCTCTGCACAAC
CACTACACGCAGAAGAGCCTCTCCCTGTCTCCGGGTAAA
```

FIG. 20E

MKRGLPLLCAVLALVLAPAGAFRNDKCGDTIKIESPGYLTSPGYPHSYHPSEKCEWLIQAPDPYQRI
MINFNPHFDLEDRDCKYDYVEVFDGENENGHFRGKFCGKIAPPPVVSSGFFLFIKFVSDYETHGAGF
SIRYELFKRGPECSQNYTTPSGVIKSPGFPEKYPNSLECTYIVFAPKMSEIILEFESFDLEPDSNPP
GGNFCRYDRLEIWDGFPDVGPHIGRYCGQKTPGRIRSSSGILSXVFYTDSAIAKEGFSANYSVLQSS
VSEDFKCMEALQMESGEIHSDQITASSQYSTNXSAERSRLNYFENGXTPGEDSYREWIQVDLGLLRP
VTAVGTQGAISKETKKKYYVKTYKIDVSSNGEDWITIKEGNKPVLFQGNTNPTDVVVAVFPKPLITR
FVRIKPATWETGISXRFEVYGCZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZDKTHTCPPCPAPE
LLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKARGQPREPQVYTLPPSREEMTKNQVSLTC
LVKGFYPSDIAVEWESNGQPENNYKTTPPVLDSDGSFFLYSKLTVDKSRWQQGNVFSCSVMHEALHN
HYTQKSLSLSPGK

```
MERGLPLLCAVLALVLAPAGAFRNDKCGDTIKIESPGYLTSPGYPHSYHPSEKCEWLIQAP
DPYQRIMINFNPHFDLEDRDCKYDYVEVFDGENENGHFRGKFCGKIAPPPVVSSGPFLFIK
FVSDYETHGAGFSIRYELFKRGPECSQNYTTPSGVIKSPGFPEKYPNSLECTYIVFAPKMS
EIILEFESFDLEPDSNPPGGMFCRYDRLEIWDGFPDVGPHIGRYCGQKTPGRIRSSSGILS
MVFYTDSAIAKEGFSANYSVLZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK
```

FIG. 20H

```
ATGGAGAGGGGGCTGCCGGCTCCTCTGCGGCGTGCTCGCCCTCGTCCTCGCCCCGGCCGGCGCTTTTC
GCAACGATAAATGTGCCGATACTATAAAAATTGAAAGCCCCGGGTACCTTACATCTCCTGGTTATCC
TCATTCTTATCACCCAAGTGAAAAATGCGAATGGCTCATTCAGGCTCCGGACCCATACCAGAGAATT
ATGATCAACTTCAACCCTCACTTCGATTTGCAGGACAGAGACTGCAAGTATGACTACGTGGAAGTCT
TCGATGGAGAAAATGAAAATGGACATTTTAGGGGAAAGTTCTGTGGAAAGATAGCCCCTCCTCCTGT
TGTGTCTTCAGGGCCATTTCTTTTTATCAAATTTGTCTCTGACTACGAAACACATGGTGCAGGATTT
TCCATACGTTATGAACTTTTCAACAGAGGTCCTGAATGTTCCAGAACTACACAACACCTAGTGGAG
TGATAAAGTCCCCCCGGATTCCCTGAAAAATATCCCAACAGCCTTGAATGCACTTATATTGTCTTTGC
GCCAAAGATGTCAGAGATTATCCTGGAATTTGAAAGCTTTGACCTGCAGCCTGACTCAAATCCTCCA
GGGGCATGTTCTGTCGCTACGACCGGCTAGAAATCTGGGATGGATTCCCTGATGTTCGCCCTCACA
TTGGGCGTTACTGTGGACAGAAAACACCAGGTCGAATCCGATCCTCATCGGGCATTCTCTCCATGGT
TTTTACACCGACAGTGCCGATAGCAAAAGAACGTTTCTCAGCAAACTACAGTGTCTTGNNNNNNNNN
NNNNNNNNNNNNNNNNNNNNNNNNNNNNNNNNNNNNNNNNNNNNNNNNNNNNNNNNNNNNNNNNNNN
[...many lines of N...]
NNNNNNNNNNNNNNNNNNNNNNNNNNNNNGACAAAACTCACACATGCCCACCGTGCCCAGCACCTGAA
CTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACTATCTCCAAAGCCAAAGGGCAGCCCCGAGA
ACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCACGAGGCTCTGCACAAC
CACTACACGCAGAAGAGCCTCTCCCTGTCTCCGGGTAAA
```

```
gagggcaacaacaactatgatacacctgagctgcggactcttccagctctctccacgcga
 E  G  N  N  N  Y  D  T  P  E  L  R  T  F  P  A  L  S  T  R
ttcatcaggatctaccccgagagagccactcatggcggactggggctcagaatggagctg
 F  I  R  I  Y  P  E  R  A  T  H  G  G  L  G  L  R  M  E  L
ctgggctgtagatctgacaaaactcacacatgcccaccgtgcccagcacctgaactcctg
 L  G  C  R  S  D  K  T  H  T  C  P  P  C  P  A  P  E  L  L
ggggacgtcagtcttcctcttccccccaaaacccaaggacacccctcatgatctcccgg
 G  G  P  S  V  F  L  F  P  P  K  P  K  D  T  L  M  I  S  R
acccctgaggtcacatgcgtggtggtggacgtgagccacgaagaccctgaggtcaagttc
 T  P  E  V  T  C  V  V  V  D  V  S  H  E  D  P  E  V  K  F
aactggtacgtggacggcgtggaggtgcataatgccaagacaaagccgcgggaggagcag
 N  W  Y  V  D  G  V  E  V  H  N  A  K  T  K  P  R  E  E  Q
tacaacagcacgtaccgtgtggtcagcgtcctcaccgtcctgcaccaggactggctgaat
 Y  N  S  T  Y  R  V  V  S  V  L  T  V  L  H  Q  D  W  L  N
ggcaaggagtacaagtgcaaggtctccaacaaagccctcccagcccccatcgagaaaacc
 G  K  E  Y  K  C  K  V  S  N  K  A  L  P  A  P  I  E  K  T
atctccaaagccaaagggcagccccgagaaccacaggtgtacaccctgcccccatcccgg
 I  S  K  A  K  G  Q  P  R  E  P  Q  V  Y  T  L  P  P  S  R
gaggagatgaccaagaaccaggtcagcctgacctgcctggtcaaaggcttctatcccagc
 E  E  M  T  K  N  Q  V  S  L  T  C  L  V  K  G  F  Y  P  S
gacatcgccgtggagtgggagagcaatgggcagccggagaacaactacaagaccacgcct
 D  I  A  V  E  W  E  S  N  G  Q  P  E  N  N  Y  K  T  T  P
cccgtgctggactccgacggctccttcttcctctacagcaagctcaccgtggacaagagc
 P  V  L  D  S  D  G  S  F  F  L  Y  S  K  L  T  V  D  K  S
aggtggcagcaggggaacgtcttctcatgctccgtgatgcatgaggctctgcacaaccac
 R  W  Q  Q  G  N  V  F  S  C  S  V  M  H  E  A  L  H  N  H
tacacgcagaagagcctctccctgtctccgggtaaa
 Y  T  Q  K  S  L  S  L  S  P  G  K
```

FIG. 20K

```
atggagagggggctgccgctcctctgcgcagtgctcgccctcgtcctcgcccggccggc
 M  E  R  G  L  P  L  L  C  A  V  L  A  L  V  L  A  P  A  G
gcttttcgaacgataaatgtggcgatactataaaattgaaagccccggtaccttaca
 A  F  R  N  Q  K  C  G  D  T  I  K  I  E  S  P  G  Y  L  T
tctcctggttatccttcattcttatcacccaagtgaaaaatgcgaatggctgattcaggct
 S  P  G  Y  P  H  S  Y  H  P  S  E  K  C  E  W  L  I  Q  A
ccggacccataccagagaattatgatcaacttcaaccctcacttcgatttggaggacaga
 P  D  P  Y  Q  R  I  M  I  N  F  N  P  H  F  D  L  E  D
gactgcaagtatgactacgtggaagtcttcgatggagaaaatgaaaatggacatttagg
 D  C  K  Y  D  Y  V  E  V  F  D  G  E  N  E  N  G  H  F  R
ggaaagttctgtggaaagatagcccctcctcctgttgtgtcttcagggccatttcttttt
 G  K  F  C  G  K  I  A  P  P  P  V  V  S  S  G  P  F  L  F
atcaaattgtctctgactatgaaacacatggtgcaggatttccatacgttatgaactt
 I  K  F  V  S  D  Y  E  T  H  G  A  G  F  S  I  R  Y  E  L
ttcaagagaggtcctgaatgttcccagaactacaccaacacctagtggagtgataaagtcc
 F  K  R  G  P  E  C  S  Q  N  Y  T  N  T  S  G  V  I  K  S
cccggattccctgaaaaatatcccaacagccttgaatgcacttatattgtctttgcgcca
 P  G  F  P  E  K  Y  P  N  S  L  E  C  T  Y  I  V  F  A  P
aagatgtcagagattatcctggaatttgaaagctttgacctggagcctgactcaaatcct
 K  M  S  E  I  I  L  E  F  E  S  F  D  L  E  P  D  S  N  P
ccaggggggatgttctgtcgctacgacggctagaaatctgggatggattccctgatgtt
 P  G  M  F  C  R  Y  D  R  L  E  I  W  D  G  F  P  D  V
ggccctcacattgggcgttactgtggacagaaaacaccaggtcgaatcgatcctcatcg
 G  P  H  I  G  R  Y  C  G  Q  K  T  P  G  R  I  S  S  S
ggcattctctccatggttttttacaccgacagcgcgatagcaaaagaaggttctcagca
 G  I  L  S  M  V  F  Y  T  D  S  A  I  A  K  E  G  F  S  A
aactacagtgtcttgcagagcagtgtctcagaagatttcaaatgtatggaagctctggc
 N  Y  S  V  L  Q  S  S  V  S  E  D  F  K  C  M  E  A  L  G
atggaatcaggagaaattcattctgaccagatcacagcttcttcccagtatagcaccaac
 M  E  S  G  E  I  H  S  D  Q  I  T  A  S  S  Q  Y  S  T  N
tggtctgcagagcgtctcccgcctgaactaccctgagaatgggtggactcccggagaggat
 W  S  A  E  R  S  R  L  N  Y  P  E  N  G  W  T  P  G  E  D
tcctaccgagagtggatacaggtagacttggggcttctgcgcttgtcacggctgtcggg
 S  Y  R  E  W  I  Q  V  D  L  G  L  L  R  F  V  T  A  V  G
acacagggcgccatttcaaaagaaaccaagaagaatattatgtcaagacttacaagatc
 T  Q  G  A  I  S  K  E  T  K  K  N  Y  V  K  T  Y  K  I
gacgttagctccaacggggaagactggatcaccataaaagaaggaaacaaacctgttctc
 D  V  S  S  N  G  E  D  W  I  T  I  K  E  G  N  K  P  V  L
tttcagggaaacaccaacctacagatgttgtggttgcagtattcccaaaccactgata
 F  Q  G  N  T  N  P  T  D  V  V  V  A  V  F  P  K  P  L
actgattgtcgaatcaagctgcaacttgggaaactggcatatctatgagattgaa
 T  D  C  R  I  K  L  Q  L  G  K  L  A  Y  L  M  R  F  E
gtatatggttgcagatctgacaaaactcacacatgcccaacgtgccagcacctgaactc
 V  Y  G  C  R  S  D  K  T  H  T  C  P  T  C  P  A  P  E  L
ctggggggaccgtcagtcttcctcttccccccaaaacccaaggacaccctcatgatctcc
 L  G  G  P  S  V  F  L  F  P  P  K  P  K  D  T  L  M  I  S
cggacccctgaggtcacatgcgtggtggtggacgtgagccacgaagaccctgaggtcaag
 R  T  P  E  V  T  C  V  V  V  D  V  S  H  E  D  P  E  V  K
ttcaactggtacgtggacggcgtggaggtgcataatgccaagacaaagccgcgggaggag
 F  N  W  Y  V  D  G  V  E  V  H  N  A  K  T  K  P  R  E  E
cagtacaacagcacgtaccgtgtggtcagcgtcctcaccgtcctgcaccaggactggctg
 Q  Y  N  S  T  Y  R  V  V  S  V  L  T  V  L  H  Q  D  W  L
```

FIG. 20L

```
aatggcaaggagtacaagtgcaaggtctccaacaaagccctcccagcccccatcgagaaa
 N  G  K  E  Y  K  C  K  V  S  N  K  A  L  P  A  P  I  E  K
accatctccaaagccaaagggcagccccgagaaccacaggtgtacaccctgcccccatcc
 T  I  S  K  A  K  G  Q  P  R  E  P  Q  V  Y  T  L  P  P  S
cgggaggagatgaccaagaaccaggtcagcctgacctgcctggtcaaaggcttctatccc
 R  E  E  M  T  K  N  Q  V  S  L  T  C  L  V  K  G  F  Y  P
agcgacatcgccgtggagtgggagagcaatgggcagccggagaacaactacaagaccacg
 S  D  I  A  V  E  W  E  S  N  G  Q  P  E  N  N  Y  K  T  T
cctcccgtgctggactccgacggctccttcttcctctacagcaagctcaccgtggacaag
 P  P  V  L  D  S  D  G  S  F  F  L  Y  S  K  L  T  V  D  K
agcaggtggcagcaggggaacgtcttctcatgctccgtgatgcatgaggctctgcacaac
 S  R  W  Q  Q  G  N  V  F  S  C  S  V  M  H  E  A  L  H  N
cactacacgcagaagagcctctccctgtctccgggtaaa
 H  Y  T  Q  K  S  L  S  L  S  P  G  K
```

FIG. 20M

```
atggagagggggctgccgctcctctgcgcgtgctcgccctcgtcctcgccccggccggc
 M  E  G  L  P  L  L  C  A  V  L  A  L  V  L  A  P  A  G
gcttttcgaacgataaatgtggcgatactataaaattgaaagcccccggtaccttaca
 A  F  R  S  K  C  G  D  T  I  K  I  E  S  P  G  Y  L  T
tctcctggttatcctcattctatcacccaagtgaaaaatgcgaatggctgattcaggct
 S  P  G  Y  P  H  S  Y  H  P  S  E  K  M  R  M  A  D  S  G
ccggacccataccagagaattatgatcaacttcaaccctcacttcgattgagacaga
 P  D  P  Y  Q  R  I  M  I  N  F  N  P  H  L  D  R
gactgcaagtatgactacgtggaagtcttcgatggagaaaatgaaaatggacatttagg
 D  C  K  Y  D  Y  V  S  V  F  D  G  E  N  E  N  G  H  L  R
ggaaagttcgtggaaagatagccccctcctcctgttgtgtcttcagggccattcttttt
 G  K  F  V  E  R  *  P  L  L  L  L  C  L  Q  G  H  S  F
atcaaatttgtctctgactacgaaacacatggtgcaggattttccatacgttatgaactt
 I  K  F  V  S  D  Y  E  T  H  G  A  G  F  S  I  R  Y  E  L
ttcaagagaggtcctgaatgtcccagaactacacaacactagtggagcgataaagtcc
 F  K  R  G  P  E  C  P  R  T  T  Q  H  L  V  E  R  *  S  P
cccggatccctgaaaatatcccaacagccttgaatgcacttatattgtcttgccca
 P  G  S  L  K  I  S  Q  Q  P  *  M  H  L  Y  C  L  A
aagatgtcagagattatcctggaatttgaaagctttgacctggagctgactcaaatcct
 K  M  S  E  I  I  L  E  F  E  S  F  D  L  E  L  T  Q  I  L
ccaggggggatgttctgtcgctaacgaccggctagaaaatctgggatggattcctgatgtt
 Q  G  G  C  S  V  A  N  D  R  L  E  N  L  G  W  I  P  D  V
ggccctaacattggcgttactgtggacagaaaacaccaggtcgaatccgatcctcatcg
 G  P  N  I  G  V  T  V  D  R  K  T  P  G  R  I  R  S  S  S
ggcattctctccaatggttttttacacgacagcgcgatagcaaaagaaggtttctcagca
 G  I  L  S  N  V  F  Y  T  D  S  A  I  A  K  E  G  F  S  A
aactacagtgtcttgagatctgacaaaactcacacatgcccaccgtgcccagcacctgaa
 N  Y  S  V  L  R  S  D  K  T  H  T  C  P  P  C  P  A  P  E
ctcctggggggaccgtcagtcttcctcttccccccaaaacccaaggacaccctcatgatc
 L  L  G  G  P  S  V  F  L  F  P  P  K  P  K  D  T  L  M  I
tcccggaccccctgaggtcacatgcgtggtggtggacgtgagccacgaagaccctgaggtc
 S  R  T  P  E  V  T  C  V  V  V  D  V  S  H  E  D  P  E  V
aagttcaactggtacgtggacggcgtggaggtgcataatgccaagacaaagccgcgggag
 K  F  N  W  Y  V  D  G  V  E  V  H  N  A  K  T  K  P  R  E
gagcagtacaacagcacgtaccgtgtggtcagcgtcctcaccgtcctgcaccaggactgg
 E  Q  Y  N  S  T  Y  R  V  V  S  V  L  T  V  L  H  Q  D  W
ctgaatggcaaggagtacaagtgcaaggtctccaacaaagccctcccagcccccatcgag
 L  N  G  K  E  Y  K  C  K  V  S  N  K  A  L  P  A  P  I  E
aaaaccatctccaaagccaaagggcagccccgagaaccacaggtgtacaccctgccccca
 K  T  I  S  K  A  K  G  Q  P  R  E  P  Q  V  Y  T  L  P  P
tcccgggaggagatgaccaagaaccaggtcagcctgacctgcctggtcaaaggcttctat
 S  R  E  E  M  T  K  N  Q  V  S  L  T  C  L  V  K  G  F  Y
cccagcgacatcgccgtggagtgggagagcaatgggcagccggagaacaactacaagacc
 P  S  D  I  A  V  E  W  E  S  N  G  Q  P  E  N  N  Y  K  T
acgcctcccgtgctggactccgacggctccttcttcctctacagcaagctcaccgtggac
 T  P  P  V  L  D  S  D  G  S  F  F  L  Y  S  K  L  T  V  D
aagagcaggtggcagcaggggaacgtcttctcatgctccgtgatgcatgaggctctgcac
 K  S  R  W  Q  Q  G  N  V  F  S  C  S  V  M  H  E  A  L  H
aaccactacacgcagaagagcctctccctgtctccgggtaaa
 N  H  Y  T  Q  K  S  L  S  L  S  P  G  K
```

```
gagggcaacaacaactatgatacacctgagctgcggactttccagtctctccacgcga
 E G N N Y D T P E L R T F P A L S T R
ttcatcaggatctaaccgagagagcaactcatggtggactggggtcagaatggagctg
 F I R I * P E R A T * G G L G * M E L
ctgggctgtgaagtggaagcccttacagctggacgacctctccaacggggaacttggtc
 L G C E V E A P T A G * T * P * G N L V
gatgaatgtgatgacgaccaggccaactgcacagtggaacaggtgatgacttccagctc
 D E C D D Q A N C * G T * D * F * L
acaggtggcacaactgtgctggcacagaaagcccacggtcatagacagcaccatacaa
 T G * T V L A * R P * V I * S T I Q
tcagagttccaacatatggttttaactgtgaatttggctgggctctcacaagacttc
 S E F * T * G F * C E F G W G * * T F
tgccactgggaacatgacaatacgtgcagtcaagtggagtgtgttgaccagcaagacg
 C H W E * D N R V Q L K * S V L T S K T
ggaccattcaggatcaacaggagatggcaacttcatctattccaagctgacgaaaat
 G * P I Q D * T * G * N F * * S Q A * E N
cagaagggcaaagtggctcgcctggtgagcctgtggttattcccagaactctgccac
 Q K G K V A R L V S P V V Y * Q N * A H
tgatgacttctggtatcacatgtctgggtccacgtggcacactcagggtcaaactg
 * N T F W Y * * S G S R V G T L * V K L
ccgctaccaggaagcagggagtacgatcagctggtctggatggccattggacaccaggt
 R Y Q * P E Y D Q L V W M A I G * Q G
gaccactggaaggaagggcgtgtcttgctccacaagtctctgaaactttatcaggtgatt
 D H W K E G * V L L H K S L K L Y Q V I
ttcgagggtgaaatcggaaaggaaaccttggtggattgctgtggatgacttagtatt
 F E G * I G K * G R * L G G * * V D * L * I
aataaccactttcacaagaagattgtgcaaaaccagcagactggataaaagaaccca
 N N H * F * S R R * V Q N Q Q T G * R K N P
gaaattaaaattgatgaaacaggagacatgccaggatacgaaggtgaaggagaaggtgac
 K I K I D E T G * * H A R I R G * R E E G D
aagacatctccaggaagccaggcaatgtgttgaagacctagaccccagatctgacaaa
 K T S R E A R Q C V E D L D P R S D K
actcaacatgccaccgtgccagacacctgaactcctggggggacgtcagtcttcctc
 T Q H A T V P R T * N * G G D V S F L
ttcccccaaaaccaaggacacctatgatctccggaccctgaggtcacatgctgtg
 F P P K P K D T * M * S R T P E V T C V
gtggtggacgtgagccacgaagaccctgaggtcaagttcaactggtacgtggacggcgtg
 V V D V S H E D P E V K F N W Y V D G V
gaggtgcataatgccaagacaaagccgcgggaggagcagtacaacagcacgtaccgtgtg
 E V H N A K T K P R E E Q Y N S T Y R V
gtcagcgtcctcaccgtcctgcaccaggactggctgaatggcaaggagtacaagtgcaag
 V S V L T V L H Q D W L N G K E Y K C K
gtctccaacaaagccctcccagcccccatcgagaaaaccatctccaaagccaaagggcag
 V S N K A L P A P I E K T I S K A K G Q
ccccgagaaccacaggtgtacaccctgcccccatcccgggaggagatgaccaagaaccag
 P R E P Q V Y T L P P S R E E M T K N Q
gtcagcctgacctgcctggtcaaaggcttctatcccagcgacatcgccgtggagtgggag
 V S L T C L V K G F Y P S D I A V E W E
agcaatgggcagccggagaacaactacaagaccacgcctcccgtgctggactccgacggc
 S N G Q P E N N Y K T T P P V L D S D G
tccttcttcctctacagcaagctcaccgtggacaagagcaggtggcagcaggggaacgtc
 S F F L Y S K L T V D K S R W Q Q G N V
ttctcatgctccgtgatgcatgaggctctgcacaaccactacacgcagaagagcctctcc
 F S C S V M H E A L H N H Y T Q K S L S
ctgtctccgggtaaa
 L S P G K
```

FIG. 20P

MERGLPLLCAVLALVLAPAGAFRNDKCGDTIKIESPGYLTSPGYPHSYHPSEKCEWLIQAP
DPYQRIMINFNPHFDLEDRDCKYDYVEVFDGENENGHFRGKFCGKIAPPPVVSSGPFLFIK
FVSDYETHGAGFSIRYELFKRGPECSQNYTTPSGVIKSPGFPEKYPNSLECTYIVFAPKMS
EIILEFESFDLEPDSNPPGGMFCRYDRLEIWDGFPDVGPHIGRYCGQKTPGRIRSSSGILS
MVFYTDSAIAKEGFSANYSVLQSSVSEDFKCMEALGMESGEIHSDQITASSQASTNWSAE
RSRLNYPENGWTPGEDSYREWIQVDLGLLRFVTAVGTQGAISKETKKKYYVKTYKIDVSS
NGEDWITIKEGNKPVLFQGNTNPTDVVVAVFPKPLITRFVRIKPATWETGISMRFEVYGCKI
TDYPCSGMLGMVSGLISDSQITSSNQGDRNWMPENIRLVTSRSGWALPPAPHSYINEWL
QIDLGEEKIVRGIIIQGGKHRENKVFMRKFKIGYSNNGSDWKMIMDDSKRKAKSFEGNNNY
DTPELRTFPALSTRFIRIYPERATHGGLGLRMELLGCZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

MKRGLPLLCAVLALVLAPAGAFRNDKCGDTIKIESPGYLTSPGYPHSYHPSEKCEWLIQA
PDPYQRIMINFNPHFDLEDRDCKYDYVEVFDGENENGHFRGKFCGKIAPPPVVSSGPFLF
IKFVSDYETHCAGFSIRYELFKRGPECSQNYTTPSGVIKSPGFPEKYPNSLECTYIVFAP
KNSEIILEFESFDLEPDSNPPCQMFCRYDRLEIWDGFPDVGPHIGRYCGQKTPGRIRSSS
GILSMVFYTDSAIAKEGFSANYSVLQSSVSEDFKCMEALGMESGEIHSDQITASSQASTN
WSAEKSRLNYPENGWTPGEDSYREWIQVDLGLLRFVTAVGTQGAISKETKKKYYVKTYKI
DVSSNGEDWITIKEGNKPVLFQGNTNPTDVVVAVFPKFLITRFVRIKPATWETGISMRFE
VYGCZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZZZZZZZZZZZZZZZZZZZZZZZZZZZZZZZZZZZZZZZZZZZ
ZZZZZZZZZZZZZZZZZDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLS
LSPGK

FIG. 20S

```
ATGGAGAGGGGCTGCCGCTCCTCTGCGCCGTGCTCGCCCTCGTCCTCGCCCCGGCCGGCGCTTTTC
GCAACGATAAATGTGGCGATACTATAAAAATTGAAAGCCCCGGGTACCTTACATCTCTGGTTATCC
TCATTCTTATCACTCAACTGAAAAATGCCAATGGCTGATTCAGCCTCCGCACCCATACCAGAGAATT
ATGATCAACTTCAACCCTCACTTCGATTTGGAGGACAGAGACTGCAAGTATGACTACGTGGAAGTCT
TCGATGGAGAAAATGAAAATGGACATTTTACGGGAAAGTTCTGTGGAAAGATAGCCCGTTCCTCCTGT
TGTGTCTTCAGGGCCATTTCTTTTTATCAAATTGTCTCTGACTACGAAACACATGGTGCAGGATTT
TCCATACGTTATGAACTTTTCAAGAGAGCTCCTGAATGTTCCCAGAACTACACAACACCTAGTGGAG
TGATAAAGTCCCTCGGATTCCCTGAAAAATATCCCAACAGCCTTGAATGCACTTATATTGTCTTTGC
GCCAAAGATGTCAGACATTATCCTGGAATTTGAAAGCTTTGACCTGGAGCCTGACTCAAATCCTCCA
GGGGGCATGTTCTGTCCCTACGACCGGCTAGAAATCTGGGATGGATTCCCTGATGTTGGCCCTCACA
TTGGGCGTTACTGTGGACAGAAAACACGAGGTCGAATCCGATCCTCATCGGGCATTCTCTCCATGGT
TTTTACACCGACAGCGCGATAGCCAAAACAAGGTTTCTCAGCAAACTACAGTGTCTTGCAGAGCAGT
GTCTCAGAACATTCAAATGTATGGAAGCTCTGGGCATGGAATCAGGAGAAATTCATTCTGACCAGA
TCACAGCTTCTTCCCAGGCTAGCACCAACTGGTCTGCAGAGCGCTCCCGCCTGAACTACCCTGACAA
TGGGTGGACTCCCGGAGAGGATTCCTACCGAGAGTGGATACAGGTAGACTTGGGCCTTCTGCCCTTT
GTCACGGCCTGTCCGGACACAGGGCGCCATTTCAAAAGAAAACCAACAAGAAATATTATGTCAAGACTT
ACAAGATCGACGTTAGCTCCAACGGGAAGACTGGATCACCATAAAAGAAGGAAACAAAGCTGTTCT
CTTTCAGGGAAACACCAACCCTACAGATGTTGTGGTTCCAGTATTCCCCAAACCACTGATAACTCGG
TTTGTCCGAATCAAGCCTGCAACTTGGGAAACTGGCATATCTATGAGATTTCAAGTATATGGTTGCN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNGACAAAACTCACACATGCCCACCGTGCCCAGCACCTGAA
CTCCTGGGGGGACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCACGAGGCTCTGCACAAC
CACTACACGCAGAAGAGCCTCTCCCTGTCTCCGGGTAAA
```

FIG. 20T

```
atggagagggggctgccgctcctctgcgcagtgctcgccctcgtcctcgcccaggcgggc
 M  E  R  G  L  P  L  L  C  A  V  L  A  L  V  L  A  P  A  G
gcttttcgcaacgataaatgtggcgatactataaaaattgaaagcccgggttaccttaca
 A  F  R  N  D  K  C  G  D  T  I  K  I  E  S  P  G  Y  L  T
tctcctggttatcctcattcttatccccaagtgaaaaatgcgaatggctgattcaggct
 S  P  G  Y  P  H  S  Y  P  S  E  K  C  E  W  L  I  Q  A
ccggacccataccagagaatatgatcaacttcaacctcacttcgatttggaggacaga
 P  D  P  Y  Q  R  I  M  I  N  F  N  P  F  D  L  E  D  R
gactgcaagtatgactacgtggaagtcttcgatggagaaaatgaaaatggacattcagg
 D  C  K  Y  D  Y  V  E  V  F  D  G  E  N  E  N  G  H  F  R
ggaaagttctgtggaaagatagccctcctcctgttgtgtcttcagggccattcttttt
 G  K  F  C  G  K  I  A  P  P  V  V  S  S  G  P  F  L  F
atcaaattgtctctgactacgaaacacatggtgcaggattttcctacgttatgaactt
 I  K  F  V  S  D  Y  E  T  H  G  A  G  F  S  Y  V  M  N  F
ttcaagagagggtcctgaatgttcccagaactacacaacacctagtggagtgataaagtcc
 F  K  R  G  P  E  C  S  Q  N  Y  T  T  P  S  G  V  I  K  S
cccggattccctgaaaaatatcccaacagccttgaatgcacttatatgtctttgcgcca
 P  G  F  P  E  K  Y  P  N  S  L  E  C  T  Y  I  V  F  A  P
aagaatgtcagagattatcctggaatttgaaagctttgacctggagcctgactcaaatcct
 K  N  S  E  I  L  E  F  E  S  F  D  L  E  P  D  S  N  P
ccagggggcatgttctgtcgctacgacggctagaaaatctgggatggattccctgatgtt
 P  G  G  M  F  C  R  Y  D  G  L  E  I  W  D  G  F  P  D  V
ggccctcacattgggcgttactgtggacagaaaacaccaggtcgaatccgatcctcatcg
 G  P  H  I  G  R  Y  C  G  Q  K  T  P  G  R  I  R  S  S
ggcattctctccatggttttttacaccgacagcgcgatagcaaaagaaggtttctcagca
 G  I  L  S  M  V  F  Y  T  D  S  A  I  A  K  E  G  F  S  A
aactacagtgtcttgcagagcagtgtctcagaagatttcaaatgtatggaagctctggc
 N  Y  S  V  L  Q  S  S  V  S  E  D  F  K  C  M  E  A  L  G
atggaatcaggagaaaattcattctgaccagatcacagttcttcccaggctagcacaac
 M  E  S  G  E  I  S  D  Q  I  T  A  S  S  Q  A  S  T  N
tggtctgcagagcgctccgcctgaactacctgagaatgggtggactcccggagaggat
 W  S  A  E  R  S  R  L  N  Y  P  E  N  G  W  T  P  G  E  D
tcctaccgagagtggatacaggtagacttggggcttctgcgcttgtcaggctgtcggg
 S  Y  R  E  W  I  Q  V  D  L  G  L  L  R  F  V  T  A  V  G
acacaggggcatttcaaaagaaaccagaagaaatattatgtcaagacttacaagatc
 T  Q  G  A  I  S  K  E  T  K  K  Y  Y  V  K  T  Y  K  I
gacgttagctccaaggggaagactggatcaccataaaagaaggaaacaaacctgttctc
 D  V  S  S  N  G  E  D  W  I  T  I  K  E  G  N  K  P  V  L
tttcaggggaaacaccaacctacagatgttgtggttgcagtattccccaaaccactgata
 F  Q  G  N  T  N  P  T  D  V  V  V  A  V  F  P  K  P  L  I
actcgatttgtccgaatcaagcctgcaacttgggaaactggcatatctatgagatttgaa
 T  R  F  V  R  I  K  P  A  T  W  E  T  G  I  S  M  R  F  E
gtatatggttgcaagataacagattatccttgctctggaatgttgggtatggtgtctgga
 V  Y  G  C  K  I  T  D  Y  P  C  S  G  M  L  G  M  V  S  G
cttattctgactcccagatcaatcatccaaccaaggggacagaaactggatgcctgaa
 L  I  S  D  S  Q  I  T  S  S  N  Q  G  D  R  N  W  M  P  E
aacatccgcctggtaaccagtcgctctggctgggcacttccacccgcacctcattcctac
 N  I  R  L  V  T  S  R  S  G  W  A  L  P  P  A  P  S  Y
atcaatgagtggctccaaatagacctgggggaggagaagatcgtgagggcatcatcatt
 I  N  E  W  L  Q  I  D  L  G  E  E  K  I  V  R  G  I  I  I
cagggtgggaagcacggagagaacaaggtgttcatgaggaagttcaagatcgggtacagc
 Q  G  G  S  N  R  E  N  K  V  F  M  R  K  F  K  I  G  Y  S
```

FIG. 20U

```
aacaacggctcggactggaagatgatcatggatgacagcaaacgcaaggcgaagtcttt
 N  N  G  S  D  W  K  M  I  M  D  D  S  K  R  K  A  K  S  F
gagggcaacaacaactatgatacacctgagctgcggacttttccagtctctccacgcga
 E  G  N  N  N  Y  D  T  P  E  L  R  T  F  P  A  L  S  T  R
ttcatcaggatctaccccgagagagccactcatggcggactggggctcagaatggagctg
 F  I  R  I  Y  P  E  R  A  T  S  G  G  L  G  L  R  M  E  L
ctgggctgtagatctgacaaaactcacacatgcccacgtgccagcactgaactcctg
 L  G  C  R  S  D  K  T  S  T  C  P  P  C  P  A  P  E  L  L
gggggaccgtcagtcttcctcttccccccaaaacccaaggacaccctcatgatctcccgg
 G  G  P  S  V  F  L  F  P  P  K  P  K  D  T  L  M  I  S  R
acccctgaggtcacatgcgtggtggtggacgtgagccacgaagaccctgaggtcaagttc
 T  P  E  V  T  C  V  V  V  D  V  S  H  E  D  P  E  V  K  F
aactggtacgtggacggcgtggaggtgcataatgccaagacaaagccgcgggaggagcag
 N  W  Y  V  D  G  V  E  V  H  N  A  K  T  K  P  R  E  E  Q
tacaacagcacgtaccgtgtggtcagcgtcctcaccgtcctgcaccaggactggctgaat
 Y  N  S  T  Y  R  V  V  S  V  L  T  V  L  H  Q  D  W  L  N
ggcaaggagtacaagtgcaaggtctccaacaaagccctcccagcccccatcgagaaaacc
 G  K  E  Y  K  C  K  V  S  N  K  A  L  P  A  P  I  E  K  T
atctccaaagccaaagggcagccccgagaaccacaggtgtacaccctgcccccatcccgg
 I  S  K  A  K  G  Q  P  R  E  P  Q  V  Y  T  L  P  P  S  R
gaggagatgaccaagaaccaggtcagcctgacctgcctggtcaaaggcttctatcccagc
 E  E  M  T  K  N  Q  V  S  L  T  C  L  V  K  G  F  Y  P  S
gacatcgccgtggagtgggagagcaatgggcagccggagaacaactacaagaccacgcct
 D  I  A  V  E  W  E  S  N  G  Q  P  E  N  N  Y  K  T  T  P
cccgtgctggactccgacggctccttcttcctctacagcaagctcaccgtggacaagagc
 P  V  L  D  S  D  G  S  F  F  L  Y  S  K  L  T  V  D  K  S
aggtggcagcaggggaacgtcttctcatgctccgtgatgcatgaggctctgcacaaccac
 R  W  Q  Q  G  N  V  F  S  C  S  V  M  H  E  A  L  H  N  H
tacacgcagaagagcctctccctgtctccgggtaaa
 Y  T  Q  K  S  L  S  L  S  P  G  K
```

FIG. 20V

```
tggagaggggctgccgctcctctgcgccgtgctggccctcgtcctcgcccggccgga
 M  E  R  G  L  P  L  L  C  A  V  L  A  L  V  L  A  P  A  G
gcttttcgaacgataaatgtggcgatactataaaattgaaagccccgggtaccttaca
 A  F  R  N  D  K  C  G  D  T  I  K  I  E  S  P  G  Y  L  T
tctcctggttatcctcattcttatcacccaagtgaaaatgcgaatggtgattcaggct
 S  P  G  Y  P  H  S  Y  H  P  S  E  N  A  N  G  D  S  G
ccggacccataccagagaattatgatcaacttcaacctcacttcgatttggaggacaga
 P  D  P  Y  Q  R  I  M  I  N  F  N  P  H  F  D  L  E  D  R
gactgcaagtatgactacgtggaagtcttcgatggagaaaatgaaaatggacatttagg
 D  C  K  Y  D  Y  V  E  V  F  D  G  E  N  E  N  G  H  L  G
ggaaagttctgtggaaagatagcccctcctcctgttgtgtcttcagggccatttctttt
 G  K  F  C  G  K  I  A  P  P  P  V  V  S  S  G  P  F  L  F
atcaaatttgtctctgactacgaaacacatggtgcaggattttcatacgttatgaactt
 I  K  F  V  S  D  Y  E  T  H  G  A  G  F  S  Y  R  Y  E  L
ttcaagagaggtcctgaatgttccagaactacacaacacctagtggagtgataaagtcc
 F  K  R  G  P  E  C  S  R  T  T  Q  H  P  S  G  V  I  K  S
ccggattccctgaaaaatatccccaacagccttgaatgcacttatattgtctttgcgca
 P  G  S  L  K  N  I  P  N  S  L  E  C  T  Y  I  V  F  A  P
aagatgtcagagattatcctggaatttgaaagctttgaccctggagcctgactcaaatcct
 K  M  S  E  I  I  L  E  F  E  S  F  D  L  E  P  D  S  N  P
ccaggggggatgttctgtcgctacgaccggctagaaatctgggatggattccctgatgtt
 P  G  G  M  F  C  R  Y  D  R  L  E  I  W  G  F  P  D  V
ggccctcacattgggcgttactgtggacagaaaaccaggtcgaatcgatcctaatcg
 G  P  H  I  G  R  Y  C  G  Q  K  T  P  G  R  I  R  S  S
ggcattctctccatggttttttacacgacagcgcgatagcaaaagaaggtttctcagca
 G  I  L  S  M  V  F  Y  T  D  S  A  I  A  K  E  G  F  S  A
aactacagtgtcttgcagagaagtgtctcagaagatttcaaatgtatggaagctctggc
 N  Y  S  V  L  Q  S  S  V  S  E  D  F  K  C  M  E  A  L  G
atggaatcaggagaaattcattctgaccagatcacagcttcttccaggctagcaccaac
 M  E  S  G  E  I  H  S  D  Q  I  T  A  S  S  Q  A  S  T  N
tggtctgcagagcgctccgcctgaactaccctgagaatgggtggactcccggagaggat
 W  S  A  R  S  L  N  Y  P  E  N  G  W  T  P  G  E  D
tcctaccgagagtggatacaggtagacttggcctttctgcgcttgtcacggctgtcggg
 S  Y  R  E  W  I  Q  V  D  L  G  L  L  R  F  V  T  A  V  G
acacagggcgccatttcaaaagaaaccaagaagaaatattatgtcaagacttacaagatc
 T  Q  G  A  I  S  K  E  T  K  K  Y  Y  V  K  T  Y  K  I
gacgttagctccaacgggagactggatcaccataaagaaggaaacaaacctgttctc
 D  V  S  S  N  G  E  D  W  I  T  I  K  E  G  N  K  P  V  L
ttcaggggaaacaccaaccctacagatgttgtggttgcagtattcccaaaccactgata
 F  Q  G  N  T  N  P  T  D  V  V  V  A  V  F  P  K  P  L  I
actcgattgtccgaatcaagcctgcaacttggaaactggcatatctatgagatttgaa
 T  R  F  V  R  I  R  P  A  T  W  E  T  G  I  S  M  R  F  E
gtatatggttgcagatctgacaaaactcacacatgcccaccgtgcccagcacctgaactc
 V  Y  G  C  R  S  D  K  T  H  T  C  P  P  C  P  A  P  E  L
ctgggggacgtcagcttcctcttcccccaaaaccaaggacaccctcatgatctcc
 L  G  D  V  S  F  L  F  P  P  K  P  K  D  T  L  M  I  S
cggacccctgaggtcacatgcgtggtggtggacgtgagccacgaagaccctgaggtcaag
 R  T  P  E  V  T  C  V  V  V  D  V  S  H  E  D  P  E  V  K
ttcaactggtacgtggacggcgtggaggtgcataatgccaagacaaagccgcgggaggag
 F  N  W  Y  V  D  G  V  E  V  H  N  A  K  T  K  P  R  E  E
cagtacaacagcacgtaccgtgtggtcagcgtcctcaccgtcctgcaccaggactggctg
 Q  Y  N  S  T  Y  R  V  V  S  V  L  T  V  L  H  Q  D  W  L
```

FIG. 20W

```
aatggcaaggagtacaagtgcaaggtctccaacaaagccctcccagcccccatcgagaaa
 N  G  K  E  Y  K  C  K  V  S  N  K  A  L  P  A  P  I  E  K
accatctccaaagccaaagggcagccccgagaaccacaggtgtacaccctgcccccatcc
 T  I  S  K  A  K  G  Q  P  R  E  P  Q  V  Y  T  L  P  P  S
cgggaggagatgaccaagaaccaggtcagcctgacctgcctggtcaaaggcttctatccc
 R  E  E  M  T  K  N  Q  V  S  L  T  C  L  V  K  G  F  Y  P
agcgacatcgccgtggagtgggagagcaatgggcagccggagaacaactacaagaccacg
 S  D  I  A  V  E  W  E  S  N  G  Q  P  E  N  N  Y  K  T  T
cctcccgtgctggactccgacggctccttcttcctctacagcaagctcaccgtggacaag
 P  P  V  L  D  S  D  G  S  F  F  L  Y  S  K  L  T  V  D  K
agcaggtggcagcaggggaacgtcttctcatgctccgtgatgcacgaggctctgcacaac
 S  R  W  Q  Q  G  N  V  F  S  C  S  V  M  H  E  A  L  H  N
cactacacgcagaagagcctctccctgtctccgggtaaa
 H  Y  T  Q  K  S  L  S  L  S  P  G  K
```

FIG. 20X

```
atggagagggggctgccgttgctgtgcgccaaggctgcccttgccctcgcctggcgggc
 M  E  R  G  L  L  L  C  A  T  L  A  L  A  L  A  G
gcttccgcagcgacaaatgtggcggaccataaaaatcgaaaacccagggtacctcaca
 A  F  R  S  D  K  C  G  T  I  K  I  E  N  P  G  Y  L  T
tctcccggttaccctcattcttacatccaagtgagaagtgtgaatggctaatccaagct
 S  P  G  Y  P  S  Y  H  P  S  E  K  C  E  W  L  I  Q  A
cgggaagctaccagagaatcatgatcaacttcaaccgacattccgatttggaggacaga
 R  E  A  Y  Q  R  I  M  I  N  F  N  R  H  S  D  L  E  D  R
gactgcaagtatgactacgtggaagtaatcgatggggagaatgaaggcggccgctgtgg
 D  C  K  Y  D  Y  V  E  V  I  D  G  E  N  E  G  R  L  W
ggaagttctgtgggaagattgcaccttctcctgtggtgtcttcagggcctttctcttc
 G  K  F  C  G  K  I  A  P  S  P  V  V  S  S  G  P  F  L  F
atcaaattgtgtctgactatgagacacatgggcagggttttccatccgctatgaaatc
 I  K  F  V  S  D  Y  E  T  H  G  A  G  F  S  I  R  Y  E  I
ttcaagagagggcccgaatgttctcagaactatacagcacctactggagtgataaagtcc
 F  K  R  G  P  E  C  S  Q  N  Y  T  A  P  T  G  V  I  K  S
cctgggttccctgaaaataccccaacagctggagtgcacctacatcatcttgcacca
 P  G  F  P  E  K  Y  P  N  S  L  E  C  T  Y  I  I  F  A  P
aagatgtctgagataatcctggagtttgaaagttttgacctggagcaagactgaatcct
 K  M  S  E  I  I  L  E  F  E  S  F  D  L  E  Q  D  S  N  P
ccggaggaatgttctgtgctatgaccggctggagatctggatggattccctgaagtt
 P  G  E  C  S  V  Y  D  R  L  E  I  W  D  G  P  P  E  V
ggcctccacattgggcgttattgtgggcagaaaactctggccggatccgctcctcttca
 G  P  H  I  G  R  Y  C  G  Q  K  T  P  G  R  I  R  S  S
ggcgttctatccatggtcttttacactgacagcgcaatagcaaaagaaggtttctcagcc
 G  V  L  S  M  V  F  Y  T  D  S  A  I  A  K  E  G  F  S  A
aactacagtgtgctacagagcagcatctctgaagattttaagtgtatggaggctctggc
 N  Y  S  V  L  Q  S  S  I  S  E  D  F  K  C  M  E  A  L  G
atggaatctggagagatccattctgatcagatcactgcatcttcacagtatggtaccaac
 M  E  S  G  E  I  H  S  D  Q  I  T  A  S  S  Q  Y  G  T  N
tggtctgtagagcgctccgctgaactaccctgaaaatgggtggactccaggagaagac
 W  S  V  E  R  S  R  L  N  Y  P  E  N  G  W  T  P  G  E  D
tcctacaaggagtggatccaggtggactggggcctcctgcgattcgttactgctgtaggg
 S  Y  K  E  W  I  Q  V  D  L  G  L  L  R  F  V  T  A  V  G
acacagggtgccatttccaaggaaaccaagaagaaatattatgtcaagacttacagagta
 T  Q  G  A  I  S  K  E  T  K  K  K  Y  Y  V  K  T  Y  R  V
gacatcagctcaacggagaggactggatctccctgaaagagggaaataaagccattatc
 D  I  S  S  N  G  E  D  W  I  S  L  K  E  G  N  K  A  I  I
tttcagggaaacacccaacccacagatgttgtcttaggagttttctcaaaaccactgata
 F  Q  G  N  T  N  P  T  D  V  V  L  G  V  F  S  K  P  L  I
actcgatttgtccgaatcaaacctgtatcctgggaaactggtatatctatgagatttgaa
 T  R  F  V  R  I  K  P  V  S  W  E  T  G  I  S  M  R  F
gtttatggctgcaagataacagattatcctcgctctggaatgttgggcatggtgtctgga
 V  Y  C  K  I  D  Y  P  C  S  G  M  L  G  M  V  S  G
cttattcaagactcccagattacagcatccaatcaagcggacaggaattggatgcagaa
 L  I  S  D  S  Q  I  T  A  S  N  Q  A  D  R  N  W  M  Q  E
aacatccgtctggtgaccagtcgtaccggctgggcactgccacccctcaccccagccatac
 N  I  R  L  V  T  S  R  T  G  W  A  L  P  P  S  P  H  P  Y
accaatgaatggctccaagtggacctgggagatgagaagatagtaagaggtgtcatcatt
 T  N  E  W  L  Q  V  D  L  G  D  E  K  I  V  R  G  V  I  I
caggtggggaagcaccgagaaaacaaggtgttcatgaggaagttcaagatcgctatagt
 Q  G  G  K  H  R  E  N  K  V  F  M  R  K  F  K  I  A  Y  S
aacaatggctctgactggaaaactatcatggatgacagcaagcgcaaggctaagtcgttc
 N  N  G  S  D  W  K  T  I  M  D  D  S  K  R  K  A  K  S  F
gaaggcaacaacaactatgacacacctgagcttcggacgttttcacctctctccacaagg
 E  G  N  N  N  Y  D  T  P  E  L  R  T  F  S  P  L  S  T  R
```

FIG. 20Y

```
ttcatcaggatctaccctgagagagccacacacagtgggcttgggctgaggatggagcta
 F  I  R  I  Y  P  E  R  A  T  H  S  G  L  G  L  R  M  E  L
ctgggtgtgaagtggaagcacctacagctggaccaaccacacccaatgggaaccagtg
 L  G  C  E  V  E  A  P  T  A  G  P  T  T  P  N  G  N  P  V
gatgagtgtgacgacgaccaggccaactgcacagtggcacaggtgatgacttccagctc
 D  E  C  D  D  Q  A  N  C  H  S  G  T  G  D  D  F  Q  L
acaggaggaccactgtcctggccacagagaaggcaaccattatagacagcaccatccaa
 T  G  G  T  T  V  L  A  T  E  K  P  T  I  D  S  T  I  Q
tcagagttccgacatacggttttaactgggagtttggctgggctctcacaagacattc
 S  E  F  P  T  Y  G  F  N  C  E  F  G  W  G  S  H  K  F
tgccactgggagcatgacagccatgcacagctcaggtggagtgtgctgaccagcaagaca
 C  H  W  E  H  D  S  H  A  Q  L  R  W  S  V  L  T  S  K  T
gggccgattcaggaccatacaggagatggcaacttcatctattcccaagctgatgaaat
 G  P  I  Q  D  H  T  G  D  G  N  F  I  Y  S  Q  A  D  E  N
cagaaaggcaaagtagccgcctggtgagccctgtggtctattcccagagctctgccac
 Q  K  G  K  V  A  R  L  V  S  P  V  V  Y  S  Q  S  S  A  T
tgtatgaccttctggtatcacatgtccggctctcatgtgggtacactgagggtcaaacta
 C  M  T  F  W  Y  H  M  S  G  S  H  V  G  T  L  R  V  K  L
cgctaccagaagccagaggaatatgatcaactggtctggatggtggttgggcaccaagga
 R  Y  Q  K  P  E  E  Y  D  Q  L  V  W  N  V  V  G  Q  Q  G
gaccactggaaagaaggacgtgtcttgctgcacaaatctctgaaactatatcaggttatt
 D  H  W  K  E  G  R  V  L  L  H  K  S  L  K  L  Y  Q  V  I
tttgaaggtgaaatcggaaaaggaaaccttggtggaattgctgtggatgatatcagtatt
 F  E  G  E  I  G  K  G  N  L  G  G  I  A  V  D  D  I  S  I
aacaaccatattctcaggaagactgtgcaaaaccaacagacctagataaaaagaacaca
 N  N  H  I  S  Q  E  D  C  A  K  P  T  D  L  D  K  K  N  T
gaaattaaaattgatgaaacagggagcactccaggatatgaaggagaaggggaaggtgac
 E  I  K  I  D  E  T  G  S  T  P  G  Y  E  G  E  G  E  G  D
aagaacatctccaggaagccaggcaatgtgcttaagaccctggatccgtctcgagcacc
 K  N  I  S  R  K  P  G  N  V  L  K  T  L  D  P  V  S  S  T
atggttagatctggttgtaagccttgcatatgtacagtcccagaagtatcatctgtcttc
 M  V  R  S  C  K  P  C  I  C  T  V  P  E  V  S  S  V  F
atcttcccccaaagcccaaggatgtgctcaaccattactctgactcctaaggtcaagtgt
 I  F  P  P  K  P  K  D  V  L  T  I  T  L  T  P  K  V  T  C
gttgtggtagacatcagcaaggatgatcccgaggtccagttcagctggtttgtagatgat
 V  V  V  D  I  S  K  D  D  P  E  V  Q  F  S  W  F  V  D  D
gtggaggtgcacacagctcagacgcaaccccgggaggagcagttcaacagcactttccgc
 V  E  V  H  T  A  Q  T  Q  P  R  E  E  Q  F  N  S  T  F  R
tcagtcagtgaacttcccatcatgcaccaggactggctcaatggcaaggagttcaaatgc
 S  V  S  E  L  P  I  M  H  Q  D  W  L  N  G  K  E  F  K  C
agggtcaacagtgcagcttccctgccccccatcgagaaaaccatctccaaaaccaaggc
 R  V  N  S  A  A  F  P  A  P  I  E  K  T  I  S  K  T  K
agaccgaaggctccacaggtgtacaccattccacctcccaaggagcagatggccaggat
 R  P  K  A  P  Q  V  Y  T  I  P  P  P  K  E  Q  M  A  K  D
aaagtcagtctgacctgcatgataacagacttcttccctgaagacattactgtggagtgg
 K  V  S  L  T  C  M  I  T  D  F  F  P  E  D  I  T  V  E  W
cagtggaatgggcagccagcggagaactacaagaacactcagcccatcatggacacagat
 Q  W  N  G  Q  P  A  E  N  Y  K  N  T  Q  P  I  M  D  T  D
ggctcttacttcgtctacagcaagctcaatgtgcagaagagcaactgggaggcaggaaat
 G  S  Y  F  V  Y  S  K  L  N  V  Q  K  S  N  W  E  A  G  N
actttcacctgctctgtgttacatgagggcctgcacaaccacatactgagaagagctc
 T  F  T  C  S  V  L  H  E  G  L  H  N  H  H  T  E  K  S  L
tcccactctcctggtaaatga
 S  H  S  P  G  K  -
```

FIG. 20Z

```
atggagagggggctgccgttgctgtgcgccacgctcgccttgcccctgcccctggcggc
 M  E  R  G  L  P  L  L  C  A  T  L  A  L  A  L  A  G
gcttccgagcgacaaatgtggggggaccataaaaatcgaaaacccagggtacctcaca
 A  F  R  S  D  K  C  G  G  T  I  K  I  E  N  P  G  Y  L  T
tctcccggtacccctcattcttaccatccaagtgagaagtgtgaatggctaatccaagct
 S  P  G  T  P  H  S  Y  H  P  S  E  K  C  E  W  L  I  Q  A
ccggaacctaccagagaatcatgatcaacttcaaccacatttcgattggaggacaga
 P  E  P  T  Q  R  I  M  I  N  F  N  P  H  F  D  L  E  D
gactgcaagtatgactacgtggaagtaatcgatgggagaatgaaggcggcgcctgtgg
 D  C  K  Y  D  Y  V  E  V  I  D  G  E  N  E  G  G  R  L  W
gggaagttctgtggaagattgcaccttctcctgtggtgtcttcaggccctttctcttc
 G  K  F  C  G  K  I  A  P  S  P  V  V  S  G  P  F  L  F
atcaaattgtctctgactatgagacatgggcagggttttccatccgctatgaaatc
 I  K  F  V  S  D  Y  E  T  H  G  A  G  F  S  I  R  Y  E  I
ttcaagagagggccggaatgtctcagaactatacagcacctactggagtgataaagtcc
 F  K  R  G  P  E  C  S  Q  N  Y  T  A  P  T  G  V  I  K  S
cctggggttccctgaaaatacccaacagcttggagtgcacctacatcatctttgcacca
 P  G  F  P  E  K  Y  P  N  S  L  E  C  T  Y  I  I  F  A  P
aagatgtctgagataatcctggagtttgaaagttttgacctggagcaagactcgaatcct
 K  M  S  E  I  I  L  E  F  E  S  F  D  L  E  Q  D  S  N  P
ccggagggaatgttctgtcgctatgaccggctggagatctggatggattccctgaagtt
 P  G  G  M  F  C  R  Y  D  R  L  E  I  W  D  G  F  P  E  V
ggccctcacattgggcgttattgtgggcagaaaactcctggccggatccgctcctctca
 G  P  H  I  G  R  Y  C  G  Q  K  T  P  G  R  I  R  S  S
ggcgttctatccatggtctttacactgacagcgtaatagcaaagaaggtttctcagcc
 G  V  L  S  M  V  F  Y  T  D  S  A  I  A  K  E  G  F  S  A
aactacagtgtgctacagagcagatctctgaagattttaagtgtatggaggctctgggc
 N  Y  S  V  L  Q  S  S  I  S  E  D  F  K  C  M  E  A  L  G
atggaatctggagagatccattctgatcagatcactgcatcttcacagtatggtaccaac
 M  E  S  G  E  I  S  D  Q  I  T  A  S  S  Q  Y  G  T  N
tggtctgtagagcgctcccgcctgaactaccctgaaaatggtggactccaggagaagat
 W  S  V  E  R  S  R  L  N  Y  P  E  N  G  W  T  P  G  E  D
tcctacaaggagtggatccaggtggacttggcctcctgcgattcgttactgctgtaggg
 S  Y  K  E  W  I  Q  V  D  L  G  L  L  R  F  V  T  A  V  G
acacagggtgccatttccaaggaaaaccaagaagaaatattatgtcaagacttacagagta
 T  Q  G  A  I  S  K  E  T  K  K  K  Y  Y  V  K  T  Y  R  V
gacatcagctccaacggagaggactggatctcccctgaaagagggaaataaagccattatc
 D  I  S  S  N  G  E  D  W  I  S  L  K  E  G  N  K  A  I  I
ttcaggggaaacaccaaccccacagatgttgtcttaggagttttctccaaaccactgata
 F  Q  G  N  T  N  P  T  D  V  V  L  G  V  F  S  K  P  L  I
actcgatttgtccgaatcaaacctgtatcctgggaaactggtatatctatgagatttgaa
 T  R  F  V  R  I  K  P  V  S  W  E  T  G  I  S  M  R  F  E
gtttatggctgcaagataacagattatcctcgtctggaatgttgggcatggtgtctgga
 V  Y  G  C  K  I  T  D  Y  P  C  S  G  M  L  G  M  V  S  G
cttatttcagactccagattacagcatccaatcaagccgacaggaattggatgccagaa
 L  I  S  D  S  Q  I  T  A  S  N  Q  A  D  R  N  W  M  P  E
aacatccgtctggtgaccagtcgtaccggctgggactgccacccctcaccctcacccctac
 N  I  R  L  V  T  S  R  T  G  W  A  L  P  P  S  P  H  P  Y
accaatgaatggctccaagtggacctggagatgaagaatagtaagaggtgtcatcatt
 T  N  E  W  L  Q  V  D  L  G  E  M  K  I  V  R  G  V  I  I
caggtgggaagcaccgagaaaacaaggtgttcatgaggaagttcaagatcgcctatagt
 Q  G  G  K  H  R  E  N  K  V  F  M  R  K  F  K  I  A  Y  S
aacaggctctgactggaaaactaccatggatgacagcaagggctaagtcgttc
 N  N  G  S  D  W  K  T  I  M  D  D  S  K  R  K  A  K  S  F
gaaggcaaaaacaactatgacactcctgagcttggagcgttttcacccctctccacaagg
 E  G  K  N  N  Y  D  T  P  E  L  R  T  F  S  P  L  S  T  R
```

```
atggagaggggctgccgttgctgtgcgccacgctggcctgcctgcctggcgga
 M  E  R  G  L  P  L  L  C  A  T  L  A  L  A  L  A  G
gcttcgcagacaaatgtggcggaccataaaaatgaaaaccagggtacctcaca
 A  F  R  D  K  C  G  T  I  K  I  E  N  P  G  Y  L  T
tctccggttaccctcattcttaccatccaagtgagaagtgtgaatggctaatccaagct
 S  P  G  Y  P  H  S  Y  H  P  S  E  K  C  E  W  L  I  Q  A
ccggaacctaccagagaatcatgatcaacttcaacccacattcgatttggaggacaga
 P  E  P  Y  Q  R  I  M  I  N  F  N  P  H  F  D  L  E  D  R
gactgcaagtatgactacgtggaagtaatcgatgggagaatgaaggcggccgctgtgg
 D  C  K  Y  D  Y  V  E  V  I  D  G  E  N  E  G  G  R  L  W
gggaagttctgtgggaagattgcacctctcctgtggtgtctcagggccctttctctc
 G  K  F  C  G  K  I  A  P  S  P  V  V  S  Q  G  P  F  L  S
atcaaattgtctctgactatgagacacatggggcagggttttcatccgctatgaaatc
 I  K  F  V  S  D  Y  E  T  H  G  A  G  F  S  I  R  Y  E  I
ttcaagagagggcccgaatgttctcagaactatacagtactactggagtgataaagtcc
 F  K  R  G  P  E  C  S  Q  N  Y  T  A  P  T  G  V  I  K  S
cctgggttcctgaaaaatacccccaacagctggagtgcactacatcatcttgcacca
 P  G  F  P  E  K  Y  P  N  S  L  E  C  T  Y  I  I  F  A  P
aagatgtctgagataatcctggagttgaaagtttgacctgagcaagactgaatcct
 K  M  S  E  I  I  L  E  F  E  S  F  D  L  E  Q  D  S  N
ccggaggaatgttctgtcgctatgacaggctggagatctggatggattcctgaagtt
 P  G  E  M  F  C  R  Y  D  R  L  E  I  W  D  G  F  P  E  V
ggccctcacattggagttattgtgggcagaaaactcctagccggatcgctcctcttca
 G  P  H  I  G  R  Y  C  G  Q  K  T  P  G  R  I  S  S  S
gggcgttctatccatggtctttacactgacagcgcaatagcaaaagaaggtttctcagcc
 G  V  L  S  M  V  F  Y  T  D  S  A  I  A  K  E  G  F  S  A
aactacagtgtgctacagagcagcatctctgaagatttaagtgtatggaggctctggc
 N  Y  S  V  L  Q  S  I  S  E  D  F  K  C  M  E  A  L  G
atggaatctggagagatccattctgatcagatcactgcatcttcacagtatggtaccaac
 M  E  S  G  E  I  H  S  D  Q  I  T  A  S  S  Q  Y  G  T  N
tggtctgtagagagctcccgcctgaactacctgaaattgggtggactccaggagaagac
 W  S  V  E  R  S  R  L  N  Y  P  E  N  G  W  T  P  G  E  D
tcctacaaggagtggatccaggtgactctggcctcctgagattgttactgctgtaggg
 S  Y  K  E  W  I  Q  V  T  L  A  S  L  R  L  V  T  A  V  G
acacaggttgccattccaaggaaaccaagaagaaatattatgtcaagacttacagagta
 T  Q  G  A  I  S  K  E  T  K  K  Y  Y  V  K  T  Y  R  V
gacatcagttcaacggagaggactggatctccctgaaagagggaaataaagccattatc
 D  I  S  S  N  G  E  D  W  I  S  L  K  E  G  N  K  A  I  I
tttcagggaaacaaccccacagatgttgtcttaggagttttctccaaacccactgata
 F  Q  G  N  N  P  T  D  V  V  L  G  V  F  S  K  P  L  I
actcgatttgtccgaatcaaacctgtatcctgggaaactggtatatctatgagattgaa
 T  R  F  V  R  I  K  P  V  S  W  E  T  G  I  S  M  R  F
gttatggtgtgctctgagcacatggttagatctggtcgtaagctctgcatagtacac
 V  Y  G  V  S  E  H  M  V  R  S  G  C  K  L  C  I  V  T
gtcccagaagtatcatctgtcttcatcttcccccaaagcccaaggatgtgctcaccatt
 V  P  E  V  S  S  V  F  I  F  P  K  P  K  D  V  L  T  I
actctgactcttaaggtcacgtgtgtgtgtgtgtagacatcagcaaggatgatcccgaggtc
 T  L  T  L  K  V  T  C  V  V  V  D  I  S  K  D  D  P  E  V
cagttcagctggtttgtagatgatgtggaggtgcacacagctcagacgcaacccgggag
 Q  F  S  W  F  V  D  D  V  E  V  H  T  A  Q  T  Q  P  R  E
gagcagttcaacagcactttccgctcagtcagtgaactcatcatcgacccaggactgg
 E  Q  F  N  S  T  F  R  S  V  S  E  L  P  I  M  H  Q  D  W
ctcaatggcaaggagttcaaatgcagggtcaacagtgcagctttccctgcccccatcgag
 L  N  G  K  E  F  K  C  R  V  N  S  A  A  F  P  A  P  I  E
```

FIG. 20CC

```
aaaaccatctccaaaaccaaaggcagaccgaaggctccacaggtgtacaccattccacct
 K  T  I  S  K  T  K  G  R  P  K  A  P  Q  V  Y  T  I  P  P
cccaaggagcagatggccaaggataaagtcagtctgacctgcatgataacagacttcttc
 P  K  E  Q  M  A  K  D  K  V  S  L  T  C  M  I  T  D  F  F
cctgaagacattactgtggagtggcagtggaatgggcagccagcggagaactacaagaac
 P  E  D  I  T  V  E  W  Q  W  N  G  Q  P  A  E  N  Y  K  N
actcagcccatcatggacacagatggctcttacttcgtctacagcaagctcaatgtgcag
 T  Q  P  I  M  D  T  D  G  S  Y  F  V  Y  S  K  L  N  V  Q
aagagcaactgggaggcaggaaatactttcacctgctctgtgttacatgagggcctgcac
 K  S  N  W  E  A  G  N  T  F  T  C  S  V  L  H  E  G  L  H
aaccatcatactgagaagagcctctcccactctcctggtaaatga
 N  H  H  T  E  K  S  L  S  H  S  P  G  K
```

FIG. 21

```
         10         20         30         40         50         60
MGWLTRIVCL FWGVLLTARA NYQMGKNWVP HLKLSYREML SSNNVITPNG LANSSSYHTF
         70         80         90        100        110        120
LLDEERSRLV GARDHIFSF DLVNIEDFQK IVNPVSYTRR GECKWAGKDI LKECANFIEV
        130        140        150        160        170        180
LKAYNQTHLY ACGTGAFHPI CTYIEIGHHP EDNIFKLENS HFENGRCESP YDPKLLTASL
        190        200        210        220        230        240
LIDGELYSGT AADFMGRDFA IFRTLGHHHP IRTEQHDSRW LNDPKFISAH LISESDNPED
        250        260        270        280        290        300
DKVIFFFREN AIDGEHSGKA THARIGQICK NDFGGHRSLV NKWTTFLKAR LICSVPGPNG
        310        320        330        340        350        360
IDTHFDELQD VFLMNFEDFK NPVVYGVFTT SSNIFKGSAV CMYSMSDVRR VFLGPYAHRD
        370        380        390        400        410        420
GPNYQWVPYQ GRVPTPRPGT CPSKTFGGFD STKDLPDDVI TFARSHPAMY NPVFPMNNRP
        430        440        450        460        470        480
IVIKIDVNTQ FTQIVVDRVD AEDQQTDVNF IGTDVGTVLK VVSIPKETWY DLEEVLLEEM
        490        500        510        520        530        540
TVFREPTAIS AMELSTRQQQ LYIGSTAGVA QLPLHRCDIY GKACAECCLA RDPYCAWDGS
        550        560        570        580        590        600
ACSRYFPTAK RRTRQRRQIRN GDPLTHCSDL HHDNHHGHSP EEHIIYGVEN SSTFLECSPK
        610        620        630        640        650        660
SQRALVYRQF QRNEERKEE IRVDHIIRT DQGLLLRSLQ QKDSGNYLCH AVEHGFIQTL
        670        680        690        700        710        720
LKVTLEVIDT EHLEELLMKD DDGDGSKTKK MSNSMTPSQK VWTRFNQLI NHPNLNTMDE
        730        740        750        760        770
FCEQVMERQR KQRRQRFQHT PGSNMEMKHL QEKEKGRMRR THEFERAPRS V
```

FIG. 22

```
  1  mergipllca vlalvlapag afrndtcgit ikiecpgyit apgyphayhp aekcewilga  a1
 61  pdpygrieln fnphfdlsdr dctydyvavf dgeneaghfr gxfcgkiapp pvvsegpflf
121  ikfvedyath gggfeiryei fkrgpecaqn yttpagvike pgfpekypas lectylvfap
181  kmseillefe afdlapdsnp pggafcrydr leiwdgfpdv gphigrycqq ktpqrirsss  a2
241  qllsmvfytd aalakegfsa nyavlqssvs adfkewaig aengethedy itssegyatn   b1
301  wsserariny psegwtpged syrewigwdi gllrfvtavg tggalsetk kkyywktyki
361  dvasngedwl likegnkpvi fgmtnptdv vvavfpxpli fxfvrikpat wetglsscfs
421  vyqckifdyp csgnlgmvag lisdsqitss nqgdrowmpe nirlvtarag walppaphay  b2
481  lnewlqidlg eekivrqiii qqgkbrenkv fmrkfkigys nngsdwkmlm ddskrkakaf
541  egnnnydtps lrtfpalstr firlyperat hggiginmel lgrsveggtt siatekgsvi  c
601  datigsglk
```

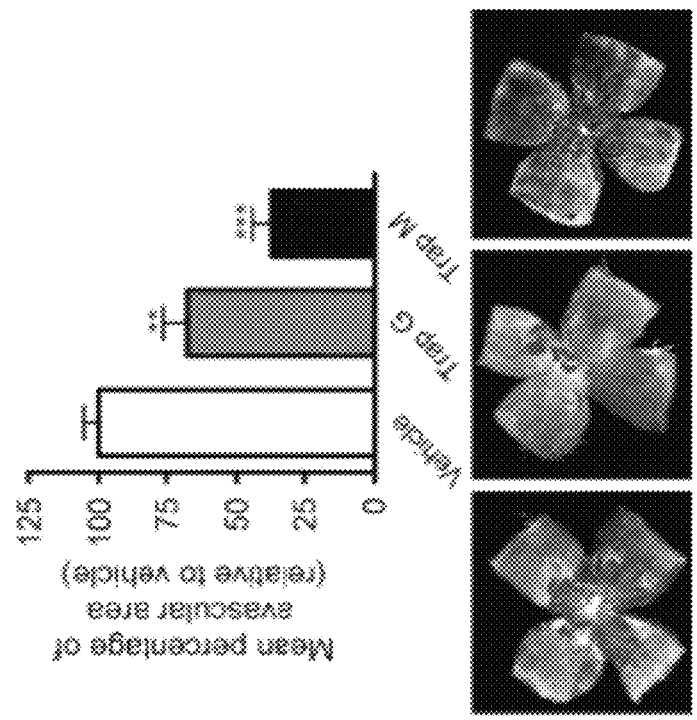
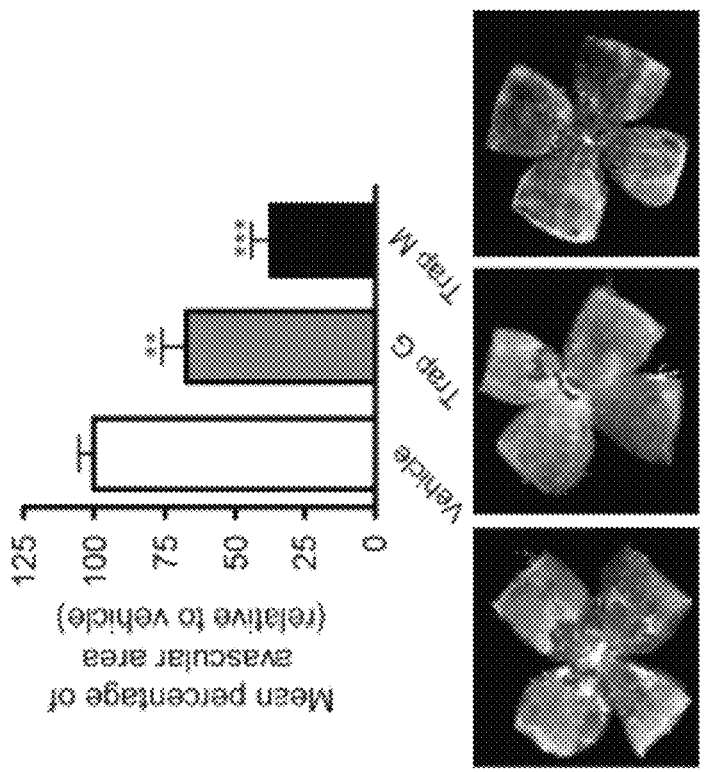
FIG. 23B

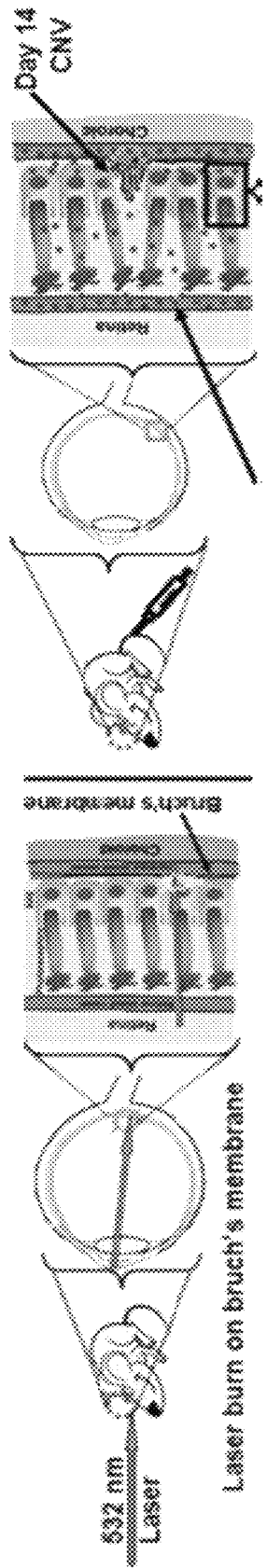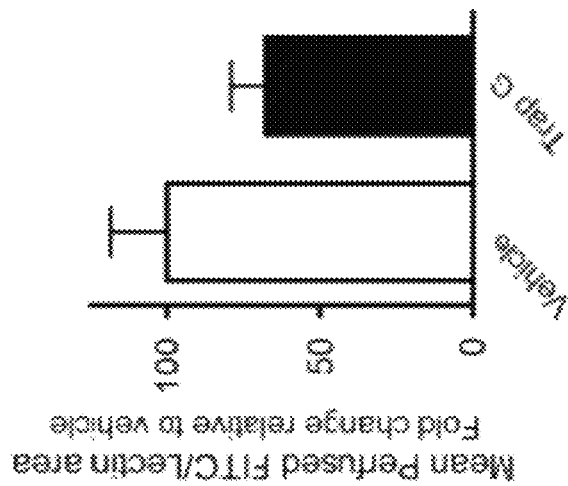
FIG. 25A
FIG. 25B

COMPOSITIONS AND METHODS FOR TREATING AND PREVENTING INFLAMMATION

CROSS REFERENCE TO RELATED APPLICATIONS

This is a divisional of U.S. application Ser. No. 15/507,407, filed Feb. 28, 2017, which is the U.S. National Stage of International Patent Application No. PCT/CA2015/050862, filed Sep. 8, 2015, which was published in English under PCT Article 21(2), which in turn claims priority of U.S. provisional application serial No. U.S. 62/046,459, filed on Sep. 5, 2014. The above-referenced applications are incorporated herein by reference in their entirety.

SEQUENCE LISTING

This application contains a Sequence Listing in computer readable form entitled "98565-02_ST25.txt", created on May 16, 2019 having a size of 579 KB. The computer readable form is incorporated herein by reference.

STATEMENT REGARDING FEDERALLY SPONSORED RESEARCH OR DEVELOPMENT

N.A.

FIELD OF THE INVENTION

The present invention relates to inflammation. More specifically, the present invention is concerned with the inhibition of the NRP1 pathway for the prevention or treatment of inflammation.

REFERENCE TO SEQUENCE LISTING

N.A.

BACKGROUND OF THE INVENTION

Local acute inflammatory responses are predominantly beneficial and constitute the body's first line of defense against infection of the host. Conversely, acute systemic inflammation such as in septic shock is a leading cause of morbidity and mortality (58). When chronic, low-grade inflammation persists, it can be at the origin of a several systemic diseases ranging from type II Diabetes Mellitus, arthritis, cancer, a number of neuro-inflammatory conditions and more.

Of all cytokines, receptors and other players thought to contribute to the inflammatory processes, one paradigm that has been largely overlooked is the influence of classical neuronal guidance cues and their receptors. These include semaphorin3A (SEMA3A, e.g., mRNA: NM_006080; and protein: NP_006071 and FIG. 21) and their receptor Neuropilin-1 (NRP1, e.g., mRNA: NM_001024628; and protein: NP_001019799, NM_003873 and FIGS. 22 (isoform 2 or b, secreted) and 26 (isoform 1). NRP1 is expressed on both lymphoid and myeloid cells (59, 31). Yet its role in inflammation is largely unknown and especially in the context of cytokine production.

The Semaphorins were initially characterized as key players in axonal guidance during embryogenesis. It is now clear that the role of Semaphorins extends beyond axonal guidance and influence vascular systems, tumor growth and the immune response. The Semaphorin family counts at least 21 vertebrate genes and 8 additional genes in invertebrates. All Semaphorins contain a ~500 amino acid SEMA domain that is required for signaling. Class 3 Semaphorins (such as SEMA3A) are the only secreted members of the family. SEMA3A is synthesized as a disulphide-linked homodimer and dimerization is essential for signaling.

In neurons, binding of SEMA3A to its cognate receptor Neuropilin-1 (NRP1) provokes cytoskeletal collapse via plexins (60); the transduction mechanism in endothelial cells remains ill-defined. NRP1 has the particular ability to bind two structurally dissimilar ligands via distinct sites on its extracellular domain (27-29). It binds not only SEMA3A (46, 47) provoking cytoskeletal collapse but also $VEGF_{165}$ (28, 29, 47, 61) enhancing binding to VEGFR2 and thus increasing its angiogenic potential (62). Crystallographic evidence revealed that $VEGF_{165}$ and SEMA3A do not directly compete for NRP1 but rather can simultaneously bind to NRP1 at distinct, non-overlapping sites (63). Moreover, genetic studies show that NRP1 distinctly regulates the effects of VEGF and SEMA3A on neuronal and vascular development (64). Finally, NRP1 has also been found to bind to TGF-β1 and to regulate its latent form.

NRP1 is a single-pass transmembrane receptor with a large 860 amino acid extracellular domain subdivided into 3 sub-domains (a1a2, b1b2 and c) and a short 40 amino acid intracellular domain (65). In neurons, binding of SEMA3A to NRP1 recruits Plexins, which transduce their intracellular signal (60) and provoke cytoskeletal collapse. The transduction mechanism in endothelial cells remains ill-defined. NRP1 binds SEMA3A (46, 47) primarily via its a1a2 (but possibly also b1-) domain (provoking cytoskeletal collapse) and $VEGF_{165}$ (28, 29, 47, 61) via its b1b2 domain (enhancing binding to VEGFR2 and thus increasing its angiogenic potential (62). The elevated levels of SEMA3A in the ischemic retina may thus partake in forcing neovessels into the vitreous by collapsing and deviating the advancing tip cells away from the source of the repellent cue (21).

The CNS had long been considered an immune-privileged system, yet it is now clear that the brain, retina and spinal cord are subjected to complex immune-surveillance (1, 2). Immunological activity in the CNS is largely dependent on an innate immune response and is present in health and heightened in diseases such as diabetic retinopathy, multiple sclerosis, amyotrophic lateral sclerosis and Alzheimer's disease. This is apparent in the retina where an intensified, largely microglial/macrophage-based immune response is associated with the progression of several sight threatening diseases such as diabetic retinopathy (DR)(3-5), age related macular degeneration (AMD)(6-8) and retinopathy of prematurity (ROP)(9, 10). Together, these retinal diseases account for the principal causes of loss of sight in industrialized countries (6, 11, 12).

Many of the current line of treatments of inflammatory diseases and conditions suffer from important side-effects and deficient long-term safety profiles. Accordingly, there remains a need for novel pharmaceutical targets and methods of treatments.

The present description refers to a number of documents, the content of which is herein incorporated by reference in their entirety.

SUMMARY OF THE INVENTION

The present inventors have sought to determine the function of myeloid-resident NRP1 in the context of the innate immune response.

The present inventors have determined that SEMA3A, VEGF and TGF-β act as potent attractants for mononuclear phagocytes (MPs, e.g., microglia and macrophages) expressing the NRP1 receptor. Inhibition of NRP1 signaling in innate immune cells was shown to result in protection against MPs-dependent inflammation and tissue damage under a variety of conditions involving hyperactivation of the innate immune-response including proliferative retinopathies, septic shock and cerebral ischemia/stroke. Furthermore, the present inventors have designed various soluble NRP1-derived traps which inhibit SEMA3A signalling and shown that inhibition of SEMA3A significantly reduce the inflammatory response in various conditions.

Accordingly, the present invention relates to the inhibition of NRP1 cell signalling (e.g., NRP1 and its ligands) for the prevention or treatment of inflammatory diseases and conditions involving hyperactivation (i.e., pathological activation) of the innate immune response. Non-limiting examples of such disease and conditions include sepsis, stroke, cerebral ischemia, and various proliferative retinopathies.

More specifically, in an aspect, the present invention concerns a method of treating or preventing inflammation comprising inhibiting NRP1-dependent cell-signaling.

In another aspect, the present invention relates to a method of preventing or reducing hyperactivation of innate immune response comprising inhibiting NRP1-dependent cell-signaling. In an embodiment, the hyperactivation of innate immune response comprises i) secretion of IL-1β and TNFα and/or activation/recruitment of mononuclear phagocytes (MPs).

In an embodiment, inhibiting NRP1-dependent cell-signaling comprises: a) reducing NRP1 expression or activity; and/or b) reducing NRP1 ligand expression or activity. In an embodiment, the NRP1 ligand is SEMA3A, $VEGF_{165}$ or TGF-β. In a particular embodiment, the NRP1 ligand is SEMA3A.

In an embodiment, reducing NRP1 activity consists of inhibiting the binding of NRP1 to at least one NRP1 ligand. In an embodiment, inhibiting the binding of NRP1 to at least one NRP1 ligand comprises administering an NRP1 antibody (e.g., a SEMA3A antibody).

In another embodiment of the above methods, reducing NRP1 activity comprises administering an effective amount of an NRP1 trap which comprises soluble NRP1 polypeptide or a functional fragment thereof. In a particular embodiment, the NRP1 trap is as set forth in FIG. 19 or 20.

In a particular embodiment, the NRP1 trap of the present invention inhibits the binding of SEMA3A to NPR-1 but does not substantially inhibit the binding of VEGF to NRP1. In an embodiment, such NRP1 trap comprises the a1a2 domain of NRP1 but does not comprise the b1 and/or b2 subdomain(s) of NRP1. In another embodiment, such trap comprises a mutation in domain b1 at a position corresponding to tyrosine 297 of the NRP1 amino acid sequence as set forth in FIG. 22 which reduces or abrogates VEGF binding to the trap. In a specific embodiment, the mutation changes the tyrosine at position 297 to an alanine.

In specific embodiments, the NRP1 trap of the present invention: a) comprises domains a1, a2, b1, b2 and c and of NRP1; b) comprises domains a1, a2, b1 and b2 of NRP1; c) comprises domains a1, a2 and b1 of NRP1; d) comprises domains a1 and a2 of NRP1; e) comprises domain b1, wherein the b1 domain comprises a mutation in amino acid corresponding to tyrosine 297 of NRP1 which reduces or abrogates the binding to VEGF; f) comprises domain b1, wherein the b1 domain comprises a mutation in amino acid corresponding to tyrosine 297 of NRP1 which changes the tyrosine to an alanine; g) does not comprise domain c of NRP1; h) does not comprise domain b1 of NRP1; i) does not comprise domains b1 and b2 of NRP1; or j) does not comprise domains b1, b2 and c of NRP1.

In an embodiment of the above methods, inhibiting NRP1 ligand expression or activity comprises specifically inhibiting SEMA3A expression or SEMA3A binding to NRP1. In a particular embodiment, inhibiting SEMA3A binding to NRP1 comprises administering a SEMA3A antibody.

In a particular embodiment, the method of the present invention comprises reducing NRP1 expression by administering a NRP1 antisense, shRNA or siRNA.

In another embodiment, the method comprises reducing SEMA3A expression by administering a SEMA3A antisense, shRNA or siRNA.

In a further aspect, the present invention concerns a compound for the prevention or treatment of inflammation wherein the compound a) reduces NRP1 expression or activity; or b) reduces NRP1 ligand expression or activity.

In another aspect, the present invention relates to a compound for preventing or reducing hyperactivation of innate immune response, wherein the compound a) reduces NRP1 expression or activity; or b) reduces NRP1 ligand expression or activity.

In an embodiment, the compound is: i) A SEMA3A antibody; ii) A NRP1 antibody; iii) A NRP1 trap; iv) A SEMA3A antisense, shRNA or siRNA; or v) A NRP1 antisense, shRNA or siRNA. In another particular embodiment the compound is a NRP1 antibody or a NRP1 trap and said compound does not substantially reduce the binding of VEGF to NRP1.

In a particular embodiment, the compound is a NRP1 trap. In an embodiment, the NRP1 trap is as set forth in FIGS. 19, 20, 27 and Table 1.

In another embodiment, the NRP1 trap of the present invention inhibits the binding of SEMA3A to NPR-1 but does not substantially inhibit the binding of VEGF to NRP1. In an embodiment, such NRP1 trap comprises the a1a2 domain of NRP1 but does not comprise the b1 and/or b2 subdomain(s) of NRP1. In another embodiment, such trap comprises a mutation in domain b1 at a position corresponding to tyrosine 297 of the NRP1 amino acid sequence as set forth in FIG. 22 which reduces or abrogates VEGF binding to the trap. In a specific embodiment, the mutation changes the tyrosine at position 297 to an alanine.

In specific embodiments, the NRP1 trap of the present invention: a) comprises domains a1, a2, b1, b2 and c and of NRP1; b) comprises domains a1, a2, b1 and b2 of NRP1; c) comprises domains a1, a2 and b1 of NRP1; d) comprises domains a1 and a2 of NRP1; e) comprises domain b1, wherein the b1 domain comprises a mutation in amino acid corresponding to tyrosine 297 of NRP1 which reduces or abrogates the binding to VEGF; f) comprises domain b1, wherein the b1 domain comprises a mutation in amino acid corresponding to tyrosine 297 of NRP1 which changes the tyrosine to an alanine; g) does not comprise domain c of NRP1; h) does not comprise domain b1 of NRP1; i) does not comprise domains b1 and b2 of NRP1; or j) does not comprise domains b1, b2 and c of NRP1.

In an embodiment, the NRP1 trap of the present invention comprises: (i) amino acids 1-856 (preferably, 22 to 856) of the NRP1 polypeptide set forth in FIG. 26 (SEQ ID NO: 69); (ii) amino acids 1 to 583 (preferably 22 to 583) of the NRP1 polypeptide set forth in FIG. 26 (SEQ ID NO: 69); (iii) amino acids 1 to 424 (preferably 22-424) the NRP1 polypeptide set forth in FIG. 26 (SEQ ID NO: 69); (iv) amino acids 1 to 265 (preferably 22 to 265) the NRP1 polypeptide set forth in FIG. 26 (SEQ ID NO: 69); (v) 1 to 430 and 584 to 856 (preferably 22-430 and 584-856) the NRP1 polypeptide set forth in FIG. 26 (SEQ ID NO: 69); (vi) amino acids 1 to 274 and 584 to 856 (preferably 22-274 and 584 to 856) the NRP1 polypeptide set forth in FIG. 26 (SEQ ID NO: 69); (vii) amino acids 1 to 430 and 584 (preferably 22 to 430 and 584 to 856) of the NRP1 polypeptide set forth in FIG. 26 (SEQ ID NO: 69). In a particular embodiment, the above noted traps comprise one or more mutation to reduce VEGF or SEMA3A binding as described above.

In another aspect, the present invention provides compositions for i) treating and preventing inflammation or ii) for preventing or reducing the hyperactivation of the innate immune response, comprising one or more compounds of the present invention together with a pharmaceutical carrier.

The present invention also relates to the use of one or more compounds of the present invention in the manufacture of a medicament for i) treating and preventing inflammation or ii) for preventing or reducing the hyperactivation of the innate immune response.

In a related aspect, the present invention concerns the use of one or more compounds of the present invention for i) treating and preventing inflammation or ii) for preventing or reducing the hyperactivation of the innate immune response.

In a particular embodiment, the methods, compounds (e.g., NRP1 polypeptide traps, nucleic acids encoding same, vectors, cells comprising vectors, etc.), compositions and uses of the present invention are for treating or preventing inflammatory diseases and conditions selected from the group consisting of septic shock, arthritis, inflammatory bowel disease (IBD), cutaneous skin inflammation, diabetes, uveitis, diabetic retinopathy, age-related macular degeneration (AMD), retinopathy of prematurity, multiple sclerosis, amyotrophic lateral sclerosis (ALS), age-related cognitive decline/Alzheimer's disease or stroke.

In an embodiment, the methods, compounds, compositions and uses of the present invention are for treating or preventing septic shock, cerebral ischemia or stroke.

More specifically, in accordance with the present invention, there is provided the following items:

1. A method of treating or preventing inflammation comprising inhibiting NRP1-dependent cell-signaling in a subject.
2. A method of preventing or reducing hyperactivation of innate immune response comprising inhibiting NRP1-dependent cell-signaling in a subject.
3. The method of item 2, wherein said hyperactivation of innate immune response comprises i) secretion of IL-6, IL-1β and TNFα and/or recruitment of mononuclear phagocytes (MPs).
4. The method of any one of items 1-3, wherein inhibiting NRP1-dependent cell-signaling comprises: (a) reducing NRP1 expression or activity; and/or (b) reducing NRP1 ligand expression or activity; wherein said NRP1 ligand is SEMA3A, VEGF and/or TGF-β.
5. The method of item 4, wherein the method comprises (i) reducing NRP1 activity by inhibiting the binding of NRP1 to at least one NRP1 ligand.
6. The method of item 5, wherein the NRP1 ligand is SEMA3A, VEGF or TGF-β.
7. The method of item 5 or 6, wherein inhibiting the binding of NRP1 to at least one NRP1 ligand comprises administering an anti-NRP1 antibody or an NRP1 trap, wherein said trap comprises a NRP1 polypeptide or a functional fragment or variant thereof.
8. The method of item 7, wherein said NRP1 polypeptide corresponds to soluble NRP1 isoform 2.
9. The method of item 8, wherein said soluble NPR1 isoform 2 comprises or consists essentially of a polypeptide having an amino acid sequence as set forth in FIG. 22 without a signal peptide.
10. The method of item 7, wherein said NRP1 polypeptide corresponds to the extracellular domain of an NRP1 isoform 1 polypeptide.
11. The method of item 10, wherein said NRP1 isoform 1 polypeptide is as set forth in FIG. 26 and wherein said extracellular domain comprises amino acids 22 to 859 corresponding to the NRP1 polypeptide shown in FIG. 26 (SEQ ID NO:66).
12. The method of any one of items 7 to 11, wherein said NRP1 trap comprises an NRP1 polypeptide comprising (i) amino acids 22 to 609 of a NRP1 polypeptide as set forth in SEQ ID NO: 65; (ii) amino acids 22 to 859 of a NRP1 polypeptide as set forth in SEQ ID NO: 66; (iii) amino acids 22 to 859 of a NRP1 polypeptide as set forth in SEQ ID NO: 69 (iv) or a functional fragment or functional variant of (i), (ii) or (iii).
13. The method of any one of items 7 to 12, wherein said anti-NRP1 antibody inhibits the binding of SEMA3A to NPR-1 but does not substantially inhibit the binding of VEGF to NRP1 and wherein said NRP1 trap binds to SEMA3A but does not substantially bind to VEGF165 or has a reduced binding affinity for VEGF165 compared to SEMA3A binding affinity.
14. The method of item 13, wherein said NRP1 trap (i) lacks completely or partially domain b1 and/or b2 of NRP1; or (ii) comprises at least one amino acid point mutation which inhibits VEGF binding to NRP1.
15. The method of item 13, wherein said anti-NRP1 antibody does not bind to domain b1 and/or b2 of NRP1.
16. The method of item 14, wherein said point mutation comprises (a) an amino acid substitution or deletion in domain b1 at an amino acid residue corresponding to tyrosine 297 of an NRP1 amino acid sequence set forth in FIG. 22 or FIG. 26; (b) an amino acid substitution or deletion in domain b1 at an amino acid residue corresponding to aspartic acid 320 of an NRP1 amino acid sequence set forth in FIG. 22 or FIG. 26; and/or (c) an amino acid substitution or deletion in domain b1 at an amino acid residue corresponding to glutamic acid 319 of an NRP1 amino acid sequence set forth in FIG. 22 or FIG. 26.
17. The method of item 16, wherein said point mutation is a Y297A substitution; a D320K substitution and/or a E319K substitution.
18. The method of any one of item 7 to 12, wherein said NRP1 trap: (a) comprises domains a1, a2, b1, b2, and c and of said NRP1 polypeptide; (b) comprises domains a1, a2, b1 and b2 of said NRP1 polypeptide; (c) comprises domains a1, a2, and b1 of said NRP1 polypeptide; (d) comprises domains a1 and a2 said NRP1 polypeptide; (f) comprises domain b1 of said NRP1 polypeptide, wherein said domain b1 comprises at least one point mutation at an amino acid residue corresponding to (i) tyrosine 297; (ii) aspartic acid 320 and/or (iii) glutamic acid 319, of a NRP1 polypeptide comprising an amino acid sequence as set forth in FIG. 26, wherein said at least one mutation reduces or abrogates binding to VEGF$_{165}$; (g) lacks completely or partially domain c of said NRP1 polypeptide; (h) lacks completely or partially domain b1 of said NRP1 polypeptide; (i) lacks completely or partially domain b2 of said NRP1 polypeptide; (j) lacks domains b1 and b2 of said NRP1 polypeptide; or (k) lacks domains b1, b2 and c of said NRP1 polypeptide.
19. The method of item 18, wherein (i) said domain a1 comprises or consists essentially of an amino acids sequence corresponding to amino acids 27 to 141 of an NRP1 polypeptide as set forth in FIG. 26; (ii) said domain a2 comprises an amino acid sequence corresponding to amino acids 147 to 265 of an NRP1 polypeptide as set forth in FIG. 26; (iii) said domain b1 comprises an amino acids sequence corresponding to amino acids 275 to 424 of an NRP1 polypeptide as set forth in FIG. 26; (iv) said domain b2 comprises an amino acids sequence corresponding to amino acids 431 to 583 of an NRP1 polypeptide as set forth in FIG. 26; and/or (v) said domain c domain comprises an amino acids sequence corresponding to amino acids 645 to 811 of an NRP1 polypeptide as set forth in FIG. 26.

20. The method of item 18, wherein (i) said domain a1 comprises or consists essentially of an amino acids sequence corresponding to amino acids 22 to 148 of an NRP1 polypeptide as set forth in FIG. 26; (ii) said domain a2 comprises an amino acid sequence corresponding to amino acids 149 to 275 of an NRP1 polypeptide as set forth in FIG. 26; (iii) said domain b1 comprises an amino acids sequence corresponding to amino acids 276 to 428 of an NRP1 polypeptide as set forth in FIG. 26; (iv) said domain b2 comprises an amino acids sequence corresponding to amino acids 429 to 589 of an NRP1 polypeptide as set forth in FIG. 26; and/or (v) said domain c domain comprises an amino acids sequence corresponding to amino acids 590 to 859 of an NRP1 polypeptide as set forth in FIG. 26.

21. The method of item 7, wherein said method comprises inhibiting the binding of NRP1 to at least one NRP1 ligand by administering a NRP1 trap consisting essentially of a trap as set forth in Table 1 or a functional variant thereof.

22. The method of any one of items 7 to 20, wherein said NRP1 trap further comprises a protein purification domain.

23. The method of 22, wherein said purification domain is a polyhistidine tag.

24. The method of any one of items 7 to 20, wherein said NRP1 trap further comprises a FC domain.

25. The method of any one of items 22 to 24, wherein said NRP1 trap comprises a protease or peptidase cleavage site enabling said protein purification domain or FC domain to be removed from said NRP1 trap.

26. The method of item 25, wherein said protease or peptidase is a TEV protease cleavage site.

27. The method of item 26, wherein said TEV protease cleavage site comprises the amino acid sequence GSKENLYFQG.

28. The method of item 4, wherein the method comprises reducing NRP1 ligand expression or activity, and wherein the NRP1 ligand is SEMA3A.

29. The method of item 28, comprising reducing SEMA3A activity by inhibiting SEMA3A binding to NRP1 by administering an anti-SEMA3A antibody which binds to the SEMA domain of SEMA3A.

30. The method of 4, wherein said method comprises reducing NRP1 expression by administering a NRP1 antisense, shRNA or siRNA.

31. The method of item 4, wherein said method comprises reducing SEMA3A expression by administering a SEMA3A antisense, shRNA or siRNA.

32. A NRP1 polypeptide trap comprising s a NRP1 polypeptide or a functional fragment or variant thereof which binds to SEMA3A, VEGF165 and/or TGF-β.

33. The NRP1 polypeptide trap of item 32, wherein said NRP1 polypeptide corresponds to soluble NRP1 isoform 2.

34. The NRP1 polypeptide trap of item 33, wherein said soluble NPR1 isoform 2 comprises or consists essentially of a polypeptide having an amino acid sequence as set forth in FIG. 22 without a signal peptide.

35. The NRP1 polypeptide trap of item 34, wherein said NRP1 polypeptide corresponds to the extracellular domain of an NRP1 isoform 1 polypeptide.

36. The NRP1 polypeptide trap of item 35, wherein said NRP1 isoform 1 polypeptide is as set forth in FIG. 26 and wherein said extracellular domain corresponds to amino acids 22 to 859.

37. The NRP1 polypeptide trap of any one of items 32 to 36, wherein said NRP1 trap comprises an NRP1 polypeptide comprising (i) amino acids 22 to 609 of a NRP1 polypeptide as set forth in SEQ ID NO: 65; (ii) amino acids 22 to 859 of a NRP1 polypeptide as set forth in SEQ ID NO: 66; (iii) amino acids 22 to 859 of a NRP1 polypeptide as set forth in SEQ ID NO: 69 (iv) or a functional fragment or functional variant of (i), (ii) or (iii).

38. The NRP1 polypeptide trap of item any one of items 32 to 37, wherein NRP1 trap binds to SEMA3A but does not substantially bind to VEGF165 or has a reduced binding affinity for VEGF165 as compared to SEMA3A binding affinity.

39. The NRP1 polypeptide trap of item 38, wherein said NRP1 trap (i) lacks completely or partially domain b1 and/or b2 of NRP1; or (ii) comprises at least one amino acid point mutation which inhibits VEGF binding to NRP1.

40. The NRP1 polypeptide trap of item 39, wherein said point mutation comprises (a) an amino acid substitution or deletion in domain b1 at an amino acid residue corresponding to tyrosine 297 of an NRP1 amino acid sequence set forth in FIG. 22 or FIG. 26; (b) an amino acid substitution or deletion in domain b1 at an amino acid residue corresponding to aspartic acid 320 of an NRP1 amino acid sequence set forth in FIG. 22 or FIG. 26; and/or (c) an amino acid substitution or deletion in domain b1 at an amino acid residue corresponding to glutamic acid 319 of an NRP1 amino acid sequence set forth in FIG. 22 or FIG. 26.

41. The NRP1 polypeptide trap of item 40, wherein said mutation point is a Y297A substitution; a D320K substitution and/or a E319K substitution.

42. The NRP1 polypeptide trap of any one of items 32 to 38, wherein said trap: (a) comprises domains a1, a2, b1, b2, and c and of said NRP1 polypeptide; (b) comprises domains a1, a2, b1 and b2 of said NRP1 polypeptide; (c) comprises domains a1, a2, and b1 of said NRP1 polypeptide; (d) comprises domains a1 and a2 said NRP1 polypeptide; (e) comprises domain b1 of said NRP1 polypeptide, wherein said domain b1 comprises at least one point mutation at an amino acid residue corresponding to (i) tyrosine 297; (ii) aspartic acid 320 and/or (iii) glutamic acid 319, of a NRP1 polypeptide comprising an amino acid sequence as set forth in FIG. 26, wherein said at least one mutation reduces or abrogates binding to VEGF165; (f) lacks completely or partially domain c of said NRP1 polypeptide; (g) lacks completely or partially domain b1 of said NRP1 polypeptide; (h) lacks completely or partially domain b2 of said NRP1 polypeptide; (i) lacks domains b1 and b2 of said NRP1 polypeptide; or (j) lacks domains b1, b2 and c of said NRP1 polypeptide.

43. The NRP1 polypeptide trap of item 42, wherein (i) said domain a1 comprises or consists essentially of an amino acids sequence corresponding to amino acids 27 to 141 of an NRP1 polypeptide as set forth in FIG. 26; (ii) said domain a2 comprises an amino acid sequence corresponding to amino acids 147 to 265 of an NRP1 polypeptide as set forth in FIG. 26; (iii) said domain b1 comprises an amino acids sequence corresponding to amino acids 275 to 424 of an NRP1 polypeptide as set forth in FIG. 26; (iv) said domain b2 comprises an amino acids sequence corresponding to amino acids 431 to 583 of an NRP1 polypeptide as set forth in FIG. 26; and/or (v) said domain c domain comprises an amino acids sequence corresponding to amino acids 645 to 811 of an NRP1 polypeptide as set forth in FIG. 26.

44. The NRP1 polypeptide trap of item 42, wherein (i) said domain a1 comprises or consists essentially of an amino acids sequence corresponding to amino acids 22 to 148 of an NRP1 polypeptide as set forth in FIG. 26; (ii) said domain a2 comprises an amino acid sequence corresponding to amino acids 149 to 275 of an NRP1 polypeptide as set forth in FIG. 26; (iii) said domain b1 comprises an amino acids sequence corresponding to amino acids 276 to 428 of an NRP1 polypeptide as set forth in FIG. 26; (iv) said domain b2 comprises an amino acids sequence corresponding to amino acids 429 to 589 of an NRP1 polypeptide as set forth in FIG. 26; and/or (v) said domain c domain comprises an amino acids sequence corresponding to amino acids 590 to 859 of an NRP1 polypeptide as set forth in FIG. 26.

45. The NRP1 polypeptide trap of item 32, wherein said trap consists essentially of a trap as set forth in Table 1 or a functional variant thereof.

46. The NRP1 polypeptide trap of any one of items 32 to 44, wherein said trap further comprises a protein purification domain.

47. The NRP1 polypeptide trap of item 46, wherein said purification domain is a polyhistidine tag.

48. The NRP1 polypeptide trap of any one of items 32 to 47, wherein said NRP1 trap further comprises a FC domain.

49. The NRP1 polypeptide trap of any one of items 46 to 48, wherein said NRP1 trap comprises a protease or peptidase cleavage site enabling said protein purification domain or FC domain to be removed from said NRP1 trap.

50. The NRP1 polypeptide trap of item 49, wherein said protease or peptidase cleavage site is a TEV protease cleavage site.

51. The NRP1 polypeptide trap of item 50, wherein said TEV protease cleavage site comprises the amino acid sequence GSKENLYFQG.

52. A nucleic acid encoding the NRP1 polypeptide trap of any one of items 32-51.

53. An expression vector comprising the nucleic acid of item 52.

54. A host cell comprising the vector of item 53.

55. A composition comprising the NRP1 polypeptide trap of any one of items 32 to 51, the nucleic acid of item 52, the vector of item 53 or the host cell of item 54 and a suitable carrier.

56. The composition of item 55 for (ii) for preventing or treating inflammation, or (ii) preventing or reducing hyperactivation of innate immune response.

57. A compound for preventing or treating inflammation, wherein said compound: (a) reduces NRP1 expression or activity; and/or (b) reduces NRP1 ligand expression or activity.

58. A compound for preventing or reducing hyperactivation of innate immune response, wherein said compound: (a) reduces NRP1 expression or activity; and/or (b) reduces NRP1 ligand expression or activity.

59. The compound of item 57 or 58, wherein said compound is: (i) A anti SEMA3A antibody; (ii) An anti VEGF165 antibody; (iii) A anti NRP1 antibody (iv) A NRP1 trap; (v) A SEMA3A antisense, shRNA or siRNA; (vi) A NRP1 antisense, shRNA or siRNA; or (vii) A VEGF antisense, shRNA or siRNA.

60. The compound item 59, wherein said compound is an NRP1 polypeptide trap.

61. A composition for treating or preventing inflammation comprising a compound as defined in any one of items 57-60 and a suitable carrier.

62. A composition for preventing or reducing hyperactivation of innate immune response comprising a compound as defined in of any one of items 57-60 and a suitable carrier.

63. Use of the NRP1 polypeptide trap of any one of items 32-51, the nucleic acid of item 52, the vector of item 53, the host cell of item 54 the compound of any one of items 57-60 or the composition of any one of items 55, 61 and 62 in the manufacture of a medicament for preventing or treating inflammation.

64. Use of the NRP1 polypeptide trap of any one of items 32-51, the nucleic acid of item 52, the vector of item 53, the host cell of item 54 the compound of any one of items 57-60 or the composition of any one of items 55, 61 and 62 in the manufacture of a medicament for preventing or treating inflammation.

65. Use of the NRP1 polypeptide trap of any one of items 32-51, the nucleic acid of item 52, the vector of item 53, the host cell of item 54 the compound as defined in any one of items 57-60 or the composition as defined in any one of items 55, 61 and 62 for preventing or treating hyperactivation of innate immune response.

66. Use of a the NRP1 polypeptide trap of any one of items 32-51, the nucleic acid of item 52, the vector of item 53, the host cell of item 54 the compound as defined in any one of items 57-60 or the composition as defined in any one of items 55, 61 and 62 for preventing or reducing hyperactivation of innate immune response.

67. The method of any one of items 1-31, wherein said subject suffers or is likely to suffer from septic shock, arthritis, inflammatory bowel disease (IBD), cutaneous skin inflammation, diabetes, uveitis, diabetic retinopathy, age-related macular degeneration (AMD), retinopathy of prematurity, multiple sclerosis, amyotrophic lateral sclerosis (ALS), age-related cognitive decline/Alzheimer's disease or stroke.

68. The method of any one of items 1-31, the NRP1 polypeptide trap of any one of items 32-51, the nucleic acid of item 52, the vector of item 53, the host cell of item 54, a compound as defined in any one of items 57-60 or a composition as defined in any one of items 55, 61 and 62 wherein said method, NRP1 polypeptide trap, nucleic acid, vector, host cell, compound, composition or use is for treating or preventing septic shock, arthritis, inflammatory bowel disease (IBD), cutaneous skin inflammation, diabetes, uveitis, diabetic retinopathy, age-related macular degeneration (AMD), retinopathy of prematurity, multiple sclerosis, amyotrophic lateral sclerosis (ALS), age-related cognitive decline/Alzheimer's disease or stroke.

69. The method of any one of items 1-31, the NRP1 polypeptide trap of any one of items 32-51, the nucleic acid of item 52, the vector of item 53, the host cell of item 54, a compound as defined in any one of items 57-60 or a composition as defined in any one of items 55, 61 and 62 wherein said method, NRP1 polypeptide trap, nucleic acid, vector, host cell, compound, composition or use is for treating or preventing septic shock or stroke.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the appended drawings:

FIGS. 1A-1T show that NRP1 identifies a population of microglia that is mobilized secondary to vascular injury. (FIG. 1A). Schematic depiction of the mouse model of oxygen-induced retinopathy (OIR). The first phase (postnatal day 7-12 (P7-P12)), under 75% oxygen, induces vasoobliteration. The second phase (under room air) from postnatal day 12 to 17 (P7-P17) allows to attain maximal pre-retinal neovascularization. (FIGS. 1B, 1E and 1H) show representative FACS plots of CD11b+/F4-80-F/Gr-1⁻ cells (microglia) in retinas collected at P10 (FIG. 1B), P14 (FIG. 1E) and P17 (FIG. 1H) from WT OIR and Normoxic control mice. (FIGS. 1C, 1F and 1I) show the fold change in the number of retinal microglia in Normoxia (N) and OIR at P10 (FIG. 1C), P14 (FIG. 1F) and P17 (FIG. 1I). The number of retinal microglia was significantly increased in OIR at all points analyzed (FIGS. 1C, 1F and 1I); n=7-8 (Normoxia, (N)), n=7-8 (OIR) (total of 28-32 retinas per condition; each "n" comprises 4 retinas). (FIGS. 1D, 1G and 1J) show the fold change in the number of NRP1 positive MPs at P10 (FIG. 1D), P14 (FIG. 1G) and P17 (FIG. 1J). A proportional increase in the number of NRP1-positive microglia was observed in OIR retinas (FIGS. 1D, 1G and 1J); n=3-5 (Normoxia, (N)), n=3-5 (OIR) (total of 12-20 retinas per condition; each "n" is comprised of 4 retinas). (FIGS. 1L, 1N and 1P), FACS analysis at P10 (FIG. 1L), P14 (FIG. 1N) and P17 (FIG. 1P) to quantify the number of MPs in LysM-Cre/Nrp1$^{fl/fl}$ mice retinas in Normoxia and OIR. (FIGS. 1M, 1O and 1Q) show the fold change in the number of MPs in LysM-Cre/Nrp1$^{fl/fl}$ mice retinas in normoxia and OIR. FACS analysis at P10 and P14 during the proliferative phase of OIR (FIG. 1L, FIG. 1N) reveals that MP-resident NRP1 is essential for MP infiltration into the ischemic retina as LysM-Cre/Nrp1$^{fl/fl}$ mice did not show an increase in numbers of CD11b-F/F4-80-F/Gr-1⁻ cells in OIR at these time points (FIG. 1M, FIG. 1O). At P17, MPs infiltrate independent of NRP1 (P, Q). n=7-8 (N), n=7-9 (OIR) (total of 28-36 retinas per condition; each "n" comprises 4 retinas). (FIG. 1R) Summary graph of MP accumulation in the retina over the course of OIR in WT and LysM-Cre/Nrp1$^{fl/fl}$ mice. (FIG. 1S, FIG. 1T) Representative FACS plots depicting that Gr1⁻/CD11b⁺/F4/80⁺ cells express high levels of CX3CR1 and intermediate/low levels of CD45. CX3CR1high and CD45low cells express NRP1 in WT retinas (S) and do not express NRP1 in retinas from LysM-Cre/Nrp1$^{fl/fl}$ mice (FIG. 1T). Data is expressed as fold change relative to control ±SEM. *P<0.05, P<0.001, *P>0.0001;

FIGS. 2A-2L show that NRP1⁺ myeloid cells localize to sites of pathological neovascularization in the retina. Confocal images of Isolectin B4 (vessel and microglia stain) and NRP1-stained retinal flatmounts at P14 with budding neovascular tufts in WT (FIG. 2A) and LysM-Cre/Nrp1$^{fl/fl}$ mice (FIG. 2G) and at P17 with mature tufts in WT (FIG. 2D) and LysM-Cre/Nrp1$^{fl/fl}$ mice (FIG. 2J). High magnification images reveal co-localization of NRP1-positive microglia (IBA1) with both nascent (FIG. 2B) and mature tufts (FIG. 2E) as confirmed by 3D reconstruction (FIG. 2C, FIG. 2D) in WT mice. (FIGS. 2C, 2F, 2I, 2L) show 3D reconstruction of tissue. White arrows in (FIG. 2A, right panel) point to sprouting tufts. White arrows in (FIG. 2B, FIG. 2E) point to NRP1⁺ MPs associated with tufts. LysM-Cre/Nrp1$^{fl/fl}$ mice had less MPs and less tufting (FIGS. 2G-2K). For all IHCs, representative images of three independent experiments are shown. Scale bars (FIGS. 2A, 2D, 2G, 2J): 100 μm, (FIGS. 2B, 2E, 2H, 2K): 50 μm;

FIGS. 3A-3J show that the NRP1 ligand, SEMA3A, is induced in patients suffering from proliferative diabetic retinopathy. Angiographies, funduscopies, spectral-domain optical coherence tomography (SD-OCT) and three-dimensional (3D) retinal maps obtained from patients selected for the study. Control patients had non-vascular pathologies and were compared to patients with proliferative diabetic retinopathy (PDR). Control ERM patients shows signs of non-diabetes-related retinal damage such as (FIG. 3A, FIG. 3B) tractional tension on vasculature (arrow) secondary to (FIG. 3C) fibrotic tissue (white arrow), posterior vitreous detachment (arrowhead) and macular bulging (angiography and 3D map). Retinas from PDR patients have (FIG. 3E) neovascularization (inset) with (FIG. 3D) highly permeable microvessels as evidenced by leakage of fluorescent dye (inset), (FIG. 3F) microaneurysms (inset arrows) and (FIG. 3G) fibrous scar tissue (arrow), indicative of advanced retinopathy. (FIG. 3H) PDR patients show some evidence of macular edema, including cystoid formation (white arrowhead) due to focal coalescence of extravasated fluid. (FIG. 3I) Vitreous humour analyzed by ELISA shows increased levels of SEMA3A protein by 5-fold in patients with PDR; n=17 for controls and 17 with PDR. (FIG. 3J) Western blot analysis of equal volumes of vitreous corroborates the increase in SEMA3A (~125 KDa and 95 KDa) in patients with PDR with respect to controls;

(FIG. 4A, FIG. 4B) Retinas from WT and myeloid deficient NRP1 k.o. mice (LysM-Cre/Nrpr$^{fl/fl}$ mice) under normoxic conditions or in OIR were collected between P10 and P17 and analyzed by RT-qPCR (oligonucleotide used were as disclosed in Example 11, Table 2). SEMA3A mRNA (FIG. 4A) expression was induced throughout OIR in both WT and LysM-Cre/Nrp1 fl/fl retinas while VEGF (FIG. 4B) was significantly less induced in k.o. mice (LysM-Cre/Nrp1$^{fl/fl}$) compared to WT retinas (stars). Data are expressed as a fold change relative to respective normoxic controls for each time point ±SEM; n=4-7; *p<0.05, p<0.01, *p<0.001. (FIG. 4C) Laser capture micro-dissection (LCM) was performed on P14 mice with care being taken to select avascular retinal zones in OIR. (FIG. 4D, FIG. 4E) RT-qPCR on LCM of retinal layers in control and OIR avascular zones showed an induction in both SEMA3A (FIG. 4D) and VEGF (FIG. 4E) mRNA in the ganglion cell layer (GCL) during OIR retinas compared to normoxic retinas. VEGF was also induced in the inner nuclear layer of OIR retinas (FIG. 4E). Data are expressed as a fold change relative to normoxic GCL±SEM;

(FIG. 6A, FIG. 6B) Primary macrophages were isolated from WT or myeloid-deficient NRP1 k.o. mice (LysM-Cre/Nrp1$^{fl/fl}$ mice) and subjected to a transwell migration assay with vehicle, MCP-1 (100 ng/ml), SEMA3A (100 ng/ml) or VEGF (50 ng/ml) added to the lower chamber. Representative images of migrated cells stained with DAPI are shown (FIG. 6A). SEMA3A or VEGF promoted macrophage migration to similar extents as the positive control MCP-1 (FIG. 6B). To ascertain that SEMA3A and VEGF were stimulating macrophage chemotaxis, cells were pre-treated with the selective ROCK inhibitor Y-27632 (100 μg/ml) (FIG. 6B) which abolished chemotaxis. Macrophages from LysM-Cre/Nrp1$^{fl/fl}$ mice were unresponsive to SEMA3A or VEGF but responsive to MCP-1 (FIG. 6C). Data are expressed as a fold change relative to control (non-treated cells); n=6-22; p<0.01, *p<0.001. Scale bars: 100 μm (FIG. 6A);

(FIG. 7A) Quantification and representative images of choroid explants isolated from LysM-Cre/Nrp1$^{+/+}$ and LysM-Cre/Nrp1$^{fl/fl}$ mice (n=6; p=0.018). (FIG. 7B, FIG. 7C) Representative images of choroid explants from LysM-Cre/Nrp1$^{+/+}$ (FIG. 7B) and LysM-Cre/Nrp1$^{1+}$ (FIG. 7C) mice following chlodronate liposome treatment (to deplete macrophages) and subsequent addition of exogenous macrophages (Ma). (FIG. 7D, FIG. 7E) Quantification of choroidal microvascular sprouting from LysM-Cre/Nrp1$^{+/+}$ (FIG. 7D) and LysM-Cre/Nrp1$^{fl/fl}$ (FIG. 7E) depicted in B and C (n=6, n.s.: not significant, * p<0.05, p<0.01, *p<0.001);

FIG. 11A. Fold change in SEMA3A (left panel) and VEGF (right panel) in mice brain. FIG. 11B. Fold change in SEMA3A (left panel) and VEGF (right panel) in mice kidneys. FIG. 11C. Fold change in SEMA3A (left panel) and VEGF (right panel) in mice lungs. FIG. 11D. Fold change in SEMA3A (left panel) and VEGF (right panel) in mice liver;

FIG. 12A. Fold change in TNF-α (left panel) and IL-1β (right panel) in mice brain. FIG. 12B. Fold change in TNF-α (left panel) and IL-1β (right panel) in mice kidneys. FIG. 12C. Fold change in TNF-α (left panel) and IL-1β (right panel) in mice lungs. FIG. 12D. Fold change in TNF-α (left panel) and IL-1β (right panel) in mice liver;

(FIG. 16A) Survival rate of control mice administered with i) a high dose of LPS (i.p., 25/mg/kg); or ii) an NRP1 trap (i.v., 0.2 mg/kg of Trap-1, FIGS. 19C and 20X-20Y but without an FC domain, NP_032763) followed by a high dose of LPS (i.p., 25/mg/kg). (FIG. 16B) Comparison of survival rate between myeloid-resident NRP1 knock out mice (LyzM/NRP1$^{fl/fl}$) and control mice administered with a high dose of LPS (i.p., 25/mg/kg);

(FIG. 18A), Coronal cerebral sections of MCAO mice treated with vehicle. (FIG. 18B) Coronal cerebral sections of MCAO mice treated with NRP1 Trap-1 (see FIGS. 19C and 20X-20Y but without an FC domain, NP_032763). (FIG. 18C) Schematic representation of average infarct size in mice treated with vehicle or NRP1 trap following MCAO. (FIG. 18D) Neurological impairment (neuroscore) of mice treated with vehicle or NRP1 trap 1h after MCAO. (FIG. 18E) Neurological impairment (neuroscore) of mice treated with vehicle or NRP1 trap 24h after MCAO;

FIGS. 19A-19F show a schematic representation of the NRP1 protein and embodiments of NRP1-traps of the present invention. (FIG. 19A). WT NRP1 representation showing SEMA3A binding domain (mainly a1a2 with a small contribution of b1 and VEGF binding domain (b1b2). The c-domain is the MEM domain that is thought to contribute to NRP dimerization to other co-receptors. (FIGS. 19B, 19D-19F) Schematic representations of human-derived NRP1 (FIG. 19C) and mouse-derived NRP1 traps;

FIGS. 20A-20CC show the nucleic acid and protein sequences of the NRP1 traps depicted in FIGS. 19B and 19C. (FIGS. 20A-20B) Trap 1/TrappeA-full NRP1-FC amino acid (SEQ ID NO: 114) and nucleotide (SEQ ID NO: 2) sequences; (FIG. 20C) Trap 2-NRP1-FC-Δc-amino acid sequence (SEQ ID NO: 115); (FIG. 20D) Trap 2-NRP1-FC-Δ c-nucleotide sequence (SEQ ID NO: 4); (FIG. 20E) Trap 3-NRP1-FC-Δ b2c-amino acid sequence (SEQ ID NO: 116); (FIG. 20F). Trap 3-NRP1-FC-Δ b2c-nucleotide sequence (SEQ ID NO: 6); (FIG. 20G) Trap 4-NRP1-FC-Δb1 b2c-amino acid sequence (SEQ ID NO: 117); (FIG. 20H) Trap 4-NRP1-FC-Δb1 b2c-nucleotide sequence (SEQ ID NO: 8); (FIGS. 20I-20J) Trap 5/Trap I-NRP1-FC Δ c-short-amino acid (SEQ ID NO: 118) and nucleotide (SEQ ID NO: 10) sequences; (FIGS. 20K-20L) Trap 6/Trap D-NRP1-FC Δ b2c-short-amino acid (SEQ ID NO: 119) and nucleotide (SEQ ID NO: 12) sequences; (FIG. 20M) Trap 7/Trap C-NRP1-FC Δ b1b2c-short-amino acid (SEQ ID NO: 120) and nucleotide (SEQ ID NO: 14) sequences; (FIGS. 20N-20O) Trap 8/TrapJ-full NRP1-FC-VEGF low-amino acid (SEQ ID NO: 121) and nucleotide (SEQ ID NO: 16) sequences; (FIG. 20P) Trap 9-NRP1-FC-Δ c-VEGF low-amino acid sequence (SEQ ID NO: 122); (FIG. 20Q) Trap 9-NRP1-FC-Δ c-VEGF low-nucleotide sequence (SEQ ID NO: 18); (FIG. 20R) Trap 10-NRP1-FC-Δ b2c-VEGF low-amino acid sequence (SEQ ID NO:123); (FIG. 20S) Trap 10-NRP1-FC-Δ b2c-VEGF low-nucleotide sequence (SEQ ID NO: 20); (FIGS. 20T-20U) Trap 11/TrapL-NRP1-FC-Δ c-VEGF low-Short-amino acid (SEQ ID NO: 124) and nucleotide (SEQ ID NO:22) sequences; (FIGS. 20V-20W) Trap 12/TrapK-NRP1-FC-Δb2 c-VEGF low-Short-amino acid (SEQ ID NO:125) and nucleotide (SEQ ID NO:24) sequences. (FIGS. 20X-20Y) Mouse Trap 1-full Nrp1-mFC amino acid (SEQ ID NO: 126) and nucleotide (SEQ ID NO: 26) sequences. (FIGS. 20Z-20AA) Mouse Trap 2-Nrp1-mFC Δ c-short amino acid (SEQ ID NO: 127) and nucleotide (SEQ ID NO: 28) sequences. (FIGS. 20BB-20CC) Mouse Trap 3-Nrp1-FC Δ b2c-short amino acid (SEQ ID NO: 128) and nucleotide (SEQ ID NO: 30) sequences;

FIG. 21 shows human SEMA3A precursor protein sequence (SEQ ID NO: 31). This sequence is further processed into mature form. Residues 1-20 correspond to the signal peptide;

FIG. 22 shows human soluble Neuropilin-1 (NRP1) receptor protein sequence (e.g., GenBank Acc. No. AAH07737.1-SEQ ID NO: 65). Domains a1, a2, b1, b2 and c are shown. Domain a1 consist of amino acids 23-148; domain a2 consist of amino acids 149-270; domain b1 consist of amino acids 271-428; domain b2 consists of amino acids 429-590 and domain c consists of amino acids 591-609;

FIGS. 23A-23B show that SEMA3A traps accelerate vascular regeneration and reduce pathological angiogenesis in ischemic mice retinas in an oxygen-induced retinopathy model. (FIG. 23A) Schematic depiction of the mouse model of oxygen-induced retinopathy (OIR) showing the four principal stages of retinopathy i.e., normoxia, vessel loss/vaso-obliteration, proliferation/neovascularization and neovascular (NV) regression. (FIG. 23B) Mean percentage (%) of avascular area (relative to vehicle) at P17 following intravitreal injection of histidine tagged Trap G or Trap M (Trap G-HIS (SEQ ID NO: 38) and TrapM-HIS (SEQ ID NO: 42)). Photographs of representative retinas showing avascular area are shown for each group. Mean percentage of neovascular area (relative to vehicle) at P17 following intravitreal injection of histidine tagged Trap G and Trap M. Photographs of representative retinas showing neovascular area are shown for each group. *p<0.05, p<0.01, *p<0.001. n=8-13 animals/group;

(FIG. 24A). Blood glucose levels of mice prior streptozotocin (STZ) treatment (week 0) and 3 weeks following STZ treatment (diabetic state). (FIG. 24B). Retinal Evans Blue permeation assay (measured at week 8) on mice retinas injected intravitreally with 0.5 ug/ml of Trap G, Trap M or 80 μg (1 ul) of anti-VEGF$_{164}$ antibody (AF-493-NA, R&D) at 6 and 7 weeks following STZ administration. (FIG. 24C) Retinal Evans Blue permeation assay (measured at week 14) on mice retinas injected intravitreally with 0.5 ug/ml of Trap G or Trap M or anti-VEGF$_{164}$ antibody (AF-493-NA, Novus Biologicals) at 12 and 13 weeks post STZ treatment. *p<0.05, n=4, from 12 animals;

FIGS. 25A-25B show that NRP1 derived trap (anti SEMA3A and VEGF) reduces choroidal neovascularization in a model of age-related macular degeneration (AMD) (FIG. 25A). Schematic representation of the method used for inducing choroidal neovascularization in mice eyes. (FIG. 25B) Choroidal Neovascularization at day 14 post laser burn (mean perfused FITC/Lectin area). Mice eyes were injected intravitreally with Trap G right after laser burn:

FIGS. 26A-26B show an alignment between rat (Access. Nos. EDL96784, NP_659566), human (SEQ ID NO: 68, Accession No. NM003873) and mouse (SEQ ID NO: 67, Accession No. NP_032763) together with an NRP1 consensus sequence (SEQ ID NO: 69). The NRP1 signal domain (amino acids 1-21), SEMA3a binding domains a1 (amino acids 22-148, SEQ ID NO:78), a2 (amino acids 149-175, SEQ ID NO:79), VEGF binding domains b1 (amino acids 276-428, SEQ ID NO:80) and b2 (amino acids 429-589, SEQ ID NO:81), domain c (amino acids 590-859, SEQ ID NO:82), transmembrane domain (amino acids 860-883, SEQ ID NO:77) and cytoplasmic domain (amino acids 884-923) are identified; and FIGS. 27A-27H show protein sequence alignments between exemplary traps of the present invention shown in FIG. 19 but without any histidine or FC tags. (FIGS. 27A-27D). protein sequence alignment between exemplary traps but lacking the 6×His tag purification domains (G (SEQ ID NO:100), R (SEQ ID NO:101), Z (SEQ ID NO:102), AB (SEQ ID NO:103), AC (SEQ ID NO:104), O (SEQ ID NO:105), Q (SEQ ID NO:106), M (SEQ ID NO:107), P (SEQ ID NO:108), N (SEQ ID NO:109), W (SEQ ID NO: 110), X (SEQ ID NO: 111) and Y (SEQ ID NO: 112)) of the present invention comprising a 6×His tag purification domain. (FIGS. 27E-27H) protein sequence alignment between exemplary traps of the present invention but lacking the FC domain ((A (SEQ ID NO:100), I (SEQ ID NO:105), D (SEQ ID NO:107), C (SEQ ID NO:109), J (SEQ ID NO:101), L (SEQ ID NO:106), K (SEQ ID NO:108), S (SEQ ID NO:113), U (SEQ ID NO:111), V (SEQ ID NO:112)).

DESCRIPTION OF ILLUSTRATIVE EMBODIMENTS

Figure 1A:
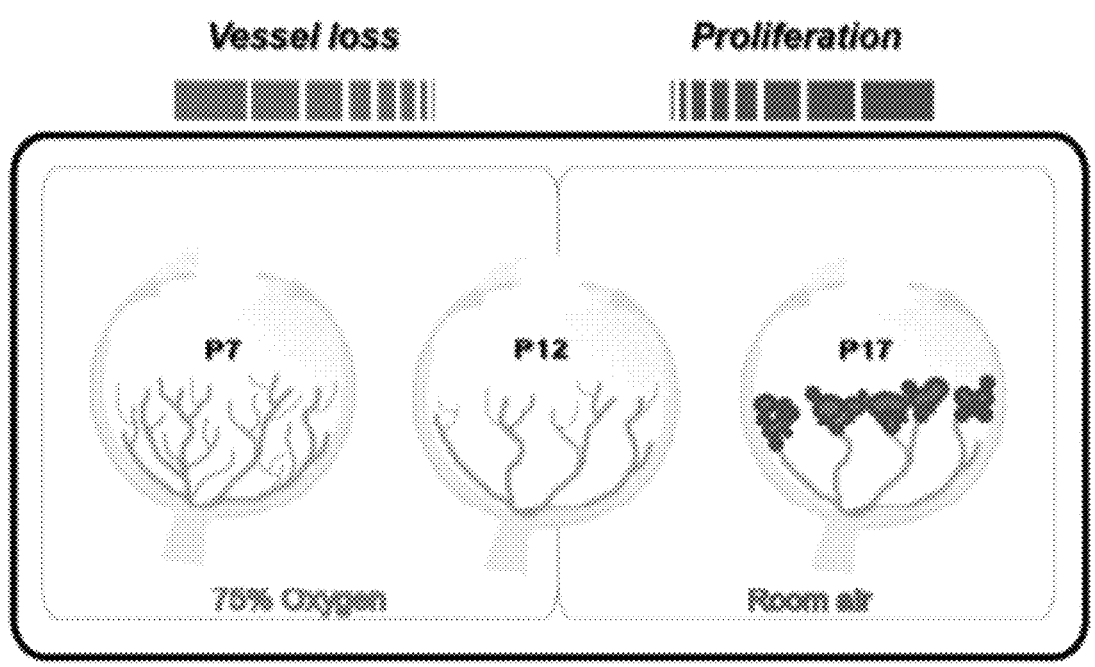

The present inventors have identified a subset of mononuclear phagocytes (MPs) that responds to local chemotactic cues such as SEMA3A that are conserved between central neurons, vessels and immune cells. NRP1 expressing MP's were shown to enter the site of injury and to contribute to (i) tissue damage and/or (ii) pathological activation of the innate immune response in models of inflammatory conditions including various forms of inflammatory, proliferative retinopathies (e.g., proliferative diabetic retinopathy, retinopathy of prematurity and age-related macular degeneration), septic shock and cerebral ischemia/stroke.

The inventors demonstrated that stressed retinal neurons and neural tissue have the inherent ability to modulate the local innate immune response via unconventional chemotactic agents. NRP1 on microglia was found to be a potent chemoattractive receptor for SEMA3A, and VEGF and inhibition of NRP1 signaling in innate immune cells (e.g., using NRP1-derived traps or NRP1 or SEMA3A antibodies) resulted in protection against MP's induced inflammation and tissue damage.

Patients suffering from late stage proliferative diabetic retinopathy (PDR) were shown to produce elevated levels of SEMA3A which counterintuitively acts as a potent attractant for Neuropilin-1 (NRP1)-positive MPs. These pro-angiogenic MPs are selectively recruited to sites of pathological neovascularization in response to locally produced SEMA3A as well as VEGF and TGF-β. Furthermore, SEMA3A was shown to be up-regulated in several organs during septic shock and to induce secretion of inflammatory cytokines by MP's. Inhibition of NRP1 also reduced the production of proinflammatory cytokines in sepsis.

Finally NRP1-positive MPs were shown to play a critical role in inflammatory disease progression. Inhibition/abrogation of NRP1 myeloid-dependent activity was shown to protect against neovascular retinal disease (vascular degeneration and pathological neovascularization), septic shock and neural damages secondary to cerebral ischemia/stroke.

Together, these findings underscore the role of NRP1-positive MPs and their ligands in inflammation (and in particular in neuroinflammation) and demonstrate the therapeutic benefit of inhibiting NRP1 cell signaling to limit hyperactivation of innate immune response (e.g., tissue damage at the site of injury through recruitment of microglia/macrophages and/or induction of production and/or secretion of proinflammatory cytokines, and/or vascular leakage/edema). The present findings finds applications in the prevention and treatment of diseases and conditions characterized by sustained (e.g., chronic, persistent) or excessive/pathological inflammation involving MP recruitment and proinflammatory cytokines production and secretion such as septic shock, arthritis, inflammatory bowel disease (IBD), cutaneous skin inflammation, diabetes, uveitis and neuroinflammatory conditions such as diabetic retinopathy, age-related macular degeneration (AMD), retinopathy of prematurity, multiple sclerosis, amyotrophic lateral sclerosis (ALS), age-related cognitive decline/Alzheimer's disease and stroke.

Inhibition of NRP1-Mediated Cellular Activity

The present inventors have found that by inhibiting NRP1-dependent cell signaling (and in particular SEMA3A-mediated cell signaling), it is possible to protect against (prevent or treat) inflammatory diseases and conditions such as those involving hyperactivation of the innate immune response. In particular, inhibition of NRP1-mediated cell-signaling reduces the unwanted (pathological) recruitment of mononuclear phagocytes (MPs, e.g., microglia, macrophages) and the production/secretion of proinflammatory cytokines which contribute to tissue damage (e.g., increased vascular degeneration, pathologic neovascularization, cell death or cell damages), inflammation and edema.

Thus, in an aspect, the present invention relates to a method of treating or preventing inflammation comprising inhibiting NRP1-dependent cell-signaling. In a particular aspect, the inflammation is neuroinflammation.

As used herein, the term "inflammation" means a disease or condition which involves the activation of the innate immune response comprising i) the recruitment of mononuclear phagocytes (e.g., microglia or macrophages) expressing the NRP1 receptor at the site of inflammation or injury; and/or ii) the NRP1 dependent production/secretion of pro-inflammatory cytokines (e.g., IL-1β, TNF-α, IL-6). The classical signs of acute inflammation are pain, heat, redness, swelling, and loss of function. Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged (sustained) inflammation, known as chronic inflammation, leads to a progressive shift in the type of cells present at the site of inflammation and is characterized by simultaneous destruction and healing of the tissue from the inflammatory process. Non-limiting examples of inflammatory conditions which may be treated or prevented in accordance with methods of the present invention include septic shock, arthritis, inflammatory bowel disease (IBD), cutaneous skin inflammation, diabetes, uveitis and neuroinflammatory conditions such as diabetic retinopathy (including proliferative diabetic retinopathy (PDR)), age-related macular degeneration (AMD), retinopathy of prematurity, multiple sclerosis, amyotrophic lateral sclerosis (ALS), age-related cognitive decline/Alzheimer's disease and stroke.

In a particular embodiment the inflammatory disease or condition is not a retinopathy. In another embodiment, the inflammatory disease or condition is not diabetic retinopathy. In another embodiment, the inflammatory disease or condition is not macular edema. In another embodiment, the inflammatory disease or condition is not diabetic macular edema.

In a related aspect, the present invention concerns a method of inhibiting hyperactivation (or pathological activation) of the innate immune response comprising inhibiting NRP1-dependent cell-signaling. Such an hyperactivation of innate immune response, is typically associated with acute or chronic activation of any given cell population of the immune system (innate and adaptive, e.g., mononuclear cell recruitment in the organ/tissue) beyond levels required to maintain tissue homeostasis. This is often accompanied by heightened production of cytokines (e.g., TNF-alpha, IL-6), increased vascular permeability, and may result in compromised tissue function.

In another aspect, the present invention concerns a method of treating or preventing vascular degeneration comprising inhibiting NRP1-dependent cell-signaling.

In a further aspect, the present invention concerns a method of treating or preventing pathological neovascularization comprising inhibiting NRP1-dependent cell-signaling.

In another aspect, the present invention concerns a method of treating or preventing septic shock comprising inhibiting NRP1-dependent cell-signaling.

In a yet another aspect, the present invention concerns a method of treating or preventing neural damages secondary to cerebral ischemia/stroke comprising inhibiting NRP1-dependent cell-signaling.

Because NRP1-mediated cell signaling (e.g., MPs recruitment and production/secretion of pro-inflammatory cytokines) depends on the binding of NRP1 to its ligands (e.g., SEMA3A, VEGF and/or TGF-β), inhibition of NRP1-mediated cellular signaling can be achieved in at least two ways: i) by targeting the expression or activity of NRP1 directly (through the use of NRP1 antibodies, NRP1 derived traps or the like); or ii) by targeting the expression or activity of one or more of its ligands (e.g., SEMA3A, VEGF and/or TGF-β).

In embodiments, the above methods comprise preferentially or specifically inhibiting SEMA3A-mediated cell signalling. "Preferentially inhibiting" means that the level of inhibition of SEMA3A-mediated cell signalling is greater than that of other NRP1 ligands (e.g., VEGF165 and TGF-beta). In certain aspects, methods of the present invention substantially do not reduce or inhibit VEGF (e.g., VEGF165) and/or TGF-beta-mediated cell signalling that occur through the interaction with NRP1. In embodiments, compounds of the present invention (e.g., NRP1 traps) "preferentially bind" to one ligand over the others (e.g., preferentially bind SEMA3A over VEGF). Such preferential interaction may be determined by measuring the dissociation constant (Kd) for each ligand. In embodiments, interaction for one ligand (e.g., SEMA3A) over the others (e.g., VEGF) is at least 1.5, 2, 3, 4, 5, 6, 7, 8, 9, 10, 12, 15, 28, 20, 22, 25, 30, 35, 40, 45, 50, 60, 75, 80, 100, 200, 300, 400, 500, 1000 times greater or more. In embodiments the kD (e.g., in nM) for one ligand is at least 1.5, 2, 3, 4, 5, 6, 7, 8, 9, 10, 12, 15, 28, 20, 22, 25, 30, 35, 40, 45, 50, 60, 75, 80, 100, 200, 300, 400, 500, 1000 times smaller than the kD for one or more of the other ligands (e.g., VEGF).

In an embodiment, methods of the present invention comprise administration to a subject likely to suffer from inflammation (e.g., likely to suffer from an inflammatory disease or condition). In other embodiment, methods of the present invention comprise administration to a subject diagnosed from inflammation (e.g., likely to suffer from an inflammatory disease or condition). In an embodiment, the subject is a mammal, preferably a human.

NRP1 Traps

Inhibition of NRP1-mediated cellular signaling can be achieved using NRP1 traps of the present invention. As used herein, the terms, "NRP1 trap", or "NRP1 polypeptide trap" encompass naturally occurring soluble NRP1 polypeptide (e.g., such as NRP1 secreted isoform b FIG. 22, SEQ ID NO: 65)), and synthetic (e.g., recombinantly produced) NRP1 polypeptide traps including any functional soluble fragment of NRP1 (e.g., NRP1 isoform 1 or 2) or any functional variant of NRP1 which competes with endogenous NRP1 for ligand binding. In an embodiment, the NRP1 traps of the present invention do not exists in nature (i.e., are not naturally occurring) but are "derived" from naturally occurring NRP1 polypeptides (i.e. they are synthetic; e.g., NRP1 traps comprising the extracellular domain of NRP1 isoform 1 or a fragment or variant thereof). NRP1 traps the present invention initially comprise a signal peptide at their N-terminal end (e.g., amino acids 1-21 (SEQ ID NO: 70) of NRP1 shown in FIG. 26 (e.g., SEQ ID NO:69) which is cleaved upon secretion by the cells. Accordingly, NRP1 polypeptide traps of the present invention lack amino acids 1-21 when administered as purified polypeptides or when prepared as pharmaceutical compositions comprising a purified or substantially pure form. Nucleic acids encoding for NRP1 traps of the present invention (e.g., SEQ ID NOs: 2, 4, 6, 8, 10, 12, 14, 16, 18, 20, 22, 24, 26, 28, 34, 32, 34, 36, 39, 41, 43, 45, 47, etc. See also Table 1) comprise a polynucleotide sequence in 5' which encodes for a signal peptide (first 63 nucleotides encoding for the first 21 amino acids at the N-terminal end) which will allow the NRP1 trap to be synthesized and secreted by the cells. In a particular embodiment, the signal peptide corresponds to the first 20 amino acids of the NRP1 polypeptide set forth in SEQ ID NO: 65 (FIG. 22) or SEQ ID NO: 69 (FIG. 26). NRP1 traps of the present invention encompass functional variants of corresponding "wild-type" NRP1 polypeptides or fragment thereof (e.g., polymorphic variations naturally found in the population).

NRP1 traps of the present invention may or may not comprise further polypeptide domains (e.g., purification domains). Exemplary traps lacking purification domains and comprising only NRP1-derived sequences are shown in FIG. 27. Non-limiting examples of NRP1 traps that may be used in accordance with the present invention are given in FIGS. 19B-F, FIG. 20, FIG. 27 and are listed Table 1 below.

TABLE 1

Exemplary NRP1-derived traps which have been prepared
in accordance with the present invention.

| Trap | Description | SEQ ID Nos. (aa and nts) |
| --- | --- | --- |
| Trap 1/A | Human, "full" extracellular domain NRP1 (corresponding to amino acids 22 to 856 of NRP1 sequences shown on FIG. 26)-FC | SEQ ID NOs: 1, 2, 100 (aa without FC, includes SP) |
| Trap 2 | Human, NRP1-FC-Δc (275 aa linker) | SEQ ID NOs: 3, 4 |
| Trap 3 | Human, NRP1-FC-Δb2c (434 aa linker) | SEQ ID NOs: 5, 6 |
| Trap 4 | Human, NRP1-FC-Δb1b2c (593 aa linker) | SEQ ID NOs: 7, 8 |
| Trap 5/Trap I | Human, NRP1-FC-Δc-short | SEQ ID NOs: 9, 10, 105 (aa, without FC, includes SP) |
| Trap 6/TrapD | Human, NRP1-FC-Δb2c-short | SEQ ID NOs: 11, 12, 107, (aa, without FC, includes SP) |
| Trap 7/TrapC | Human, NRP1-FC-Δb1b2c-short | SEQ ID NOs: 13, 14 109, (aa, without FC, includes SP) |
| Trap 8/TrapJ | Human, "full" extracellular domain NRP1-FC-VEGF low (Y297A mutation) | SEQ ID NOs: 15, 16, 101 (aa, without FC, includes SP) |
| Trap 9 | Human, NRP1-FC-Δc-VEGF low (Y297A mutation, 275 aa linker) | SEQ ID NOs: 17, 18 |
| Trap 10 | Human, NRP1-FC-Δb2c-VEGF low (Y297A mutation, 434 aa linker) | SEQ ID NOs: 19, 20 |
| Trap 11/Trap L | Human, NRP1-FC-Δc-VEGF low-short (Y297A mutation) | SEQ ID NOs: 21, 22, 106 (aa, without FC, includes SP) |
| Trap 12Trap K | Human, NRP1-FC-Δb2c-VEGF low-short (Y297A mutation) | SEQ ID NOs: 23, 24, 108 (aa, without FC, includes SP) |
| mTrap 1 | Mouse, "full" extracellular domain NRP1-FC Amino acids residues 22-856 | SEQ ID NOs: 25, 26 |
| mTrap 2 | Mouse, NRP1-FC-Δc-short | SEQ ID NOs: 27, 28 |
| mTrap 3 | Mouse, NRP1-FC-Δb2c-short | SEQ ID NOs: 29, 30 |
| Trap S | Human, NRP1-FC-Δb2-short | SEQ ID NOs: 31, 32, 113 (aa without FC, includes SP) |
| Trap U | Human, NRP1-FC-Δb2-VEGF low-short (Y297A mutation) | SEQ ID NOs: 33, 34, 111 (aa, without FC, includes SP) |
| Trap V | Human, NRP1-FC-Δb1b2-short | SEQ ID NOs: 35, 36, 112 (aa, without FC, includes SP) |
| Trap G | Human, "full" extracellular domain NRP1-His | SEQ ID NOs: 38, 39, 100 (aa without his tag, includes SP) |
| Trap O | Human, NRP1-His-Δc-short | SEQ ID NOs: 40, 41, 105 (aa without his tag, includes SP) |
| Trap M | Human, NRP1-His-Δb2c-short | SEQ ID NOs: 42, 43, 107 (aa without his tag, includes SP) |
| Trap N | Human, NRP1-His-Δb1b2c-short | SEQ ID NOs: 44, 45, 109 (aa without his tag, includes SP) |
| Trap R | Human, NRP1-His-Δc-VEGF low | SEQ ID NOs: 46, 47, 101 (aa without his tag) |
| Trap Q | Human, NRP1-His-Δc-VEGF low-short | SEQ ID NOs: 48, 49, 106 (aa without his tag, includes SP) |
| Trap P | Human, NRP1-His-Δb2c-VEGF low-short | SEQ ID NOs: 50, 51, 108 (aa without his tag, includes SP) |
| Trap W | Human, NRP1- His-Δb2 -short | SEQ ID NOs: 52, 53, 110 (aa without his tag, includes SP) |
| Trap X | Human, NRP1- His-Δb2 - VEGF low-short | SEQ ID NOs: 54, 55, 111 (aa, without his tag, includes SP) |
| Trap Y | Human, NRP1- His-Δb1b2 -short | SEQ ID NOs: 56, 57, 112 (aa, without his tag, includes SP) |
| Trap AB | Human, "full" extracellular domain NRP1-His-SEMA3A low (S346A et E348K mutations) | SEQ ID NOs: 58, 59, 103 (aa, without his tag, includes SP) |

TABLE 1-continued

Exemplary NRP1-derived traps which have been prepared in accordance with the present invention.

| Trap | Description | SEQ ID Nos. (aa and nts) |
|---|---|---|
| Trap AC | Human, "full" extracellular domain NRP1-His-VEGF- low (D320K mutation) | SEQ ID NOs: 60, 61, 104 (aa without his tag, includes SP) |
| Trap Z | Human, "full" extracellular domain NRP1-His, VEGF165-Low (E319K/D320K mutations) | SEQ ID NOs: 62, 63, 102 (aa, without his tag, includes SP) |
| Trap 1bis | Human, Trap 1 without FC | SEQ ID NO: 83, 84 |

SP: Signal peptide

Given that NRP1 distinctly regulates the effects of its ligands on signal transduction and cellular responses, it may be advantageous to specifically inhibit the binding of one specific ligand to NRP1 but not that of the others. For example, as shown herein, at early time points of retinal disease, where SEMA3A levels are elevated, VEGF levels remain low and relatively unchanged compared to non-diabetic controls. Also, in septic shock, SEMA3A was the sole NRP1 ligand which had a long term effect and stayed up-regulated for more than 24 hours following induction of sepsis. Thus, given the differences in expression kinetics for each ligand and the fact that neutralization of one ligand (e.g., VEGF) may be ineffective in certain conditions (or be associated with undesired side effects), specific inhibition of one ligand (e.g., SEMA3A) binding to NRP1, (but not that of the other(s) (e.g., VEGF)) is advantageous. Thus, in certain aspects of the methods of the present invention, inhibition of SEMA3A-mediated cell signaling, is accomplished by providing NRP1 Traps having greater affinity for SEMA3 than VEGF or to which VEGF (e.g., VEGF165) does not bind or does not bind substantially.

Accordingly, in an embodiment, the soluble NRP1 polypeptide or functional fragment or variant thereof (NRP1 trap) of the present invention binds to all natural ligands of NRP1 (e.g., SEMA3A, VEGF and TGF-beta, e.g., a soluble NRP1 trap comprising the extracellular domain (e.g., amino acids 22-856 or 22-959 of SEQ ID NO: 66 or 69), Trap 1, (SEQ ID NO: 1) or Trap G (SEQ ID NO: 38)—See also, FIGS. 19 and 27 and Table 1). In an embodiment, the NRP1-derived trap of the present invention inhibits SEMA3 and VEGF signaling by binding to both SEMA3A and VEGF.

In another embodiment, the NRP1 trap of the present invention is a polypeptide which binds to SEMA3A but not to VEGF. For example the NRP1 trap may comprise the a1 (e.g., SEQ ID NO:71) and/or a2 subdomain(s) (e.g., SEQ ID NO:72) which bind(s) to SEMA3A but not the b1 (e.g., SEQ ID NO:73) and/or b2 (e.g., SEQ ID NO: 74) subdomain(s) required for VEGF binding (e.g., Trap M, (SEQ ID NO: 42), Trap N (SEQ ID NO: 44), Trap 12/Trap K(SEQ ID NO: 23), Trap 4 (SEQ ID NO:7), Trap 7/C (SEQ ID NO: 13), See also, FIGS. 19 and 27 and Table 1). In an embodiment, the NRP1-derived trap comprises domains a1 and a2 corresponding to amino acids 22 to 275 of the NRP1 amino acid sequence set forth in FIG. 26 (e.g., amino acids 22-275 of SEQ ID NO: 66 or SEQ ID NO: 22-275 of SEQ ID NO: 69). The NRP1 trap may also comprise a mutation (e.g., a deletion or substitution) which abrogates or reduces significantly the binding of VEGF to NRP1 but not that of SEMA3A to NRP1 (e.g., Trap 8/trap J (SEQ ID NO:15), Trap 9 (SEQ ID NO: 17), Trap 10 (SEQ ID NO: 19), TRAP 11/L (SEQ ID NO:21), Trap12/K (SEQ ID NO: 23), Trap U (SEQ ID NO: 34), Trap R (SEQ ID NO: 46), Trap Q (SEQ ID NO: 48), Trap P (SEQ ID NO: 50, Trap X (SEQ ID NO:54, Tarp AC (SEQ ID NO: 60), TRAP Z (SEQ ID NO: 62) See also, FIGS. 19 and 27 and Table 1). One non-limiting example of such mutation is a substitution at tyrosine 297 in the b1 domain of NRP1 (e.g., Y297A, FIGS. 19B-D, FIG. 27 and Table 1, e.g., Traps 8, 9, 10, 11, 12, V, R, Q, P and X). Other examples of such mutations comprise a substitution at the glutamic acid at position 319 and at aspartic acid at position 320 in NRP1 (e.g., E319K and D320K such as in Trap AC and Z (SEQ ID NOs: 60, 62)).

In another embodiment, the NRP1 trap is a soluble NRP1 polypeptide or functional fragment or variant thereof which binds to VEGF but not to SEMA3A. For example, the NRP1 trap may comprise the b1 (e.g., SEQ ID NO: 73) and/or b2 (e.g., SEQ ID NO: 74) domain(s) to bind to VEGF but not the a1 (e.g., SEQ ID NO: 71) and/or a2 (e.g., SEQ ID NO: 72) subdomain(s) which bind to SEMA3A. In an embodiment, the NRP1 trap comprises domains b1b2 corresponding to amino acids 276 to 589 of the NRP1 amino acid sequence set forth in FIG. 26 (e.g., amino acids 276-589 of SEQ ID NO: 66 or 276-289 of SEQ ID NO: 69). In another embodiment, the NRP1 trap may comprise a mutation which reduces or abrogate SEMA3A binding but not that of VEGF. One non-limiting example of such mutation is a substitution at serine 346 and/or glutamic acid 348 of NRP1 (e.g., S346A and E348K mutations, such as in trap AB (SEQ ID NO: 58)—See also FIGS. 19 and 27).

In an embodiment, the soluble NRP1 polypeptide or functional fragment thereof comprises or consists of traps as set forth in FIGS. 19B-F, 20, 27 and Table 1.

In preferred embodiments, the NRP1 traps of the present invention lack the transmembrane domain (e.g., corresponding to amino acids residues 860 to 883 of the NRP1 polypeptide sequences shown in FIG. 26 (such as SEQ ID NO: 66 and 69)) and cytosolic domain (e.g., corresponding to amino acids residues 884-923 of the NRP1 polypeptide isoform 1 sequences shown in FIG. 26 (such as SEQ ID NO: 66 and 69)) found in for example NRP1 isoform 1. In embodiments, the NRP1 traps of the present invention lacks completely or partially domain c of NRP1. NRP1 isoform 1 comprises a larger c domain (see FIG. 26), while that of isoform 2 is shorter (e.g., amino acid sequence VLATEKPT-VIDSTIQSGIK (SEQ ID NO: 99) shown in FIG. 22). Particularly, domain c is not essential to SEMA3A and VEGF binding and thus may be excluded from the NRP1 traps used to inhibit NRP1-dependent cell signaling (or SEMA3A-mediated cell signaling). In an embodiment, the NRP1 trap lacks the c domain corresponding to amino acids 590 to 859 of the NRP1 amino acid sequence set forth in FIG. 26 (e.g., amino acids 590 to 859 of SEQ ID NO: 66 or SEQ ID NO: 69). In an embodiment the NRP1 traps of the present invention lack completely or partially the c domain of isoform 2 as set forth in FIG. 22 (e.g., SEQ ID NO: 99). In an embodiment, NRP1 traps of the present invention comprise domain c of NRP1 isoform 2. In another embodiment, the NRP1 derived trap lacks a portion of domain c corresponding to the amino acids set forth in SEQ ID NO: 75.

The soluble NRP1 polypeptide or functional fragment or variant thereof of the present invention may comprise one or more additional polypeptide domain(s) to increase in vivo stability and/or facilitate purification. For example, NRP1 traps of the present invention may include a FC domain (or part thereof such as the human FC domain set forth in SEQ ID NO: 37.) or a purification tag (e.g., a 6x-histidine tag). Such additional polypeptide domain(s) may be linked directly or indirectly (through a linker) to the soluble NRP1 polypeptide or functional fragment thereof.

The soluble NPR1 polypeptide or functional fragment thereof of the present invention may optionally include one or more polypeptide linkers. Such linkers may be used to link one or more additional polypeptide domain(s) to the soluble polypeptide of the present invention (e.g., a polypeptide domain which increases the stability of the polypeptide in vivo and/or a domain which facilitates purification of the polypeptide). Linker sequence may optionally include peptidase or protease cleavage sites which may be used to remove one or more polypeptide fragments or domains (e.g., removal of purification tag prior to in vivo administration of the soluble NRP1 polypeptides or functional fragment thereof). One non-limiting example of a linker or domain which enables cleavage of the polypeptide and removal of, for example, polypeptide domain(s) (e.g., 6xhis tag purification domain) includes a polypeptide comprising a TEV protease cleavage site (e.g., GSKENLYFQ'G, SEQ ID NO:76). Many other TEV cleavage sites are known and many other protease/peptidase cleavage sites are known to the skilled person and may be introduced in the polypeptides of the present invention to optionally remove one or more polypeptide domains or fragments.

Polypeptide linkers may also be used to replace totally or partially domains which are normally found in the wild-type NRP1 polypeptide but which are absent in the soluble NRP1 polypeptide or functional fragment thereof of the present invention. For example, in the NRP1 traps of the present invention, synthetic linkers may replace totally or partially domains a1, a2, b1, b2 and c. The length of the linker may correspond to the entire length of the domain removed or to a portion of it. Such linkers may increase protein folding, stability or binding to NRP1 ligands. Non-limiting examples of NRP1 traps comprising linkers are shown in FIGS. 19 and 20 (e.g., Trap 2, Trap 3, Trap 4, Trap 9 and Trap 10 listed in Table 1). One non-limiting example of a useful polypeptide linker is a polyarginine polypeptide. Other linkers are known in the art and may be used in accordance with the present invention.

In an embodiment, the NRP1 trap of the present invention comprises: (i) amino acids 1-856 (preferably, 22 to 856) of the NRP1 polypeptide set forth in FIG. 26 (SEQ ID NO: 69); (ii) amino acids 1 to 583 (preferably 22 to 583) of the NRP1 polypeptide set forth in FIG. 26 (SEQ ID NO: 69); (iii) amino acids 1 to 424 (preferably 22-424) the NRP1 polypeptide set forth in FIG. 26 (SEQ ID NO: 69); (iv) amino acids 1 to 265 (preferably 22 to 265) the NRP1 polypeptide set forth in FIG. 26 (SEQ ID NO: 69); (v) 1 to 430 and 584 to 856 (preferably 22-430 and 584-856) the NRP1 polypeptide set forth in FIG. 26 (SEQ ID NO: 69); (vi) amino acids 1 to 274 and 584 to 856 (preferably 22-274 and 584 to 856) the NRP1 polypeptide set forth in FIG. 26 (SEQ ID NO: 69); (vii) amino acids 1 to 430 and 584 (preferably 22 to 430 and 584 to 856) of the NRP1 polypeptide set forth in FIG. 26 (SEQ ID NO: 69). In a particular embodiment, the above noted traps comprise one or more mutation to reduce VEGF or SEMA3A binding as described above.

In a related aspect, the present invention provides nucleic acids encoding the NRP1 traps (e.g., traps listed in Table 1 and shown on FIGS. 19, 20 and 27). Such nucleic acids may be included in an expression vector for expression in cells. Accordingly, the present invention further relates to vectors comprising nucleic acids encoding soluble NRP1 polypeptide or functional fragments thereof and cells comprising such expression vectors. Nucleic acids encoding a soluble NRP1 polypeptide or functional fragment thereof (i.e., NRP-derived trap) of the present invention may include a polynucleotide portion encoding a signal sequence (e.g., encoding amino acids 1-21 of SEQ ID NO: 65, 66 or 69, or SEQ ID NO: 70) for secretion by the cells. Furthermore, nucleic acids of the present invention include nucleic acids with and without a translation termination "stop" codon at their 3' end. The translation termination stop codon may be provided, for example, by an expression vector into which the nucleic acids of the present invention may be cloned.

As used herein, a "functional fragment" or "functional variant" of NRP1 (e.g., a functional fragment of soluble NRP1 polypeptide or polynucleotide of the present invention such as an NRP1) refers to a molecule which retains substantially the same desired activity as the original molecule but which differs by any modifications, and/or amino acid/nucleotide substitutions, deletions or additions (e.g., fusion with another polypeptide). Modifications can occur anywhere including the polypeptide/polynucleotide backbone (e.g., the amino acid sequence, the amino acid side chains and the amino or carboxy termini). Such substitutions, deletions or additions may involve one or more amino acids or in the case of polynucleotide, one or more nucleotide. The substitutions are preferably conservative, i.e., an amino acid is replaced by another amino acid having similar physico-chemical properties (size, hydrophobicity, charge/polarity, etc.) as well known by those of ordinary skill in the art. Functional fragments of the soluble NRP1 include a fragment or a portion of a soluble NRP1 polypeptide (e.g., the a1 and/or a2 domain(s)) or a fragment or a portion of a homologue or allelic variant of NRP1 which retains inhibiting activity, i.e., binds to SEMA3A, VEGF and/or TGF-β and inhibits the transduction of NRP1-mediated cellular activity. Non-limiting examples of NRP1-mediated cellular activity include i) vascular hyperpermeability; ii) MPs activation and recruitment; iii) inducement of apoptosis; iv) induction of pro-inflammatory cytokines (e.g., TNF-α, IL-1β) production and/or secretion. In an embodiment, the NRP1 polypeptide is at least 80, 85, 88, 90, 95, 98 or 99% identical to the polypeptide sequence of FIG. 22 (NRP1 isoform 2, SEQ ID NO: 65) or amino acids 1-859 or 22-859 of the NRP1 isoform 1 set forth in FIG. 26 (SEQ ID Nos: 66 and 69). In an embodiment, the NRP1 functional fragment comprises subdomains a1, a2, b1, b2 and/c which are/is at least 80, 85, 88, 90, 95, 98 or 99% identical to subdomain(s) a1 (e.g., SEQ ID NO: 71 or amino acids 22-148 of SEQ ID NO: 66), a2 (e.g., SEQ ID NO: 72, or amino acids 149-275 of SEQ ID NO: 66), b1 (e.g., SEQ ID NO:73 or amino acids), b2 (e.g., SEQ ID NO: 74 or amino acids 429-589 of SEQ ID NO:66) and/or c (e.g., SEQ ID NO: 75 or amino acids 590-859 of SEQ ID NO: 66) of NRP1 as depicted in FIG. 22 or 26 (SEQ ID NOs:65 and 66 respectively). In an embodiment, the NRP1 is a functional variant which includes variations (conservative or non-conservative substitution(s) and/or deletion(s)) in amino acids which are not conserved between rat, mouse and human NRP1 (see FIG. 26 and consensus sequence set forth in SEQ ID NO: 69). Preferably, the NRP1 polypeptide/polynucleotide or fragment thereof is human.

TABLE 2

Non-limiting examples of substitutions in the soluble NRP1 polypeptide/NRP1 traps of the present invention.

| WT Amino acid (with ref. to FIG. 26, SEQ ID NO: 66) | Domain | Exemplary substitution(s) |
|---|---|---|
| N24 | a1 | Serine |
| E26 | a1 | Lysine |
| D29 | a1 | Glycine |
| S35 | a1 | Asparagine |
| D62 | a1 | Glutamic acid |
| M68 | a1 | Isoleucine |
| F90 | a1 | Isoleucine |
| N96 | a1 | Glycine |
| H98 | a1 | Arginine |
| F99 | a1 | Leucine |
| R100 | a1 | Tryptophan |
| P110 | a1 | Serine |
| T153 | a2 | Alanine |
| S155 | a2 | Threonine |
| S170 | a2 | Cysteine |
| V177 | a2 | Isoleucine |
| P196 | a2 | Glutamine |
| D219 | a2 | Glutamic acid |
| I242 | a2 | Valine |
| 269 | a2 | Isoleucine |
| 298 | b1 | Glycine |
| A303 | b1 | valine |
| N323 | b1 | Lysine |
| K359 | b1 | Arginine |
| I360 | b1 | Valine |
| V362 | b1 | Isoleucine |
| T371 | b1 | Serine |
| I372 | b1 | Leucine |
| P378 | b1 | Alanine |
| V379 | b1 | Isoleucine |
| L380 | b1 | Isoleucine |
| V392 | b1 | Phenylalanine, leucine |
| A393 | b1 | Glycine |
| P396 | b1 | Proline, serine |
| A409 | b1 | Valine |
| T410 | b1 | Serine |
| T410 | b1 | Serine |
| S449 | b2 | Alanine |
| G453 | b2 | Alanine |
| S469 | b2 | Threonine |
| A476 | b2 | Serine |
| S479 | b2 | Proline |
| I481 | b2 | Threonine |
| I487 | b2 | Valine |
| E491 | b2 | Aspartic acid |
| 498 | b2 | Valine |
| G518 | b2 | Alanine |
| M528 | b2 | Threonine |
| A553 | b2 | Alanine |
| P555 | b2 | Serine, threonine |
| A556 | b2 | Proline |
| G572 | b2 | Serine |
| A587 | c | Valine |
| L599 | c | Proline |
| D601 | c | Histidine |
| V634 | c | Isoleucine |
| N667 | c | Serine |
| 669 | c | Alanine |
| K672 | c | Arginine |
| S674 | c | Arginine |
| N717 | c | Serine |
| R741 | c | Histidine |
| A755 | c | Valine |
| I756 | c | Valine |
| S805 | c | Proline |
| A813 | c | Threonine |
| P820 | c | Threonine |
| G835 | c | deletion |
| E838 | c | Lysine |
| E854 | c | Aspartic acid |
| T410 | b1 | Serine |
| S449 | b2 | Alanine |

Antibodies

NRP1 cellular activity can be inhibited by using an agent which blocks NRP1 binding to one or more of its ligands (e.g., SEMA3A, VEGF and/or TGF-β). One example of such agent is an antibody which binds to NRP1 and blocks the binding of NRP1 to SEMA3A, VEGF and/or TGF-β.

Alternatively, inhibition of NRP1-mediated cellular signaling can be achieved by using an agent which blocks binding of an NRP1 ligand to the NRP1 polypeptide. Non-limiting examples of such agent includes an antibody which binds to SEMA3A, VEGF or TGF-3 and blocks their respective binding to NRP1.

In a particular aspect of the present invention, antibodies targeting NRP1 block SEMA3A binding to the receptor but do not substantially interfere with VEGF and/or TGF-3 binding to NRP1. In an embodiment, the anti NRP1 antibody binds to the a1a2 domains of the NRP1 polypeptide. In another embodiment, the anti NRP1 antibody binds to subdomains a1 or a2 of the NRP1 polypeptide.

As noted above, anti SEMA3A antibodies may be used to inhibit (i.e., reduce completely or partially) NRP1-mediated cellular signaling by blocking SEMA3A binding to NRP1. Useful anti SEMA3A antibodies bind to the SEMA domain of SEMA3A and block the interaction with NRP1. In embodiments the anti-SEMA3A antibodies used in accordance with the present invention include antibodies binding to SEMA3A polypeptide domains comprising amino acid residues 252-260, 359-366 or 363-380 of SEMA3A. SEMA3A antibodies which inhibit the binding of SEMA3A to NRP1 are known in art and may be used in accordance with the present invention.

As used herein, the expression "anti NRP1 antibody" refers to an antibody that specifically binds to (interacts with) a NRP1 protein and displays no substantial binding to other naturally occurring proteins other than the ones sharing the same antigenic determinants as the NRP1 protein. Similarly, the expression "anti SEMA3A antibody", "anti VEGF antibody" or "anti TGF-3 antibody" refers to an antibody that specifically binds to (interacts with) a SEMA3A, VEGF or TGF-β protein respectively and displays no substantial binding to other naturally occurring proteins other than the ones sharing the same antigenic determinants as the targeted SEMA3A/VEGF/TGF-β protein.

Antibodies that can be used in accordance with the present invention include polyclonal, monoclonal, humanized as well as chimeric antibodies. The term antibody or immunoglobulin is used in the broadest sense, and covers monoclonal antibodies (including full length monoclonal antibodies), polyclonal antibodies, multispecific antibodies and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), nanobodies, shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies™, antibody-T-cell epitope fusions (Troybodies) or Peptibodies.

Anti-human NRP1/sem3A/VEGF/TGF-β antibodies have been previously prepared and are also commercially available from various sources including Santa Cruz, AbCam, and Cell Signaling.

In general, techniques for preparing antibodies (including monoclonal antibodies, hybridomas and humanized antibodies when their sequences are known) and for detecting antigens using antibodies are well known in the art and various protocols are well known and available.

Inhibition of the Expression of NRP1 or NRP1 Ligands

Various approaches are available for decreasing the expression (at the mRNA or protein level) of NRP1 or its ligands (e.g., SEMA3A, VEGF or TGF-β) to inhibit NRP1 mediated cell signaling and thus reduce inflammation and hyperactivation of innate immune response (i.e., i) production and/or secretion of pro-inflammatory cytokines; ii) recruitment of mononuclear phagocytes (MPs); iii) vascular hyperpermeabilization; and/or iv) edema, v) neuronal damage, choroidal neovascularization etc.). Non-limiting example includes the use of small hairpin shRNA (RNAi), antisense, ribozymes, TAL effectors targeting the NRP1, SEMA3A, VEGF or Tgf-β promoter or the like.

Expression in cells of shRNAs, siRNAs, antisense oligonucleotides or the like can be obtained by delivery of plasmids or through viral (e.g., lentiviral vector) or bacterial vectors.

Therefore, in alternative embodiments, the present invention provides antisense, shRNA molecules and ribozymes for exogenous administration to effect the degradation and/or inhibition of the translation of mRNA of interest. Preferably, the antisense, shRNA molecules and ribozymes target human NRP1, SEMA3A, VEGF and/or Tgf-β expression. Examples of therapeutic antisense oligonucleotide applications include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. Nos. 5,276,019 and 5,264,423; BioWorld Today, Apr. 29, 1994, p. 3.

Preferably, in antisense molecules, there is a sufficient degree of complementarity to the mRNA of interest to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as Shc inhibitors of the invention is disclosed in U.S. Pat. No. 5,932,435.

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n$ $NH_2$ or $O(CH_2)_n$ $CH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

In a further embodiment, expression of a nucleic acid encoding a polypeptide of interest (e.g., SEMA3A or NRP1), or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example published US patent applications 20020173478 (Gewirtz; published Nov. 21, 2002) and 20020132788 (Lewis et al.; published Nov. 7, 2002). Reagents and kits for performing RNAi are available commercially from for example Ambion Inc. (Austin, Tex., USA) and New England Biolabs Inc. (Beverly, Mass., USA).

The initial agent for RNAi in some systems is a dsRNA molecule corresponding to a target nucleic acid. The dsRNA (e.g., shRNA) is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA (shRNAs) or siRNA-like molecules into cells. RNAi may for example be performed using chemically-synthesized RNA. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods and various methods for introducing such vectors into cells, either in vitro or in vivo (e.g. gene therapy) are known in the art.

Accordingly, in an embodiment expression of a nucleic acid encoding a polypeptide of interest (or a fragment thereof e.g., soluble NRP1, NRP1 derived traps, may be inhibited by introducing into or generating within a cell an siRNA or siRNA-like molecule corresponding to a nucleic acid encoding a polypeptide of interest (e.g. SEMA3A or NRP1), or a fragment thereof, or to an nucleic acid homologous thereto. "siRNA-like molecule" refers to a nucleic acid molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a nucleic acid encoding a polypeptide of interest, or a fragment or variant (or a fragment of a variant) thereof. Such a variant is capable of encoding a protein having activity similar to the polypeptide of interest.

A variety of viral vectors can be used to obtain shRNA/RNAi expression in cells including adeno-associated viruses (AAVs), adenoviruses, and lentiviruses. With adeno-associated viruses and adenoviruses, the genomes remain episomal. This is advantageous as insertional mutagenesis is avoided. It is disadvantageous in that the progeny of the cell will lose the virus quickly through cell division unless the cell divides very slowly. AAVs differ from adenoviruses in that the viral genes have been removed and they have diminished packing capacity. Lentiviruses integrate into sections of transcriptionally active chromatin and are thus passed on to progeny cells. With this approach there is increased risk of insertional mutagenesis; however, the risk can be reduced by using an integrase-deficient lentivirus.

Pharmaceutical Compositions and Kits

Agents which inhibit NRP1-dependent cell signaling (i.e., NRP1 inhibitors) of the present invention can be administered to a human subject by themselves or in pharmaceutical compositions where they are mixed with suitable carriers or excipient(s) at doses to treat or prevent the targeted disease or condition or to raise the desired cellular response.

Mixtures of these compounds (e.g., NRP1 trap, antibodies, dominant negative, small inhibitory peptides or the like) can also be administered to the subject as a simple mixture or in suitable formulated pharmaceutical compositions. A therapeutically effective dose further refers to that amount of the compound or compounds sufficient to result in the prevention or treatment of the targeted inflammatory disease or condition (e.g., such as septic shock, arthritis, inflammatory bowel disease (IBD), cutaneous skin inflammation, diabetes, uveitis and neuroinflammatory conditions such as diabetic retinopathy, age-related macular degeneration (AMD), retinopathy of prematurity, multiple sclerosis, amyotrophic lateral sclerosis (ALS), age-related cognitive decline/Alzheimer's disease) or to provide the desired cellular or physiological response (e.g., amount sufficient to i) reduce edema, ii) reduce activation/recruitment of mononuclear phagocytes (e.g., microglia or macrophages), iii) reduce production or secretion of inflammatory cytokines (e.g., IL-1β, TNF-α, IL-6, etc.); iv) reduce pathological neovascularization; v) reduce vascular degeneration, etc.,).

As used herein "pharmaceutically acceptable carrier" or "excipient" includes any and all solvents, dispersion media, coatings, antibacterial and antifungal agents, physiological media, and the like that are physiologically compatible. In embodiments the carrier is suitable for ocular administration. In other embodiments the carrier is suitable for systemic administration. In other embodiments the carrier is suitable for oral administration.

Pharmaceutically acceptable carriers include sterile aqueous solutions or dispersions and sterile powders for the extemporaneous preparation of sterile injectable solutions or dispersion. The use of such media and agents, such as for ocular, systemic or oral application, is well known in the art. Except insofar as any conventional media or agent is incompatible with the compounds of the invention, use thereof in the compositions of the invention is contemplated. Supplementary active compounds can also be incorporated into the compositions.

Techniques for formulation and administration of the compounds of the instant application may be found in "Remington's Pharmaceutical Sciences, "Mack Publishing Co., Easton, Pa., latest edition.

The present invention also concerns kits or commercial packages for use in the methods of the present invention. Such kits may comprises compounds of the present invention (e.g., compounds which inhibit NRP1 cell signaling, including SEMA3A-mediated cell signaling such as traps, antibodies, shRNA, cells, vectors, nucleic acids) optionally with instructions to use the kit.

Routes of Administration/Formulations

Suitable routes of administration may, for example, include systemic, oral and ocular (eye drops or intraocular injections). Preferred routes of administration comprise eye drops and intraocular injections for eye conditions, oral for chronic inflammatory conditions and systemic for sepsis and certain neuronal conditions such as stroke. The formulations may also be in the form of sustained release formulations.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents of the invention may be formulated in aqueous solutions, preferably in physiologically compatible buffers such as Hanks's solution, Ringer's solution, or physiological saline buffer.

The compounds may be formulated for ocular administration e.g., eye drops or ocular injections. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Furthermore, one may administer the drug in a targeted drug delivery system, for example, in a liposome coated with a cell-specific antibody or other delivery system (e.g., to target for example a specific tissue (e.g., brain) or cell type (e.g., microglia or macrophages)). Nanosystems and emulsions are additional well known examples of delivery vehicles or carriers for drugs. Another example is the Encapsulated Cell Therapy (ECT) delivery system from Neurotech's, for eye diseases. ECT is a genetically engineered ocular implant that enables continuous production of therapeutic proteins to the eye for over 2 years. Additionally, the therapy is reversible by simply removing the implant. The ECT implant is inserted into the vitreous through a single incision and sutured in place in a 20-minute outpatient surgical procedure.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

The effective dose of the compound inhibits the cellular signaling function of NRP1 sufficiently to reduce or prevent one or more physiological or cellular responses (e.g., vascular hyperpermeability, blood retinal barrier leakage, edema, MPs activation and/or recruitment, proinflammatory cytokines production and/or secretion, neovascularization, neuronal damage, etc.) or to prevent or treat a given inflammatory disease or condition, without causing significant adverse effects. Certain compounds which have such activity can be identified by in vitro assays that determine the dose-dependent inhibition of NRP1-mediated cell signaling inhibitors (e.g., agents which directly target the expression or activity of NRP1 or agents which targets the expression or activity (e.g., binding) of ligands of NRP1.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of the cellular signaling function of NRP1, usually in response to inflammatory mediators such as $II$-$1\beta$ or other activating stimulus such as hypoxia, ischemia, cellular stress, ER stress, etc.

A therapeutically effective amount refers to that amount of the compound that results in amelioration of symptoms in a subject. Similarly, a prophylactically effective amount refers to the amount necessary to prevent or delay symptoms in a patient (e.g., NRP1-mediated vascular hyperpermeability, spotted and/or blurry vision, pericytes loss, macular edema, retinal swelling, blood retinal barrier leakage, mononuclear phagocytes recruitment, production and secretion of pro-inflammatory cytokines, vascular degeneration, pathological neovascularization, neuronal damage, etc.). Toxicity and therapeutic efficacy of such compounds can be determined by standard pharmaceutical procedures in cell cultures or experimental animals, e.g., determining the maximum tolerated dose (MTD) and the ED (effective dose for 50% maximal response) The dose ratio between toxic and therapeutic effects is the therapeutic index and it can be expressed as the ratio between MTD and ED50. Compounds which exhibit high therapeutic indices are preferred. The exact formulation, route of administration and dosage can be chosen by the individual physician in view of the patient's condition.

Dosage amount and interval may be adjusted individually to provide levels of the active compound which are sufficient to maintain the NRP1 modulating effects, or minimal effective concentration (MEC). The MEC will vary for each compound but can be estimated from in vitro data; e. g. the concentration necessary to achieve substantial inhibition of SEMA3A expression or activity (e.g., binding to NRP1 receptor) Dosages necessary to achieve the MEC will depend on individual characteristics and route of administration.

The amount of composition administered will, of course, be dependent on the subject being treated, on the subject's weight, the severity of the affliction, the manner of administration and the judgment of the prescribing physician.

Definitions

For clarity, definitions of the following terms in the context of the present invention are provided.

As used herein, the term "Neuropilin-1 receptor" or "NRP1" receptor refers to neuropilin-1 and its isoforms, and allelic/polymorphic forms (e.g., HGNC: 8004; Entrez Gene: 8829; Ensembl: ENSG00000099250; OMIM: 602069; and UniProtKB: O14786; GenBank Acc. No. AAH07737.1, FIG. 22, SEQ ID NO: 65). NRP1 is a non-tyrosine kinase multifunctional receptor having the particular ability to bind three structurally dissimilar ligands via distinct sites on its extracellular domain. It binds SEMA3A[18,19] (for example provoking cytoskeletal collapse) and $VEGF_{165}$, enhancing binding to VEGFR2 (for example increasing its angiogenic potential). It also binds to TGF-β. Moreover, genetic studies show that NRP1 distinctly regulates the effects of VEGF and SEMA3A on neuronal and vascular development. Hence, depending on the ligand, NRP1-mediated cellular response varies.

The basic structure of neuropilin-1 comprises 5 domains: Three extracellular domains (a1a2 (CUB), b1b2 (FV/FVIII) and c (MAM)), a transmembrane domain and a cytoplasmic domain (See FIGS. 19A and 22 and SEQ ID NO: 65 and 66 and 68). The a1a2 domain is homologous to complement components C1r and C1s (CUB) which generally contain 4 cysteine residues forming disulfide bridges. This domain binds SEMA3A. Domains b1b2 (FV/FVIII) binds to VEGF. Amino acid Y297 in subdomain b1 is important for binding to VEGF as substitution of Y297 to an alanine significantly reduces VEGF binding to NRP1. There exists several splice variants isoforms and soluble forms of NRP1 which are all encompassed by the present invention.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid/polynucleotide sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90%, 95%, 98% or 99% identical. As used herein, a given percentage of homology between sequences denotes the degree of sequence identity in optimally aligned sequences. An "unrelated" or "non-homologous" sequence shares less than 40% identity, though preferably less than about 25% identity, with any of the nucleic acids and polypeptides disclosed herein.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 98%, or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH. For example, in an embodiment, the compound of the present invention is an antisense/RNAi or shRNA that hybridizes to an NRP1 or SEMA3A nucleic acid sequence (preferably a human sequence).

As used herein the term "treating" or "treatment" in reference to inflammatory diseases or conditions (e.g., retinopathies, cerebral ischemia, stroke, sepsis, ect.) is meant to refer to a reduction/improvement in one or more symptoms or pathological physiological responses associated with said disease or condition. Non-limiting examples include edema, swelling, itching, pain, vascular hyperpermeability; blood retinal barrier integrity, increase in SEMA3A, VEGF and/or TGF-beta expression, mononuclear phagocyte recruitment/chemotaxis, production and/or secretion of proinflammatory cytokines, vascular or neuronal degeneration, etc.

As used herein the term "preventing" or "prevention" in reference to inflammatory diseases or conditions is meant to refer to a reduction in the progression or a delayed onset of at least one symptom associated with the disease or condition.

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

The present invention is illustrated in further details by the following non-limiting examples.

Example 1

Materials and Methods (Examples 2-9 and 12)

Generation of LyzM-cre/Nrpfl/fl mice. C57Bl/6 wild-type (WT) were purchased from The Jackson Laboratory. LyzM-Cre (Lyz2 tm1(cre)lfo/J; no. 004781) and NRP1 floxed mice (Nrp1 tm2Ddg/J; no. 005247) were purchased from The Jackson Laboratory and bread to obtain LyzM-cre/Nrpfl/fl with NRP1-deficient myeloid cells.

$O_2$-induced retinopathy. Mouse pups (WT or LyzM-Cre (Jackson Laboratory) or LysM-Cre/Nrp1$^{fl/fl}$) and their fostering mothers (CD1, Charles River) were exposed to 75% $O_2$ from postnatal day 7 (P7) to day 12 and returned to room air (52). This model serves as a proxy to human ocular neovascular diseases such as diabetic retinopathy characterized by a late phase of destructive pathological angiogenesis (53, 54). Upon return to room air, hypoxia-driven neovascularization (NV) develops from P14 onwards (26). Eyes were enucleated at different time points and the retinas dissected for FACS analysis or mRNA analysis as described. In other experiments, dissected retinas were flatmounted and incubated overnight with fluoresceinated isolectin B4 (1:100) in 1 mM $CaCl_2$ to determine extent of avascular area or neovascularization area at P17 using ImageJ and the SWIFT-NV method (55).

FACS of digested retinas and spleen. Retinas from WT or LysM-Cre/Nrp1$^{fl/fl}$ mice were homogenized and incubated in a solution of 750 U/mL DNaseI (Sigma) and 0.5 mg/mL of collagenase D (Roche) for 15 min at 37° C. with gentle shaking. Homogenates were then filtered with a 70 μm cell strainer and washed in PBS+3% fetal bovine serum. Spleen samples were homogenized and incubated with 1 mg/mL of collagenase D for 10 min at 37° C. Homogenates were washed in PBS+3% fetal bovine serum and the pellets were resuspended and incubated in lysis buffer (10 mM $KCHO_3$; 150 mM $NH_4Cl$; 0.1 mM EDTA) for 5 min at room temperature. Cell suspensions (retina or spleen) were incubated with LEAF™ purified anti-mouse CD16/32 (Biolegend) for 15 min at room temperature to block Fc receptors. Cells were then incubated for 30 min at room temperature with the following antibodies: FITC anti-mouse/human CD11b (Biolegend), PE/CY7 anti-mouse Ly-6G/Ly-6C (Gr-1; Biolegend), Pacific Blue™ anti-mouse F4/80 (Biolegend), 7AAD (BD Biosciences) and anti-mNeuropilin-1 Allophycocyanin conjugated Rat IgG2A (R&D Systems) or Rat IgG2A Isotype Control Allophycocyanin conjugated (R&D Systems).

For analysis of CX3CR1 and CD45 expression, additional extracellular staining was performed using the above mentioned antibodies supplemented with Alexa Fluor 700 anti-mouse CD45.2 (Biolegend) and anti-mouse CX3CR1 Phycoerythrin conjugated Goat IgG (R&D Systems) or Goat IgG Isotype. Control Phycoerythrin conjugated FACS was performed on a LSRII (BD Biosciences) device and data were analysed using FlowJo™ software (version 7.6.5).

BrdU injections. Wild-type mice subjected to OIR or kept in normoxic conditions were injected intraperitoneally with 5-bromo-2-deoxyuridine (BrdU; Sigma) at the dose of 1 mg/mouse dissolved in PBS at P13.

Analysis of BrdU incorporation. The staining was performed on the retinal cells from P14 WT mice. Samples were obtained as described above. Extracellular staining was performed as described above (CD45.2 (intermediate/low); Gr-1-; CD11b+,F4/80+; 7AAD). Cells were then fixed with Cytofix/Cytoperm™ Buffer (BD Biosciences) for 30 min and permeabilised with Perm/Wash™ Buffer (BD Biosciences) for 10 min. Next, cells were treated with 300 ug/mL of DNAse for 1h at 37° C. and washed with Perm/Wash™. Intracellular staining of BrdU was performed using anti-BrdU-PE antibodies (Ebioscience) or mouse IgG1 κ Isotype Control PE conjugated (Ebioscience) for 25 min at 4° C. Cells were then washed in Perm/Wash™ and resuspended in PBS+3% fetal bovine serum before FACS analysis on a LSRII (BD Biosciences).

Vitrectomy. All patients previously diagnosed with PDR were followed and operated by a single vitreoretinal surgeon (FAR). Control patients were undergoing surgical treatment for non-vascular pathology (ERM (epiretinal membrane) or MH (macular hole)) by the same surgeon. In an operating room setting, patients underwent surgery under local retro/peribulbar anesthesia. A 5% povidone-iodine solution was used to clean the periocular skin and topical instillation into the eye and within the cul-de-sac was left in place for 5 minutes. Three-port 25-gauge transconjunctival pars plana vitrectomy was performed through 25-gauge valved cannulas (Alcon). Under microscope visualization using a wide-angle viewing system (Resight™, Zeiss), undiluted vitreous was collected with a 25-gauge vitrector. After vitreous biopsy, the infusion line was opened and vitrectomy and membrane peeling was performed in the usual fashion to treat diabetic vitreous hemorrhage and tractional retinal detachment. This was followed by panretinal endolaser photocoagulation, fluid-air exchange, and intravitreal anti-VEGF injection.

Quantification of SEMA3A protein by ELISA. Vitreous samples were frozen on dry ice and immediately after biopsy and stored at −80°. Samples were centrifuged at 15000×g for 5 minutes at 4° C. prior to analysis. SEMA3A levels were quantified in supernatants using enzyme-linked immunosorbent assays (ELISAs) following manufacturer's instructions (USCN Life Science Inc.).

Assessment of SEMA3A protein levels by Western-blot. Equal volumes of vitreous fluid (20 uL) from PDR and control patients were assessed by standard SDS-PAGE technique for the presence of SEMA3A (Abcam).

Real-time PCR analysis. RNA was isolated using the GenElute™ Mammalian Total RNA Miniprep Kit (Sigma)

and digested with DNase I to prevent amplification of genomic DNA. Reversed transcription was performed using M-MLV reverse transcriptase (Life Technologies) and gene expression analyzed using Sybr™ Green (BioRad) in an ABI Biosystems Real-Time PCR machine. 1-actin was used as a reference gene (see Table 2 in Example 10 for details on the sequence of the oligonucleotides used.

Immunohistochemistry. For visualization of pan-retinal vasculature, flatmount retinas were stained with stained with Rhodamine labeled Griffonia (Bandeiraea) Simplicifolia Lectin I (Vector Laboratories, Inc.) in 1 mM $CaCl_2$ in PBS for retinal vasculature and anti-rat Neuropilin-1 antibody, (goat IgG; R&D Systems) and IBA1 (rabbit polyclonal; Wako).

Primary peritoneal macrophages culture. Adult WT or LyzMcre/NRP1 fl/fl mice were anesthetized with 2% isoflurane in oxygen 2 L/min and then euthanized by cervical dislocation. Then, a small incision in abdominal skin of mouse was performed. Skin was pulled to each size of the mouse and peritoneal cavity was washed with 5 ml of PBS plus 3% FBS for 2 min. Then, the harvested cells were centrifuged for 5 min at 1000 rpm, resuspended in medium (DMEM F12 plus 10% FBS and 1% Streptomycin/Penicillin) and plated. After 1h of culture at 37° C. under a 5% $CO_2$ atmosphere the medium was changed and cells were cultured for the next 24h in the same conditions before use in cytokine or transwell migration assay.

Transwell migration assay. Migration assays were performed in 24-well plates with 8 μm pore inserts. Primary peritoneal macrophages (5×105 cells) resuspended in 200 μl of medium (DMEM F12 plus 10% FBS and 1% Streptomycin/Penicillin) were added to the upper chamber. 800 μl of medium with or without migratory factors: MCP-1 (100 ng/ml), SEMA3A (100 ng/ml), and $VEGF_{165}$ (50 ng/ml) was added to the lower chamber. Cells were allowed to migrate through the insert membrane overnight at 37° C. under a 5% $CO_2$ atmosphere. In some experiments, cells were first pretreated with Y-27632 (Sigma), selective ROCK (Rho-associated coiled coil forming protein serine/threonine kinase) inhibitor (100 μg/ml) for 1 h at 37° C. The inserts were then washed with PBS, and nonmigrating cells were swabbed from the upper surface of the insert membrane with cotton buds. Then the membranes with migrated cells were fixed with 4% paraformaldehyde (PFA) for 20 minutes, washed twice with PBS and mounted on the slide. The cells were stained using mounting medium with DAPI (Vector Laboratories, Inc.). Then, 9 random fields per each membrane were photographed using an inverted fluorescence microscope at 20× magnification and the cells were counted using ImageJ software.

Choroidal explants and microvascular sprouting assay. The ex vivo choroid explants and quantification of microvascular sprouting as described previously (56). Briefly, choroids from LysM-Cre/Nrp1$^{+/+}$ and LysM-Cre/Nrp1$^{fl/fl}$ mice (n=6 for each condition) were dissected shortly after enucleating eyes. After plating segmented choroids into 24 well tissue culture plates and covering with Matrigel™ (BD Biosciences), samples were treated with either EGM™-2 medium, EGM-2 medium with PBS filled liposome (liposome-PBS), or EGM™-2 medium with Dichloromethylene-diphosphonic acid disodium salt filled liposome (liposome-Clodronate) (Sigma). The packaging of liposomes was performed according to (57). Twelve hours later, liposomes containing passenger compounds were removed from the wells followed by washing with PBS. Macrophages from primary peritoneal macrophage cultures (from either LysM-Cre/Nrp1$^{+/+}$ or LysM-Cre/Nrp1$^{fl/fl}$ mice) were added to choroidal explant cultures to investigate the impact of macrophages on microvascular sprouting.

Soluble recombinant NRP1. Wild-type mice subjected to OIR were intravitreally injected with rmNRP1 trap-1 (FIGS. 19C and 20X-20Y, SEQ ID NO: 25) from plasmid (29) or R&D Systems at P12.

Recombinant proteins used. Recombinant mouse CCL2/JE/MCP-1 (from E. coli) (R&D Systems) concentration used in vitro 100 ng/ml. Recombinant human SEMA3A Fc chimera (from murine myeloma cell line, NS0) (R&D Systems) concentration used in vitro 100 ng/ml. -Recombinant human $VEGF_{165}$ (PeproTech) concentration used in vitro 50 ng/ml.

Statistical analyses. Data are presented as mean±s.e.m. Student's T-test and ANOVA were used, where appropriate, to compare the different groups; a P<0.05 was considered statistically different. For ELISA, statistical analysis was performed using nonparametric Mann-Whitney test (GraphPad Prism).

Study approval: Human samples. We obtained approval of human clinical protocol and informed consent form by Maisonneuve-Rosemont Hospital (HMR) ethics committee (Ref. CER: 10059) and recruitment of patients for local core vitreal biopsy sampling from patients afflicted with T1DM or T2DM. The entire procedure was performed as an outpatient procedure in the minor procedure room within the ambulatory clinic from the Department of Ophthalmology at Maisonneuve-Rosemont Hospital. All instruments were opened and handled in a sterile manner. The study conforms to the tenets of the declaration Helsinki.

Study approval: Animals. All studies were performed according to the Association for Research in Vision and Ophthalmology (ARVO) Statement for the Use of Animals in Ophthalmic and Vision Research and were approved by the Animal Care Committee of the University of Montreal in agreement with the guidelines established by the Canadian Council on Animal Care. C57Bl/6 wild-type (WT) were purchased from The Jackson Laboratory. LyzM-Cre (Lyz2 tm1(cre)lfo/J; no. 004781) and Neuropilin 1 floxed mice (Nrp1 tm2Ddg/J; no. 005247) were purchased from The Jackson Laboratory.

TABLE 3

Characteristics of Vitrectomy Patients

| Sample | Age | Db type | Duration (years) | Retinopathy | Analysis |
|---|---|---|---|---|---|
| C1 | 74 | na | na | MH | WB/ELISA |
| C2 | 54 | na | na | MMD | WB/ELISA |
| C3 | 72 | na | na | ERM | WB/ELISA |
| C4 | 77 | na | na | ERM | WB/ELISA |
| C5 | 82 | na | na | MH | WB/ELISA |
| C6 | 62 | na | na | ERM | ELISA |
| C7 | 65 | na | na | MH | ELISA |
| C8 | 69 | na | na | ERM | ELISA |
| C9 | 75 | na | na | MH/Cataract | ELISA |
| C10 | 77 | na | na | Ret. Det. | ELISA |
| C11 | 69 | na | na | ERM | ELISA |
| C12 | 68 | na | na | ERM | ELISA |
| C13 | 81 | na | na | ERM | ELISA |
| C14 | 70 | na | na | ERM | ELISA |
| C15 | 65 | na | na | MH | ELISA |
| C16 | 74 | na | na | MH | ELISA |
| C17 | 75 | na | na | MH | ELISA |
| PDR1 | 62 | 2 | 13 | PDR | WB/ELISA |
| PDR2 | 79 | 2 | 33 | PDR | WB/ELISA |
| PDR3 | 73 | 2 | 15 | PDR | WB/ELISA |
| PDR4 | 74 | 2 | 10 | PDR | WB/ELISA |
| PDR5 | 54 | 1 | 20 | PDR | WB/ELISA |

TABLE 3-continued

Characteristics of Vitrectomy Patients

| Sample | Age | Db type | Duration (years) | Retinopathy | Analysis |
|---|---|---|---|---|---|
| PDR6 | 60 | 2 | 34 | PDR | WB/ELISA |
| PDR7 | 77 | 2 | 34 | PDR | WB/ELISA |
| PDR8 | 71 | 2 | 10 | PDR | ELISA |
| PDR9 | 35 | — | — | PDR | ELISA |
| PDR10 | 69 | 2 | 40 | PDR | ELISA |
| PDR11 | 78 | — | 5 | PDR | ELISA |
| PDR12 | 36 | 2 | — | PDR | ELISA |
| PDR13 | 81 | 1 | 30 | PDR | ELISA |
| PDR14 | 70 | 2 | 30 | PDR | ELISA |
| PDR15 | 74 | — | 35 | PDR | ELISA |
| PDR16 | 67 | 2 | 30 | PDR | ELISA |
| PDR17 | 69 | 2 | 2 | PDR | ELISA |

MH: Macular hole
MMD: Myopic Macular Degeneration
ERM: Epiretinal Membrane
PDR: Proliferative Diabetic Retinopathy
Ret. Det.: Retinal Detachement Example 2

Nrp1 Identifies a Population of Mononuclear Phagocytes (MPs) that are Mobilized Secondary to Vascular Injury To determine whether MPs (mononuclear phagocytes) such as microglia or macrophages partake in the vascular pathogenesis associated with proliferative retinopathies, FACS analysis was first carried-out on whole mouse retinas to elucidate the kinetics of macrophage/microglial accumulation throughout the evolution of oxygen-induced retinopathy (OIR, FIG. 1A, 75% oxygen from P7-P12 (postnatal day 7-12) to induce vasoobliteration and room air until P17 to attain maximal pre-retinal neovascularization (26,33)) (FIG. 1B,E,H). Results revealed significantly higher numbers of retinal macrophage/microglial cells (Gr-1-, F4/80+, CD11b+, cells, data not shown) in OIR at all time points analysed including a 36% increase during the vaso-obliterative phase at P10 (P=0.0004) (FIG. 1C), a 63% rise during the neovascular phase at P14 (P<0.0001) (FIG. 1F) and a 172% surge during maximal neovascularization at P17 (P=0.0006) (FIG. 1I).

Importantly, at each time point investigated, we observed a proportional increase in NRP1-positive MPs in OIR with a rise of 37% at P10 (P=0.0240) (FIG. 1D), 61% at P14 (P=0.0196) (FIG. 1G) and 155% at P17 (P=0.0058) (FIG. 1J) suggesting that this subpopulation of NRP1-positive MPs was being recruited to the neuroretina during the progression of the disease. For all OIR experiments, weights of mouse pups were recorded (data not shown) to ascertain adequate metabolic health (35).

Figure 1K:
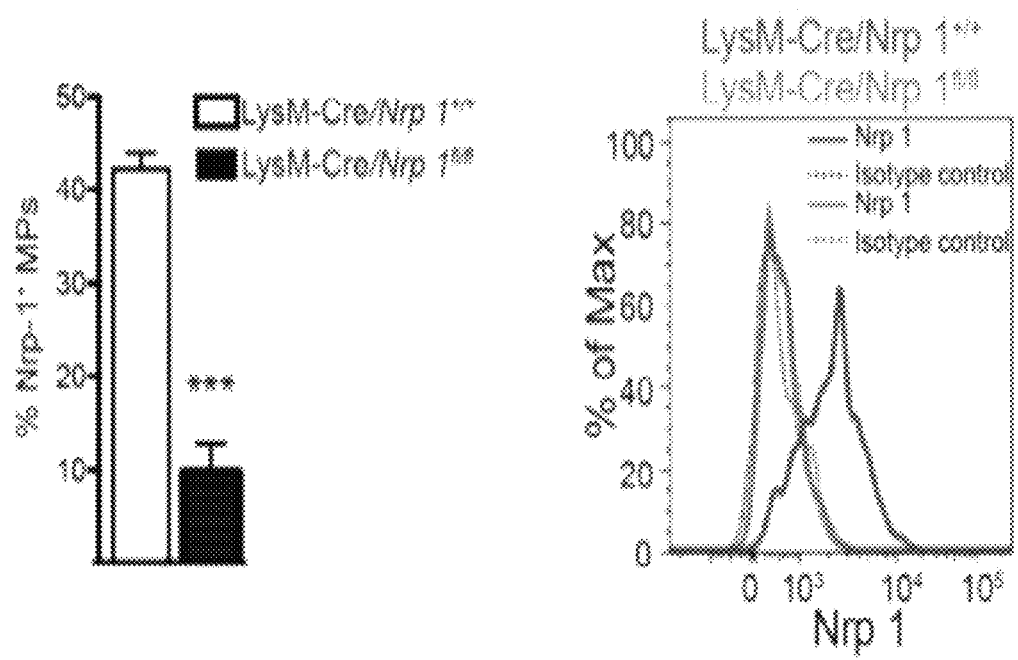
(FIG. 1K). To investigate the role of MP-resident NRP1, LysM-Cre/Nrp1$^{fl/fl}$ mice which have significantly compromised NRP1 expression in retinal microglia were generated (n=3 (WT), n=4 (LysM-Cre/Nrp1$^{fl/fl}$, total of 12-16 retinas per condition). Left panel shows the % of NPR-1 positive MPs in WT (LysM-Cre/NRP1$^{+/+}$) and mice deficient in NRP1 in their myeloid cells (LysM-Cre/Nrp1$^{fl/fl}$) as determined by FACS (right panel).
Figures 1L, 1M:
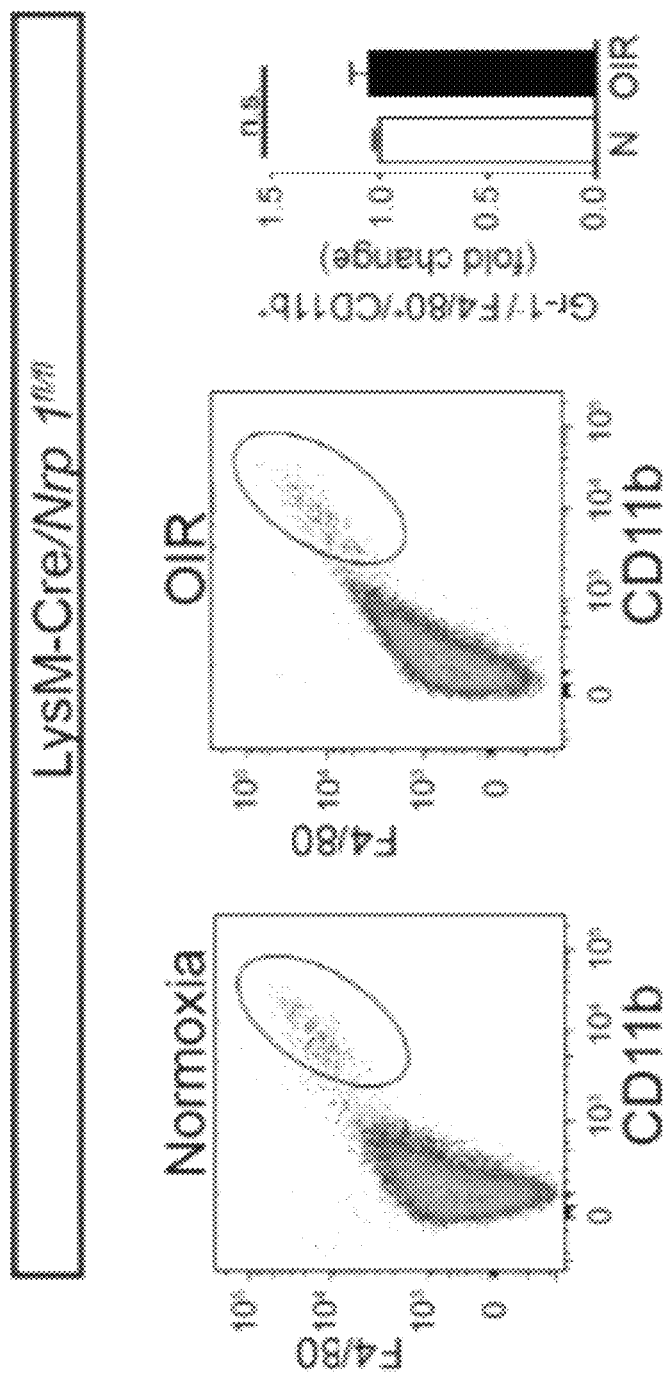

In order to establish the role of MP-resident NRP1 in retinopathy, a myeloid specific knockout of NRP1 was generated by intercrossing Nrp1 floxed mice with LysM-Cre mice (36) yielding LysM-Cre/Nrp1$^{fl/fl}$ progeny. The resulting mice showed an ~80% decrease in NRP1 expression in retinal MPs when compared to LysM-Cre/Nrp1$^{+/+}$ littermate controls (P=0.0004) (FIG. 1K). Of note, mice tested negative for the rd8 mutation of the Crb1 gene (37). LysM-Cre/Nrp1$^{fl/fl}$ mice did not show any difference in body weight, size, or open-field activity when compared with littermates throughout the period of experimentation (from P1-P17) (data not shown) and had similar numbers of resident retinal microglia (data not shown). Remarkably, deletion of NRP1 on myeloid cells fully abrogated the entry of macrophages/microglia at P10 and P14 OIR (FIG. 1L-O) revealing the critical role for this receptor in MP chemotaxis during the early stages of ischemic retinal injury. At P17, following maximal pathological neovascularization, MP infiltration occurs largely independent of NRP1 (FIGS. 1P, Q and R). Consistent with a potential microglial identity, the NRP1-expressing Gr1-/CD11b+/F4/80+ cells identified above express high levels of CX3CR1 and intermediate/low levels of CD45 (FIG. 1S and data not shown). As expected, in LysM-Cre/Nrp1$^{fl/fl}$ retinas, CD45low/CX3CR1 high MPs are devoid of NRP1 (FIG. 1T).

Example 3

Nrp1$^+$ Myeloid Cells Localize to Sites of Pathological Neovascularization in the Retina Given the pronounced influx of NRP1$^+$ macrophage/microglia during OIR, the localization of these cells during the progression of disease was next determined. Immunofluorescence on retinal flatmounts revealed that NRP1-positive macrophage/microglia (co-labelled with IBA1 and NRP1) were intimately associated with nascent pathological tufts at P14 of OIR (FIG. 2A-C) as well as mature tufts at P17 of OIR (FIG. 2D-F). White arrows in FIGS. 2B and 2E point to NRP1-positive MPs associated with pre-retinal tufts. NRP1 was also expressed by endothelial cell on the endothelium of neovascular tufts as previously reported (21). Consistent with data presented in FIG. 1, LysM-Cre/Nrp1 fl/fl mice had lower numbers of macrophage/microglia and less pronounced neovascularization (see below for full quantification) (FIG. 2 G-K).

Example 4

Figure 3H:
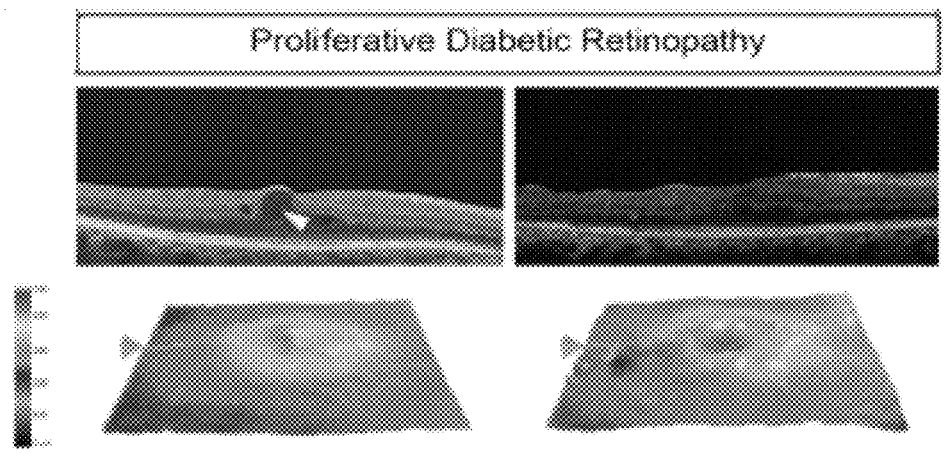

SEMA3A is Elevated in the Vitreous of Patients Suffering from Active Proliferative Diabetic Retinopathy To establish the clinical relevance of our findings on the obligate role of NRP1 in MP chemotaxis in retinopathy, the concentrations of SEMA3A directly in the vitreous of patients suffering from active PDR was determined. Seventeen samples of undiluted vitreous were obtained from patients suffering from PDR and 17 from control patients with nonvascular pathology. Detailed characteristics of patients are included in Table 1 (Example 1). Control patients (20) presented with non-vascular pathology and showed signs of non-diabetes-related retinal damage such as tractional tension on vasculature (FIG. 3A,B (white arrow)) secondary to fibrotic tissue and macular bulging (FIG. 3C). In contrast, all retinas from PDR patients showed signs of disc (FIG. 3D) or pre-retinal neovascularization (FIG. 3F), with highly permeable microvessels (leakage of fluorescent dye) (FIG. 3D,G insets), microaneurisms (FIG. 3D-G) and fibrous scar tissue, indicative of advanced retinopathy (FIG. 3G). In addition, patients showed some evidence of macular edema due to compromised vascular barrier function, including cystoid formation (white arrowhead) due to focal coalescence of extravasated fluid (FIG. 3H).

Figure 3I:
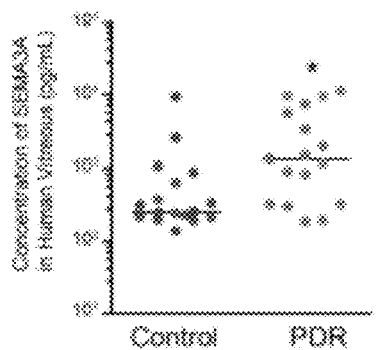
Figure 3J:
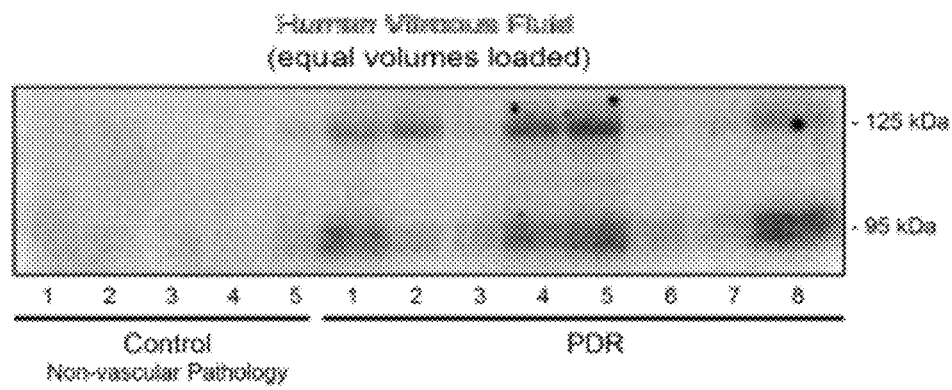

Consistent with a role in PDR, ELISA-based detection of SEMA3A revealed a 5-fold higher concentrations of the protein in the vitreous humor of patients with PDR when compared to vitreous from control patients (P=0.0132) (FIG. 3I). Results were confirmed by Western blot analysis on equal volumes of vitreous where SEMA3A (125 and 95 kDa isoforms)(38, 39) were elevated in patients with PDR (FIG. 3J). Thus, upregulation of SEMA3A in the vitreous is induced in diabetic ocular pathology.

Example 5

NRP1 Ligands are Induced in the Retinal Ganglion Cell Layer During OIR

Figure 4A:
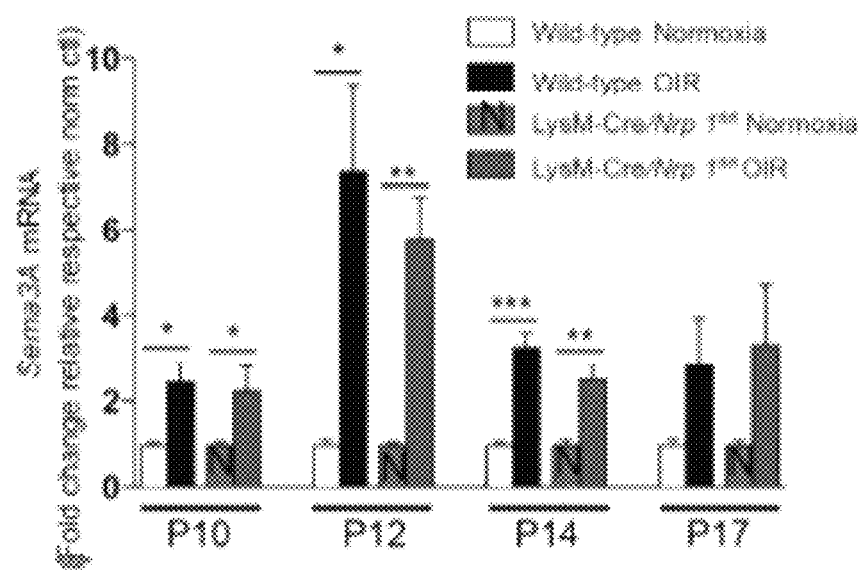
FIGS. 4A-4E show that ligands of NRP1 are induced in the retinal ganglion cell layer during OIR.
Figure 4B:
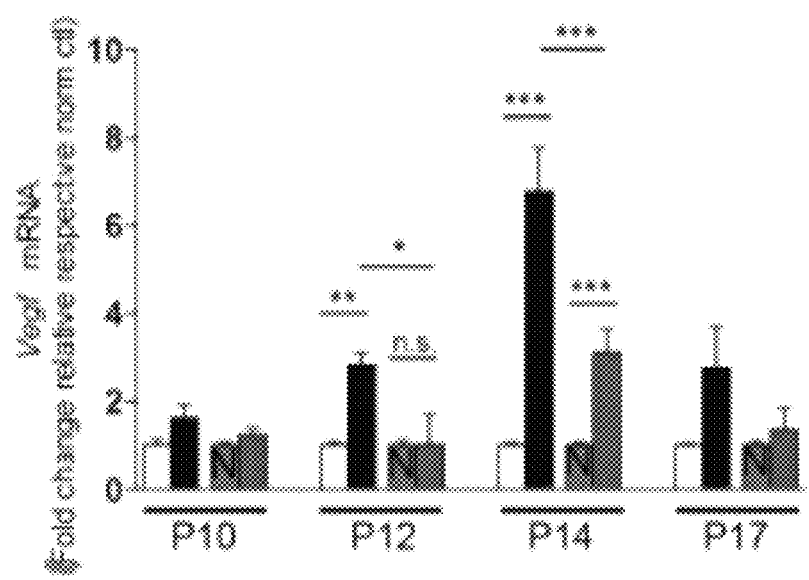

To obtain an accurate kinetic profile of expression of the two prominent ligands of NRP1 in proliferative retinopathy, levels of SEMA3A and VEGF messages in the mouse model of OIR were determined. Real-time quantitative PCR (RT-qPCR) on whole retinas revealed that SEMA3A was robustly induced in OIR both during the hyperoxic (vaso-degenerative) phase at P10 and the ischemic/neovascular stage from P12 to P17 (FIG. 4A). The observed induction occurred in both wild-type and LysM-Cre/Nrp1 fl/fl retinas. Conversely, as expected, VEGF transcripts rose exclusively in the ischemic phase of OIR from P12 to P17 (FIG. 4B). Importantly, VEGF was significantly less induced in LysM-Cre/Nrp1 fl/fl when compared to wild-type retinas (minimally increased at P12 (P=0.0451) and ~55% lower at P14 when compared wild-type OIR (P=0.0003)) (FIG. 4B) indicative of a healthier retina.

Figure 4C:
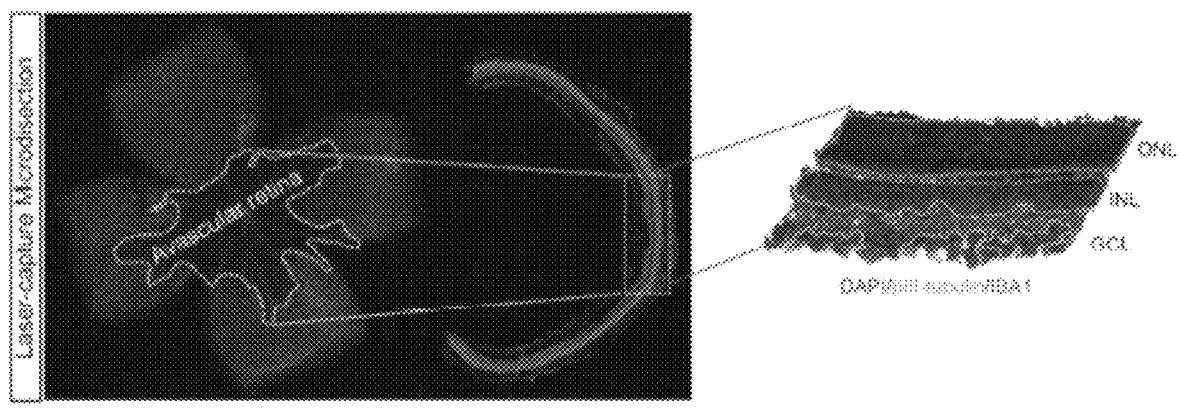
Figure 4D:
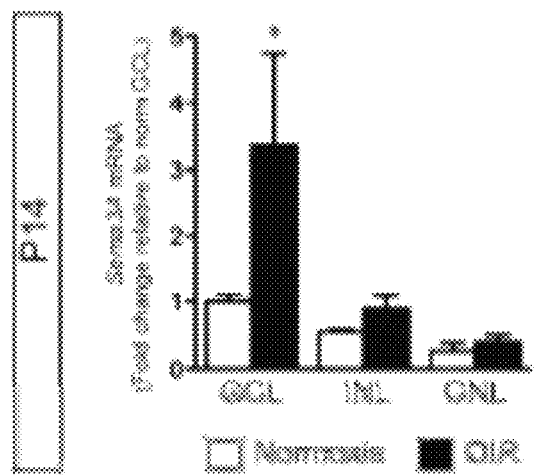
Figure 4E:
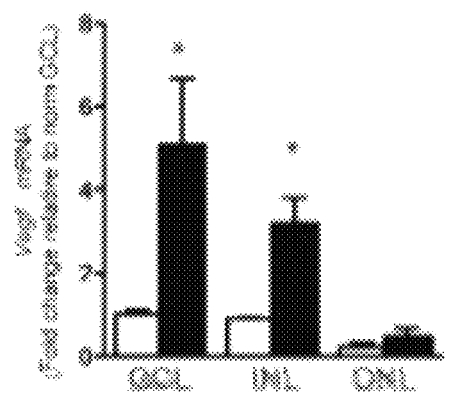

Next, laser capture micro-dissection (LCM) followed by RT-qPCR was performed on retinal layers in avascular zones to pinpoint the source of SEMA3A and VEGF messages in OIR (FIG. 4C). Both SEMA3A and VEGF where robustly induced in the ganglion cell layer with VEGF also increasing in the inner nuclear layer (FIG. 4D, E). Thus, the source of both ligands is geographically consistent with the localization of retinal MPs (FIG. 2).

Example 6

Figure 5A:
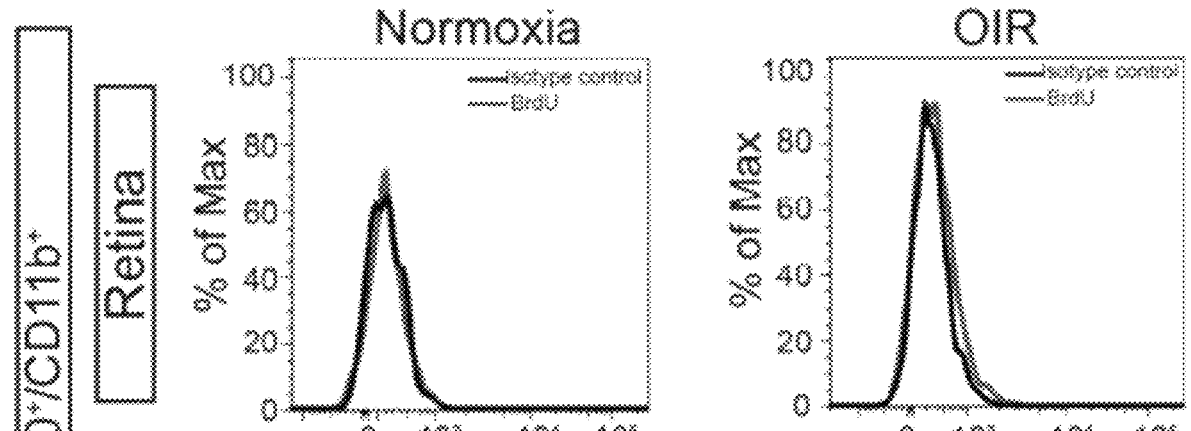
FIGS. 5A-5C show that NRP1⁺ MPs do not proliferate in the retina after vascular injury. Representative FACS histograms of CD11b-F/F4-80-F/Gr-1⁻ cells obtained from retinas (FIG. 5A) and spleens (FIG. 5B) collected at P14 from WT OIR (right panel) and Normoxic (left panel) control mice injected with BrdU at P13. The number of BrdU⁺ cells was considerably higher in spleens but did not change significantly between OIR and Normoxic mice (FIG. 5C). n=4 (Normoxic, N), n=4 (OIR) (total of 16 retinas per condition; each "n" is comprised of 4 retinas). Data are expressed as a percentage of BrdU+Gr-1⁻/CD11b+/F4-80+ cells±SEM.
Figure 5B:
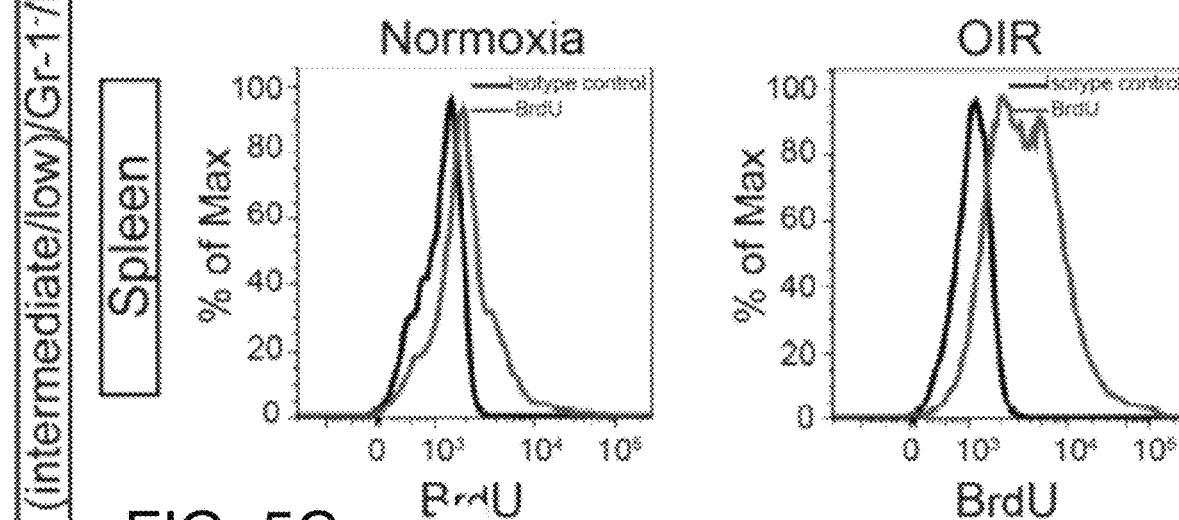
Figure 5C:
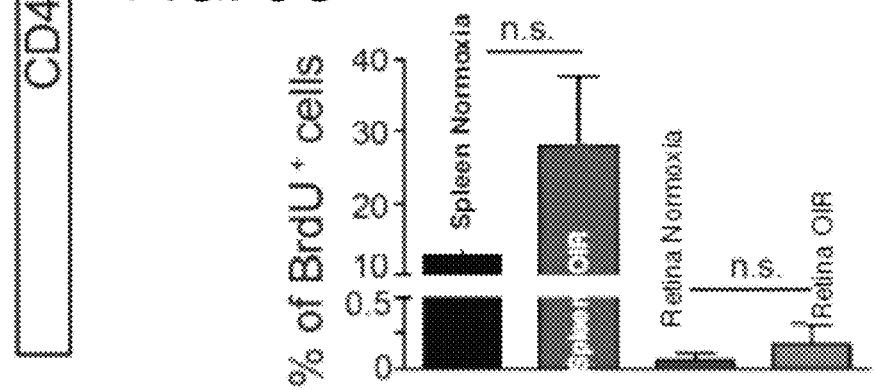

Mononuclear Phagocytes (MPs) do not Proliferate in the Retina after Vascular Injury In order to determine if the noted rise in NRP1+ MPs was due to an influx from systemic circulation or an increase in MP proliferation within the retina, the local retinal proliferation of these cells was investigated. Mice were systemically injected with BrdU at P13 (24 hours prior to sacrifice) and FACS analysis was carried out on retinas (FIG. 5A) and spleens (FIG. 5B). Within the retina, Gr1−/CD11b+/F4/80+ MPs did not show significant proliferation (P=0.4708). Considerably more proliferation was observed in spleens. No significant difference was observed between Normoxia and OIR (FIG. 5C). The lack of proliferation of MPs in the retina suggest that noted accretion NRP1+ MPs during retinopathy has a systemic origin.

Example 7

SEMA3A and $VEGF_{165}$ Mobilize MPs Via Nrp1

Figure 6A:
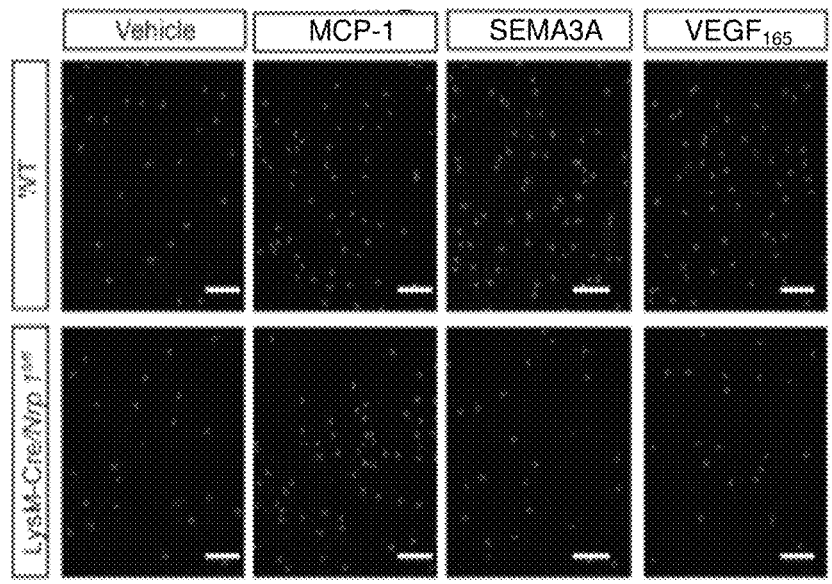
FIGS. 6A-6C show that SEMA3A and VEGF are chemo-attractive towards macrophages via NRP1.
Figure 6B:
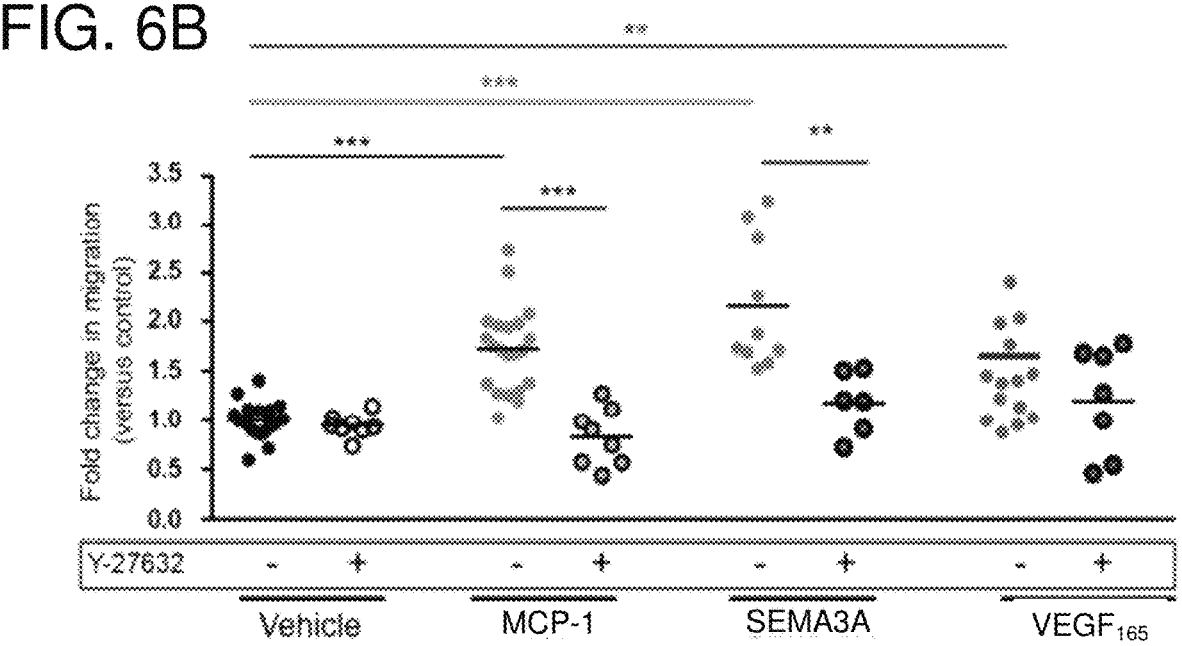
Figure 6C:
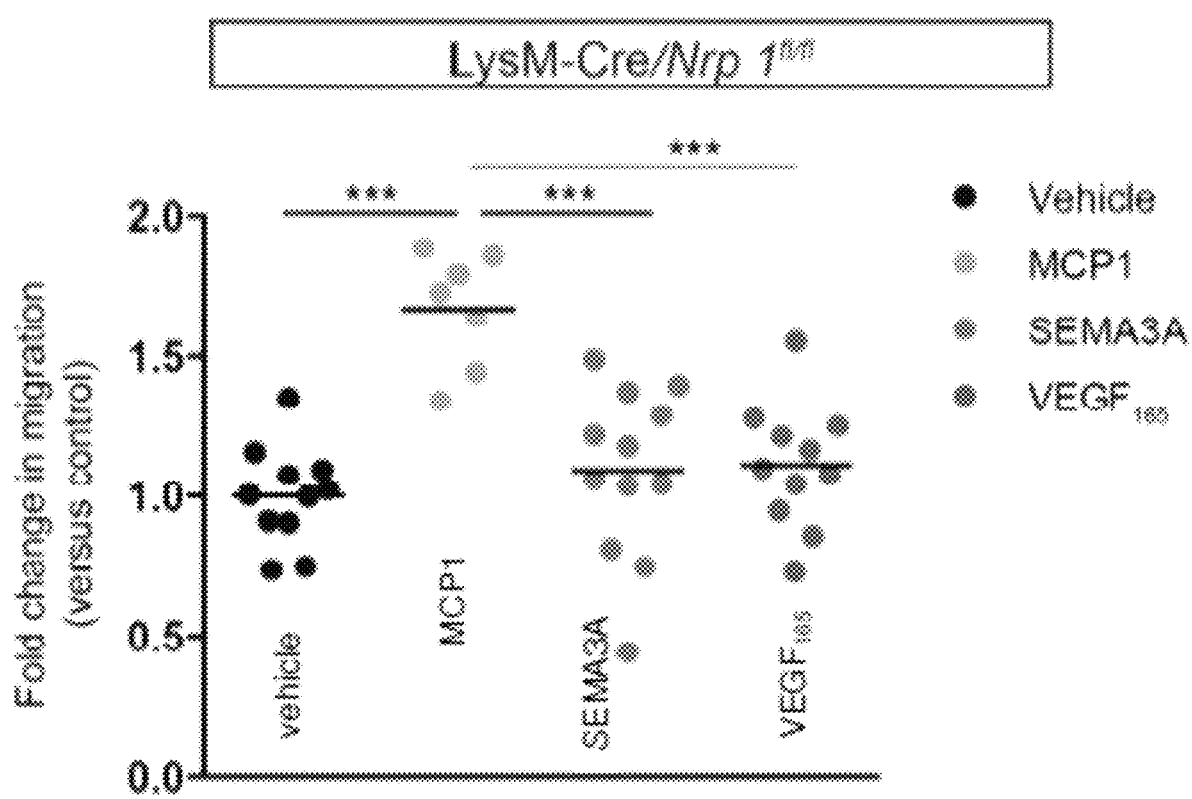

In light of the requirement of NRP1 for myeloid cell mobilization to sites of vascular lesion (FIG. 1) as well as the induction of the principal ligands of NRP1 in retinopathy (FIG. 3-4) and the likely systemic origin of these cells (FIG. 5), the propensity of these cues to provoke chemotaxis of MPs was determined. Primary macrophage cultures were isolated from wild-type mice and subjected to a Transwell Boyden chamber migration assay. Both SEMA3A (100 ng/ml) (P<0.0001) and $VEGF_{165}$ (50 ng/ml) (P=0.0027) provoked macrophage chemotaxis to similar magnitudes as positive control MCP-1 (100 ng/ml) (P<0.0001) (FIGS. 6A, B). These data were validated by demonstrating that Y-27632, a selective inhibitor ROCK (Rho-associated coiled coil forming protein serine/threonine kinase) abolished their chemotactic properties. ROCK is downstream of NRP1 signaling (40) and is known to mediate monocyte migration (41). VEGF migration was partially yet not significantly diminished suggesting a contribution from alternate receptors such as VEGFR1 as recently reported (33). Consistent with a role for NRP1 in SEMA3A and VEGF-mediated chemotaxis, macrophages from LysM-Cre/Nrp1$^{fl/fl}$ mice were uniquely responsive to MCP-1 and not mobilized by SEMA3A or VEGF (FIG. 6C).

Example 8

NRP1+ Macrophages Potentiate Microvascular Sprouting Ex Vivo

Figure 7A:
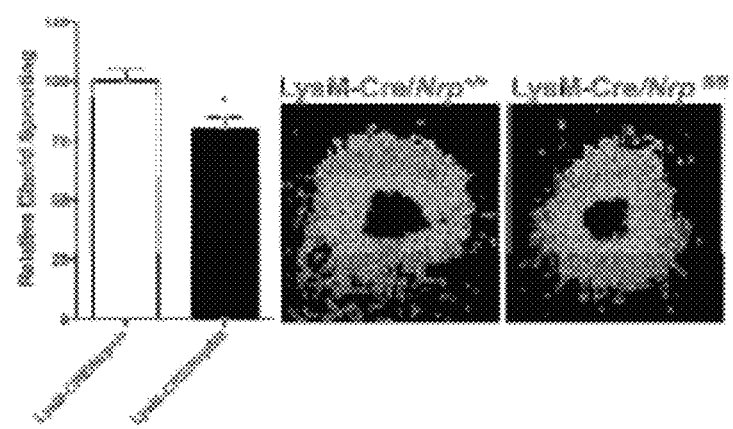
FIGS. 7A-7E show that Nrp1⁺ macrophages promote microvascular growth in ex vivo choroid explants.
Figure 7B:
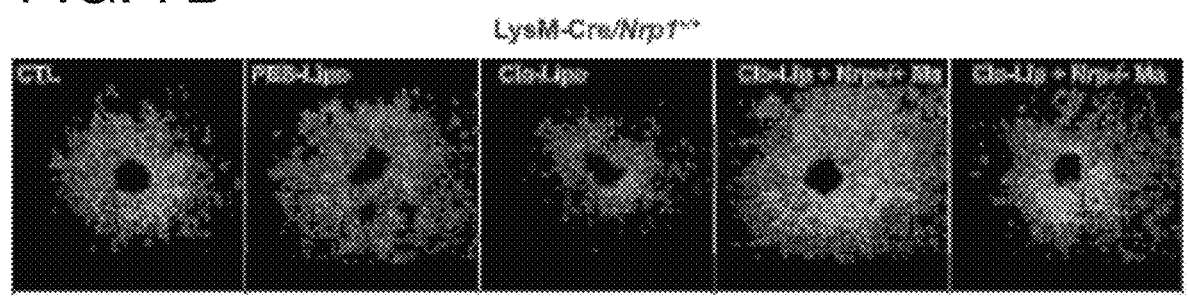
Figure 7C:
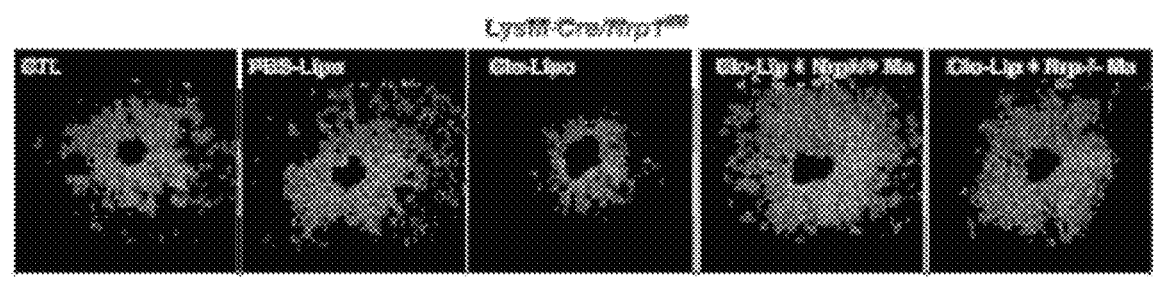
Figure 7D:
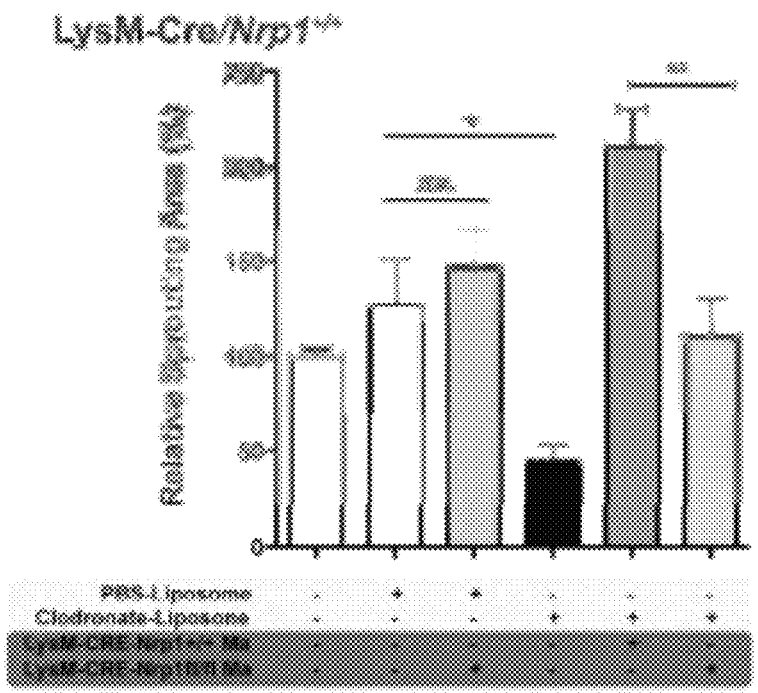
Figure 7E:
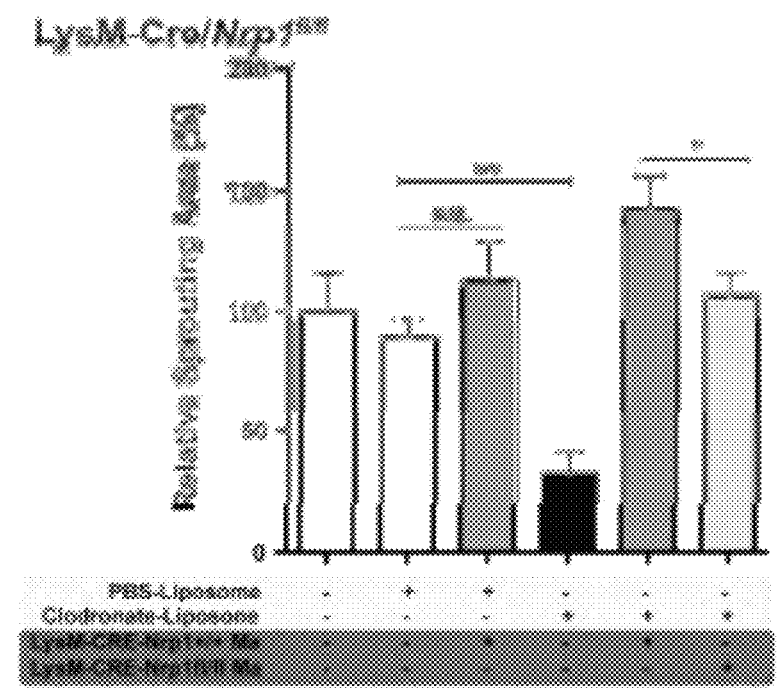

To investigate the impact of NRP1 expressing macrophages on microvascular angiogenesis, choroid tissue from either LysM-Cre/Nrp1$^{+/+}$ mice or LysM-Cre/Nrp$^{fl/fl}$ mice was isolated and grew in Matrigel™ to assess microvascular sprouting. Choroids from LysM-Cre/Nrp$^{fl/fl}$ mice sprout ~20% less microvessels when compared to ones from LysM-Cre/Nrp1$^{+/+}$ mice (P=0.018) (FIG. 7A). To investigate the role of NRP1+ macrophages in promoting microvascular sprouting, clodronate-liposomes were used to eliminate endogenous macrophages from the isolated choroid tissues. In explants from both LysM-Cre/Nrp1$^{fl/fl}$ and LysM-Cre/Nrp1$^{+/+}$/mice, PBS containing liposomes (i.e. vehicle control) had no impact on vascular sprouting, but clodronate-liposomes reduced microvascular sprouting by ~60% (P=0.0114 for LysM-Cre/Nrp1$^{+/+}$ choroid and P=0.0007 for LysM-Cre/Nrp1$^{fl/fl}$ choroid) (FIGS. 7B-E). To verify whether NRP1$^{+/+}$ macrophages have a propensity to promote angiogenesis, peritoneal macrophages were extracted from LysM-Cre/Nrp1$^{+/+}$ or LysM-Cre/Nrp$^{fl/fl}$ mice, and introduced into choroid explant cultures that had previously been treated with clodronate liposomes and washed. LysM-Cre/Nrp1$^{+/+}$ macrophages robustly potentiated microvascular sprouting by 50-100% when compared to macrophages from LysM-Cre/Nrp1$^{fl/fl}$ mice (P=0.0068 for LysM-Cre/Nrp1$^{+/+}$ choroid and P=0.0491 for LysM-Cre/Nrp1$^{fl/fl}$ choroid) (FIGS. 7D and E) and independent of the genotype of the choroidal explant.

Example 9

Figures 8A, 8B:
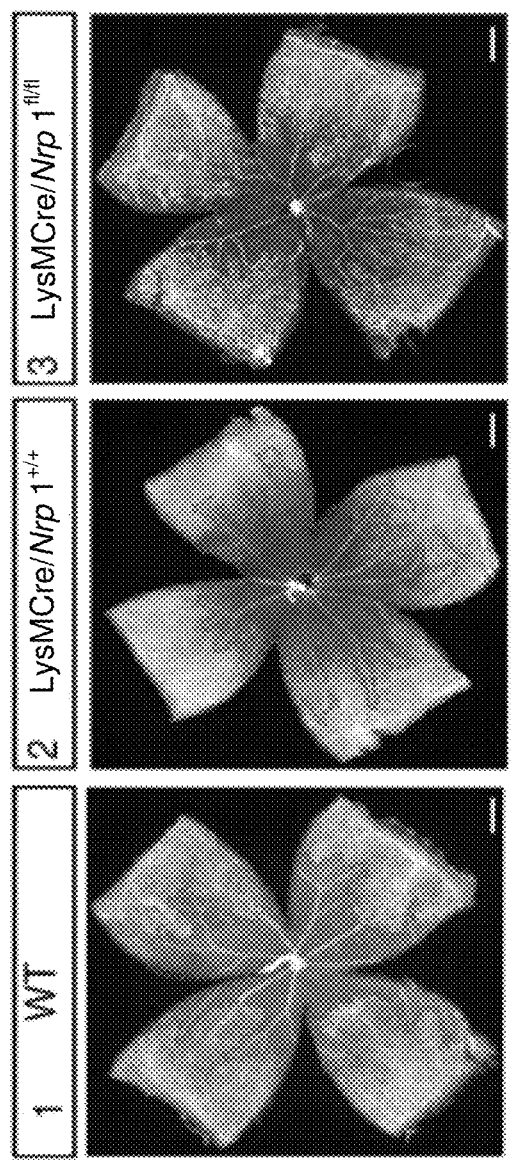
FIGS. 8A-8F show that deficiency in myeloid-resident NRP1 reduces vascular degeneration and pathological neovascularization in retinopathy. Wild-type, LysMCre/Nrp1$^{+/+}$ and LysM-Cre/Nrp1$^{fl/fl}$ mice were subjected to OIR and retinas collected at P12 and P17, flatmounted and stained with Isolectin B4. LysM-Cre/Nrp1$^{fl/fl}$ mice had less vasoobliteration at P12 (#3 in FIG. 8A, FIG. 8B) and reduced avascular areas (#3 in FIG. 8C, FIG. 8D) and preretinal neovascularization (#3 in FIG. 8E, FIG. 8F) at P17 compared to both control WT (#1) or control LysMCre/Nrp1$^{+/+}$ mice (#2). Results are expressed as percentage of avascular or neovascular area versus the whole retinal area; n=5-19. Scale bars: B&D: 1 mm and F:500 μm. p<0.01, *p<0.001.
Figure 8C:
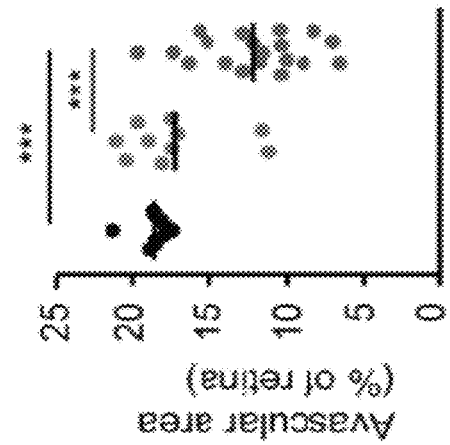
Figure 8D:
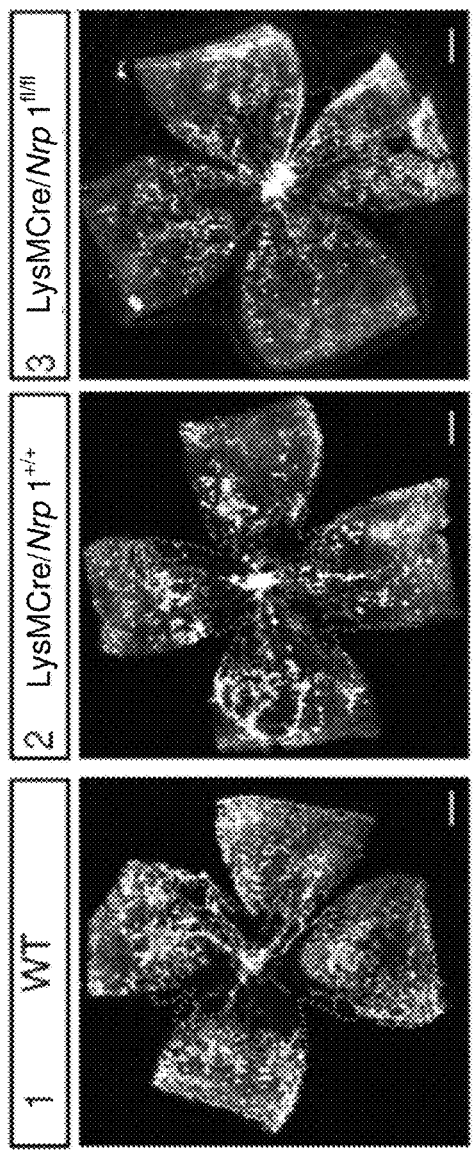

Deficiency in Myeloid-Resident NRP1 Reduces Vascular Degeneration and Pathological Neovascularization in Retinopathy Given the obligate role of NRP1 cell signaling in MP infiltration during the early stages of OIR (FIG. 1), the impact of myeloid cell-specific ablation of NRP1 on the progression of disease was next determined. Upon exit from 75% $O_2$ at P12, LysM-Cre/Nrp1fl/fl mice showed significantly lower levels of retinal vasoobliteration when compared to wild-type (P=0.0011) and LysM-Cre/Nrp+l+ (P<0.0001) controls (FIGS. 8A, B). This may be attributed to lower levels of IL-1β present in the retinas of LysM-Cre/Nrp1fl/fl mice (Data not shown). Importantly, at P17 when pathological neovascularization peaks (26), deletion of myeloid-resident NRP1 profoundly reduced avascular areas (~35% when compared to wild-type (P<0.0001) and ~30% compared to LysM-Cre/Nrp1$^{+/+}$ mice (P=0.0008)) (FIGS.

Figure 8E:
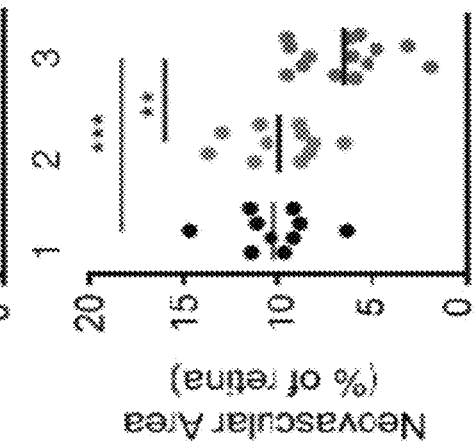
Figure 8F:
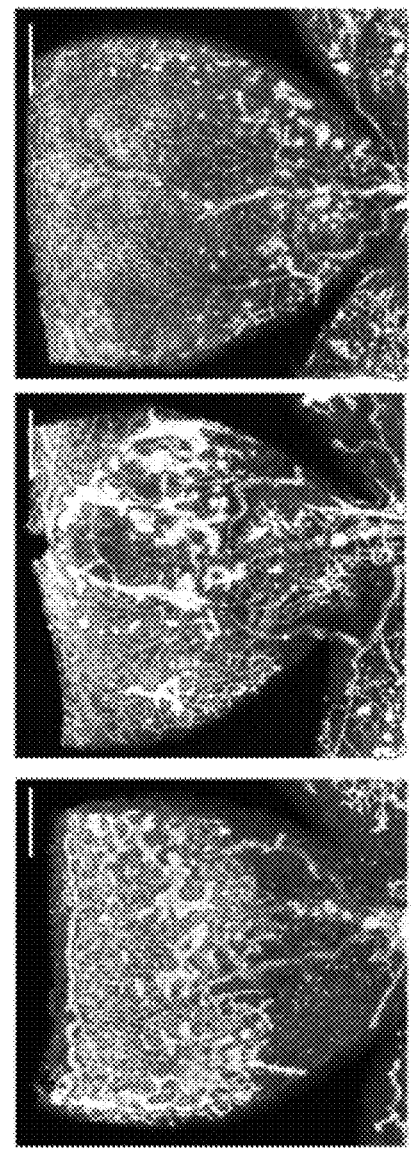

8C, D). In turn, significant reductions in destructive pre-retinal neovascularization associated with ischemic retinopathy were observed (~36% when compared to wild-type (P=0.0008) and ~34% compared to LysM-Cre/Nrp1+I+ mice (P=0.0013)) (FIGS. 8E, F).

Example 10

Preparation of Soluble SEMA3A Neutralizing Traps

High affinity traps to inhibit/neutralize SEMA3A were generated. These traps were derived from Neuropilin 1 (NRP1) and were optionally coupled to 6x-His tag or FC proteins (see FIGS. 19, 20 and 27, and Table 1). Various variants comprising either the entire NRP1 extracellular domain or functional variants capable of maintaining SEMA3A binding were generated. Traps containing a b1 domain (which binds to VEGF) and including a neutralizing VEGF165 mutation were generated. The traps were shown to be highly expressed and secreted in transformed human cells.

Simple purification and formulation protocols were developed to produce trap samples for SAR and in vivo efficacies studies to follow.
Methods Cell culture and material. The human Neuropilin 1 (GenBank™ accession NM_003873, SEQ ID NO: 66) was acquired from Origene Inc. The Origen clone comprises a conservative mutation at amino acid 140 which changes the leucine for an isoleucine. The 293T (ATCC) cells were grown in Dulbecco's modified Eagle's medium supplemented with 10% fetal calf serum. The pFUSE-hIgG1-Fc1 vector was purchased from InvivoGen Inc.

Cloning. The extracellular domain of Neuropilin-1 (residues 1-856), or portions of it, were PCR amplified from Origene clone RC217035 using the Phusion™ high fidelity polymerase (New England Biolabs) and cloned in the EcoR1-BglII of pFUSE-hIgG1-Fc1 in frame with the human FC-1 coding sequence. Constructs coding for the soluble versions of the traps were generated by inserting a sequence coding for a TEV protease cleavage site followed by 6x His residues and a stop codon upstream of the FC coding portion of the corresponding FC constructs. Additional deletions (b1, b1b2) or VEGF165 binding mutations (e.g., Y297A) were introduced using the Q5 site directed mutagenesis kit (NEB). All constructs sequences were verified by Sanger sequencing (Genome Quebec). The nucleotides and amino acid sequences of the assembled traps are depicted in FIGS. 20 and 27.

Evaluation of traps' expression in human cells. Constructs coding for the mouse and human traps were transfected in 293T cells. Cells were grown for 48 hrs post transfection in FreeStyle™ 293 medium (Invitrogen). Cell lysates were prepared from 293T cells 48 hours post-transfections. Cells were extensively washed with PBS and lysed in ice cold lysis buffer (50 mM HEPES pH7.5, 150 mM NaCL, 1.5 mM MgCl2, 1% Triton X-100 and 10% glycerol) supplemented with standard amounts of protease inhibitors (AEBSF, TPCK, TLCK, aprotinin, leupeptin, pepstatin and E64, Sigma). Cell lysates were cleared by micro centrifugation (12000 g, 20 minutes). Lysates concentrations were determined by standard micro BCA (Sigma). Equal amounts of protein were loaded on 5-20% PAGE-SDS gradient gels and transferred to PVDF (Amersham). Cleared conditioned media from transfected cells were incubated with either Protein A sepharose (Pharmacia) or Talon resin (Clontech) for FC or 6xHis tag. Resins were washed with PBS and diluted in 2xPAGE-SDS sample buffer prior to gel separation and transfer. The antibody used in immunoblottings were the anti-human Neuropilin-1 (Cell signaling), the mouse monoclonal anti-6x-HIS (In Vitrogen) and the reporter HRP linked anti-human, mouse and rabbit IgG (BioRAD). All antibodies were used at a 1/2000 dilution. Chemiluminescent signal was captured using a Fuji imaging system after incubation of membranes with ECL (Amersham).

Traps expression and purification. 293-T cells were transfected with plasmids encoding the various traps by either the Polyethylamine (PEI) or the calcium phosphate precipitation standard transfections methods. The next day cells were washed twice with serum free media and fed with serum free complete media (Free style 293 media, InVitrogen). Conditioned medium were collected after 60-72 hrs of growth in serum free media and cleared from cellular debris by swing bucket centrifugation (2000 RPM, 20 minutes). FC traps were purified from conditioned media of transfected 293T cells by passage on Protein A or G sepharose (Pharmacia) followed by extensive washes with PBS and elutions with 0.1 M glycine pH 3.0. Elution fractions were neutralised immediately by the addition of 1/10 volume 1 M Tris pH 8 and 1/10 volume of 10xPBS pH 7.4. Soluble 6xHIS tagged traps were purified from conditioned media of transfected 293T cell by passage on Talon agarose (Clontech) followed by extensive washes with PBS and stepwise imidazole elutions (Range 10-150 uM typically). Samples of purification fractions of traps were analysed on 5-15% or 5-20% gradient PAGE-SDS gels. Gel were stained using the Safely Blue staining kit (InVitrogen).

Sterile formulation of purified traps for in vivo injections. Purifications elution fractions from 40 ml of conditioned media were pooled and diluted to a total volume of 10 ml in PBS. Diluted trap proteins were sterilized by filtration through a 0.2 uM low protein binding filter (Progene). Protein solutions were concentrated and buffer exchanged with PBS on sterile PES concentration devices (Pierce, nominal MWCO 30 KD). Sterile concentrated Traps samples (~30-50 ul) were analysed and stained on PAGE-SDS as described above.

Example 11

Affinity of Traps for SEMA3A and VEGF

Production of AP-VEGF$_{165}$. the coding sequence of the human VEGF165 variant 1 (NM_001025366) was subcloned in the pAPtag5 vector (GenHunter), in-frame with an Alkaline Phosphatase domain (AP-VEGF165). HEK293T cells were transfected with the AP-VEGF165 construct using a polyethylenimine (PEI) transfection method. Following the overnight transfection step, cells were cultured for an additional 60 hr in serum free media (Invitrogen). The cell media were collected and concentrated on a PES device (Pierce). The concentrated AP-VEGF165 ligand was analysed on PAGE-SDS and quantified using SimplyBlue safe stain (Life technologies).

Sema 3A and AP-VEGF$_{165}$ binding assays. Saturation curves for the determinations of KD of binding to SEMA 3A or VEGF165 were obtained as follow. Wells of high protein binding 96 well plates (Maxisorp, Nunc) were coated with purified traps diluted in PBS and blocked afterward with binding buffer (PBS containing 2% casein and 0.05% Tween 20). The SEMA3A-FC (R&D systems) or AP-VEGF165 ligands were diluted in binding buffer over an extensive range of concentrations and added to wells. Following an overnight incubation, wells were washed with PBS containing 0.05% tween. Bound SEMA3a-FC was detected using an HRP-linked anti-Human IgG (Biorad) and ECL substrate (Pierce). Alternatively, bound AP-VEGF165 was detected using CPD star substrate (Roche). The Chemiluminescent signal was acquired on a TECAN reader. Dissociation constant (KD) were determined by non-linear curve fitting using the Graph Pad prism software.

The relative affinity of traps of the present invention to SEMA3A and VEGF has been assessed. Traps were prepared as described in Example 10. Schematic representation of traps tested is also provided in FIG. 19.

TABLE 4

Dissociation constant of SEMA3A and VEGF for various Traps

| Trap | SEMA 3A-FC binding (nM) | VEGF165 binding (nM) | SEQ ID NOs: (aa and nts) |
|---|---|---|---|
| G | 0.8 | 6.75 | SEQ ID NOs: 38, 39 |
| O | 1.05 | N.D. | SEQ ID NOs: 40, 41 |
| M | 0.95 | 20.13 | SEQ ID NOs: 42, 43 |
| N | >1000 | >250 | SEQ ID Nos: 44, 45 |
| R | 6.15 | N.D. | SEQ ID NOs: 46, 47 |
| W | 1.14 | 20.73 | SEQ ID NOs: 52, 53 |
| Y | >750 | N.D. | SEQ ID NOs: 56, 57 |
| Z | 4.44 | 66.96 | SEQ ID NOs: 62, 63 |
| AB | N.D. | 29.51 | SEQ ID NOs: 58, 59 |
| AC | 4 | No binding | SEQ ID NOs: 60, 61 |

Soluble NRP1 traps of the present invention bind more efficiently to SEMA3A than VEGF. Such preference for SEMA3A was found surprising since SEMA3A and VEGF are considered to normally have the same general affinity for NRP1. Increased affinity for SEMA3A may be advantageous in conditions where SEMA3A inhibition is preferred over inhibition of VEGF and may reduce side effects associated with VEGF inhibition.

Example 12

Figure 9A:
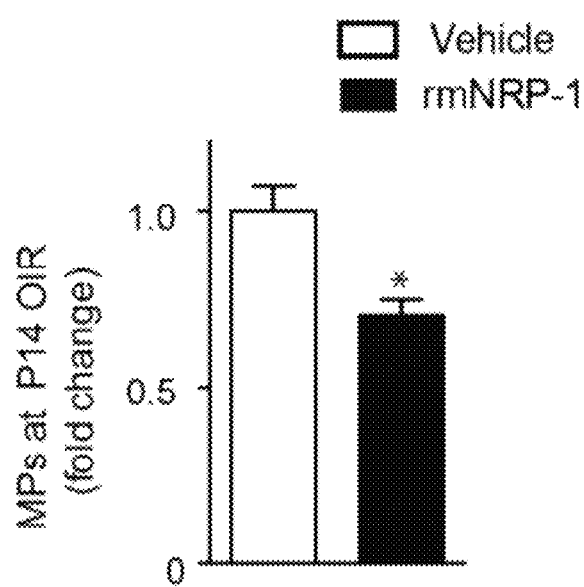
FIGS. 9A-9C show that therapeutic intravitreal administration of soluble NRP1 reduces MP infiltration and pathological neovascularization in retinopathy. WT mice were subjected to OIR and injected intravitreally at P12 with soluble recombinant mouse NRP1 (rmNRP1 comprising domains a1, a2, b1, b2 and c, see also FIGS. 19C and 20X-20Y) as a trap to sequester OIR-induced ligands of NRP1. At P14, FACS analysis revealed a decrease of over 30% in the number of retinal MPs in rmNRP1 injected retinas (FIG. 9A). Data are expressed as a fold change relative to control (vehicle-injected retinas)±SEM; n=3-4 (total of 12-16 retinas per condition; each "n" comprises 4 retinas). Treatment with rmNRP1 efficiently decreased pathological neovascularization at P17 when compared to vehicle-injected eyes (FIG. 9B, FIG. 9C). Results are expressed as percentage of neovascular area versus the whole retinal area; n=11. Scale bars: 500 μm. *p<0.05, **p<0.01.
Figure 9B:
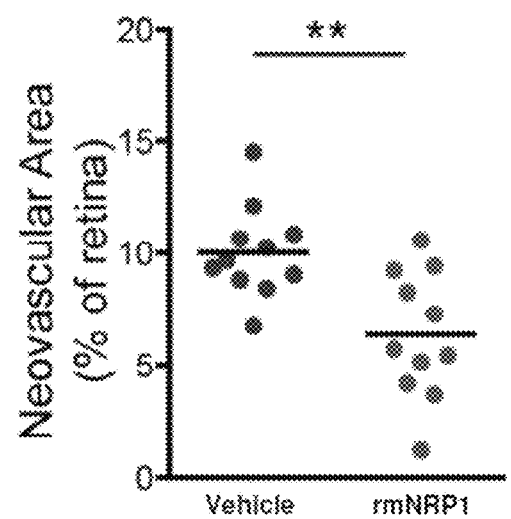
Figure 9C:
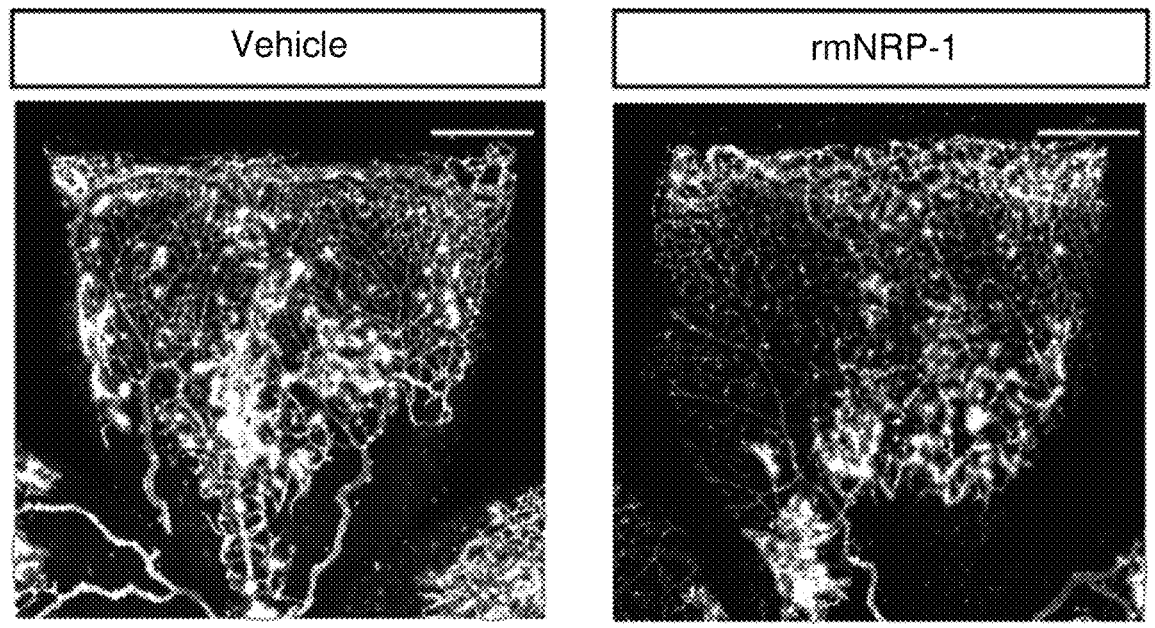
Figure 10:
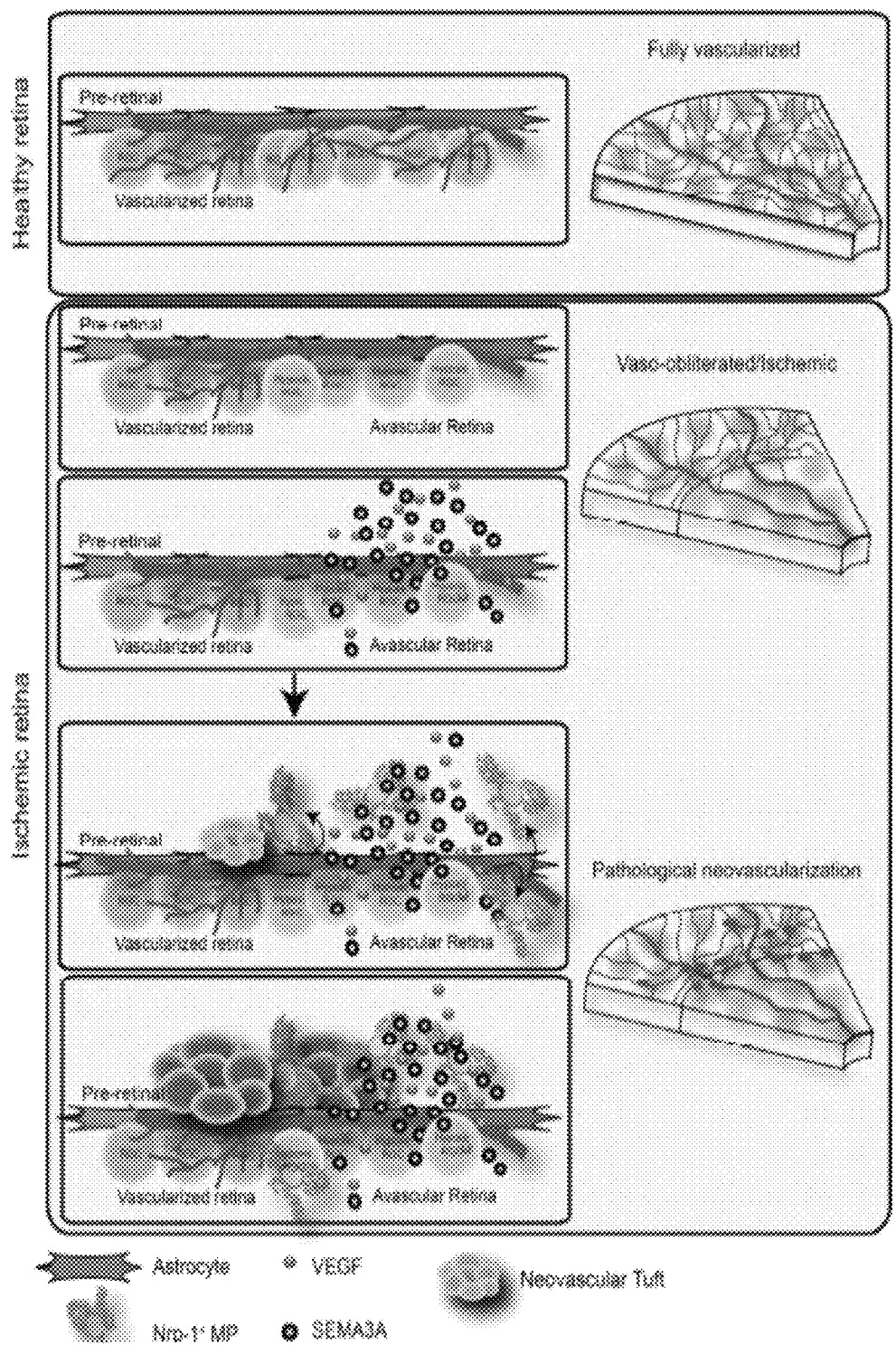
FIG. 10 is a schematic depiction of the instant findings illustrating that during ischemic retinopathies such as that of diabetes, avascular zones of the retina, ischemic neurons and neural tissue produces ligands of NRP1 (SEMA3A and VEGF), which in turn act as potent chemo-attractive agents for pro-angiogenic microglia. The NRP1⁺ microglia then partake in the pathogenesis of proliferative retinopathy.
Figure 11A:
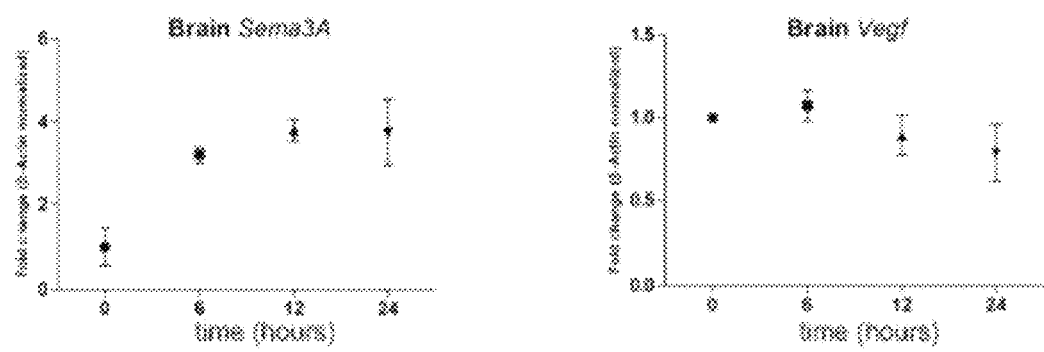
FIGS. 11A-11D show that SEMA3A is upregulated in several organs during septic shock. mRNA levels of SEMA3A (left panels) and VEGF (right panels) were assessed by qRT-PCR following LPS-induced (15 mg/kg) sepsis in mice. SEMA3A and VEGF mRNA levels were normalized with 1-actin expression and fold changes in mRNA levels were determined at 0, 6, 12 and 24 hours following LPS administration.
Figure 11B:
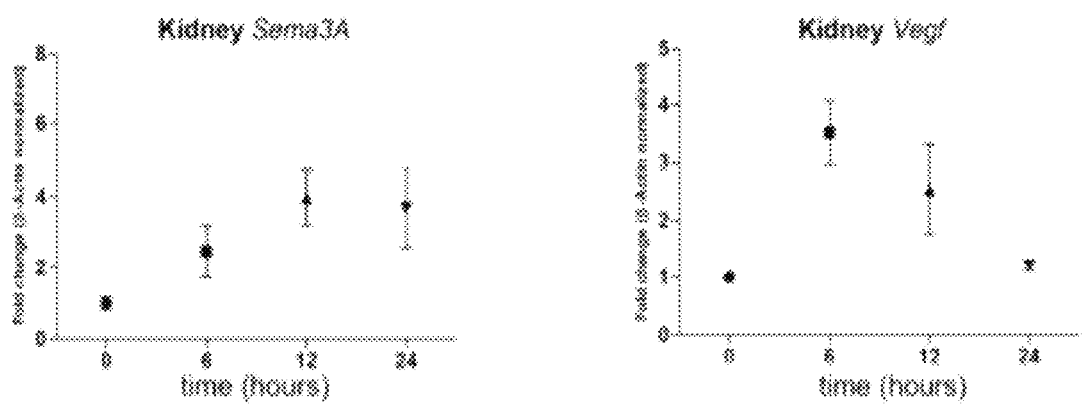
Figure 11C:
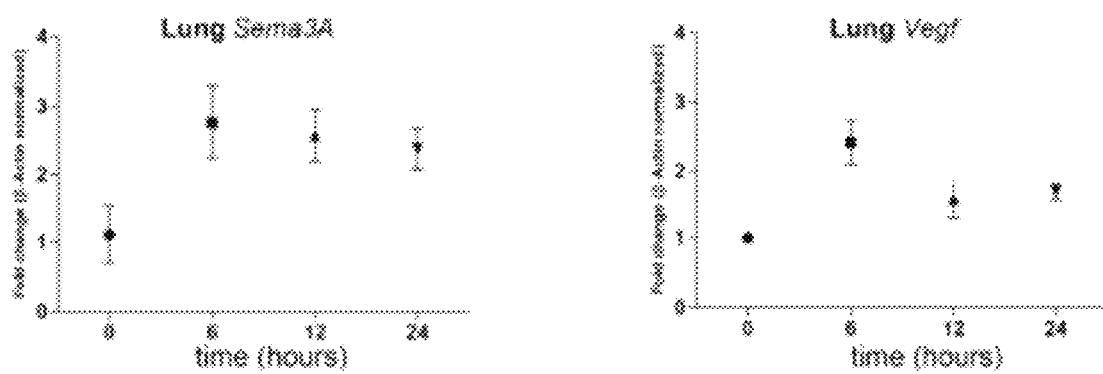
Figure 11D:
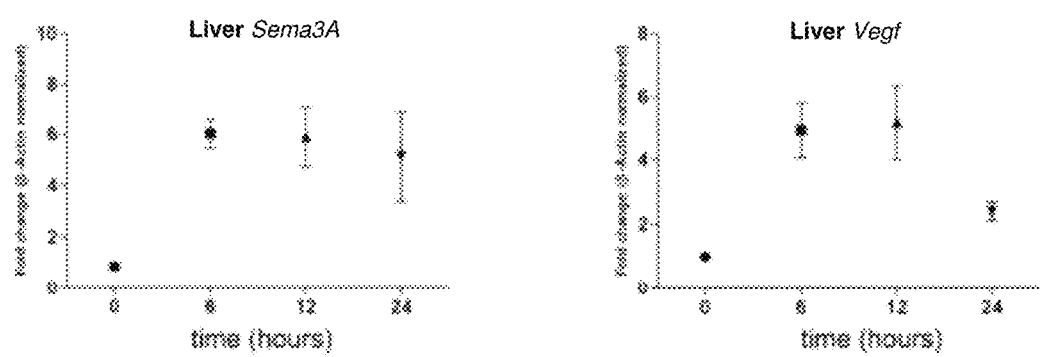
Figure 12A:
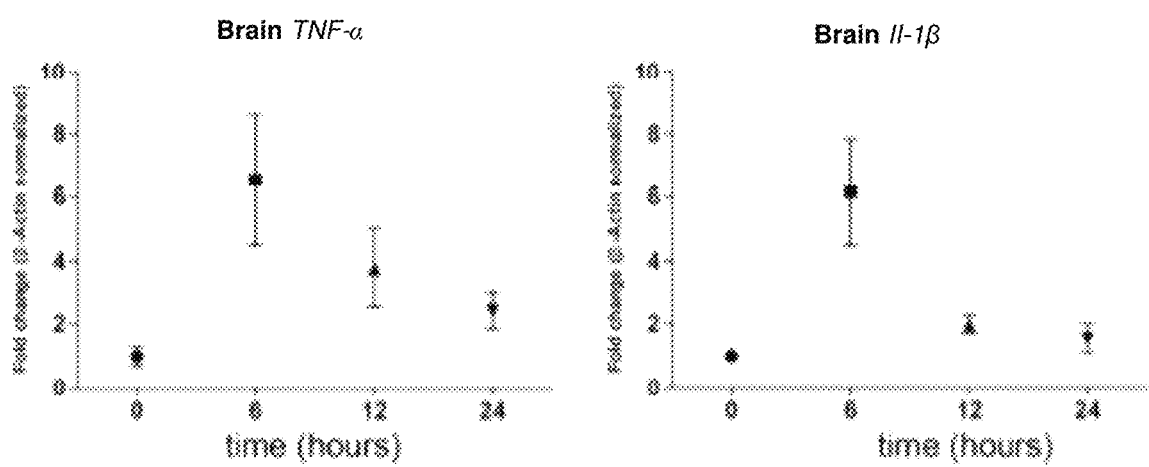
FIGS. 12A-12D show cytokines expression following LPS-induced sepsis. mRNA levels of TNF-α and IL-1β were assessed by qRT-PCR following LPS-induced sepsis (15 mg/kg) in mice. mRNA levels were normalized with β-actin expression an fold changes in mRNA levels were determined at 0, 6, 12 and 24 hours following LPS administration.
Figure 12B:
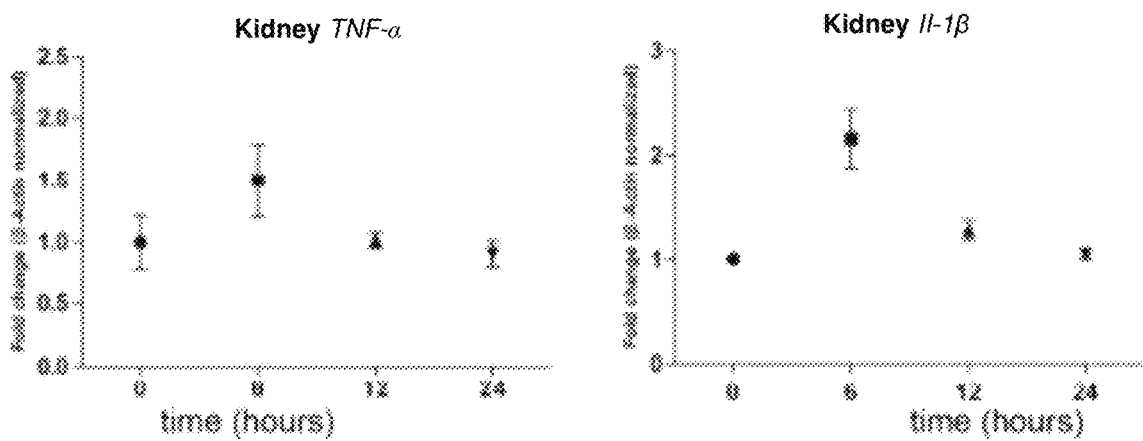
Figure 12C:
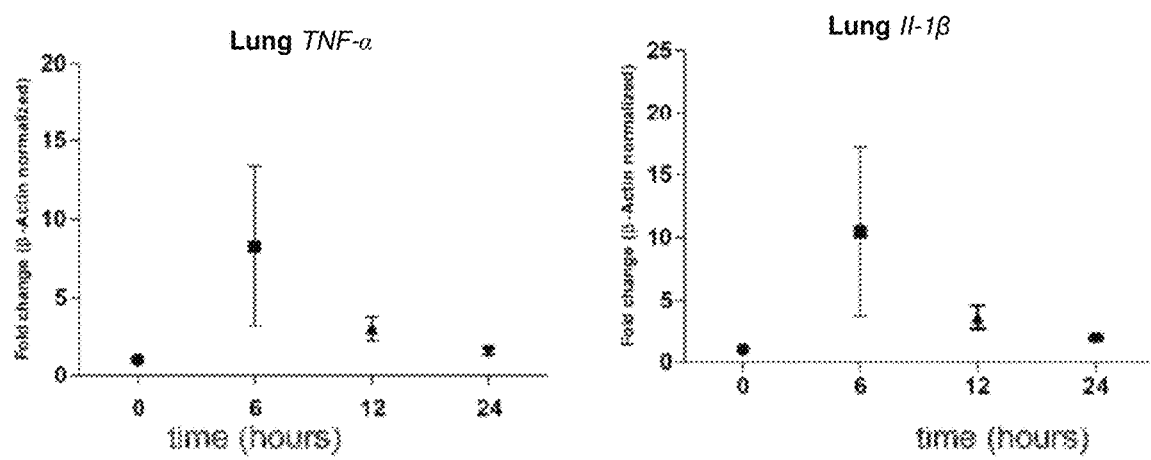
Figure 12D:
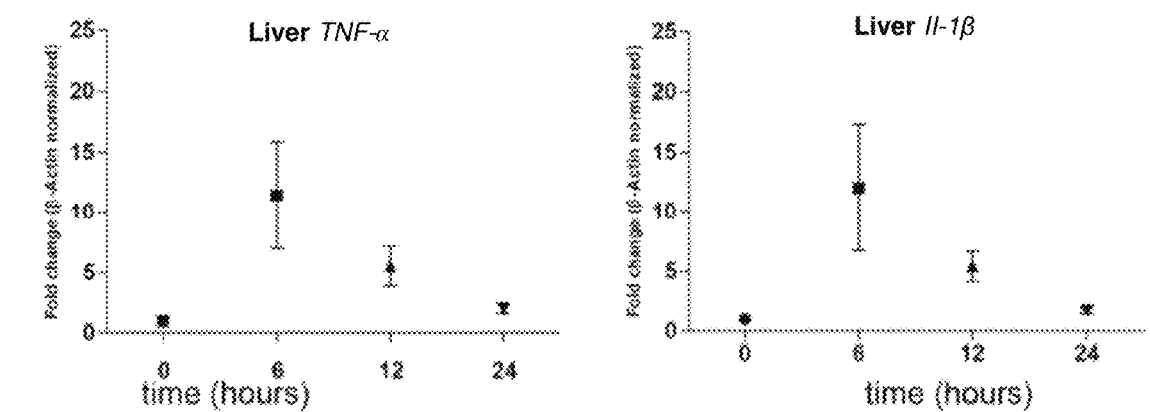

Therapeutic Intravitreal Administration of Soluble NRP1 Reduces MP Infiltration and Pathological Neovascularization in Retinopathy To determine the translational potential of the above findings, a soluble recombinant mouse (rm)NRP1 mTrap 1 polypeptide (FIGS. 19C and 20X-20Y comprising domains a1, a2, b1, b2 and c of SEQ ID NO.25) was next employed as a trap to sequester OIR-induced ligands of NRP1. A single intravitreal injection of rmNRP1 at P12 lead to a 30% reduction at P14 (P=0.0282) in the number of microglia present in retinas subjected to OIR (FIG. 9A). This finding attests to the potency of soluble NRP1 (1 µl of 50 µg/ml) to compromise microglial mobilization. Intravitreal administration of soluble NRP1 provoked a significant ~40% decrease in pathological pre-retinal angiogenesis when compared to vehicle injected controls (P=0.0025) (FIGS. 9B,C). Together, these data suggest that neutralization of ligands of NRP1 is an effective strategy to reduce destructive neovascularization in retinopathy.

Example 13

Materials and Methods for Sepsis Model—Examples 14 to 19

Mouse model of sepsis. Studies were performed according to the regulations from the Canadian Guidelines for the Use of Animals in Research by the Canadian Council on Animal Care. LPS injections were delivered intraperitoneally (i.p) in 6-8 weeks old C57BL/6 mice.

Survival assay. For generation of survival data, mice were challenged with a single intraperitoneal injection of LPS at 25 mg/kg, in a volume of nearly 100 ul adjusted to mouse weight. Mice were then monitored until reaching critical limit points defined by the Canadian Council of Animal Care.

Measurement of pro-inflammatory cytokines. For assessment of pro-inflammatory cytokines, mice were challenged i.p. with a single intraperitoneal injection of LPS at 15 mg/kg and sacrificed at various time points up to 24 hours. Tissues (Brain, Liver, Kidney) were removed and mRNA was isolated using the GenElute™ Mammalian Total RNA Miniprep Kit (Sigma) and digested with DNase I to prevent amplification of genomic DNA. Reversed transcription was performed using M-MLV reverse transcriptase and gene expression analyzed using SybrGreen in an ABI Biosystems Real-Time PCR machine. 1-actin was used as a reference gene.

Primary peritoneal macrophages culture. Adult WT or LyzMcre/NRP1fl/fl mice were anesthetized with 2% isoflurane in oxygen 2 L/min and then euthanized by cervical dislocation. Then, a small incision in abdominal skin of mouse was performed. Skin was pulled to each size of the mouse and peritoneal cavity was washed with 5 ml of PBS plus 3% FBS for 2 min. Then, the harvested cells were centrifuged for 5 min at 1000 rpm, resuspended in medium (DMEM F12 plus 10% FBS and 1% Streptomycin/Penicillin) and plated. After 1h of culture at 37° C. under a 5% $CO_2$ atmosphere the medium was changed.

Cytometric Bead Array (CBA). CBA was performed according to manufacturer's guidelines (BD Bioscience). Macrophages were isolated from wild type or LyzMcre/NRP1fl/fl mice and subjected to SEMA3A (100 ng/ml) or vehicle for 12 hours and processed by CBA.

Trap and anti-VEGF antibody administration. Mice experimental model of sepsis were treated with human or mice NRP1 trap-1 (FIGS. 19B, C and 20A-20B, 20X-20Y, SEQ ID NO: 25 or SEQ ID NO: 83) or VEGF neutralizing antibody (R&D Systems, AF-493-NA).

Experimental design: 3 mice per group. Groups: 1-Vehicle, 2-LPS, and 3-LPS+NRP1 Trap 1-Vehicle: NaCl, 2-LPS: 15 mg/kg; and 3-LPS+NRP1-trap: Mice received i.v. a single injection of 4 ug (in a volume of 100 uL) of recombinant mouse NRP1-trap corresponding to 0.2 mg/kg, few minutes after LPS injection.

Permeability tests. For permeability assays, mice were challenged i.p. with a single intraperitoneal injection of LPS at 15 mg/kg, and sacrificed 24 hrs later for tissue sampling. Changes in liver, kidney, and brain vascular permeability were assessed by quantifying Evans Blue (EB) extravasation in tissue. After 24 hrs, a solution of 10 mg/ml of EB was injected intravenously (55 mg/kg). Two hours later, mice were sacrificed and perfused through the heart with PBS. Tissues were then removed, allowed to dry at room temperature 24 hrs, and dry weights were determined. EB was extracted in formamide overnight at 65° C. EB was then measured at 620 and 740 nm in spectrophotometer.

Real-time PCR analysis. RNA was isolated using the GenElute™ Mammalian Total RNA Miniprep Kit (Sigma) and digested with DNase I to prevent amplification of genomic DNA. Reversed transcription was performed using M-MLV reverse transcriptase (Life Technologies) and gene expression analyzed using SybrGreen (BioRad) in an ABI Biosystems Real-Time PCR machine. β-actin was used as a reference gene. See Table 3 below for details on the sequence of the oligonucleotides used.

TABLE 3

Primer sequences used for RT-PCR analysis

| Target | Primer sequence | SEQ ID NO: |
|---|---|---|
| β-actin (fwd) | GAC GGC CAG GTC ATC ACT ATT G | SEQ ID NO: 85 |
| β-actin (rev) | CCA CAG GAT TCC ATA CCC AAG A | SEQ ID NO: 86 |
| SEMA3A (fwd) | GCT CCT GCT CCG TAG CCT GC | SEQ ID NO: 87 |
| SEMA3A (rev) | TCG GCG TTG CTT TCG GTC CC | SEQ ID NO: 88 |
| VEGF (fwd) | GCC CTG AGT CAA GAG GAC AG | SEQ ID NO: 89 |
| VEGF (rev) | CTC CTA GGC CCC TCA GAA GT | SEQ ID NO: 90 |
| Tnf-α(fwd) | CCC TCA CAC TCA GAT CAT CTT CT | SEQ ID NO: 91 |
| Tnf-α(rev) | GCT ACG TGG GCT ACA G | SEQ ID NO: 92 |
| IL-1β(fwd) | CTG GTA CAT CAG GAC CTC ACA | SEQ ID NO: 93 |
| IL-1β(rev) | GAG CTC CTT AAC ATG CCC TG | SEQ ID NO: 94 |
| IL-6 (fwd) | AGA CAA AGC CAG AGT CCT TCA GAG A | SEQ ID NO: 095 |
| IL-6 (Rev) | GCC ACT CCT TCT GTG ACT CGA GC | SEQ ID NO: 96 |

Example 14

Semaphorin 3A is Upregulated in Several Organs During Septic Shock

Given the link between SEMA3A, NRP1 and the innate immune response in OIR (as demonstrated in Examples 2-9 above), the implication of the NRP1-dependent cellular response in general systemic inflammation was next assessed. This was first explored by determining the kinetics of SEMA3A expression during septic shock.

LPS was administrated (15 mg/kg) to 6-8 weeks old C57BL/6 mice (n=5) and mice were sacrificed at 0, 4, 8, 12 and 24 hours following LPS administration. Key organs such as brain, kidney, lung and liver were collected and mRNA isolated. Levels of SEMA3A mRNA were robustly induced in all organs analyzed as soon as 6 hours after LPS injection and persisted for 24 hours (FIG. 11 A-D). Similarly, expression levels of another NRP1 ligand, VEGF, were also profoundly increased in kidney (FIG. 11B), lung (FIG. 11C) and liver (FIG. 11D) within the first 6 hours of septic shock. Increases in classical pro-inflammatory cytokines TNF-α and IL1-β rose at 6 hours post LPS administration and diminished similarly to VEGF mRNA (FIG. 12). Hence, of all investigated mediators of inflammation, SEMA3A had a long-term kinetic profile and stayed elevated for at least 24 hours following induction of sepsis. This particular expression profile for SEMA3A suggests that its contribution to septic shock may be long lasting when compared to other cytokines.

Example 15

SEMA3A Induces Secretion of Pro-Inflammatory Cytokines in Myeloid Cells Via NRP1

Given the contribution of monocytes and myeloid cells to the acute inflammatory response and the presence of NRP1 on myeloid cells, the contribution of SEMA3A and myeloid-resident NRP1 in the production of inflammatory cytokines was determined.

Figure 13A:
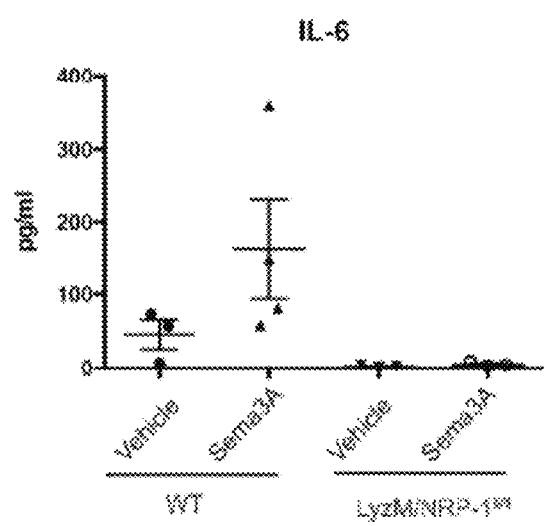
FIGS. 13A-13C show that SEMA3A induces secretion of pro-inflammatory cytokines in myeloid cells via NRP1. Wild-type and NRP1 knock out (LyzM/NRP1$^{fl/fl}$) myeloid cells were treated with SEMA3A (100 ng/nml) or vehicle and IL-6 (FIG. 13A), TNF-α (FIG. 13B) and IL-1β (FIG. 13C) protein secretion was analyzed by Cytometric Bead Array (CBA)
Figure 13B:
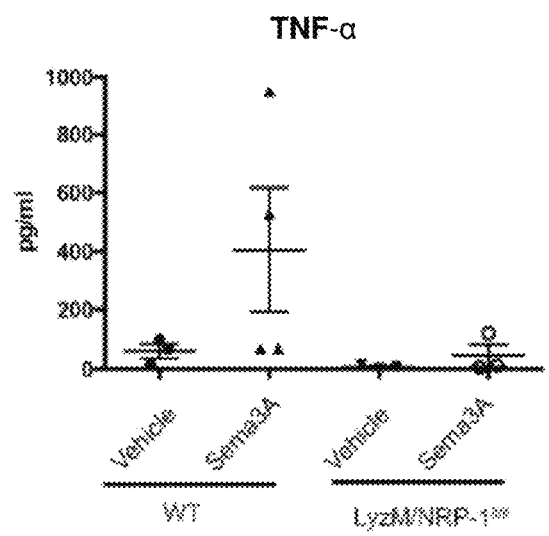
Figure 13C:
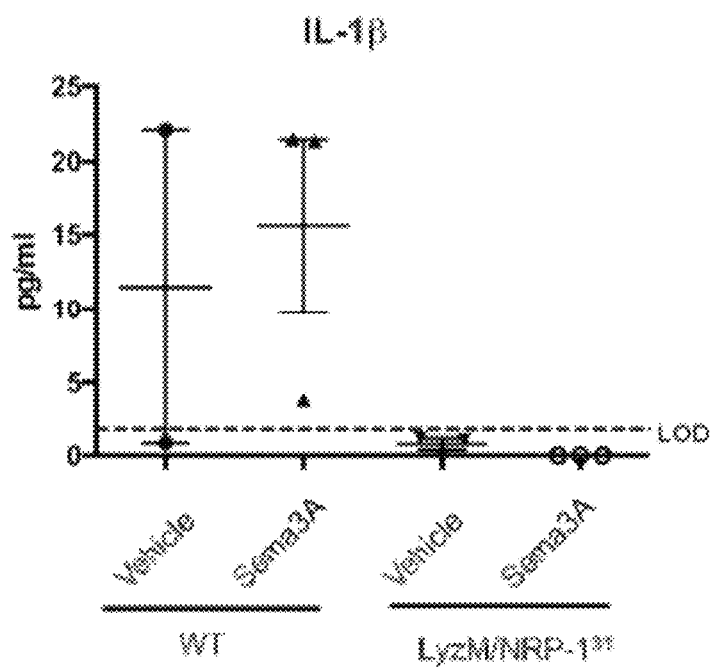

Isolated macrophages were exposed to SEMA3A (100 ng/ml) or vehicle and the production of cytokines was analyzed by Cytometric Bead Array (CBA). Results presented in FIG. 13 indicate that SEMA3A can induce the production/secretion of pro-inflammatory cytokines, known to contribute to septic shock such as IL-6 (FIG. 13A) and TNF-α (FIG. 13B). Of particular importance, a specific knockout of NRP1 (LyzM/NRP1$^{fl/fl}$) in myeloid cells abrogated SEMA3A-induced production of IL-6 and TNF-α. Notably, vehicle-treated control LyzM/NRP1$^{fl/fl}$ macrophages showed lesser production of IL-6, TNF-α and IL-1β then wild-type controls, highlighting the role of myeloid-resident NRP1 in sepsis-induced inflammation.

Example 16

Figure 14B:
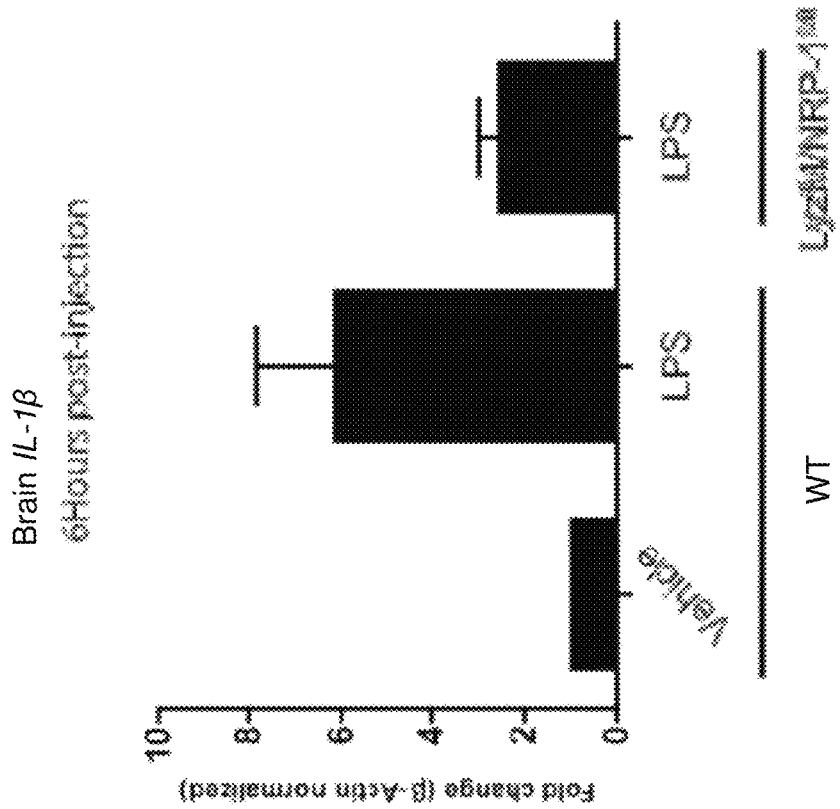
FIGS. 14A-14D show that myeloid deficiency in NRP1 reduces production of inflammatory cytokines during sepsis in vivo. NRP1 knock out mice (LyzM/NRP1') and control wild type mice were administered vehicle or LPS (15 mg/kg) to induce sepsis. Brains and livers were collected 6 hours post LPS injection and mRNA extracted. TNF-α (FIG. 14A, FIG. 14C) and IL-1β (FIG. 14B, FIG. 14D) expression was analyzed by real-time RT-PCR and levels normalized with β-actin expression level.
Figure 14A:
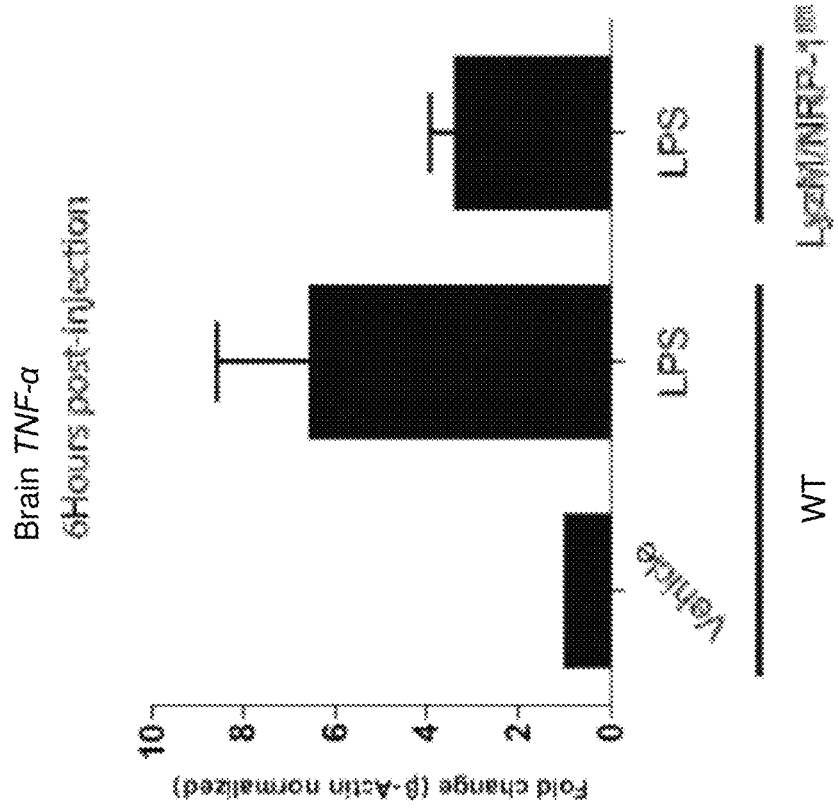
Figure 14D:
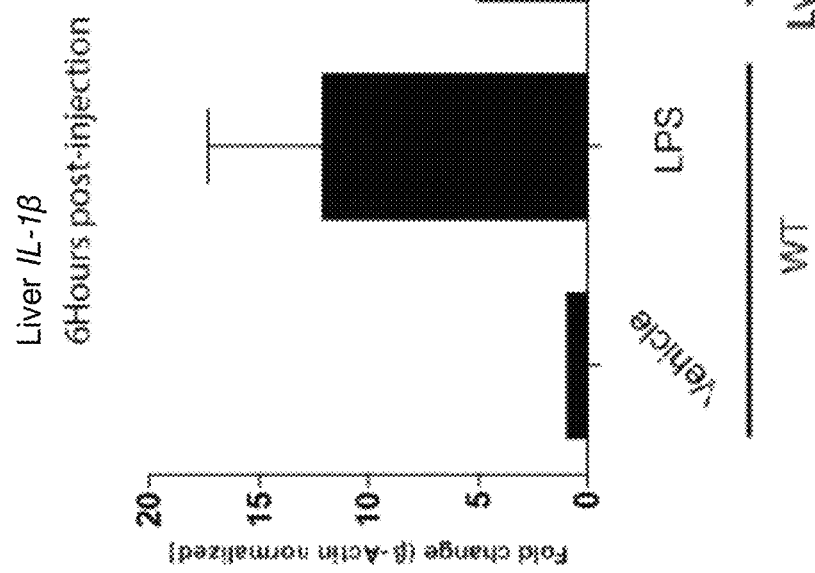
Figure 14C:
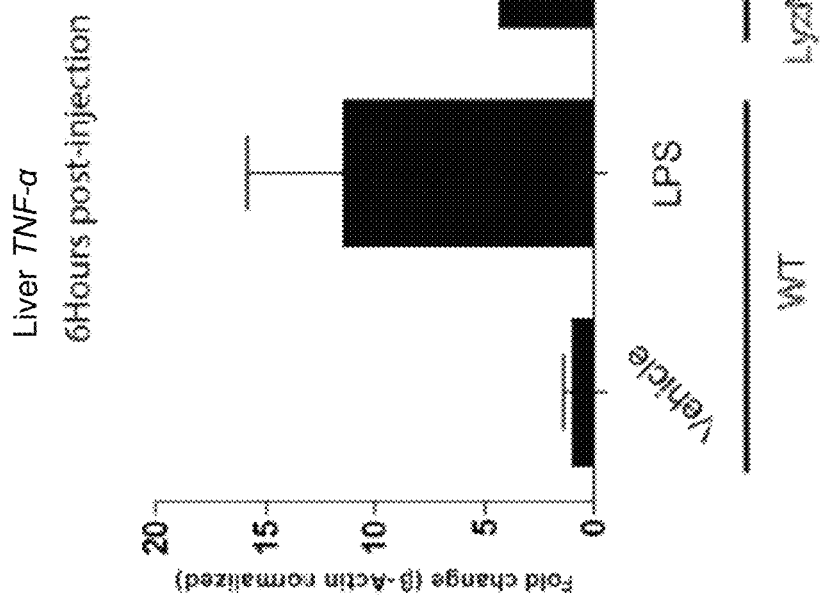

Deficiency in Myeloid-Resident NRP1 Reduces Production of Pro-Inflammatory Cytokines In Vivo in Sepsis Because myeloid-resident NRP1 was important for the release of pro-inflammatory cytokines such as IL-6 and TNF-α in vitro, its contribution was next explored in vivo. LyzM/NRP1$^{fl/fl}$ and control wild-type mice were administered vehicle or LPS (15 mg/kg) and brains and livers were collected 6 hours post LPS injection. Real-time PCR analysis of TNF-α (FIGS. 14A,C) and IL-1b (FIG. 14B,D) levels revealed a robust drop in these cytokines in LyzM/NRP1$^{fl/fl}$. These results underscore the profound contribution of NRP1 and its ligands to the development of sepsis in vivo.

Example 17

Figure 15A:
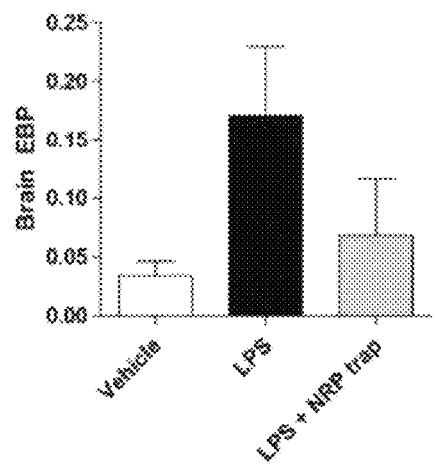
FIGS. 15A-15C show that in vivo inhibition of NRP1 activity prevents sepsis-induced barrier function breakdown. Mice were administered with i) vehicle, ii) LPS (15 mg/kg); or iii) LPS (15 mg/kg) and an NRP1 trap (Trap-1, FIGS. 19C and 20X-20Y but without an FC domain, NP_032763, 4 ug/0.2 mg/kg, i.v.). Vascular permeability in brain (FIG. 15A), kidney (FIG. 15B) and liver (FIG. 15C) was then assessed using an Evan blue permeation assay (EBP)
Figure 15B:
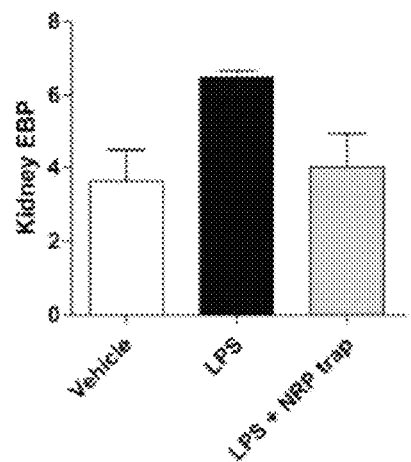
Figure 15C:
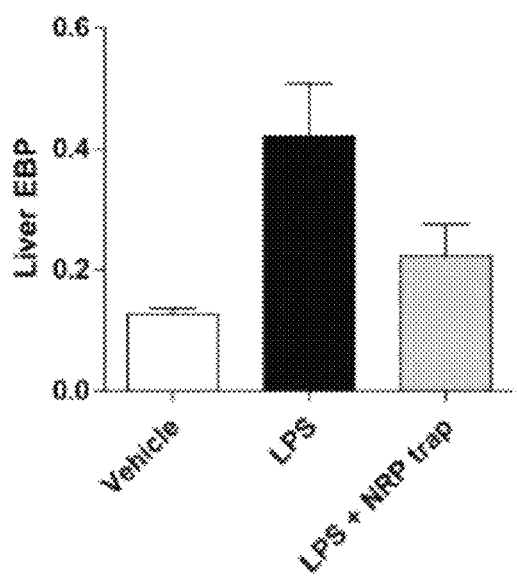

Inhibition of NRP1 Signalling Prevents Sepsis-Induced Barrier Function Breakdown One of the pathological features of severe septic shock though to contribute to organ failure is the compromise of blood barriers (blood and air in lung, blood and urine in the kidney, blood and bile in liver, and humoral molecules in the brain). Given a role for SEMA3A in the breakdown of the blood retinal barrier (46) and the present novel data on the expression of SEMA3A during sepsis, the effect of neutralizing SEMA3A with a trap derived from the extracellular domain of human NRP1 was assessed (Trap-1, without FC, FIG. 19B, SEQ ID NO:83). Using an Evans Blue Permeation (EBP) assay, we found that in all organs studied namely brain (FIG. 15A), kidney (FIG. 15B) and liver (FIG. 15C), a pronounced reduction in LPS-induced barrier function breakdown was observed when mice were treated with 4 ug of NRP1 derived trap (0.2 mg/kg, i.v.). These results strongly suggest that traps of soluble NRP1 and their derivatives are compelling therapeutic agents to counter sepsis.

Example 18

NRP1-Derived Trap Protects Against Sepsis

Figure 16A:
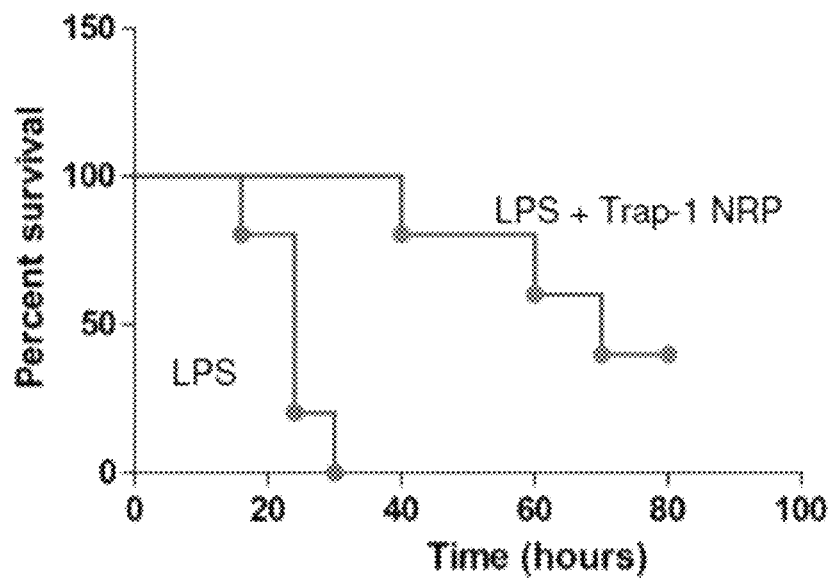
FIGS. 16A-16B show that in vivo inhibition of NRP1 activity protects against sepsis.

To determine the therapeutic benefits of neutralization of NRP1 ligands or NRP1 inhibition during sepsis, survival studies were performed. A high dose of LPS (25 mg/kg) was administered to mice. Mice were then monitored, and ethically sacrificed, when appropriate endpoints were achieved. In the second group, mice were injected i.v. with 4 ug of recombinant Trap-1 without FC (0.2 mg/kg, FIGS. 19B and 20A-20B, SEQ ID NO: 83) followed by LPS intraperitoneal injection. In the control group, 5/5 mice (100%) died within first 30 hrs (FIG. 16A) following LPS injection. Conversely, all mice treated with the trap were still alive after 30 hours and showed significant improved survival rate after 60 hours (3/5). Mortality was thus reduced from 100% (in the control group) after 30 hours to 40% (FIG. 16A) after 60 hours. Furthermore, 40% of Trap treated-mice remained alive 80 hours following LPS injection. Thus, survival time was at least doubled in 60% of the case and almost tripled in 40% of the case when cell signaling through NRP1 was inhibited.

Figure 16B:
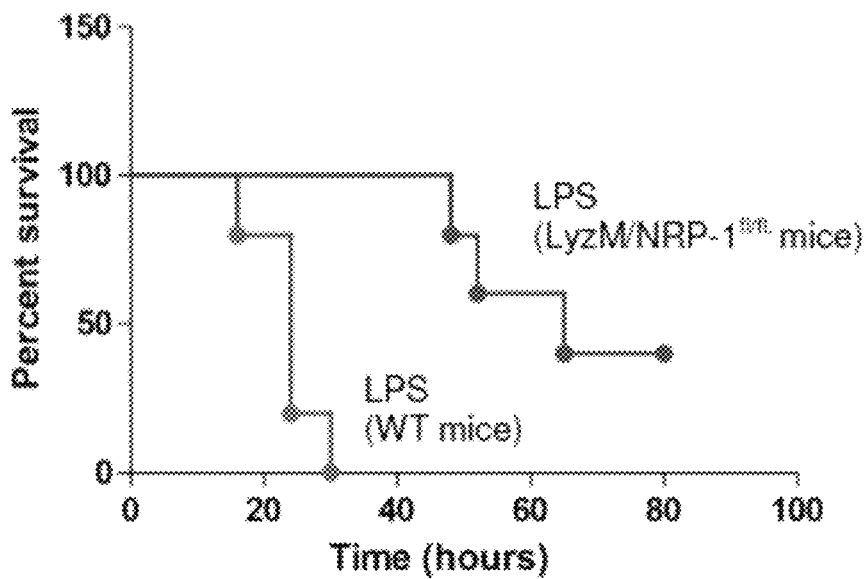

Similar results were obtained with mice harboring a specific knock out of NPR1 in myeloid cells (FIG. 16B). Absence of NRP1 in myeloid cells increased survival time and reduced sepsis-induced mortality (3/5) from 100% to 40% (FIG. 16B) after 30 hours and from 100% to 40% after 60 hours. Also, 40% of NRP1 K.O. mice remained alive 80 hours following LPS injection.

Taken together, these results highlight the therapeutic value of inhibiting NRP1-dependent cell signaling in sepsis treatment.

Example 19

NRP1-Derived Trap Lowers Production of Inflammatory Cytokines in Septic Shock

Figure 17A:
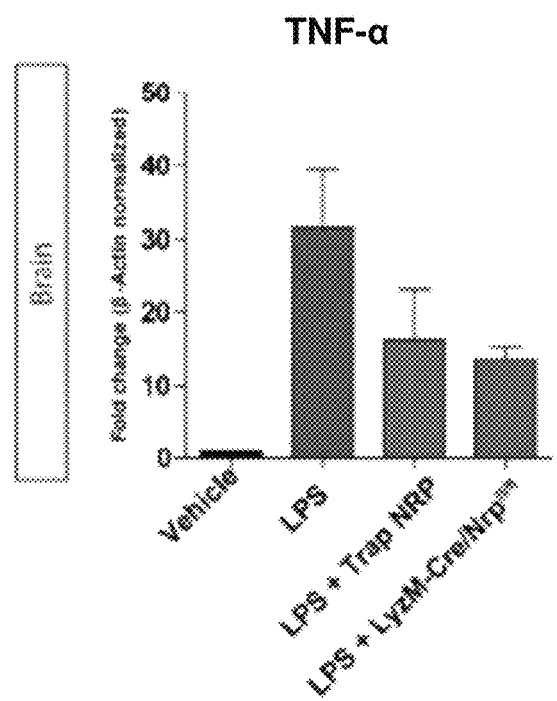
FIGS. 17A-17B show that administration of NRP1 derived trap or myeloid deficiency in NRP1 lowers inflammatory cytokine production in septic shock. Wild-type mice were administered i) vehicle (n=3), ii) LPS (15 mg/kg, n=3) or iii) LPS and an NRP1 trap (Trap-1, FIGS. 19C and 20X-20Y but without an FC domain, NP_032763). Mice with NRP1 deficient myeloid cells (LyzM-Cre/Nrp$^{f/f}$) were administered LPS (15 mg/kg, n=3). Brains were collected 6 hours post LPS injection and production of TNF-α (FIG. 17A) and IL-6 (FIG. 17B) was measured.
Figure 17B:
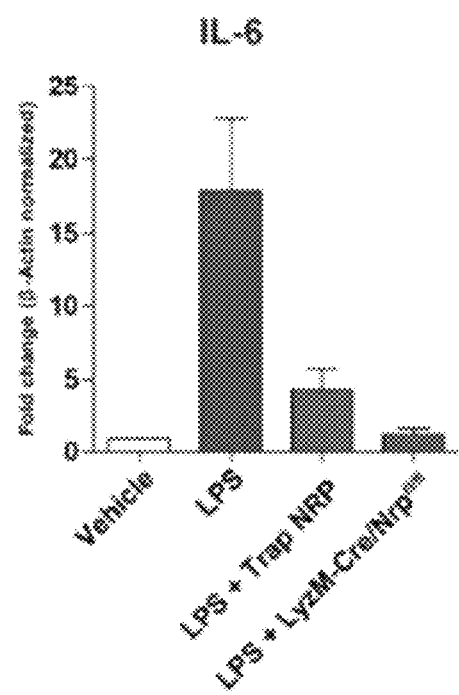

Given the therapeutic benefit of NRP1-trap on survival rates in septic shock, the impact of neutralization of NRP1 ligands on production of inflammatory cytokines during septic shock was next determined. Wild-type mice were administered i) vehicle (n=3); ii) LPS (15 mg/kg) (n=3) or iii) LPS and NRP1 mouse Trap 1 (without FC, FIG. 19C SEQ ID NO: 25, but without FC region) and brains were collected 6 hours post LPS injection. Injection of NRP1 trap-1 profoundly reduced production of TNF-α (FIG. 17A) and IL-6 (FIG. 17B). Similarly, mice with NRP1 deficient myeloid cells (LyzM-Cre/Nrp$^{fl/fl}$) (n=3) produced considerably less TNF-α and IL-6, underscoring the contribution of this cellular pathway to the progression of septic shock.

Example 20

Materials and Method for the Cerebral Ischemiaistroke Model Described in Example 21

The mice used in this study were 2- to 3-month old male C57Bl/6 mice (22-28 g).

MCAO model. MCAO mouse model was performed using the intraluminal suture technique described by Rousselet et al. (66). Briefly, mice were anesthetized in a chamber with 3% isoflurane in oxygen (1 L/min) and analgesized with buprenorphine (0.1 mg/kg body weight subcutaneously). Anesthesia was maintained during the operation using 1.5% isoflurane in oxygen provided via a face mask. The rectal temperature was recorded and kept stable at 37±0.5° C. with a heating pad. After a midline incision at the neck, the right carotid bifurcation was exposed and the common carotid artery (CCA) was temporarily occluded using 5-0 silk suture. The bifurcation of the right internal common carotid artery (ICA) and external common carotid artery (ECA) was separated. A permanent suture was placed around the ECA, as distally as possible, and another temporary suture slightly tight was placed on the ECA distal to the bifurcation. The right ICA was temporarily occluded with 5-0 silk suture to avoid bleeding. Then, a small hole in the ECA was cut between permanent and temporary sutures through which a 12 mm-long 6-0 silicon-coated (about 9-10 mm was coated with silicon) monofilament suture was introduced. The filament was advanced from the ECA into the lumen of the ICA until it blocked the origin of the middle cerebral artery (MCA) in the circle of Willis. Sham animals were obtained by inserting the monofilament into the CCA, but without advancing it to the MCA. The suture on the ECA was tightly tied to fix the monofilament in position. Thirty minutes after MCAO, the monofilament was completely removed to allow reperfusion. The temporary suture on the CCA was also removed to allow blood recirculation. After the wound was closed, 1 ml of saline solution was injected subcutaneously to avoid postsurgical dehydration. The mouse was placed in a cage and kept on the heating pad for 1 h. Meantime, when the mouse was fully awake from anesthesia, it was checked for some basic motor deficits (circling while walking and bending while hold by tail; indicators of the success of the operation) and NRP1-Trap-1 without FC (FIG. 19B SEQ ID NO:83) at the dose of 0.4 ug in 125 ul of PBS was administered to the tail vein (about 15 min after reperfusion had been started). Control animals operated in the same way as NRP1-treated animals received, after MCAO, a vehicle (PBS). Because post-surgical weight loss is generally observed, mashed food was placed in a Petri dish to encourage eating.

Determination of infarct volume. Following neurological evaluation (see section below) performed 24 h after MCAO the animals were deeply anesthetized with 3% isoflurane in oxygen (1 L/min) and decapitated. The brains were immediately isolated and transferred into isopentane cooled on dry ice and then stored at −80° C. Then, the frozen brains were coronally cut into 20-μm sections in a cryostat at −22° C. and every 15$^{th}$ slice was mounted on positively charged glass slides. Cerebral sections were stained with cresyl violet for 15 min. Each section was photographed. The areas of infarction were delineated on the basis of the relative lack of staining in the ischemic region and measured by using NIH ImageJ software. Infarct area in each section was determined as the total area of the contralateral hemisphere minus the non-affected area of the ipsilateral hemisphere.

Neurological evaluation. One hour after operation, as well as 24 h after MCAO, animals were subjected to a series of motor tests performed. The examinations and scoring were as follows: 0, Normal; 1, Contralateral front or rear limb flexion upon lifting of the whole animal by the tail; 2, Circling to the contralateral side while walking and C-shaped lateral bending while hold by tail; 4 Circling to the contralateral side while walking and C-shaped lateral bending while hold by tail with limb flexion; 5, Comatose or moribund. The magnitude of the obtained neuroscore is directly proportional to the severity of impairment.

Example 21

NRP1-Trap Protects Against Cerebral Ischemia and Stroke

Figure 18A:
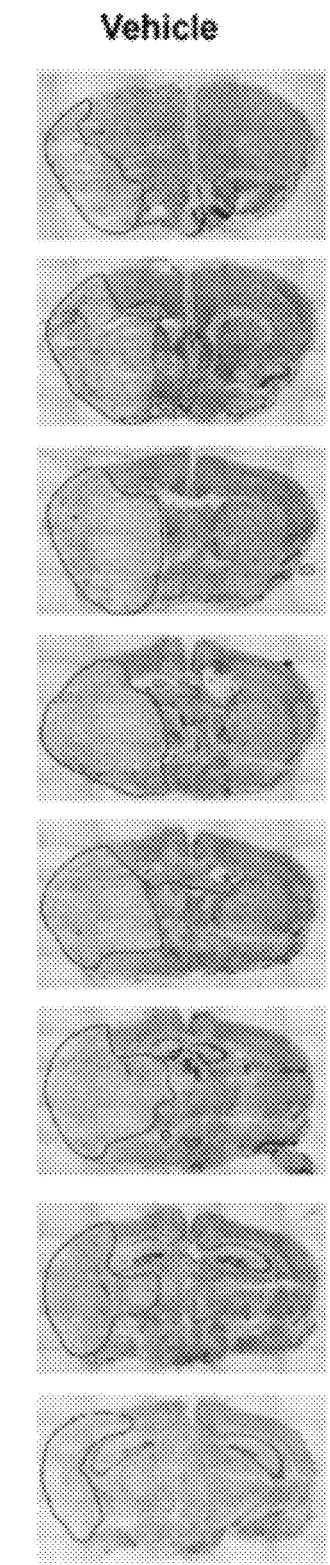
FIGS. 18A-18E shows that administration of NRP1 derived trap protects against ischemic stroke. Mice were subjected to transient middle cerebral artery occlusion (MCAO) and administered vehicle or NRP1 trap and the size of the infarct (stroke) measured on coronal cerebral sections stained with cresyl violet. The unstained area corresponds to the damaged area.
Figure 18B:
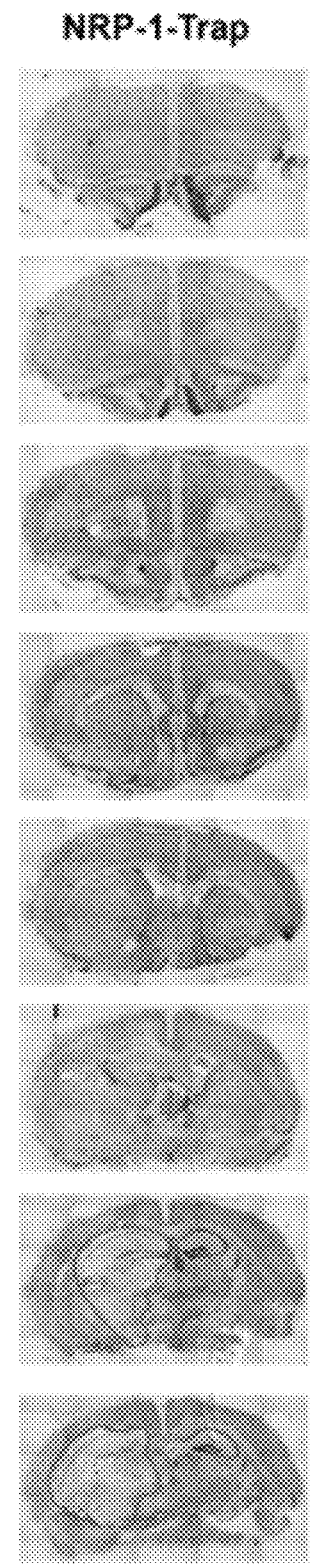
Figure 18C:
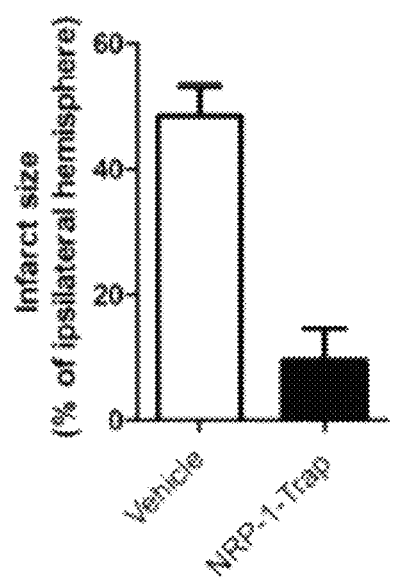

In order to assess the outcome of SEMA3A neutralization on cerebral ischemia or stroke, adult (8-12 week-old) mice were subjected to the transient middle cerebral artery occlusion (MCAO) model. Experimental details are provided in Example 20. Briefly, following termination of MCAO, mouse NRP1-trap (Trap-1, without FC,), 0.4 ug in 125 ul of PBS, (FIG. 19C, FIG. 20X-20Y; SEQ ID NO: 25) was administered to the tail vein (about 15 min after reperfusion had been started). In order to visualize brain damage induced by MCAO, coronal cerebral sections were stained with cresyl violet. On each section, the unstained area corresponded to the ischemic region of the brain (FIG. 18A). Measurement of these areas on serial coronal sections revealed that 24 h after MCAO, the infarcted zone constituted 48% of the ipsilateral hemisphere in occluded mice compared to sham operated animals whose brains were not injured. NRP1 treatment reduced brain damage; the infarct volume of the ipsilateral hemisphere was decreased by 80% (FIG. 18B,C).

Figure 18D:
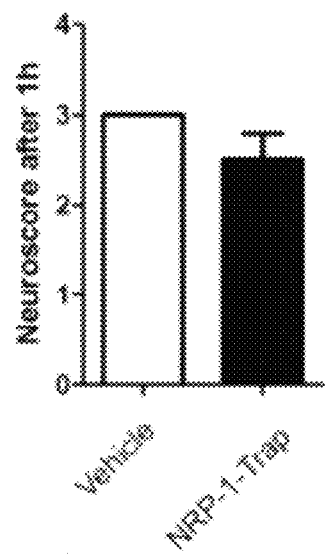
Figure 18E:
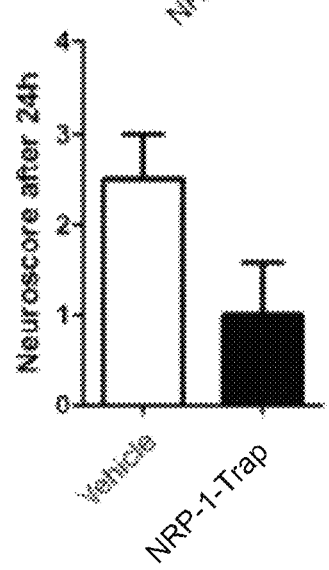
Figure 19D:
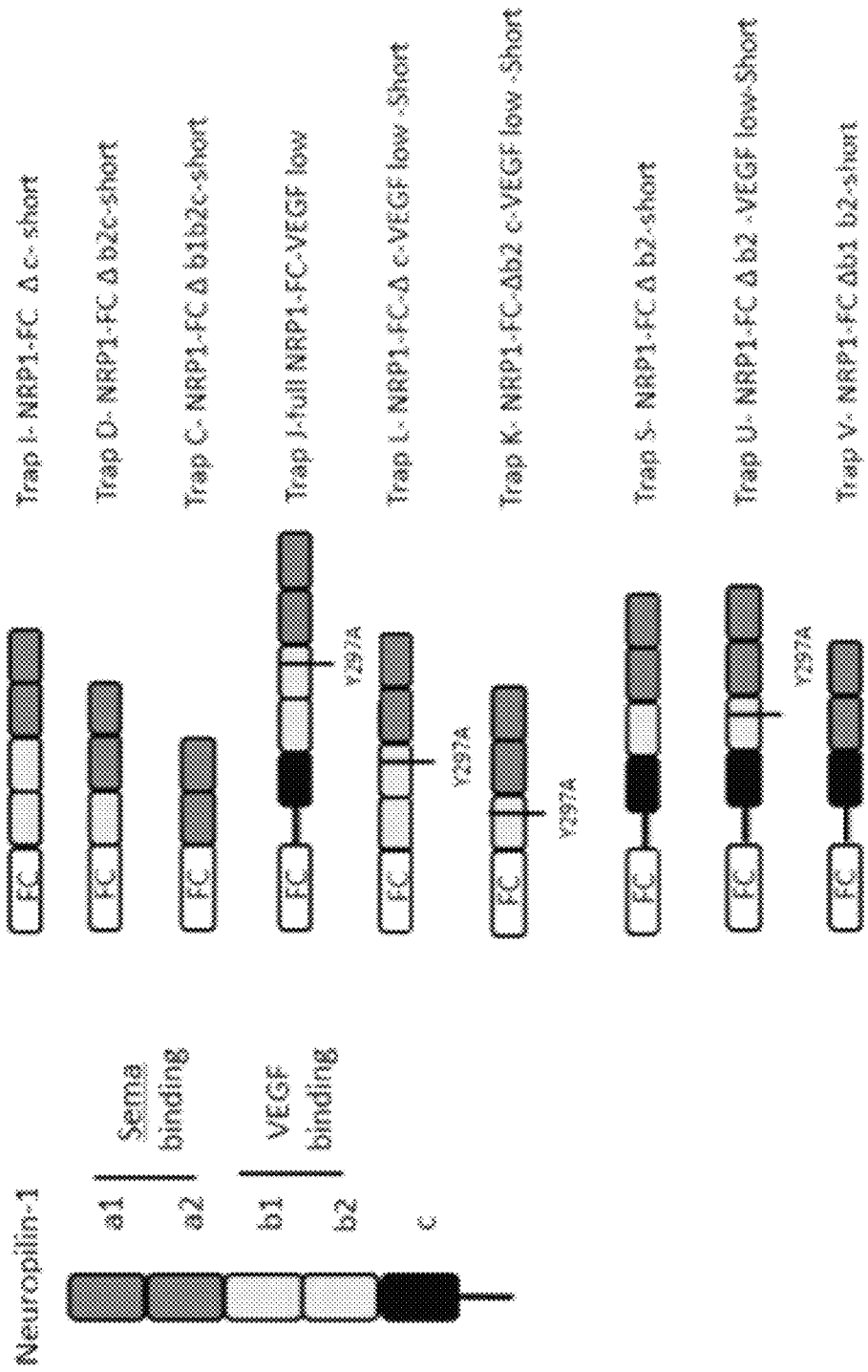
Figure 19E:
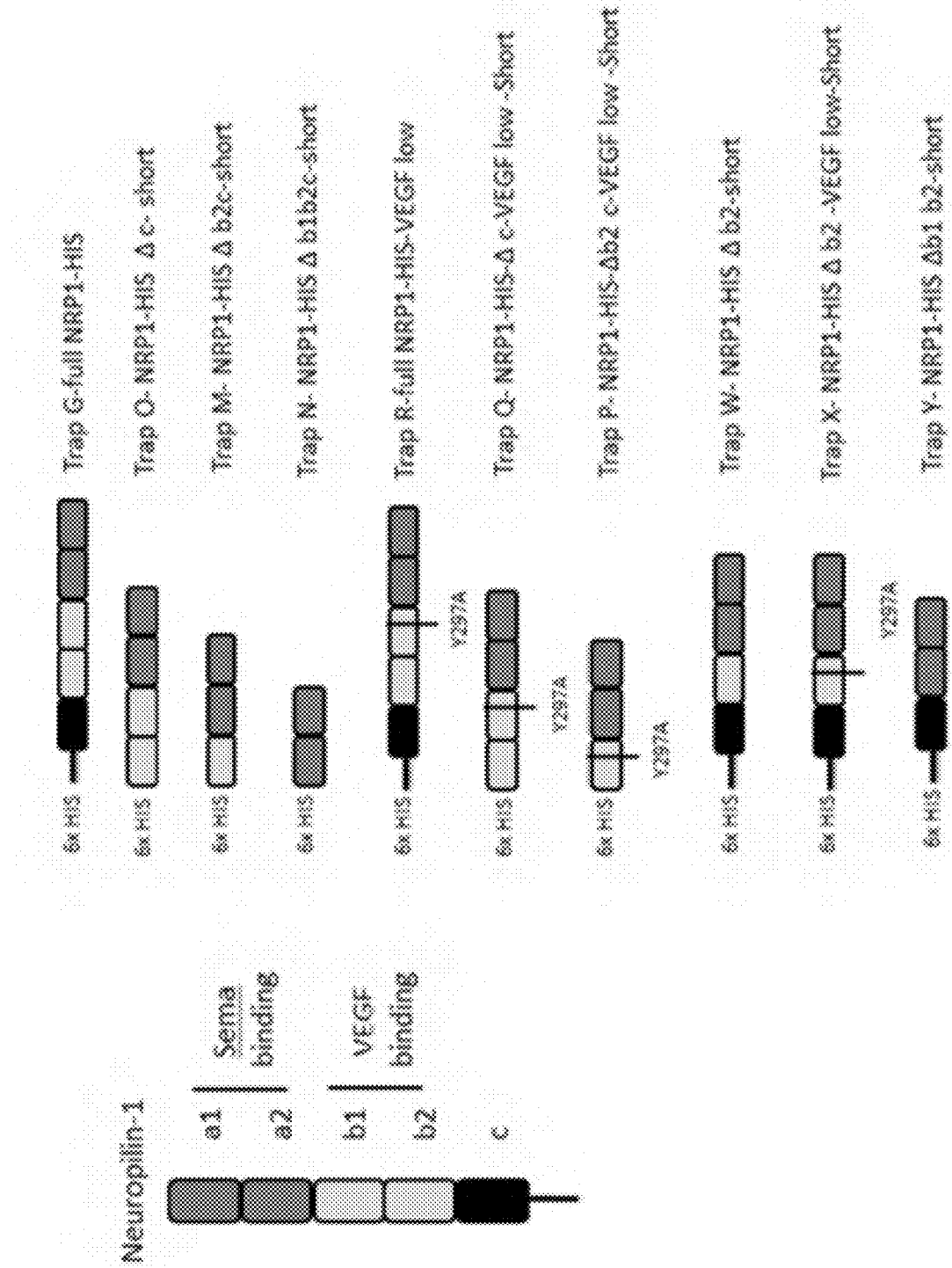
Figure 19F:
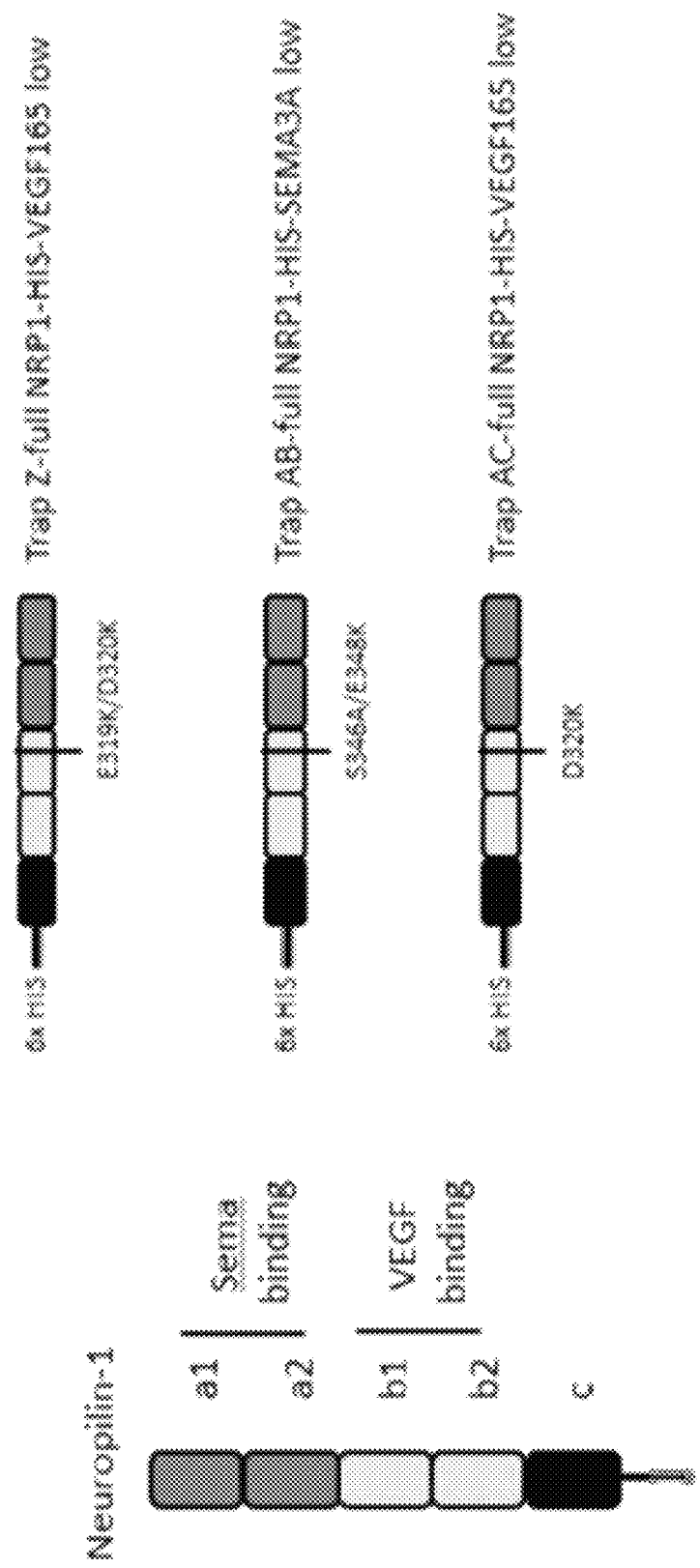

Neurological impairment was assessed by neurological scoring of the presence of limb flexion, C-shaped lateral bending of the body and circling movements. MCAO mice that were not showing circling and bending behaviour 1 hour after operation were excluded from the further study (FIG. 18D). Forelimb or hindlimb flexion, C-shaped lateral bending of the body, circling movements were observed in mice subjected to MCAO compared to sham operated animals. NRP1 treatment dramatically improved neurological scores of ischemic mice by 60% compared to non-treated MCAO mice when evaluated 24 hours after surgery (FIG. 18E).

Taken together, these results show that inhibition of the NRP1 pathway protects against cerebral ischemia and stroke and reduce the neurological impairment associated with cerebral ischemia and stroke.

Example 22

Neuropilin-Derived Traps Enhance Vascular Regeneration and Prevent Pathological Neovascularization in Ischemic Retinas in Mouse Model of Diabetic Retinopathy and Retinopathy of Prematurity Pathological vascular degeneration as well as pre-retinal vascular proliferation were studied using the well-established mouse model of oxygen-induced proliferative retinopathy (OIR)(Smith et al., 1994). This model is based on retinopathy of prematurity (ROP) and is regularly used as a proxy for the proliferative (angiogenic phase) of diabetic retinopathy and ROP.

Nursing mothers and their pups were exposed to 75% oxygen from P7-P12. Both vaso-degenerative (assessed at P12) and vaso-proliferative (assessed at P17) phases are present and are highly reproducible making evaluation of interventions on disease progression accurate and swift. Trap G (SEQ ID NO: 38), or Trap M (lacking the b2 and c domains, SEQ ID NO: 42), was injected into the vitreous at P12 (1 ul at 0.5 ug/ul). Dissected retinas were flatmounted and incubated overnight with fluoresceinated isolectin B4 (1:100) in 1 mM $CaCl_2$ to determine extent of avascular area or neovascularization area at P17. Avascular areas were determined in lectin stained retinas as zones devoid of staining. Neovascularization was determined as areas of saturated lectin staining which demarcates pre-retinal tufts (54, 55).

Figure 23A:
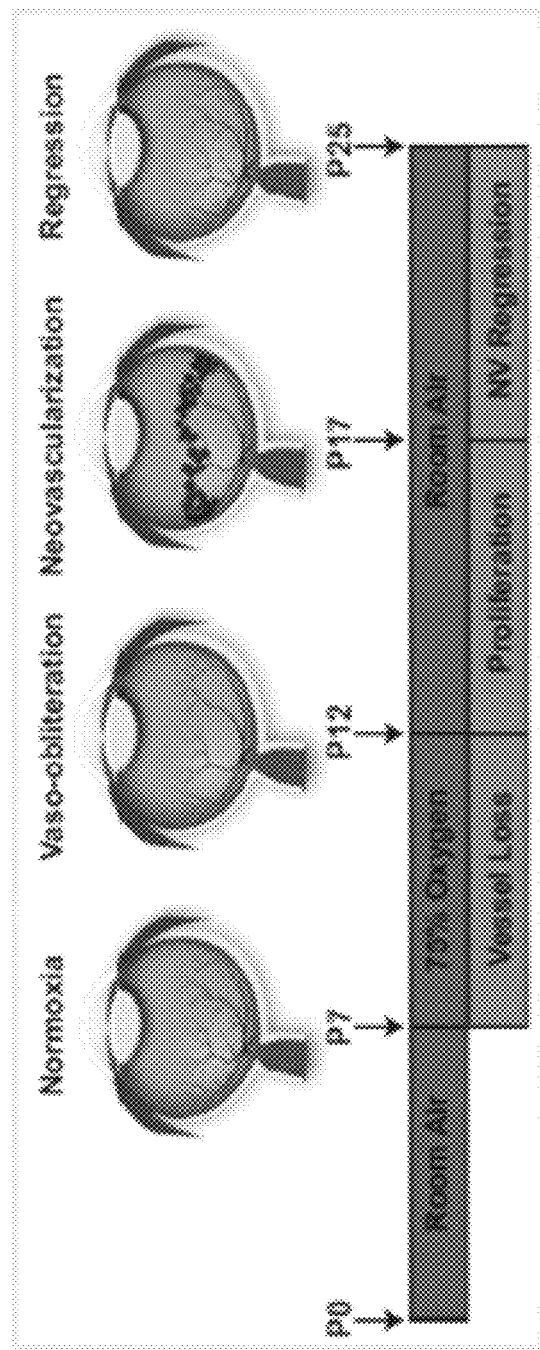

Trap G, was shown to effectively enhance vascular regeneration by over 40% when compared to vehicle control (FIG. 23B). Similarly, Trap G was shown to inhibit pathological neovascularization by ~45% (FIG. 23C). Trap-M enhanced vascular regeneration by ~60% (FIG. 23B) and inhibited pathological neovascularization by ~60% when compared to vehicle controls (FIG. 23C). Hence, Trap M, with compromised VEGF binding, more effectively prevents pathological angiogenesis and more readily leads to enhanced vascular regeneration in the ischemic retina.

Example 23

Neuropilin-Derived Traps Decrease Vascular Leakage in Diabetic Retinas

Figure 24A:
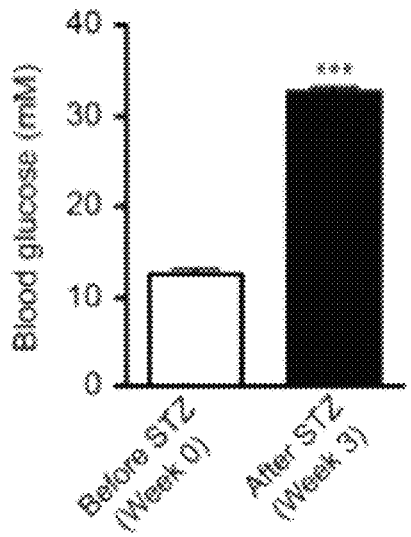
FIGS. 24A-24C show that SEMA3A trap prevents vascular leakage and edema in diabetic retinas.

The influence of Traps on vascular leakage/permeability in diabetic retinopathy was also studied in the streptozotocin (STZ) model of Type 1 diabetes. STZ (55 mg/kg) was administered over 5 consecutive days to ~6 week-old C57BL/6J mice and glycemia was monitored. Mice were considered diabetic if their non-fasted glycemia was higher than 17 mM (300 mg/dL). Mice were administered intravitreally with 0.5 ug (0.5 ug/ul) of Trap G (SEQ ID NO: 38) or M (SEQ ID NO: 42) or with mouse anti-VEGF antibody (AF-493-NA, from R&D) at 6 and 7 weeks after STZ administration. Alternatively, mice were injected intravitreally at 12 and 13 weeks post STZ and vascular permeability assessed at 14 weeks. Mice were hyperglycemic/diabetic at least 3 weeks prior to intravitreal injections with SEMA traps (see FIG. 24A) or anti VEGF antibody. Retinal vascular leakage was determined by Evans Blue assay at 8 weeks post STZ injections as follows. Retinal Evans Blue (EB) permeation was performed using 3 retinas per reading. Evan Blue was injected at 45 mg/kg intravenously and allowed to circulate for 2 hours prior to retinal extraction. Evans Blue Permeation was quantified in retinas by fluorimetry (620 nm max absorbance-740 nm min absorbance (background) with a TECAN Infinite® M1000 PRO. Evan Blue Permeation (EBP) [measured in uL/(grams*hour)] was calculated as follows: [EB (ug)/Wet retinal weight (g)]/[plasma EB (ug/uL)*Circulation time (hours)]. Evans Blue permeation was expressed relative to controls.

Figure 24B:
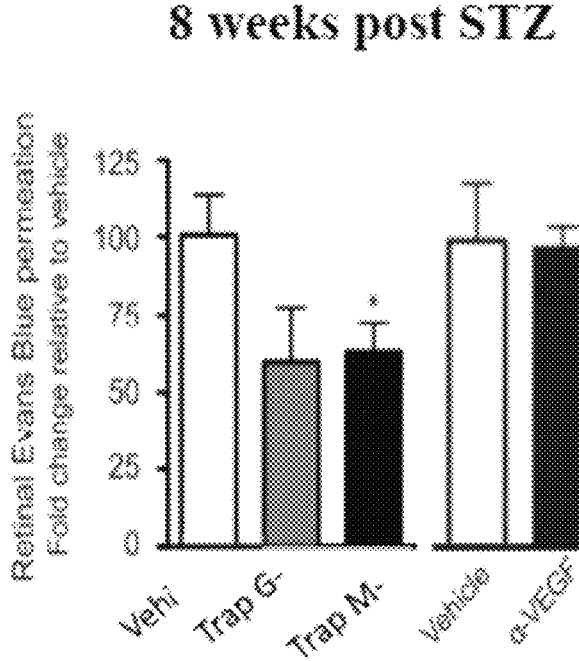

Both Trap-G (SEQ ID NO: 38) and Trap-M (SEQ ID NO: 42) significantly reduced vascular permeability by over 40% (FIG. 24B). The mouse anti-VEGF antibody (AF-493-NA) did not prevent vascular permeability at this early stage.

Figure 24C:
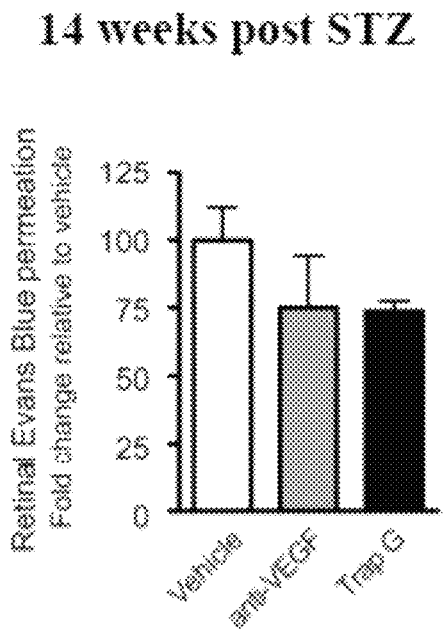

Trap G was effective at reducing vascular leakage as was the anti-VEGF neutralizing Ab at P17 (FIG. 24C), *p<0.05, n=4, from 12 animals.

Example 24

Neuropilin-Derived Traps Decrease Choroidal Neovascularization in Model of Age-Related Macular Degeneration The effect of NRP1 trap G (SEQ ID NO: 38) on choroidal neovascularization (CNV) was determined in a mouse model of age-related macular degeneration (AMD). To induce CNV and thus mimic wet AMD in mice, laser coagulations on 6-8 week old mice (1-2 disc diameters) were performed from the papillae using an Argon laser (532 nm) mounted on a Coherent slit lamp (400 mW, 50 ms and 50 µm) (Combadiere et al., 2007). Following laser burn, treated mice were injected intravitreally with 0.5 ug of Trap G. Fourteen days (P14) later, choroids were radially incised, flat-mounted and stained with the endothelial cell marker fluoresceinated Isolectin B4 (animals were also optionally perfused with fluorescein dextran to visualize luminal vessels) and volumes of CNV were measured by scanning laser confocal microscopy (Takeda et al., 2009).

Trap G was shown to significantly reduce choroidal neovascularization at day 14 post laser-burn (FIG. 25 B).

The scope of the claims should not be limited by the preferred embodiments set forth in the examples, but should be given the broadest interpretation consistent with the description as a whole.

REFERENCES

1. Lampron, A., Elali, A., and Rivest, S. 2013. Innate immunity in the CNS: redefining the relationship between the CNS and Its environment. *Neuron* 78:214-232.
2. Ousman, S. S., and Kubes, P. 2012. Immune surveillance in the central nervous system. *Nat Neurosci* 15:1096-1101.
3. Adamis, A. P., and Berman, A. J. 2008. Immunological mechanisms in the pathogenesis of diabetic retinopathy. *Semin Immunopathol* 30:65-84.
4. Antonetti, D. A., Klein, R., and Gardner, T. W. 2012. Diabetic retinopathy. *N Engl J Med* 366:1227-1239.
5. Joussen, A. M., Poulaki, V., Le, M. L., Koizumi, K., Esser, C., Janicki, H., Schraermeyer, U., Kociok, N., Fauser, S., Kirchhof, B., et al. 2004. A central role for inflammation in the pathogenesis of diabetic retinopathy. *FASEB J* 18:1450-1452.
6. Ambati, J., and Fowler, B. J. 2012. Mechanisms of age-related macular degeneration. *Neuron* 75:26-39.
7. Sennlaub, F., Auvynet, C., Calippe, B., Lavalette, S., Poupel, L., Hu, S. J., Dominguez, E., Camelo, S., Levy, O., Guyon, E., et al. 2013. CCR2(+) monocytes infiltrate atrophic lesions in age-related macular disease and mediate photoreceptor degeneration in experimental subretinal inflammation in Cx3cr1 deficient mice. *EMBO Mol Med* 5:1775-1793.
8. Combadiere, C., Feumi, C., Raoul, W., Keller, N., Rodero, M., Pezard, A., Lavalette, S., Houssier, M., Jonet, L., Picard, E., et al. 2007. CX3CR1-dependent subretinal microglia cell accumulation is associated with cardinal features of age-related macular degeneration. *J Clin Invest* 117:2920-2928.
9. Dammann, O. 2010. Inflammation and retinopathy of prematurity. *Acta Paediatr* 99:975-977.
10. Tremblay, S., Miloudi, K., Chaychi, S., Favret, S., Binet, F., Polosa, A., Lachapelle, P., Chemtob, S., and Sapieha, P. 2013. Systemic inflammation perturbs developmental retinal angiogenesis and neuroretinal function. *Invest Ophthalmol Vis Sci* 54:8125-8139.
11. Hartnett, M. E., and Penn, J. S. 2012. Mechanisms and management of retinopathy of prematurity. *N Engl J Med* 367:2515-2526.
12. Kempen, J. H., O'Colmain, B. J., Leske, M. C., Haffner, S. M., Klein, R., Moss, S. E., Taylor, H. R., and Hamman, R. F. 2004. The prevalence of diabetic retinopathy among adults in the United States. *Arch Ophthalmol* 122:552-563.
13. Sapieha, P., Hamel, D., Shao, Z., Rivera, J. C., Zaniolo, K., Joyal, J. S., and Chemtob, S. 2010. Proliferative retinopathies: angiogenesis that blinds. *Int J Biochem Cell Biol* 42:5-12.
14. Robinson, G. S., Ju, M., Shih, S. C., Xu, X., McMahon, G., Caldwell, R. B., and Smith, L. E. 2001. Nonvascular role for VEGF: VEGFR-1, 2 activity is critical for neural retinal development. *FASEB J* 15:1215-1217.
15. Saint-Geniez, M., Maharaj, A. S., Walshe, T. E., Tucker, B. A., Sekiyama, E., Kurihara, T., Darland, D. C., Young, M. J., and D'Amore, P. A. 2008. Endogenous VEGF is required for visual function: evidence for a survival role on muller cells and photoreceptors. *PLoS One* 3:e3554.
16. Hellstrom, A., Smith, L. E., and Dammann, O. 2013. Retinopathy of prematurity. *Lancet*.
17. Sapieha, P. 2012. Eyeing central neurons in vascular growth and reparative angiogenesis. *Blood* 120:2182-2194.
18. Kern, T. S., and Barber, A. J. 2008. Retinal ganglion cells in diabetes. *J Physiol* 586:4401-4408.
19. Binet, F., Mawambo, G., Sitaras, N., Tetreault, N., Lapalme, E., Favret, S., Cerani, A., Leboeuf, D., Tremblay, S., Rezende, F., et al. 2013. Neuronal ER Stress Impedes Myeloid-Cell-Induced Vascular Regeneration through IRElalpha Degradation of Netrin-1. *Cell Metab* 17:353-371.
20. Cerani A, T. N., Menard C, Lapalme E, Patel C, Sitaras N, Beaudoin F, Leboeuf D, De Guire V, Binet F, Dejda A, Rezende F, Miloudi K, Sapieha P. 2013. Neuron-Derived Semaphorin 3A is an Early Inducer of Vascular Permeability in Diabetic Retinopathy via Neuropilin-1. *Cell Metabolism.*, 18(4): 505-518.
21. Joyal, J.-S., Sitaras, N., Binet, F., Rivera, J. C., Stahl, A., Zaniolo, K., Shao, Z., Polosa, A., Zhu, T., Hamel, D., et al. 2011. Ischemic neurons prevent vascular regeneration of neural tissue by secreting semaphorin 3A. *Blood* 117: 6024-6035.
22. Checchin, D., Sennlaub, F., Levavasseur, E., Leduc, M., and Chemtob, S. 2006. Potential role of microglia in retinal blood vessel formation. *Invest Ophthalmol Vis Sci* 47:3595-3602.
23. Connor, K. M., SanGiovanni, J. P., Lofqvist, C., Aderman, C. M., Chen, J., Higuchi, A., Hong, S., Pravda, E. A., Majchrzak, S., Carper, D., et al. 2007. Increased dietary intake of omega-3-polyunsaturated fatty acids reduces pathological retinal angiogenesis. *Nat Med* 13:868-873.
24. Sapieha, P., Stahl, A., Chen, J., Seaward, M. R., Willett, K. L., Krah, N. M., Dennison, R. J., Connor, K. M., Aderman, C. M., Liclican, E., et al. 2011. 5-Lipoxygenase Metabolite 4-HDHA Is a Mediator of the Antiangiogenic Effect of {omega}-3 Polyunsaturated Fatty Acids. *Sci Transl Med* 3:69ra12.
25. Stahl, A., Sapieha, P., Connor, K. M., Sangiovanni, J. P., Chen, J., Aderman, C. M., Willett, K. L., Krah, N. M., Dennison, R. J., Seaward, M. R., et al. 2010. Short communication: PPAR gamma mediates a direct antiangiogenic effect of omega 3-PUFAs in proliferative retinopathy. *Circ Res* 107(4):495-500.

26. Smith, L. E., Wesolowski, E., McLellan, A., Kostyk, S. K., D'Amato, R., Sullivan, R., and D'Amore, P. A. 1994. Oxygen-induced retinopathy in the mouse. *Invest Ophthalmol Vis Sci* 35:101-111.

27. Lee, P., Goishi, K., Davidson, A. J., Mannix, R., Zon, L., and Klagsbrun, M. 2002. Neuropilin-1 is required for vascular development and is a mediator of VEGF-dependent angiogenesis in zebrafish. *Proc Natl Acad Sci USA* 99:10470-10475.

28. Gluzman-Poltorak, Z., Cohen, T., Shibuya, M., and Neufeld, G. 2001. Vascular endothelial growth factor receptor-1 and neuropilin-2 form complexes. *J Biol Chem* 276:18688-18694.

29. Mamluk, R., Gechtman, Z., Kutcher, M. E., Gasiunas, N., Gallagher, J., and Klagsbrun, M. 2002. Neuropilin-1 binds vascular endothelial growth factor 165, placenta growth factor-2, and heparin via its b1 b2 domain. *J Biol Chem* 277:24818-24825.

30. Soker, S., Takashima, S., Miao, H. Q., Neufeld, G., and Klagsbrun, M. 1998. Neuropilin-1 is expressed by endothelial and tumor cells as an isoform-specific receptor for vascular endothelial growth factor. *Cell* 92:735-745.

31. Fantin, A., Vieira, J. M., Gestri, G., Denti, L., Schwarz, Q., Prykhozhij, S., Peri, F., Wilson, S. W., and Ruhrberg, C. 2010. Tissue macrophages act as cellular chaperones for vascular anastomosis downstream of VEGF-mediated endothelial tip cell induction. *Blood* 116:829-840.

32. Carrer, A., Moimas, S., Zacchigna, S., Pattarini, L., Zentilin, L., Ruozi, G., Mano, M., Sinigaglia, M., Maione, F., Serini, G., et al. 2012. Neuropilin-1 identifies a subset of bone marrow Gr1− monocytes that can induce tumor vessel normalization and inhibit tumor growth. *Cancer Res* 72:6371-6381.

33. Casazza, A., Laoui, D., Wenes, M., Rizzolio, S., Bassani, N., Mambretti, M., Deschoemaeker, S., Van Ginderachter, J. A., Tamagnone, L., and Mazzone, M. 2013. Impeding Macrophage Entry into Hypoxic Tumor Areas by SEMA3A/Nrp1 Signaling Blockade Inhibits Angiogenesis and Restores Antitumor Immunity. *Cancer Cell* 24:695-709.

34. Ritter, M. R., Banin, E., Moreno, S. K., Aguilar, E., Dorrell, M. I., and Friedlander, M. 2006. Myeloid progenitors differentiate into microglia and promote vascular repair in a model of ischemic retinopathy. *J Clin Invest* 116:3266-3276.

35. Stahl, A., Chen, J., Sapieha, P., Seaward, M. R., Krah, N. M., Dennison, R. J., Favazza, T., Bucher, F., Lofqvist, C., Ong, H., et al. 2010. Postnatal Weight Gain Modifies Severity and Functional Outcome of Oxygen-Induced Proliferative Retinopathy. *Am J Pathol.* 177(6): 2715-2733.

36. Clausen, B. E., Burkhardt, C., Reith, W., Renkawitz, R., and Forster, I. 1999. Conditional gene targeting in macrophages and granulocytes using LysMcre mice. *Transgenic Res* 8:265-277.

37. Mattapallil, M. J., Wawrousek, E. F., Chan, C. C., Zhao, H., Roychoudhury, J., Ferguson, T. A., and Caspi, R. R. 2012. The Rd8 mutation of the Crb1 gene is present in vendor lines of C57BL/6N mice and embryonic stem cells, and confounds ocular induced mutant phenotypes. *Invest Ophthalmol Vis Sci* 53:2921-2927.

38. Klebanov, O., Nitzan, A., Raz, D., Barzilai, A., and Solomon, A. S. 2009. Upregulation of Semaphorin 3A and the associated biochemical and cellular events in a rat model of retinal detachment. *Graefes Arch Clin Exp Ophthalmol* 247:73-86.

39. Koppel, A. M., and Raper, J. A. 1998. Collapsin-1 covalently dimerizes, and dimerization is necessary for collapsing activity. *J Biol Chem* 273:15708-15713.

40. Neufeld, G., and Kessler, O. 2008. The semaphorins: versatile regulators of tumour progression and tumour angiogenesis. *Nat Rev Cancer* 8:632-645.

41. Worthylake, R. A., and Burridge, K. 2003. RhoA and ROCK promote migration by limiting membrane protrusions. *J Biol Chem* 278:13578-13584.

42. Dammann, O., Brinkhaus, M. J., Bartels, D. B., Dordelmann, M., Dressier, F., Kerk, J., Dork, T., and Dammann, C. E. 2009. Immaturity, perinatal inflammation, and retinopathy of prematurity: a multi-hit hypothesis. *Early Hum Dev* 85:325-329.

43. Kastelan, S., Tomic, M., Gverovic Antunica, A., Salopek Rabatic, J., and Ljubic, S. 2013. Inflammation and pharmacological treatment in diabetic retinopathy. *Mediators Inflamm* 2013:213130.

44. Silva, P. S., Cavallerano, J. D., Sun, J. K., Aiello, L. M., and Aiello, L. P. 2010. Effect of systemic medications on onset and progression of diabetic retinopathy. *Nat Rev Endocrinol* 6:494-508.

45. Cerani, A., Tetreault, N., Menard, C., Lapalme, E., Patel, C., Sitaras, N., Beaudoin, F., Leboeuf, D., De Guire, V., Binet, F., et al. 2013. Neuron-derived semaphorin 3A is an early inducer of vascular permeability in diabetic retinopathy via neuropilin-1. *Cell Metab* 18:505-518.

46. Miao, H. Q., Soker, S., Feiner, L., Alonso, J. L., Raper, J. A., and Klagsbrun, M. 1999. Neuropilin-1 mediates collapsin-1/semaphorin III inhibition of endothelial cell motility: functional competition of collapsin-1 and vascular endothelial growth factor-165. *J Cell Biol* 146:233-242.

47. Klagsbrun, M., and Eichmann, A. 2005. A role for axon guidance receptors and ligands in blood vessel development and tumor angiogenesis. *Cytokine Growth Factor Rev* 16:535-548.

48. Guttmann-Raviv, N., Shraga-Heled, N., Varshavsky, A., Guimaraes-Sternberg, C., Kessler, O., and Neufeld, G. 2007. Semaphorin-3A and semaphorin-3F work together to repel endothelial cells and to inhibit their survival by induction of apoptosis. *J Biol Chem* 282:26294-26305.

49. Neufeld, G., Sabag, A. D., Rabinovicz, N., and Kessler, O. 2012. Semaphorins in angiogenesis and tumor progression. Cold Spring Harb Perspect Med 2:a006718.

50. Bussolino, F., Valdembri, D., Caccavari, F., and Serini, G. 2006. Semaphoring vascular morphogenesis. *Endothelium* 13:81-91.

51. Yancopoulos, G. D. 2010. Clinical application of therapies targeting VEGF. *Cell* 143:13-16.

52. Miloudi, K., Dejda, A., Binet, F., Lapalme, E., Cerani, A., and Sapieha, P. 2014. Assessment of vascular regeneration in the CNS using the mouse retina. *J Vis Exp.* 88: e51351.

53. Sapieha, P., Joyal, J. S., Rivera, J. C., Kermorvant-Duchemin, E., Sennlaub, F., Hardy, P., Lachapelle, P., and Chemtob, S. 2010. Retinopathy of prematurity: understanding ischemic retinal vasculopathies at an extreme of life. *J Clin Invest* 120:3022-3032.

54. Stahl, A., Connor, K. M., Sapieha, P., Chen, J., Dennison, R. J., Krah, N. M., Seaward, M. R., Willett, K. L., 54. Aderman, C. M., Guerin, K. I., et al. 2010. The mouse retina as an angiogenesis model. *Invest Ophthalmol Vis Sci* 51:2813-2826.
55. Stahl, A., Connor, K. M., Sapieha, P., Willett, K. L., Krah, N. M., Dennison, R. J., Chen, J., Guerin, K. I., and Smith, L. E. 2009. Computer-aided quantification of retinal neovascularization. *Angiogenesis* 12:297-301.
56. Shao, Z., Friedlander, M., Hurst, C. G., Cui, Z., Pei, D. T., Evans, L. P., Juan, A. M., Tahir, H., Duhamel, F., Chen, J., et al. 2013. Choroid sprouting assay: an ex vivo model of microvascular angiogenesis. *PLoS One* 8:e69552.
57. Van Rooijen, N., and van Kesteren-Hendrikx, E. 2003. "In vivo" depletion of macrophages by liposome-mediated "suicide". *Methods Enzymol* 373:3-16.
58. Deutschman, C. S., and Tracey, K. J. 2014. Sepsis: current dogma and new perspectives. *Immunity* 40:463-475.
59. Bruder, D., Probst-Kepper, M., Westendorf, A. M., Geffers, R., Beissert, S., Loser, K., von Boehmer, H., Buer, J., and Hansen, W. 2004. Neuropilin-1: a surface marker of regulatory T cells. *Eur J Immunol* 34:623-630.
60. Takahashi, T., Fournier, A., Nakamura, F., Wang, L. H., Murakami, Y., Kalb, R. G., Fujisawa, H., and Strittmatter, S. M. 1999. Plexin-neuropilin-1 complexes form functional semaphorin-3A receptors. *Cell* 99:59-69.
61. Klagsbrun, M., Takashima, S., and Mamluk, R. 2002. The role of neuropilin in vascular and tumor biology. *Adv Exp Med Biol* 515:33-48.
62. Soker, S., Miao, H. Q., Nomi, M., Takashima, S., and Klagsbrun, M. 2002. VEGF165 mediates formation of complexes containing VEGFR-2 and neuropilin-1 that enhance VEGF165-receptor binding. *J Cell Biochem* 85:357-368.
63. Appleton, B. A., Wu, P., Maloney, J., Yin, J., Liang, W. C., Stawicki, S., Mortara, K., Bowman, K. K., Elliott, J. M., Desmarais, W., et al. 2007. Structural studies of neuropilin/antibody complexes provide insights into semaphorin and VEGF binding. *EMBO J* 26:4902-4912.
64. Vieira, J. M., Schwarz, Q., and Ruhrberg, C. 2007. Role of the neuropilin ligands $VEGF_{164}$ and SEMA3A in neuronal and vascular patterning in the mouse. *Novartis Found Symp* 283:230-235; discussion 235-241.
65. Geretti, E., Shimizu, A., and Klagsbrun, M. 2008. Neuropilin structure governs VEGF and semaphorin binding and regulates angiogenesis. *Angiogenesis* 11:31-39.
66. Rousselet, E., Kriz, J., Seidah, N. G. Mouse model of intraluminal MCAO: cerebral infarct evaluation by cresyl violet staining. *J Vis Exp.* 2012 Nov. 6; (69). pii: 4038. doi: 10.3791/4038.
67. Combadiere, C., C. Feumi, W. Raoul, N. Keller, M. Rodero, A. Pezard, S. Lavalette, M. Houssier, L. Jonet, E. Picard, P. Debre, M. Sirinyan, P. Deterre, T. Ferroukhi, S. Y. Cohen, D. Chauvaud, J. C. Jeanny, S. Chemtob, F. Behar-Cohen, and F. Sennlaub. 2007. CX3CR1-dependent subretinal microglia cell accumulation is associated with cardinal features of age-related macular degeneration. *J Clin Invest* 117:2920-2928.
68. Takeda, A., J. Z. Baffi, M. E. Kleinman, W. G. Cho, M. Nozaki, K. Yamada, H. Kaneko, R. J. Albuquerque, S. Dridi, K. Saito, B. J. Raisler, S. J. Budd, P. Geisen, A. Munitz, B. K. Ambati, M. G. Green, T. Ishibashi, J. D. Wright, A. A. Humbles, C. J. Gerard, Y. Ogura, Y. Pan, J. R. Smith, S. Grisanti, M. E. Hartnett, M. E. Rothenberg, and J. Ambati. 2009. CCR3 is a target for age-related macular degeneration diagnosis and therapy. *Nature* 460: 225-230.

---

The invention claimed is:

1. A fusion polypeptide comprising a neuropilin-1 (NRP1) polypeptide consisting of an amino acid sequence having at least 90% identity with residues 22-424 of SEQ ID NO: 107, wherein said fusion polypeptide does not comprise the b2 and c domains of native human NRP1 and has a purification tag linked to said NRP1 polypeptide.

2. The fusion polypeptide of claim 1, wherein said NRP1 polypeptide consists of an amino acid sequence having at least 95% identity with residues 22-424 of SEQ ID NO: 107.

3. The fusion polypeptide of claim 1, wherein said NRP1 polypeptide consists of residues 22-424 of SEQ ID NO: 107.

4. The fusion polypeptide of claim 3, further comprising a polypeptide linker between the NRP1 polypeptide and the purification tag.

5. The fusion polypeptide of claim 3, wherein the purification tag comprises a polyhistidine (His) tag.

6. The fusion polypeptide of claim 1, wherein said purification tag is carboxy-terminal relative to the NRP1 polypeptide in the fusion polypeptide.

7. The fusion polypeptide of claim 1, further comprising a polypeptide linker between the NRP1 polypeptide and the purification tag.

8. The fusion polypeptide of claim 7, wherein the purification tag comprises a polyhistidine (His) tag.

9. The fusion polypeptide of claim 7, wherein the polypeptide linker comprises a protease cleavage site.

10. The fusion polypeptide of claim 9, wherein the protease cleavage site comprises the sequence set forth in SEQ ID NO: 76.

11. The fusion polypeptide of claim 1, wherein the purification tag comprises a fragment crystallizable (Fc) domain.

12. The fusion polypeptide of claim 11, wherein said Fc domain comprises the amino acid sequence of SEQ ID NO: 37.

13. The fusion polypeptide of claim 1, wherein the purification tag comprises a polyhistidine (His) tag.

14. A pharmaceutical composition comprising the fusion polypeptide of claim 1 and at least one pharmaceutically acceptable excipient.

15. The pharmaceutical composition of claim 14, wherein said composition is an ophthalmic or ocular composition.

16. The pharmaceutical composition of claim 14, wherein said ophthalmic or ocular composition is an eye drop or injectable composition.

17. A pharmaceutical composition comprising the fusion polypeptide of claim 3 and at least one pharmaceutically acceptable excipient.

18. The pharmaceutical composition of claim 17, wherein said composition is an ophthalmic or ocular composition.

19. The pharmaceutical composition of claim 18, wherein said composition ophthalmic or ocular composition is an eye drop or injectable composition.

* * * * *

SEQUENCE LISTING

```
<160> NUMBER OF SEQ ID NOS: 128

<210> SEQ ID NO 1
<211> LENGTH: 1064
<212> TYPE: PRT
<213> ORGANISM: artificial sequence
<220> FEATURE:
<223> OTHER INFORMATION: Synthetic polypeptide

<400> SEQUENCE: 1

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125
```

-continued

```
Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
                260                 265                 270

Ser Ser Gln Tyr Ser Thr Asn Trp Ser Ala Glu Arg Ser Arg Leu Asn
    275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
                340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
    435                 440                 445

Gly Trp Ala Leu Pro Pro Ala Pro His Ser Tyr Ile Asn Glu Trp Leu
450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
    515                 520                 525

Glu Leu Arg Thr Phe Pro Ala Leu Ser Thr Arg Phe Ile Arg Ile Tyr
    530                 535                 540

Pro Glu Arg Ala Thr His Gly Gly Leu Gly Leu Arg Met Glu Leu Leu
```

-continued

```
545                 550                 555                 560
Gly Cys Glu Val Glu Ala Pro Thr Ala Gly Pro Thr Thr Pro Asn Gly
                565                 570                 575
Asn Leu Val Asp Glu Cys Asp Asp Gln Ala Asn Cys His Ser Gly
                580                 585                 590
Thr Gly Asp Asp Phe Gln Leu Thr Gly Gly Thr Thr Val Leu Ala Thr
                595                 600                 605
Glu Lys Pro Thr Val Ile Asp Ser Thr Ile Gln Ser Glu Phe Pro Thr
                610                 615                 620
Tyr Gly Phe Asn Cys Glu Phe Gly Trp Gly Ser His Lys Thr Phe Cys
625                 630                 635                 640
His Trp Glu His Asp Asn His Val Gln Leu Lys Trp Ser Val Leu Thr
                645                 650                 655
Ser Lys Thr Gly Pro Ile Gln Asp His Thr Gly Asp Gly Asn Phe Ile
                660                 665                 670
Tyr Ser Gln Ala Asp Glu Asn Gln Lys Gly Lys Val Ala Arg Leu Val
                675                 680                 685
Ser Pro Val Val Tyr Ser Gln Asn Ser Ala His Cys Met Thr Phe Trp
                690                 695                 700
Tyr His Met Ser Gly Ser His Val Gly Thr Leu Arg Val Lys Leu Arg
705                 710                 715                 720
Tyr Gln Lys Pro Glu Glu Tyr Asp Gln Leu Val Trp Met Ala Ile Gly
                725                 730                 735
His Gln Gly Asp His Trp Lys Glu Gly Arg Val Leu His Lys Ser
                740                 745                 750
Leu Lys Leu Tyr Gln Val Ile Phe Glu Gly Glu Ile Gly Lys Gly Asn
                755                 760                 765
Leu Gly Gly Ile Ala Val Asp Asp Ile Ser Ile Asn Asn His Ile Ser
                770                 775                 780
Gln Glu Asp Cys Ala Lys Pro Ala Asp Leu Asp Lys Lys Asn Pro Glu
785                 790                 795                 800
Ile Lys Ile Asp Glu Thr Gly Ser Thr Pro Gly Tyr Glu Gly Glu Gly
                805                 810                 815
Glu Gly Asp Lys Asn Ile Ser Arg Lys Pro Gly Asn Val Leu Lys Thr
                820                 825                 830
Leu Asp Pro Arg Ser Asp Lys Thr His Thr Cys Pro Pro Cys Pro Ala
                835                 840                 845
Pro Glu Leu Leu Gly Gly Pro Ser Val Phe Leu Phe Pro Pro Lys Pro
850                 855                 860
Lys Asp Thr Leu Met Ile Ser Arg Thr Pro Glu Val Thr Cys Val Val
865                 870                 875                 880
Val Asp Val Ser His Glu Asp Pro Glu Val Lys Phe Asn Trp Tyr Val
                885                 890                 895
Asp Gly Val Glu Val His Asn Ala Lys Thr Lys Pro Arg Glu Glu Gln
                900                 905                 910
Tyr Asn Ser Thr Tyr Arg Val Val Ser Val Leu Thr Val Leu His Gln
                915                 920                 925
Asp Trp Leu Asn Gly Lys Glu Tyr Lys Cys Lys Val Ser Asn Lys Ala
                930                 935                 940
Leu Pro Ala Pro Ile Glu Lys Thr Ile Ser Lys Ala Lys Gly Gln Pro
945                 950                 955                 960
Arg Glu Pro Gln Val Tyr Thr Leu Pro Pro Ser Arg Glu Glu Met Thr
                965                 970                 975
```

```
Lys Asn Gln Val Ser Leu Thr Cys Leu Val Lys Gly Phe Tyr Pro Ser
                980                 985                 990

Asp Ile Ala Val Glu Trp Glu Ser  Asn Gly Gln Pro Glu  Asn Asn Tyr
            995                 1000                1005

Lys Thr  Thr Pro Pro Val Leu  Asp Ser Asp Gly Ser  Phe Phe Leu
        1010                1015                1020

Tyr Ser  Lys Leu Thr Val Asp  Lys Ser Arg Trp Gln  Gln Gly Asn
        1025                1030                1035

Val Phe  Ser Cys Ser Val Met  His Glu Ala Leu His  Asn His Tyr
        1040                1045                1050

Thr Gln  Lys Ser Leu Ser Leu  Ser Pro Gly Lys
        1055                1060

<210> SEQ ID NO 2
<211> LENGTH: 3255
<212> TYPE: DNA
<213> ORGANISM: artificial sequence
<220> FEATURE:
<223> OTHER INFORMATION: Synthetic polynucleotide

<400> SEQUENCE: 2
atggagaggg ggctgccgct cctctgcgcc gtgctcgccc tcgtcctcgc cccggccggc       60
gcttttcgca acgataaatg tggcgatact ataaaaattg aaagccccgg gtaccttaca      120
tctcctggtt atcctcattc ttatcaccca agtgaaaaat gcgaatggct gattcaggct      180
ccggacccat accagagaat tatgatcaac ttcaaccctc acttcgattt ggaggacaga      240
gactgcaagt atgactacgt ggaagtcttc gatggagaaa atgaaaatgg acattttagg      300
ggaaagttct gtggaaagat agcccctcct cctgttgtgt cttcagggcc atttcttttt      360
atcaaatttg tctctgacta cgaaacacat ggtgcaggat tttccatacg ttatgaactt      420
ttcaagagag gtcctgaatg ttcccagaac tacacaacac ctagtggagt gataaagtcc      480 cccgattcc ctgaaaaata tcccaacagc cttgaatgca cttatattgt ctttgcgcca      540
aagatgtcag agattatcct ggaatttgaa agctttgacc tggagcctga ctcaaatcct      600
ccagggggga tgttctgtcg ctacgaccgg ctagaaatct gggatggatt ccctgatgtt      660
ggccctcaca ttgggcgtta ctgtggacag aaaacaccag tcgaatccg atcctcatcg      720 ggcattctct ccatggtttt ttacaccgac agcgcgatag caaagaagg tttctcagca      780 aactacagtg tcttgcagag cagtgtctca gaagatttca atgtatgga agctctgggc      840 atggaatcag agaaattca ttctgaccag atcacagctt cttcccagta tagcaccaac      900
tggtctgcag agcgctcccg cctgaactac cctgagaatg ggtggactcc cggagaggat      960
tcctaccgag agtggataca ggtagacttg ggccttctgc gctttgtcac ggctgtcggg     1020
acacagggcg ccatttcaaa agaaaccaag aagaaatatt atgtcaagac ttacaagatc     1080
gacgttagct ccaacgggga agactggatc accataaaag aaggaaacaa acctgttctc     1140
tttcagggaa acaccaaccc tacagatgtt gtggttgcag tattccccaa ccactgataa     1200
actcgatttg tccgaatcaa gcctgcaact tgggaaactg gcatatctat gagatttgaa     1260
gtatatggtt gcaagataac agattatcct tgctctggaa tgttgggtat ggtgtctgga     1320
cttatttctg actcccagat cacatcatcc aaccaagggg acagaaactg atgcctgaa      1380 aacatccgcc tggtaaccag tcgctctggc tgggcacttc acccgcacc tcattcctac      1440 atcaatgagt ggctccaaat agacctgggg gaggagaaga tcgtgagggg catcatcatt     1500
```

-continued

```
cagggtggga agcaccgaga gaacaaggtg ttcatgagga agttcaagat cgggtacagc    1560
aacaacggct cggactggaa gatgatcatg gatgacagca aacgcaaggc gaagtctttt    1620
gagggcaaca acaactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg aacttggtg     1800 gatgaatgtg atgacgacca ggccaactgc cacagtggaa caggtgatga cttccagctc    1860
acaggtggca ccactgtgct ggccacagaa aagcccacgg tcatagacag caccatacaa    1920
tcagagtttc aacatatgg ttttaactgt gaatttggct ggggctctca caagaccttc     1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca aagtggctcg cctggtgagc cctgtggttt attcccagaa ctctgcccac    2160
tgcatgacct tctggtatca catgtctggg tcccacgtcg gcacactcag ggtcaaactg    2220
cgctaccaga agccagagga gtacgatcag ctggtctgga tggccattgg acaccaaggt    2280
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400
aataaccaca tttcacaaga agattgtgca aaaccagcag acctggataa aaagaaccca    2460
gaaattaaaa ttgatgaaac agggagcacg ccaggatacg aaggtgaagg agaaggtgac    2520
aagaacatct ccaggaagcc aggcaatgtg ttgaagacct tagaccccag atctgacaaa    2580
actcacacat gcccaccgtg cccagcacct gaactcctgg ggggaccgtc agtcttcctc    2640
ttccccccaa aacccaagga caccctcatg atctcccgga cccctgaggt cacatgcgtg    2700
gtggtggacg tgagccacga agaccctgag gtcaagttca actggtacgt ggacggcgtg    2760
gaggtgcata atgccaagac aaagccgcgg gaggagcagt acaacagcac gtaccgtgtg    2820
gtcagcgtcc tcaccgtcct gcaccaggac tggctgaatg gcaaggagta caagtgcaag    2880
gtctccaaca aagccctccc agcccccatc gagaaaacca tctccaaagc caaagggcag    2940
ccccgagaac cacaggtgta caccctgccc ccatcccggg aggagatgac caagaaccag    3000
gtcagcctga cctgcctggt caaaggcttc tatcccagcg acatcgccgt ggagtgggag    3060
agcaatgggc agccggagaa caactacaag accacgcctc ccgtgctgga ctccgacggc    3120
tccttcttcc tctacagcaa gctcaccgtg gacaagagca ggtggcagca ggggaacgtc    3180
ttctcatgct ccgtgatgca cgaggctctg cacaaccact acacgcagaa gagcctctcc    3240
ctgtctccgg gtaaa                                                    3255
```

<210> SEQ ID NO 3
<211> LENGTH: 1064
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (563)..(837)
<223> OTHER INFORMATION: Xaa can be any naturally occurring amino acid

<400> SEQUENCE: 3

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30
```

```
Cys Glu Trp Leu Ile Gln Ala Pro Asp Pro Tyr Gln Arg Ile Met Ile
         35                  40                  45

Asn Phe Asn Pro His Phe Asp Leu Glu Asp Arg Cys Lys Tyr Asp
 50                  55                  60

Tyr Val Glu Val Phe Asp Gly Glu Asn Glu Asn Gly His Phe Arg Gly
 65                  70                  75                  80

Lys Phe Cys Gly Lys Ile Ala Pro Pro Val Val Ser Ser Gly Pro
                 85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
        130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Ser Gly Ile Leu Ser Met
        210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
                260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
    370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
            405                 410                 415

Val Ser Gly Leu Ile Ser Asp Ser Gln Ile Thr Ser Ser Asn Gln Gly
        420                 425                 430

Asp Arg Asn Trp Met Pro Glu Asn Ile Arg Leu Val Thr Ser Arg Ser
        435                 440                 445
```

-continued

```
Gly Trp Ala Leu Pro Pro Ala Pro His Ser Tyr Ile Asn Glu Trp Leu
450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
                500                 505                 510

Lys Arg Lys Ala Lys Ser Phe Glu Gly Asn Asn Asn Tyr Asp Thr Pro
            515                 520                 525

Glu Leu Arg Thr Phe Pro Ala Leu Ser Thr Arg Phe Ile Arg Ile Tyr
530                 535                 540

Pro Glu Arg Ala Thr His Gly Gly Leu Gly Leu Arg Met Glu Leu Leu
545                 550                 555                 560

Gly Cys Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
                580                 585                 590

Xaa Xaa Xaa Xaa Xaa Xaa Xaa Xaa Xaa Xaa Xaa Xaa Xaa Xaa Xaa Xaa
595                 600                 605

Xaa Xaa Xaa Xaa Xaa Xaa Xaa Xaa Xaa Xaa Xaa Xaa Xaa Xaa Xaa Xaa
            610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
                660                 665                 670

Xaa Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa Xaa
690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa Xaa
                725                 730                 735

Xaa Xaa Xaa Xaa Xaa Xaa Xaa Xaa Xaa Xaa Xaa Xaa Xaa Xaa Xaa Xaa
                740                 745                 750

Xaa Xaa Xaa Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa Xaa
770                 775                 780

Xaa Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa Xaa
                820                 825                 830

Xaa Xaa Xaa Xaa Xaa Asp Lys Thr His Thr Cys Pro Pro Cys Pro Ala
            835                 840                 845

Pro Glu Leu Leu Gly Gly Pro Ser Val Phe Leu Phe Pro Pro Lys Pro
850                 855                 860

Lys Asp Thr Leu Met Ile Ser Arg Thr Pro Glu Val Thr Cys Val Val
```

```
                865                 870                 875                 880
Val Asp Val Ser His Glu Asp Pro Glu Val Lys Phe Asn Trp Tyr Val
                        885                 890                 895

Asp Gly Val Glu Val His Asn Ala Lys Thr Lys Pro Arg Glu Glu Gln
                900                 905                 910

Tyr Asn Ser Thr Tyr Arg Val Val Ser Val Leu Thr Val Leu His Gln
                915                 920                 925

Asp Trp Leu Asn Gly Lys Glu Tyr Lys Cys Lys Val Ser Asn Lys Ala
            930                 935                 940

Leu Pro Ala Pro Ile Glu Lys Thr Ile Ser Lys Ala Lys Gly Gln Pro
945                 950                 955                 960

Arg Glu Pro Gln Val Tyr Thr Leu Pro Pro Ser Arg Glu Glu Met Thr
                    965                 970                 975

Lys Asn Gln Val Ser Leu Thr Cys Leu Val Lys Gly Phe Tyr Pro Ser
                980                 985                 990

Asp Ile Ala Val Glu Trp Glu Ser  Asn Gly Gln Pro Glu  Asn Asn Tyr
                995                 1000                1005

Lys Thr  Thr Pro Pro Val Leu  Asp Ser Asp Gly Ser  Phe Phe Leu
    1010                1015                1020

Tyr Ser  Lys Leu Thr Val Asp  Lys Ser Arg Trp Gln  Gln Gly Asn
    1025                1030                1035

Val Phe  Ser Cys Ser Val Met  His Glu Ala Leu His  Asn His Tyr
    1040                1045                1050

Thr Gln  Lys Ser Leu Ser Leu  Ser Pro Gly Lys
    1055                1060

<210> SEQ ID NO 4
<211> LENGTH: 3255
<212> TYPE: DNA
<213> ORGANISM: artificial sequence
<220> FEATURE:
<223> OTHER INFORMATION: Synthetic polynucleotide
<220> FEATURE:
<221> NAME/KEY: misc_feature
<222> LOCATION: (1750)..(2574)
<223> OTHER INFORMATION: n is a, c, g, or t

<400> SEQUENCE: 4
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acatttagg      300 ggaaagttct gtggaaagat agccctcct cctgttgtgt cttcagggcc atttctttt      360 atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa gctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag tcgaatccg atcctcatcg     720 ggcattctct ccatggtttt ttacaccgac agcgcgatag caaagaagg tttctcagca     780 aactacagtg tcttgcagag cagtgtctca gaagatttca atgtatgga agctctgggc     840
```

```
atggaatcag gagaaattca ttctgaccag atcacagctt cttcccagta tagcaccaac      900
tggtctgcag agcgctcccg cctgaactac cctgagaatg ggtggactcc cggagaggat      960
tcctaccgag agtggataca ggtagacttg ggccttctgc gctttgtcac ggctgtcggg     1020
acacagggcg ccatttcaaa agaaaccaag aagaaatatt atgtcaagac ttacaagatc     1080
gacgttagct ccaacgggga agactggatc accataaaag aaggaaacaa acctgttctc     1140
tttcagggaa acaccaaccc tacagatgtt gtggttgcag tattcccaa ccactgata       1200
actcgatttg tccgaatcaa gcctgcaact tgggaaactg catatctat gagatttgaa      1260
gtatatggtt gcaagataac agattatcct tgctctggaa tgttgggtat ggtgtctgga     1320
cttatttctg actcccagat cacatcatcc aaccaagggg acagaaactg gatgcctgaa     1380
aacatccgcc tggtaaccag tcgctctggc tgggcacttc cacccgcacc tcattcctac     1440
atcaatgagt ggctccaaat agacctgggg gaggagaaga tcgtgagggg catcatcatt     1500
cagggtggga agcaccgaga gaacaaggtg ttcatgagga agttcaagat cgggtacagc     1560
aacaacggct cggactggaa gatgatcatg gatgacagca acgcaaggc gaagtctttt      1620
gagggcaaca caactatga tacacctgag ctgcggactt ttccagctct ctccacgcga      1680
ttcatcagga tctaccccga gagagccact catggcggac tggggctcag aatggagctg     1740
ctgggctgtn nnnnnnnnn nnnnnnnnnn nnnnnnnnnn nnnnnnnnnn nnnnnnnnnn      1800
nnnnnnnnnn nnnnnnnnnn nnnnnnnnnn nnnnnnnnnn nnnnnnnnnn nnnnnnnnnn      1860
nnnnnnnnnn nnnnnnnnnn nnnnnnnnnn nnnnnnnnnn nnnnnnnnnn nnnnnnnnnn      1920
nnnnnnnnnn nnnnnnnnnn nnnnnnnnnn nnnnnnnnnn nnnnnnnnnn nnnnnnnnnn      1980
nnnnnnnnnn nnnnnnnnnn nnnnnnnnnn nnnnnnnnnn nnnnnnnnnn nnnnnnnnnn      2040
nnnnnnnnnn nnnnnnnnnn nnnnnnnnnn nnnnnnnnnn nnnnnnnnnn nnnnnnnnnn      2100
nnnnnnnnnn nnnnnnnnnn nnnnnnnnnn nnnnnnnnnn nnnnnnnnnn nnnnnnnnnn      2160
nnnnnnnnnn nnnnnnnnnn nnnnnnnnnn nnnnnnnnnn nnnnnnnnnn nnnnnnnnnn      2220
nnnnnnnnnn nnnnnnnnnn nnnnnnnnnn nnnnnnnnnn nnnnnnnnnn nnnnnnnnnn      2280
nnnnnnnnnn nnnnnnnnnn nnnnnnnnnn nnnnnnnnnn nnnnnnnnnn nnnnnnnnnn      2340
nnnnnnnnnn nnnnnnnnnn nnnnnnnnnn nnnnnnnnnn nnnnnnnnnn nnnnnnnnnn      2400
nnnnnnnnnn nnnnnnnnnn nnnnnnnnnn nnnnnnnnnn nnnnnnnnnn nnnnnnnnnn      2460
nnnnnnnnnn nnnnnnnnnn nnnnnnnnnn nnnnnnnnnn nnnnnnnnnn nnnnnnnnnn      2520
nnnnnnnnnn nnnnnnnnnn nnnnnnnnnn nnnnnnnnnn nnnnnnnnnn nnnngacaaa     2580
actcacacat gcccaccgtg cccagcacct gaactcctgg gggaccgtc agtcttcctc       2640
ttccccccaa aacccaagga caccctcatg atctcccgga cccctgaggt cacatgcgtg     2700
gtggtggacg tgagccacga agaccctgag gtcaagttca actggtacgt ggacggcgtg     2760
gaggtgcata atgccaagac aaagccgcgg gaggagcagt acaacagcac gtaccgtgtg     2820
gtcagcgtcc tcaccgtcct gcaccaggac tggctgaatg gcaaggagta caagtgcaag     2880
gtctccaaca aagccctccc agcccccatc gagaaaacca tctccaaagc caaagggcag     2940
ccccgagaac acaggtgta caccctgccc ccatcccggg aggagatgac caagaaccag      3000
gtcagcctga cctgcctggt caaaggcttc tatcccagcg acatcgccgt ggagtgggag     3060
agcaatgggc agccggagaa caactacaag accacgcctc ccgtgctgga ctccgacggc     3120
tccttcttcc tctacagcaa gctcaccgtg gacaagagca ggtggcagca ggggaacgtc     3180
```

-continued

```
ttctcatgct ccgtgatgca cgaggctctg cacaaccact acacgcagaa gagcctctcc    3240
ctgtctccgg gtaaa                                                     3255
```

<210> SEQ ID NO 5
<211> LENGTH: 1064
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (404)..(837)
<223> OTHER INFORMATION: Xaa can be any naturally occurring amino acid

<400> SEQUENCE: 5

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Lys Tyr Tyr Val Lys Thr
```

```
            325                 330                 335
Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
            595                 600                 605

Xaa Xaa Xaa Xaa Xaa Xaa Xaa Xaa Xaa Xaa Xaa Xaa Xaa Xaa Xaa Xaa
610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa Xaa
                725                 730                 735

Xaa Xaa Xaa Xaa Xaa Xaa Xaa Xaa Xaa Xaa Xaa Xaa Xaa Xaa Xaa Xaa
            740                 745                 750
```

```
Xaa Xaa Xaa Xaa Xaa Xaa Xaa Xaa Xaa Xaa Xaa Xaa Xaa Xaa
        755                 760                 765

Xaa Xaa Xaa Xaa Xaa Xaa Xaa Xaa Xaa Xaa Xaa Xaa Xaa
        770                 775                 780

Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa
            820                 825                 830

Xaa Xaa Xaa Xaa Xaa Asp Lys Thr His Thr Cys Pro Pro Cys Pro Ala
        835                 840                 845

Pro Glu Leu Leu Gly Gly Pro Ser Val Phe Leu Phe Pro Pro Lys Pro
        850                 855                 860

Lys Asp Thr Leu Met Ile Ser Arg Thr Pro Glu Val Thr Cys Val Val
865                 870                 875                 880

Val Asp Val Ser His Glu Asp Pro Glu Val Lys Phe Asn Trp Tyr Val
                885                 890                 895

Asp Gly Val Glu Val His Asn Ala Lys Thr Lys Pro Arg Glu Glu Gln
            900                 905                 910

Tyr Asn Ser Thr Tyr Arg Val Val Ser Val Leu Thr Val Leu His Gln
        915                 920                 925

Asp Trp Leu Asn Gly Lys Glu Tyr Lys Cys Lys Val Ser Asn Lys Ala
    930                 935                 940

Leu Pro Ala Pro Ile Glu Lys Thr Ile Ser Ala Lys Gly Gln Pro
945                 950                 955                 960

Arg Glu Pro Gln Val Tyr Thr Leu Pro Pro Ser Arg Glu Glu Met Thr
                965                 970                 975

Lys Asn Gln Val Ser Leu Thr Cys Leu Val Lys Gly Phe Tyr Pro Ser
            980                 985                 990

Asp Ile Ala Val Glu Trp Glu Ser Asn Gly Gln Pro Glu Asn Asn Tyr
        995                 1000                1005

Lys Thr Thr Pro Pro Val Leu Asp Ser Asp Gly Ser Phe Phe Leu
        1010                1015                1020

Tyr Ser Lys Leu Thr Val Asp Lys Ser Arg Trp Gln Gln Gly Asn
        1025                1030                1035

Val Phe Ser Cys Ser Val Met His Glu Ala Leu His Asn His Tyr
        1040                1045                1050

Thr Gln Lys Ser Leu Ser Leu Ser Pro Gly Lys
        1055                1060

<210> SEQ ID NO 6
<211> LENGTH: 3255
<212> TYPE: DNA
<213> ORGANISM: artificial sequence
<220> FEATURE:
<223> OTHER INFORMATION: Synthetic polynucleotide
<220> FEATURE:
<221> NAME/KEY: misc_feature
<222> LOCATION: (1273)..(2574)
<223> OTHER INFORMATION: n is a, c, g, or t

<400> SEQUENCE: 6
atggagaggg ggctgccgct cctctgcgcc gtgctcgccc tcgtcctcgc cccggccggc      60
gcttttcgca acgataaatg tggcgatact ataaaaattg aaagcccgg gtaccttaca     120
```

```
tctcctggtt atcctcattc ttatcaccca agtgaaaaat gcgaatggct gattcaggct      180
ccggacccat accagagaat tatgatcaac ttcaaccctc acttcgattt ggaggacaga      240
gactgcaagt atgactacgt ggaagtcttc gatggagaaa atgaaaatgg acattttagg      300
ggaaagttct gtggaaagat agcccctcct cctgttgtgt cttcagggcc atttcttttt      360
atcaaatttg tctctgacta cgaaacacat ggtgcaggat tttccatacg ttatgaactt      420
ttcaagagag gtcctgaatg ttcccagaac tacacaacac ctagtggagt gataaagtcc      480
cccggattcc ctgaaaaata tcccaacagc cttgaatgca cttatattgt ctttgcgcca      540
aagatgtcag agattatcct ggaatttgaa agctttgacc tggagcctga ctcaaatcct      600
ccagggggga tgttctgtcg ctacgaccgg ctagaaatct gggatggatt ccctgatgtt      660
ggccctcaca ttgggcgtta ctgtggacag aaaacaccag gtcgaatccg atcctcatcg      720
ggcattctct ccatggtttt ttacaccgac agcgcgatag caaaagaagg tttctcagca      780
aactacagtg tcttgcagag cagtgtctca gaagatttca atgtatgga agctctgggc      840 atggaatcag gagaaattca ttctgaccag atcacagctt cttcccagta tagcaccaac      900
tggtctgcag agcgctcccg cctgaactac cctgagaatg ggtggactcc cggagaggat      960
tcctaccgag agtggataca ggtagacttg ggccttctgc gctttgtcac ggctgtcggg     1020
acacagggcg ccatttcaaa agaaaccaag aagaaatatt atgtcaagac ttacaagatc     1080
gacgttagct ccaacgggga agactggatc accataaaag aaggaaacaa acctgttctc     1140
tttcagggaa acaccaaccc tacagatgtt gtggttgcag tattccccaa accactgata     1200
actcgatttg tccgaatcaa gcctgcaact tgggaaactg gcatatctat gagatttgaa     1260
gtatatggtt gcnnnnnnnn nnnnnnnnnn nnnnnnnnnn nnnnnnnnnn nnnnnnnnnn     1320
nnnnnnnnnn nnnnnnnnnn nnnnnnnnnn nnnnnnnnnn nnnnnnnnnn nnnnnnnnnn     1380
nnnnnnnnnn nnnnnnnnnn nnnnnnnnnn nnnnnnnnnn nnnnnnnnnn nnnnnnnnnn     1440
nnnnnnnnnn nnnnnnnnnn nnnnnnnnnn nnnnnnnnnn nnnnnnnnnn nnnnnnnnnn     1500
nnnnnnnnnn nnnnnnnnnn nnnnnnnnnn nnnnnnnnnn nnnnnnnnnn nnnnnnnnnn     1560
nnnnnnnnnn nnnnnnnnnn nnnnnnnnnn nnnnnnnnnn nnnnnnnnnn nnnnnnnnnn     1620
nnnnnnnnnn nnnnnnnnnn nnnnnnnnnn nnnnnnnnnn nnnnnnnnnn nnnnnnnnnn     1680
nnnnnnnnnn nnnnnnnnnn nnnnnnnnnn nnnnnnnnnn nnnnnnnnnn nnnnnnnnnn     1740
nnnnnnnnnn nnnnnnnnnn nnnnnnnnnn nnnnnnnnnn nnnnnnnnnn nnnnnnnnnn     1800
nnnnnnnnnn nnnnnnnnnn nnnnnnnnnn nnnnnnnnnn nnnnnnnnnn nnnnnnnnnn     1860
nnnnnnnnnn nnnnnnnnnn nnnnnnnnnn nnnnnnnnnn nnnnnnnnnn nnnnnnnnnn     1920
nnnnnnnnnn nnnnnnnnnn nnnnnnnnnn nnnnnnnnnn nnnnnnnnnn nnnnnnnnnn     1980
nnnnnnnnnn nnnnnnnnnn nnnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn     2100
nnnnnnnnnn nnnnnnnnnn nnnnnnnnnn nnnnnnnnnn nnnnnnnnnn nnnnnnnnnn     2160
nnnnnnnnnn nnnnnnnnnn nnnnnnnnnn nnnnnnnnnn nnnnnnnnnn nnnnnnnnnn     2220
nnnnnnnnnn nnnnnnnnnn nnnnnnnnnn nnnnnnnnnn nnnnnnnnnn nnnnnnnnnn     2280
nnnnnnnnnn nnnnnnnnnn nnnnnnnnnn nnnnnnnnnn nnnnnnnnnn nnnnnnnnnn     2340
nnnnnnnnnn nnnnnnnnnn nnnnnnnnnn nnnnnnnnnn nnnnnnnnnn nnnnnnnnnn     2400
nnnnnnnnnn nnnnnnnnnn nnnnnnnnnn nnnnnnnnnn nnnnnnnnnn nnnnnnnnnn     2460
nnnnnnnnnn nnnnnnnnnn nnnnnnnnnn nnnnnnnnnn nnnnnnnnnn nnnnnnnnnn     2520
```

-continued

```
nnnnnnnnnn nnnnnnnnnn nnnnnnnnnn nnnnnnnnnn nnnnnnnnnn nnnngacaaa    2580
actcacacat gcccaccgtg cccagcacct gaactcctgg ggggaccgtc agtcttcctc    2640
ttccccccaa aacccaagga caccctcatg atctcccgga cccctgaggt cacatgcgtg    2700
gtggtggacg tgagccacga agaccctgag gtcaagttca actggtacgt ggacggcgtg    2760
gaggtgcata atgccaagac aaagccgcgg gaggagcagt acaacagcac gtaccgtgtg    2820
gtcagcgtcc tcaccgtcct gcaccaggac tggctgaatg gcaaggagta caagtgcaag    2880
gtctccaaca aagccctccc agcccccatc gagaaaacca tctccaaagc caaagggcag    2940
ccccgagaac acaggtgta cccctgccc ccatcccggg aggagatgac caagaaccag    3000
gtcagcctga cctgcctggt caaaggcttc tatcccagcg acatcgccgt ggagtgggag    3060
agcaatgggc agccggagaa caactacaag accacgcctc ccgtgctgga ctccgacggc    3120
tccttcttcc tctacagcaa gctcaccgtg gacaagagca ggtggcagca ggggaacgtc    3180
ttctcatgct ccgtgatgca cgaggctctg cacaaccact acacgcagaa gagcctctcc    3240
ctgtctccgg gtaaa                                                     3255
```

<210> SEQ ID NO 7
<211> LENGTH: 1064
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (245)..(837)
<223> OTHER INFORMATION: Xaa can be any naturally occurring amino acid

<400> SEQUENCE: 7

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
            85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205
```

```
Gln Lys Thr Pro Gly Arg Ile Arg Ser Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
            595                 600                 605

Xaa Xaa Xaa Xaa Xaa Xaa Xaa Xaa Xaa Xaa Xaa Xaa Xaa Xaa Xaa
            610                 615                 620
```

```
Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa
            820                 825                 830

Xaa Xaa Xaa Xaa Xaa Asp Lys Thr His Thr Cys Pro Pro Cys Pro Ala
            835                 840                 845

Pro Glu Leu Leu Gly Gly Pro Ser Val Phe Leu Phe Pro Pro Lys Pro
850                 855                 860

Lys Asp Thr Leu Met Ile Ser Arg Thr Pro Glu Val Thr Cys Val Val
865                 870                 875                 880

Val Asp Val Ser His Glu Asp Pro Glu Val Lys Phe Asn Trp Tyr Val
            885                 890                 895

Asp Gly Val Glu Val His Asn Ala Lys Thr Lys Pro Arg Glu Glu Gln
            900                 905                 910

Tyr Asn Ser Thr Tyr Arg Val Val Ser Val Leu Thr Val Leu His Gln
            915                 920                 925

Asp Trp Leu Asn Gly Lys Glu Tyr Lys Cys Lys Val Ser Asn Lys Ala
930                 935                 940

Leu Pro Ala Pro Ile Glu Lys Thr Ile Ser Lys Ala Lys Gly Gln Pro
945                 950                 955                 960

Arg Glu Pro Gln Val Tyr Thr Leu Pro Pro Ser Arg Glu Glu Met Thr
            965                 970                 975

Lys Asn Gln Val Ser Leu Thr Cys Leu Val Lys Gly Phe Tyr Pro Ser
            980                 985                 990

Asp Ile Ala Val Glu Trp Glu Ser Asn Gly Gln Pro Glu Asn Asn Tyr
            995                 1000                1005

Lys Thr Thr Pro Pro Val Leu Asp Ser Asp Gly Ser Phe Phe Leu
            1010                1015                1020

Tyr Ser Lys Leu Thr Val Asp Lys Ser Arg Trp Gln Gln Gly Asn
            1025                1030                1035

Val Phe Ser Cys Ser Val Met His Glu Ala Leu His Asn His Tyr
```

Thr Gln Lys Ser Leu Ser Leu Ser Pro Gly Lys
    1055            1060

<210> SEQ ID NO 8
<211> LENGTH: 3255
<212> TYPE: DNA
<213> ORGANISM: artificial sequence
<220> FEATURE:
<223> OTHER INFORMATION: Synthetic polynucleotide
<220> FEATURE:
<221> NAME/KEY: misc_feature
<222> LOCATION: (796)..(2574)
<223> OTHER INFORMATION: n is a, c, g, or t

<400> SEQUENCE: 8

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaatg | tggcgatact | ataaaaattg | aaagccccgg | gtaccttaca | 120 |
| tctcctggtt | atcctcattc | ttatcaccca | agtgaaaaat | gcgaatggct | gattcaggct | 180 |
| ccggacccat | accagagaat | tatgatcaac | ttcaaccctc | acttcgattt | ggaggacaga | 240 |
| gactgcaagt | atgactacgt | ggaagtcttc | gatggagaaa | atgaaaatgg | acattttagg | 300 |
| ggaaagttct | gtggaaagat | agcccctcct | cctgttgtgt | cttcagggcc | atttcttttt | 360 |
| atcaaatttg | tctctgacta | cgaaacacat | ggtgcaggat | tttccatacg | ttatgaactt | 420 |
| ttcaagagag | gtcctgaatg | ttcccagaac | tacacaacac | ctagtggagt | gataaagtcc | 480 |
| cccggattcc | ctgaaaaata | tcccaacagc | cttgaatgca | cttatattgt | ctttgcgcca | 540 |
| aagatgtcag | agattatcct | ggaatttgaa | agctttgacc | tggagcctga | ctcaaatcct | 600 |
| ccaggggga | tgttctgtcg | ctacgaccgg | ctagaaatct | gggatggatt | ccctgatgtt | 660 |
| ggccctcaca | ttgggcgtta | ctgtggacag | aaaacaccag | gtcgaatccg | atcctcatcg | 720 |
| ggcattctct | ccatggtttt | ttacaccgac | agcgcgatag | caaaagaagg | tttctcagca | 780 |
| aactacagtg | tcttgnnnnn | nnnnnnnnnn | nnnnnnnnnn | nnnnnnnnnn | nnnnnnnnnn | 840 |
| nnnnnnnnnn | nnnnnnnnnn | nnnnnnnnnn | nnnnnnnnnn | nnnnnnnnnn | nnnnnnnnnn | 900 |
| nnnnnnnnnn | nnnnnnnnnn | nnnnnnnnnn | nnnnnnnnnn | nnnnnnnnnn | nnnnnnnnnn | 960 |
| nnnnnnnnnn | nnnnnnnnnn | nnnnnnnnnn | nnnnnnnnnn | nnnnnnnnnn | nnnnnnnnnn | 1020 |
| nnnnnnnnnn | nnnnnnnnnn | nnnnnnnnnn | nnnnnnnnnn | nnnnnnnnnn | nnnnnnnnnn | 1080 |
| nnnnnnnnnn | nnnnnnnnnn | nnnnnnnnnn | nnnnnnnnnn | nnnnnnnnnn | nnnnnnnnnn | 1140 |
| nnnnnnnnnn | nnnnnnnnnn | nnnnnnnnnn | nnnnnnnnnn | nnnnnnnnnn | nnnnnnnnnn | 1200 |
| nnnnnnnnnn | nnnnnnnnnn | nnnnnnnnnn | nnnnnnnnnn | nnnnnnnnnn | nnnnnnnnnn | 1260 |
| nnnnnnnnnn | nnnnnnnnnn | nnnnnnnnnn | nnnnnnnnnn | nnnnnnnnnn | nnnnnnnnnn | 1320 |
| nnnnnnnnnn | nnnnnnnnnn | nnnnnnnnnn | nnnnnnnnnn | nnnnnnnnnn | nnnnnnnnnn | 1380 |
| nnnnnnnnnn | nnnnnnnnnn | nnnnnnnnnn | nnnnnnnnnn | nnnnnnnnnn | nnnnnnnnnn | 1440 |
| nnnnnnnnnn | nnnnnnnnnn | nnnnnnnnnn | nnnnnnnnnn | nnnnnnnnnn | nnnnnnnnnn | 1500 |
| nnnnnnnnnn | nnnnnnnnnn | nnnnnnnnnn | nnnnnnnnnn | nnnnnnnnnn | nnnnnnnnnn | 1560 |
| nnnnnnnnnn | nnnnnnnnnn | nnnnnnnnnn | nnnnnnnnnn | nnnnnnnnnn | nnnnnnnnnn | 1620 |
| nnnnnnnnnn | nnnnnnnnnn | nnnnnnnnnn | nnnnnnnnnn | nnnnnnnnnn | nnnnnnnnnn | 1680 |
| nnnnnnnnnn | nnnnnnnnnn | nnnnnnnnnn | nnnnnnnnnn | nnnnnnnnnn | nnnnnnnnnn | 1740 |
| nnnnnnnnnn | nnnnnnnnnn | nnnnnnnnnn | nnnnnnnnnn | nnnnnnnnnn | nnnnnnnnnn | 1800 |

```
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnngacaaa    2580
actcacacat gcccaccgtg cccagcacct gaactcctgg ggggaccgtc agtcttcctc    2640
ttccccccaa aacccaagga caccctcatg atctcccgga cccctgaggt cacatgcgtg    2700
gtggtggacg tgagccacga agaccctgag gtcaagttca actggtacgt ggacggcgtg    2760
gaggtgcata atgccaagac aaagccgcgg gaggagcagt acaacagcac gtaccgtgtg    2820
gtcagcgtcc tcaccgtcct gcaccaggac tggctgaatg gcaaggagta caagtgcaag    2880
gtctccaaca aagcccctcc cagcccccatc gagaaaacca tctccaaagc caagggcag    2940 ccccgagaac cacaggtgta caccctgccc ccatcccggg aggagatgac caagaaccag    3000
gtcagcctga cctgcctggt caaaggcttc tatcccagcg acatcgccgt ggagtgggag    3060
agcaatgggc agccggagaa caactacaag accacgcctc ccgtgctgga ctccgacggc    3120
tccttcttcc tctacagcaa gctcaccgtg gacaagagca ggtggcagca ggggaacgtc    3180
ttctcatgct ccgtgatgca cgaggctctg cacaaccact acacgcagaa gagcctctcc    3240
ctgtctccgg gtaaa                                                     3255

<210> SEQ ID NO 9
<211> LENGTH: 791
<212> TYPE: PRT
<213> ORGANISM: artificial sequence
<220> FEATURE:
<223> OTHER INFORMATION: Synthetic polypeptide

<400> SEQUENCE: 9

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
```

```
                100             105             110
Phe Ser Ile Arg Tyr Glu Leu Phe Lys Arg Gly Pro Glu Cys Ser Gln
            115             120             125

Asn Tyr Thr Thr Pro Ser Gly Val Ile Lys Ser Pro Gly Phe Pro Glu
130             135             140

Lys Tyr Pro Asn Ser Leu Glu Cys Thr Tyr Ile Val Phe Ala Pro Lys
145             150             155             160

Met Ser Glu Ile Ile Leu Glu Phe Glu Ser Phe Asp Leu Glu Pro Asp
            165             170             175

Ser Asn Pro Pro Gly Gly Met Phe Cys Arg Tyr Asp Arg Leu Glu Ile
            180             185             190

Trp Asp Gly Phe Pro Asp Val Gly Pro His Ile Gly Arg Tyr Cys Gly
            195             200             205

Gln Lys Thr Pro Gly Arg Ile Arg Ser Ser Gly Ile Leu Ser Met
            210             215             220

Val Phe Tyr Thr Asp Ser Ala Ile Ala Lys Glu Gly Phe Ser Ala Asn
225             230             235             240

Tyr Ser Val Leu Gln Ser Ser Val Ser Glu Asp Phe Lys Cys Met Glu
            245             250             255

Ala Leu Gly Met Glu Ser Gly Glu Ile His Ser Asp Gln Ile Thr Ala
            260             265             270

Ser Ser Gln Tyr Ser Thr Asn Trp Ser Ala Glu Arg Ser Arg Leu Asn
            275             280             285

Tyr Pro Glu Asn Gly Trp Thr Pro Gly Glu Asp Ser Tyr Arg Glu Trp
            290             295             300

Ile Gln Val Asp Leu Gly Leu Leu Arg Phe Val Thr Ala Val Gly Thr
305             310             315             320

Gln Gly Ala Ile Ser Lys Glu Thr Lys Lys Tyr Tyr Val Lys Thr
            325             330             335

Tyr Lys Ile Asp Val Ser Ser Asn Gly Glu Asp Trp Ile Thr Ile Lys
            340             345             350

Glu Gly Asn Lys Pro Val Leu Phe Gln Gly Asn Thr Asn Pro Thr Asp
            355             360             365

Val Val Val Ala Val Phe Pro Lys Pro Leu Ile Thr Arg Phe Val Arg
370             375             380

Ile Lys Pro Ala Thr Trp Glu Thr Gly Ile Ser Met Arg Phe Glu Val
385             390             395             400

Tyr Gly Cys Lys Ile Thr Asp Tyr Pro Cys Ser Gly Met Leu Gly Met
            405             410             415

Val Ser Gly Leu Ile Ser Asp Ser Gln Ile Thr Ser Ser Asn Gln Gly
            420             425             430

Asp Arg Asn Trp Met Pro Glu Asn Ile Arg Leu Val Thr Ser Arg Ser
            435             440             445

Gly Trp Ala Leu Pro Pro Ala Pro His Ser Tyr Ile Asn Glu Trp Leu
            450             455             460

Gln Ile Asp Leu Gly Glu Glu Lys Ile Val Arg Gly Ile Ile Ile Gln
465             470             475             480

Gly Gly Lys His Arg Glu Asn Lys Val Phe Met Arg Lys Phe Lys Ile
            485             490             495

Gly Tyr Ser Asn Asn Gly Ser Asp Trp Lys Met Ile Met Asp Asp Ser
            500             505             510

Lys Arg Lys Ala Lys Ser Phe Glu Gly Asn Asn Asn Tyr Asp Thr Pro
            515             520             525
```

Glu Leu Arg Thr Phe Pro Ala Leu Ser Thr Arg Phe Ile Arg Ile Tyr
    530                 535                 540

Pro Glu Arg Ala Thr His Gly Gly Leu Gly Leu Arg Met Glu Leu Leu
545                 550                 555                 560

Gly Cys Arg Ser Asp Lys Thr His Thr Cys Pro Pro Cys Pro Ala Pro
            565                 570                 575

Glu Leu Leu Gly Gly Pro Ser Val Phe Leu Phe Pro Pro Lys Pro Lys
            580                 585                 590

Asp Thr Leu Met Ile Ser Arg Thr Pro Glu Val Thr Cys Val Val Val
        595                 600                 605

Asp Val Ser His Glu Asp Pro Glu Val Lys Phe Asn Trp Tyr Val Asp
    610                 615                 620

Gly Val Glu Val His Asn Ala Lys Thr Lys Pro Arg Glu Glu Gln Tyr
625                 630                 635                 640

Asn Ser Thr Tyr Arg Val Val Ser Val Leu Thr Val Leu His Gln Asp
            645                 650                 655

Trp Leu Asn Gly Lys Glu Tyr Lys Cys Lys Val Ser Asn Lys Ala Leu
            660                 665                 670

Pro Ala Pro Ile Glu Lys Thr Ile Ser Lys Ala Lys Gly Gln Pro Arg
        675                 680                 685

Glu Pro Gln Val Tyr Thr Leu Pro Pro Ser Arg Glu Glu Met Thr Lys
    690                 695                 700

Asn Gln Val Ser Leu Thr Cys Leu Val Lys Gly Phe Tyr Pro Ser Asp
705                 710                 715                 720

Ile Ala Val Glu Trp Glu Ser Asn Gly Gln Pro Glu Asn Asn Tyr Lys
            725                 730                 735

Thr Thr Pro Pro Val Leu Asp Ser Asp Gly Ser Phe Phe Leu Tyr Ser
            740                 745                 750

Lys Leu Thr Val Asp Lys Ser Arg Trp Gln Gln Gly Asn Val Phe Ser
        755                 760                 765

Cys Ser Val Met His Glu Ala Leu His Asn His Tyr Thr Gln Lys Ser
    770                 775                 780

Leu Ser Leu Ser Pro Gly Lys
785                 790

<210> SEQ ID NO 10
<211> LENGTH: 2436
<212> TYPE: DNA
<213> ORGANISM: artificial sequence
<220> FEATURE:
<223> OTHER INFORMATION: Synthetic polynucleotide

<400> SEQUENCE: 10
atggagaggg ggctgccgct cctctgcgcc gtgctcgccc tcgtcctcgc cccggccggc     60
gcttttcgca acgataaatg tggcgatact ataaaaattg aaagccccgg gtaccttaca    120
tctcctggtt atcctcattc ttatcaccca agtgaaaaat gcgaatggct gattcaggct    180
ccggacccat accagagaat tatgatcaac ttcaaccctc acttcgattt ggaggacaga    240
gactgcaagt atgactacgt ggaagtcttc gatggagaaa atgaaaatgg acatttaggt    300
ggaaagttct gtggaaagat agcccctcct cctgttgtgt cttcagggcc atttctttt     360 atcaaatttg tctctgacta cgaaacacat ggtgcaggat tttccatacg ttatgaactt    420
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540

```
aagatgtcag agattatcct ggaatttgaa agctttgacc tggagcctga ctcaaatcct    600
ccagggggga tgttctgtcg ctacgaccgg ctagaaatct gggatggatt ccctgatgtt    660
ggccctcaca ttgggcgtta ctgtggacag aaaacaccag gtcgaatccg atcctcatcg    720
ggcattctct ccatggtttt ttacaccgac agcgcgatga caaaagaagg tttctcagca    780
aactacagtg tcttgcagag cagtgtctca gaagatttca atgtatggaa gctctgggc    840 atggaatcag gagaaattca ttctgaccag atcacagctt cttcccagta tagcaccaac    900
tggtctgcag agcgctcccg cctgaactac cctgagaatg ggtggactcc cggagaggat    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa accactgata   1200
actcgatttg tccgaatcaa gcctgcaact tgggaaactg gcatatctat gagatttgaa   1260
gtatatggtt gcaagataac agattatcct tgctctggaa tgttgggtat ggtgtctgga   1320
cttatttctg actcccagat cacatcatcc aaccaagggg acagaaactg gatgcctgaa   1380
aacatccgcc tggtaaccag tcgctctggc tgggcacttc cacccgcacc tcattcctac   1440
atcaatgagt ggctccaaat agacctgggg gaggagaaga tcgtgagggg catcatcatt   1500
cagggtggga agcaccgaga gaacaaggtg ttcatgagga agttcaagat cgggtacagc   1560
aacaacggct cggactggaa gatgatcatg gatgacagca acgcaaggc gaagtctttt   1620 gagggcaaca caactatga tacacctgag ctgcggactt ttccagctct ctccacgcga   1680
ttcatcagga tctaccccga gagagccact catggcggac tggggctcag aatggagctg   1740
ctgggctgta gatctgacaa aactcacaca tgcccaccgt gcccagcacc tgaactcctg   1800 ggggaccgt cagtcttcct cttcccccca aaacccaagg acaccctcat gatctcccgg   1860
acccctgagg tcacatgcgt ggtggtggac gtgagccacg aagaccctga ggtcaagttc   1920
aactggtacg tggacggcgt ggaggtgcat aatgccaaga caaagccgcg ggaggagcag   1980
tacaacagca cgtaccgtgt ggtcagcgtc ctcaccgtcc tgcaccagga ctggctgaat   2040
ggcaaggagt acaagtgcaa ggtctccaac aaagccctcc cagcccccat cgagaaaacc   2100
atctccaaag ccaaagggca gccccgagaa ccacaggtgt acaccctgcc cccatcccgg   2160
gaggagatga ccaagaacca ggtcagcctg acctgcctgg tcaaaggctt ctatcccagc   2220
gacatcgccg tggagtggga gagcaatggg cagccggaga caactacaa gaccacgcct   2280 cccgtgctgg actccgacgg ctccttcttc ctctacagca agctcaccgt ggacaagagc   2340
aggtggcagc aggggaacgt cttctcatgc tccgtgatgc acgaggctct gcacaaccac   2400
tacacgcaga agagcctctc cctgtctccg ggtaaa                              2436
```

<210> SEQ ID NO 11
<211> LENGTH: 632
<212> TYPE: PRT
<213> ORGANISM: artificial sequence
<220> FEATURE:
<223> OTHER INFORMATION: Synthetic polypeptide

<400> SEQUENCE: 11

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys

-continued

```
                  20                  25                  30
    Cys Glu Trp Leu Ile Gln Ala Pro Asp Pro Tyr Gln Arg Ile Met Ile
                  35                  40                  45
    Asn Phe Asn Pro His Phe Asp Leu Glu Asp Arg Asp Cys Lys Tyr Asp
                  50                  55                  60
    Tyr Val Glu Val Phe Asp Gly Glu Asn Glu Asn Gly His Phe Arg Gly
     65                  70                  75                  80
    Lys Phe Cys Gly Lys Ile Ala Pro Pro Val Val Ser Ser Gly Pro
                      85                  90                  95
    Phe Leu Phe Ile Lys Phe Val Ser Asp Tyr Glu Thr His Gly Ala Gly
                     100                 105                 110
    Phe Ser Ile Arg Tyr Glu Leu Phe Lys Arg Gly Pro Glu Cys Ser Gln
                     115                 120                 125
    Asn Tyr Thr Thr Pro Ser Gly Val Ile Lys Ser Pro Gly Phe Pro Glu
                     130                 135                 140
    Lys Tyr Pro Asn Ser Leu Glu Cys Thr Tyr Ile Val Phe Ala Pro Lys
    145                 150                 155                 160
    Met Ser Glu Ile Ile Leu Glu Phe Glu Ser Phe Asp Leu Glu Pro Asp
                     165                 170                 175
    Ser Asn Pro Pro Gly Gly Met Phe Cys Arg Tyr Asp Arg Leu Glu Ile
                     180                 185                 190
    Trp Asp Gly Phe Pro Asp Val Gly Pro His Ile Gly Arg Tyr Cys Gly
                     195                 200                 205
    Gln Lys Thr Pro Gly Arg Ile Arg Ser Ser Gly Ile Leu Ser Met
                     210                 215                 220
    Val Phe Tyr Thr Asp Ser Ala Ile Ala Lys Glu Gly Phe Ser Ala Asn
    225                 230                 235                 240
    Tyr Ser Val Leu Gln Ser Ser Val Ser Glu Asp Phe Lys Cys Met Glu
                     245                 250                 255
    Ala Leu Gly Met Glu Ser Gly Glu Ile His Ser Asp Gln Ile Thr Ala
                     260                 265                 270
    Ser Ser Gln Tyr Ser Thr Asn Trp Ser Ala Glu Arg Ser Arg Leu Asn
                     275                 280                 285
    Tyr Pro Glu Asn Gly Trp Thr Pro Gly Glu Asp Ser Tyr Arg Glu Trp
                     290                 295                 300
    Ile Gln Val Asp Leu Gly Leu Leu Arg Phe Val Thr Ala Val Gly Thr
    305                 310                 315                 320
    Gln Gly Ala Ile Ser Lys Glu Thr Lys Lys Tyr Tyr Val Lys Thr
                     325                 330                 335
    Tyr Lys Ile Asp Val Ser Ser Asn Gly Glu Asp Trp Ile Thr Ile Lys
                     340                 345                 350
    Glu Gly Asn Lys Pro Val Leu Phe Gln Gly Asn Thr Asn Pro Thr Asp
                     355                 360                 365
    Val Val Val Ala Val Phe Pro Lys Pro Leu Ile Thr Arg Phe Val Arg
                     370                 375                 380
    Ile Lys Pro Ala Thr Trp Glu Thr Gly Ile Ser Met Arg Phe Glu Val
    385                 390                 395                 400
    Tyr Gly Cys Arg Ser Asp Lys Thr His Thr Cys Pro Cys Pro Ala
                     405                 410                 415
    Pro Glu Leu Leu Gly Gly Pro Ser Val Phe Leu Phe Pro Pro Lys Pro
                     420                 425                 430
    Lys Asp Thr Leu Met Ile Ser Arg Thr Pro Glu Val Thr Cys Val Val
                     435                 440                 445
```

```
Val Asp Val Ser His Glu Asp Pro Glu Val Lys Phe Asn Trp Tyr Val
    450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
        515                 520                 525

Arg Glu Pro Gln Val Tyr Thr Leu Pro Pro Ser Arg Glu Glu Met Thr
    530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
    610                 615                 620

Ser Leu Ser Leu Ser Pro Gly Lys
625                 630

<210> SEQ ID NO 12
<211> LENGTH: 1959
<212> TYPE: DNA
<213> ORGANISM: artificial sequence
<220> FEATURE:
<223> OTHER INFORMATION: Synthetic polynucleotide

<400> SEQUENCE: 12
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaatgg acattttagg     300 ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag tcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaaccaccag gtcgaatccg atcctcatcg     720
ggcattctct ccatggtttt ttacaccgac agcgcgatag caaagaagg tttctcagca     780 aactacagtg tcttgcagag cagtgtctca gaagatttca atgtatgga gctctgggc     840 atggaatcag gagaaattca ttctgaccag atcacagctt cttcccagta tagcaccaac     900
tggtctgcag agcgctcccg cctgaactac cctgagaatg gtggactcc cggagaggat     960
```

-continued

```
tcctaccgag agtggataca ggtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg gcatatctat gagatttgaa    1260
gtatatggtt gcagatctga caaaactcac acatgcccac cgtgcccagc acctgaactc    1320 ctgggggac cgtcagtctt cctcttcccc ccaaaaccca aggacaccct catgatctcc    1380
cggacccctg aggtcacatg cgtggtggtg gacgtgagcc acgaagaccc tgaggtcaag    1440
ttcaactggt acgtggacgg cgtggaggtg cataatgcca agacaaagcc gcgggaggag    1500
cagtacaaca gcacgtaccg tgtggtcagc gtcctcaccg tcctgcacca ggactggctg    1560
aatggcaagg agtacaagtg caaggtctcc aacaaagccc tcccagcccc catcgagaaa    1620
accatctcca aagccaaagg gcagccccga gaaccacagg tgtacaccct gcccccatcc    1680
cgggaggaga tgaccaagaa ccaggtcagc ctgacctgcc tggtcaaagg cttctatccc    1740
agcgacatcg ccgtggagtg ggagagcaat gggcagccgg agaacaacta caagaccacg    1800
cctcccgtgc tggactccga cggctccttc ttcctctaca gcaagctcac cgtggacaag    1860
agcaggtggc agcaggggaa cgtcttctca tgctccgtga tgcacgaggc tctgcacaac    1920
cactacacgc agaagagcct ctccctgtct ccgggtaaa                           1959
```

<210> SEQ ID NO 13
<211> LENGTH: 473
<212> TYPE: PRT
<213> ORGANISM: artificial sequence
<220> FEATURE:
<223> OTHER INFORMATION: Synthetic polypeptide

<400> SEQUENCE: 13

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190
```

```
Trp Asp Gly Phe Pro Asp Val Gly Pro His Ile Gly Arg Tyr Cys Gly
            195                 200                 205
Gln Lys Thr Pro Gly Arg Ile Arg Ser Ser Ser Gly Ile Leu Ser Met
    210                 215                 220
Val Phe Tyr Thr Asp Ser Ala Ile Ala Lys Glu Gly Phe Ser Ala Asn
225                 230                 235                 240
Tyr Ser Val Leu Arg Ser Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Glu Glu Met
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
    450                 455                 460
Lys Ser Leu Ser Leu Ser Pro Gly Lys
465                 470

<210> SEQ ID NO 14
<211> LENGTH: 1482
<212> TYPE: DNA
<213> ORGANISM: artificial sequence
<220> FEATURE:
<223> OTHER INFORMATION: Synthetic polynucleotide

<400> SEQUENCE: 14
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
```

```
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccagggggga tgttctgtcg ctacgaccgg ctagaaatct gggatggatt ccctgatgtt    660
ggccctcaca ttgggcgtta ctgtggacag aaaacaccag gtcgaatccg atcctcatcg    720
ggcattctct ccatggtttt ttacaccgac agcgcgatag caaaagaagg tttctcagca    780
aactacagtg tcttgagatc tgacaaaact cacacatgcc caccgtgccc agcacctgaa    840
ctcctggggg gaccgtcagt cttcctcttc cccccaaaac ccaaggacac cctcatgatc    900
tcccggaccc ctgaggtcac atgcgtggtg gtggacgtga gccacgaaga ccctgaggtc    960
aagttcaact ggtacgtgga cggcgtggag gtgcataatg ccaagacaaa gccgcgggag   1020
gagcagtaca acagcacgta ccgtgtggtc agcgtcctca ccgtcctgca ccaggactgg   1080
ctgaatggca aggagtacaa gtgcaaggtc tccaacaaag ccctcccagc ccccatcgag   1140
aaaaccatct ccaaagccaa agggcagccc cgagaaccac aggtgtacac cctgcccca    1200 tcccgggagg agatgaccaa gaaccaggtc agcctgacct gcctggtcaa aggcttctat   1260
cccagcgaca tcgccgtgga gtgggagagc aatgggcagc cggagaacaa ctacaagacc   1320
acgcctcccg tgctggactc cgacggctcc ttcttcctct acagcaagct caccgtggac   1380
aagagcaggt ggcagcaggg gaacgtcttc tcatgctccg tgatgcacga ggctctgcac   1440
aaccactaca cgcagaagag cctctccctg tctccgggta aa                       1482

<210> SEQ ID NO 15
<211> LENGTH: 1064
<212> TYPE: PRT
<213> ORGANISM: artificial sequence
<220> FEATURE:
<223> OTHER INFORMATION: Synthetic polypeptide

<400> SEQUENCE: 15

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175
```

-continued

```
Ser Asn Pro Pro Gly Gly Met Phe Cys Arg Tyr Asp Arg Leu Glu Ile
            180                 185                 190
Trp Asp Gly Phe Pro Asp Val Gly Pro His Ile Gly Arg Tyr Cys Gly
        195                 200                 205
Gln Lys Thr Pro Gly Arg Ile Arg Ser Ser Gly Ile Leu Ser Met
    210                 215                 220
Val Phe Tyr Thr Asp Ser Ala Ile Ala Lys Glu Gly Phe Ser Ala Asn
225                 230                 235                 240
Tyr Ser Val Leu Gln Ser Ser Val Ser Glu Asp Phe Lys Cys Met Glu
                245                 250                 255
Ala Leu Gly Met Glu Ser Gly Glu Ile His Ser Asp Gln Ile Thr Ala
            260                 265                 270
Ser Ser Gln Ala Ser Thr Asn Trp Ser Ala Glu Arg Ser Arg Leu Asn
    275                 280                 285
Tyr Pro Glu Asn Gly Trp Thr Pro Gly Glu Asp Ser Tyr Arg Glu Trp
    290                 295                 300
Ile Gln Val Asp Leu Gly Leu Leu Arg Phe Val Thr Ala Val Gly Thr
305                 310                 315                 320
Gln Gly Ala Ile Ser Lys Glu Thr Lys Lys Tyr Tyr Val Lys Thr
            325                 330                 335
Tyr Lys Ile Asp Val Ser Ser Asn Gly Glu Asp Trp Ile Thr Ile Lys
            340                 345                 350
Glu Gly Asn Lys Pro Val Leu Phe Gln Gly Asn Thr Asn Pro Thr Asp
            355                 360                 365
Val Val Val Ala Val Phe Pro Lys Pro Leu Ile Thr Arg Phe Val Arg
370                 375                 380
Ile Lys Pro Ala Thr Trp Glu Thr Gly Ile Ser Met Arg Phe Glu Val
385                 390                 395                 400
Tyr Gly Cys Lys Ile Thr Asp Tyr Pro Cys Ser Gly Met Leu Gly Met
            405                 410                 415
Val Ser Gly Leu Ile Ser Asp Ser Gln Ile Thr Ser Ser Asn Gln Gly
            420                 425                 430
Asp Arg Asn Trp Met Pro Glu Asn Ile Arg Leu Val Thr Ser Arg Ser
            435                 440                 445
Gly Trp Ala Leu Pro Pro Ala Pro His Ser Tyr Ile Asn Glu Trp Leu
450                 455                 460
Gln Ile Asp Leu Gly Glu Glu Lys Ile Val Arg Gly Ile Ile Gln
465                 470                 475                 480
Gly Gly Lys His Arg Glu Asn Lys Val Phe Met Arg Lys Phe Lys Ile
            485                 490                 495
Gly Tyr Ser Asn Asn Gly Ser Asp Trp Lys Met Ile Met Asp Asp Ser
            500                 505                 510
Lys Arg Lys Ala Lys Ser Phe Glu Gly Asn Asn Asn Tyr Asp Thr Pro
            515                 520                 525
Glu Leu Arg Thr Phe Pro Ala Leu Ser Thr Arg Phe Ile Arg Ile Tyr
            530                 535                 540
Pro Glu Arg Ala Thr His Gly Gly Leu Gly Leu Arg Met Glu Leu Leu
545                 550                 555                 560
Gly Cys Glu Val Glu Ala Pro Thr Ala Gly Pro Thr Thr Pro Asn Gly
                565                 570                 575
Asn Leu Val Asp Glu Cys Asp Asp Gln Ala Asn Cys His Ser Gly
            580                 585                 590
Thr Gly Asp Asp Phe Gln Leu Thr Gly Gly Thr Thr Val Leu Ala Thr
```

```
            595                 600                 605
Glu Lys Pro Thr Val Ile Asp Ser Thr Ile Gln Ser Glu Phe Pro Thr
610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                    645                 650                 655

Ser Lys Thr Gly Pro Ile Gln Asp His Thr Gly Asp Gly Asn Phe Ile
                660                 665                 670

Tyr Ser Gln Ala Asp Glu Asn Gln Lys Gly Lys Val Ala Arg Leu Val
            675                 680                 685

Ser Pro Val Val Tyr Ser Gln Asn Ser Ala His Cys Met Thr Phe Trp
        690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
                725                 730                 735

His Gln Gly Asp His Trp Lys Glu Gly Arg Val Leu Leu His Lys Ser
                740                 745                 750

Leu Lys Leu Tyr Gln Val Ile Phe Glu Gly Glu Ile Gly Lys Gly Asn
            755                 760                 765

Leu Gly Gly Ile Ala Val Asp Asp Ile Ser Ile Asn Asn His Ile Ser
770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
            820                 825                 830

Leu Asp Pro Arg Ser Asp Lys Thr His Thr Cys Pro Pro Cys Pro Ala
        835                 840                 845

Pro Glu Leu Leu Gly Gly Pro Ser Val Phe Leu Phe Pro Pro Lys Pro
850                 855                 860

Lys Asp Thr Leu Met Ile Ser Arg Thr Pro Glu Val Thr Cys Val Val
865                 870                 875                 880

Val Asp Val Ser His Glu Asp Pro Glu Val Lys Phe Asn Trp Tyr Val
                885                 890                 895

Asp Gly Val Glu Val His Asn Ala Lys Thr Lys Pro Arg Glu Glu Gln
            900                 905                 910

Tyr Asn Ser Thr Tyr Arg Val Val Ser Val Leu Thr Val Leu His Gln
        915                 920                 925

Asp Trp Leu Asn Gly Lys Glu Tyr Lys Cys Lys Val Ser Asn Lys Ala
        930                 935                 940

Leu Pro Ala Pro Ile Glu Lys Thr Ile Ser Lys Ala Lys Gly Gln Pro
945                 950                 955                 960

Arg Glu Pro Gln Val Tyr Thr Leu Pro Pro Ser Arg Glu Glu Met Thr
                965                 970                 975

Lys Asn Gln Val Ser Leu Thr Cys Leu Val Lys Gly Phe Tyr Pro Ser
            980                 985                 990

Asp Ile Ala Val Glu Trp Glu Ser  Asn Gly Gln Pro Glu  Asn Asn Tyr
        995                 1000                1005

Lys Thr  Thr Pro Pro Val Leu  Asp Ser Asp Gly Ser  Phe Phe Leu
    1010                1015                1020
```

| Tyr | Ser | Lys | Leu | Thr | Val | Asp | Lys | Ser | Arg | Trp | Gln | Gln | Gly | Asn |
|-----|-----|-----|-----|-----|-----|-----|-----|-----|-----|-----|-----|-----|-----|-----|
| 1025 | | | | 1030 | | | | | 1035 | | | | | |

| Val | Phe | Ser | Cys | Ser | Val | Met | His | Glu | Ala | Leu | His | Asn | His | Tyr |
|-----|-----|-----|-----|-----|-----|-----|-----|-----|-----|-----|-----|-----|-----|-----|
| 1040 | | | | | 1045 | | | | | 1050 | | | | |

| Thr | Gln | Lys | Ser | Leu | Ser | Leu | Ser | Pro | Gly | Lys |
|-----|-----|-----|-----|-----|-----|-----|-----|-----|-----|-----|
| 1055 | | | | | 1060 | | | | | |

<210> SEQ ID NO 16
<211> LENGTH: 3255
<212> TYPE: DNA
<213> ORGANISM: artificial sequence
<220> FEATURE:
<223> OTHER INFORMATION: Synthetic polynucleotide

<400> SEQUENCE: 16

| | |
|---|---|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acattttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccaggggga tgttctgtcg ctacgaccgg ctagaaatct gggatggatt ccctgatgtt | 660 |
| ggccctcaca ttgggcgtta ctgtggacag aaaacaccag tcgaatccg atcctcatcg | 720 |
| ggcattctct ccatggtttt ttacaccgac agcgcgatag caaagaagg tttctcagca | 780 |
| aactacagtg tcttgcagag cagtgtctca gaagatttca atgtatgga agctctgggc | 840 |
| atggaatcag agaaaattca ttctgaccag atcacagctt cttcccaggc tagcaccaac | 900 |
| tggtctgcag agcgctcccg cctgaactac cctgagaatg ggtggactcc cggagaggat | 960 |
| tcctaccgag agtggataca ggtagacttg ggccttctgc gctttgtcac ggctgtcggg | 1020 |
| acacagggcg ccatttcaaa agaaaccaag aagaaatatt atgtcaagac ttacaagatc | 1080 |
| gacgttagct ccaacgggga agactggatc accataaaag aaggaaacaa acctgttctc | 1140 |
| tttcagggaa acaccaaccc tacagatgtt gtggttgcag tattccccaa accactgata | 1200 |
| actcgatttg tccgaatcaa gcctgcaact tgggaaactg gcatatctat gagatttgaa | 1260 |
| gtatatggtt gcaagataac agattatcct tgctctggaa tgttgggtat ggtgtctgga | 1320 |
| cttatttctg actccagat cacatcatcc aaccaagggg acagaaactg gatgcctgaa | 1380 |
| aacatccgcc tggtaaccag tcgctctggc tgggcacttc acccgcacc tcattcctac | 1440 |
| atcaatgagt ggctccaaat agacctgggg gaggagaaga tcgtgagggg catcatcatt | 1500 |
| cagggtggga gcaccgaga gaacaaggtg ttcatgagga agttcaagat cgggtacagc | 1560 |
| aacaacggct cggactggaa gatgatcatg gatgacagca acgcaaggc gaagtctttt | 1620 |
| gagggcaaca caactatga tacacctgag ctgcggactt ttccagctct ctccacgcga | 1680 |
| ttcatcagga tctaccccga gagagccact catggcggac tggggctcag aatggagctg | 1740 |
| ctgggctgtg aagtggaagc ccctacagct ggaccgacca ctcccaacgg gaacttggtg | 1800 |

```
gatgaatgtg atgacgacca ggccaactgc cacagtggaa caggtgatga cttccagctc  1860
acaggtggca ccactgtgct ggccacagaa aagcccacgg tcatagacag caccatacaa  1920
tcagagtttc aacatatgg ttttaactgt gaatttggct ggggctctca caagaccttc   1980
tgccactggg aacatgacaa tcacgtgcag ctcaagtgga gtgtgttgac cagcaagacg  2040
ggacccattc aggatcacac aggagatggc aacttcatct attcccaagc tgacgaaaat  2100
cagaagggca aagtggctcg cctggtgagc cctgtggttt attcccagaa ctctgcccac  2160
tgcatgacct tctggtatca catgtctggg tcccacgtcg gcacactcag ggtcaaactg  2220
cgctaccaga agccagagga gtacgatcag ctggtctgga tggccattgg acaccaaggt  2280
gaccactgga aggaagggcg tgtcttgctc cacaagtctc tgaaacttta tcaggtgatt  2340
ttcgagggcg aaatcggaaa aggaaacctt ggtgggattg ctgtggatga cattagtatt  2400
aataaccaca tttcacaaga agattgtgca aaaccagcag acctggataa aagaaaccca  2460
gaaattaaaa ttgatgaaac agggagcacg ccaggatacg aaggtgaagg agaaggtgac  2520
aagaacatct ccaggaagcc aggcaatgtg ttgaagacct tagaccccag atctgacaaa  2580
actcacacat gcccaccgtg cccagcacct gaactcctgg ggggaccgtc agtcttcctc  2640
ttccccccaa aacccaagga caccctcatg atctcccgga cccctgaggt cacatgcgtg  2700
gtggtggacg tgagccacga agaccctgag gtcaagttca actggtacgt ggacggcgtg  2760
gaggtgcata atgccaagac aaagccgcgg gaggagcagt acaacagcac gtaccgtgtg  2820
gtcagcgtcc tcaccgtcct gcaccaggac tggctgaatg gcaaggagta caagtgcaag  2880
gtctccaaca aagccctccc agcccccatc gagaaaacca tctccaaagc caaagggcag  2940
ccccgagaac cacaggtgta caccctgccc ccatcccggg aggagatgac caagaaccag  3000
gtcagcctga cctgcctggt caaaggcttc tatcccagcg acatcgccgt ggagtgggag  3060
agcaatgggc agccggagaa caactacaag accacgcctc ccgtgctgga ctccgacggc  3120
tccttcttcc tctacagcaa gctcaccgtg gacaagagca ggtggcagca ggggaacgtc  3180
ttctcatgct ccgtgatgca cgaggctctg cacaaccact acacgcagaa gagcctctcc  3240
ctgtctccgg gtaaa                                                    3255

<210> SEQ ID NO 17
<211> LENGTH: 1064
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (563)..(837)
<223> OTHER INFORMATION: Xaa can be any naturally occurring amino acid

<400> SEQUENCE: 17

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80
```

```
Lys Phe Cys Gly Lys Ile Ala Pro Pro Val Ser Ser Gly Pro
            85              90              95

Phe Leu Phe Ile Lys Phe Val Ser Asp Tyr Glu Thr His Gly Ala Gly
                100             105             110

Phe Ser Ile Arg Tyr Glu Leu Phe Lys Arg Gly Pro Glu Cys Ser Gln
            115             120             125

Asn Tyr Thr Thr Pro Ser Gly Val Ile Lys Ser Pro Gly Phe Pro Glu
            130             135             140

Lys Tyr Pro Asn Ser Leu Glu Cys Thr Tyr Ile Val Phe Ala Pro Lys
145             150             155             160

Met Ser Glu Ile Ile Leu Glu Phe Glu Ser Phe Asp Leu Glu Pro Asp
                165             170             175

Ser Asn Pro Pro Gly Gly Met Phe Cys Arg Tyr Asp Arg Leu Glu Ile
            180             185             190

Trp Asp Gly Phe Pro Asp Val Gly Pro His Ile Gly Arg Tyr Cys Gly
            195             200             205

Gln Lys Thr Pro Gly Arg Ile Arg Ser Ser Ser Gly Ile Leu Ser Met
        210             215             220

Val Phe Tyr Thr Asp Ser Ala Ile Ala Lys Glu Gly Phe Ser Ala Asn
225             230             235             240

Tyr Ser Val Leu Gln Ser Ser Val Ser Glu Asp Phe Lys Cys Met Glu
                245             250             255

Ala Leu Gly Met Glu Ser Gly Glu Ile His Ser Asp Gln Ile Thr Ala
            260             265             270

Ser Ser Gln Ala Ser Thr Asn Trp Ser Ala Glu Arg Ser Arg Leu Asn
        275             280             285

Tyr Pro Glu Asn Gly Trp Thr Pro Gly Glu Asp Ser Tyr Arg Glu Trp
        290             295             300

Ile Gln Val Asp Leu Gly Leu Leu Arg Phe Val Thr Ala Val Gly Thr
305             310             315             320

Gln Gly Ala Ile Ser Lys Glu Thr Lys Lys Tyr Tyr Val Lys Thr
            325             330             335

Tyr Lys Ile Asp Val Ser Ser Asn Gly Glu Asp Trp Ile Thr Ile Lys
            340             345             350

Glu Gly Asn Lys Pro Val Leu Phe Gln Gly Asn Thr Asn Pro Thr Asp
        355             360             365

Val Val Val Ala Val Phe Pro Lys Pro Leu Ile Thr Arg Phe Val Arg
        370             375             380

Ile Lys Pro Ala Thr Trp Glu Thr Gly Ile Ser Met Arg Phe Glu Val
385             390             395             400

Tyr Gly Cys Lys Ile Thr Asp Tyr Pro Cys Ser Gly Met Leu Gly Met
            405             410             415

Val Ser Gly Leu Ile Ser Asp Ser Gln Ile Thr Ser Ser Asn Gln Gly
            420             425             430

Asp Arg Asn Trp Met Pro Glu Asn Ile Arg Leu Val Thr Ser Arg Ser
        435             440             445

Gly Trp Ala Leu Pro Pro Ala Pro His Ser Tyr Ile Asn Glu Trp Leu
    450             455             460

Gln Ile Asp Leu Gly Glu Glu Lys Ile Val Arg Gly Ile Ile Ile Gln
465             470             475             480

Gly Gly Lys His Arg Glu Asn Lys Val Phe Met Arg Lys Phe Lys Ile
            485             490             495
```

```
Gly Tyr Ser Asn Asn Gly Ser Asp Trp Lys Met Ile Met Asp Ser
            500                 505                 510

Lys Arg Lys Ala Lys Ser Phe Glu Gly Asn Asn Asn Tyr Asp Thr Pro
        515                 520                 525

Glu Leu Arg Thr Phe Pro Ala Leu Ser Thr Arg Phe Ile Arg Ile Tyr
    530                 535                 540

Pro Glu Arg Ala Thr His Gly Gly Leu Gly Leu Arg Met Glu Leu Leu
545                 550                 555                 560

Gly Cys Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa
            595                 600                 605

Xaa Xaa Xaa Xaa Xaa Xaa Xaa Xaa Xaa Xaa Xaa Xaa Xaa Xaa Xaa
            610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Asp Lys Thr His Thr Cys Pro Pro Cys Pro Ala
            835                 840                 845

Pro Glu Leu Leu Gly Gly Pro Ser Val Phe Leu Phe Pro Pro Lys Pro
    850                 855                 860

Lys Asp Thr Leu Met Ile Ser Arg Thr Pro Glu Val Thr Cys Val Val
865                 870                 875                 880

Val Asp Val Ser His Glu Asp Pro Glu Val Lys Phe Asn Trp Tyr Val
                885                 890                 895

Asp Gly Val Glu Val His Asn Ala Lys Thr Lys Pro Arg Glu Glu Gln
            900                 905                 910

Tyr Asn Ser Thr Tyr Arg Val Val Ser Val Leu Thr Val Leu His Gln
```

```
              915                 920                 925
Asp Trp Leu Asn Gly Lys Glu Tyr Lys Cys Lys Val Ser Asn Lys Ala
        930                 935                 940
Leu Pro Ala Pro Ile Glu Lys Thr Ile Ser Lys Ala Lys Gly Gln Pro
945                 950                 955                 960
Arg Glu Pro Gln Val Tyr Thr Leu Pro Pro Ser Arg Glu Glu Met Thr
                965                 970                 975
Lys Asn Gln Val Ser Leu Thr Cys Leu Val Lys Gly Phe Tyr Pro Ser
            980                 985                 990
Asp Ile Ala Val Glu Trp Glu Ser  Asn Gly Gln Pro Glu  Asn Asn Tyr
                995                 1000                1005
Lys Thr  Thr Pro Pro Val Leu  Asp Ser Asp Gly Ser  Phe Phe Leu
     1010                1015                1020
Tyr Ser  Lys Leu Thr Val Asp  Lys Ser Arg Trp Gln  Gln Gly Asn
     1025                1030                1035
Val Phe  Ser Cys Ser Val Met  His Glu Ala Leu His  Asn His Tyr
     1040                1045                1050
Thr Gln  Lys Ser Leu Ser Leu  Ser Pro Gly Lys
     1055                1060

<210> SEQ ID NO 18
<211> LENGTH: 3255
<212> TYPE: DNA
<213> ORGANISM: artificial sequence
<220> FEATURE:
<223> OTHER INFORMATION: Synthetic polynucleotide
<220> FEATURE:
<221> NAME/KEY: misc_feature
<222> LOCATION: (1750)..(2574)
<223> OTHER INFORMATION: n is a, c, g, or t

<400> SEQUENCE: 18
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agccctcct cctgttgtgt cttcagggcc atttctttt      360 atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag tcgaatccg atcctcatcg      720 ggcattctct ccatggtttt ttacaccgac agcgcgatag caaagaagg tttctcagca     780 aactacagtg tcttgcagag cagtgtctca gaagatttca atgtatgga agctctgggc     840 atggaatcag agaaattca ttctgaccag atcagcttc ttcccaggc tagcaccaac      900 tggtctgcag agcgctcccg cctgaactac cctgagaatg ggtggactcc ggagaggat      960 tcctaccgag agtggataca ggtagacttg ggccttctgc gctttgtcac ggctgtcggg     1020
acacagggcg ccatttcaaa agaaaccaag aagaatatt atgtcaagac ttacaagatc     1080
```

```
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg gcatatctat gagatttgaa    1260
gtatatggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca aacgcaaggc gaagtctttt    1620
gagggcaaca caactatga tacacctgag ctgcggactt ttccagctct ctccacgcga    1680
ttcatcagga tctaccccga gagagccact catggcggac tggggctcag aatggagctg    1740
ctgggctgtn nnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnngacaaa    2580
actcacacat gcccaccgtg cccagcacct gaactcctgg ggggaccgtc agtcttcctc    2640
ttccccccaa aacccaagga caccctcatg atctcccgga cccctgaggt cacatgcgtg    2700
gtggtggacg tgagccacga agaccctgag gtcaagttca actggtacgt ggacggcgtg    2760
gaggtgcata atgccaagac aaagccgcgg gaggagcagt acaacagcac gtaccgtgtg    2820
gtcagcgtcc tcaccgtcct gcaccaggac tggctgaatg gcaaggagta caagtgcaag    2880
gtctccaaca aagccctccc agcccccatc gagaaaacca tctccaaagc caaagggcag    2940
ccccgagaac cacaggtgta caccctgccc ccatcccggg aggagatgac caagaaccag    3000
gtcagcctga cctgcctggt caaaggcttc tatcccagcg acatcgccgt ggagtgggag    3060
agcaatgggc agccggagaa caactacaag accacgcctc ccgtgctgga ctccgacggc    3120
tccttcttcc tctacagcaa gctcaccgtg gacaagagca ggtggcagca ggggaacgtc    3180
ttctcatgct ccgtgatgca cgaggctctg cacaaccact acacgcagaa gagcctctcc    3240
ctgtctccgg gtaaa                                                    3255
```

<210> SEQ ID NO 19
<211> LENGTH: 1064
<212> TYPE: PRT
<213> ORGANISM: artificial sequence -continued

```
<220> FEATURE:
<223> OTHER INFORMATION: Synthetic polypeptide
<220> FEATURE:
<221> NAME/KEY: misc_feature
<222> LOCATION: (404)..(837)
<223> OTHER INFORMATION: Xaa can be any naturally occurring amino acid

<400> SEQUENCE: 19

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
```

```
            370                 375                 380
Ile Lys Pro Ala Thr Trp Glu Thr Gly Ile Ser Met Arg Phe Gl

```
Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa
            820                 825                 830

Xaa Xaa Xaa Xaa Xaa Asp Lys Thr His Thr Cys Pro Pro Cys Pro Ala
            835                 840                 845

Pro Glu Leu Leu Gly Gly Pro Ser Val Phe Leu Phe Pro Pro Lys Pro
    850                 855                 860

Lys Asp Thr Leu Met Ile Ser Arg Thr Pro Glu Val Thr Cys Val Val
865                 870                 875                 880

Val Asp Val Ser His Glu Asp Pro Glu Val Lys Phe Asn Trp Tyr Val
                885                 890                 895

Asp Gly Val Glu Val His Asn Ala Lys Thr Lys Pro Arg Glu Glu Gln
                900                 905                 910

Tyr Asn Ser Thr Tyr Arg Val Val Ser Val Leu Thr Val Leu His Gln
            915                 920                 925

Asp Trp Leu Asn Gly Lys Glu Tyr Lys Cys Lys Val Ser Asn Lys Ala
930                 935                 940

Leu Pro Ala Pro Ile Glu Lys Thr Ile Ser Lys Ala Lys Gly Gln Pro
945                 950                 955                 960

Arg Glu Pro Gln Val Tyr Thr Leu Pro Pro Ser Arg Glu Glu Met Thr
                965                 970                 975

Lys Asn Gln Val Ser Leu Thr Cys Leu Val Lys Gly Phe Tyr Pro Ser
            980                 985                 990

Asp Ile Ala Val Glu Trp Glu Ser Asn Gly Gln Pro Glu Asn Asn Tyr
        995                 1000                1005

Lys Thr Thr Pro Pro Val Leu Asp Ser Asp Gly Ser Phe Phe Leu
    1010                1015                1020

Tyr Ser Lys Leu Thr Val Asp Lys Ser Arg Trp Gln Gln Gly Asn
    1025                1030                1035

Val Phe Ser Cys Ser Val Met His Glu Ala Leu His Asn His Tyr
    1040                1045                1050

Thr Gln Lys Ser Leu Ser Leu Ser Pro Gly Lys
    1055                1060

<210> SEQ ID NO 20
<211> LENGTH: 3255
<212> TYPE: DNA
<213> ORGANISM: artificial sequence
<220> FEATURE:
<223> OTHER INFORMATION: Synthetic polynucleotide
<220> FEATURE:
<221> NAME/KEY: misc_feature
<222> LOCATION: (1273)..(2574)
<223> OTHER INFORMATION: n is a, c, g, or t

<400> SEQUENCE: 20
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttctttt      360 atcaaatttg tctctgacta cgaaacacat ggtgcaggat tttccatacg ttatgaactt     420
```

```
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccagggggga tgttctgtcg ctacgaccgg ctagaaatct gggatggatt ccctgatgtt    660
ggccctcaca ttgggcgtta ctgtggacag aaaacaccag gtcgaatccg atcctcatcg    720
ggcattctct ccatggtttt ttacaccgac agcgcgatag caaaagaagg tttctcagca    780
aactacagtg tcttgcagag cagtgtctca gaagatttca aatgtatgga agctctgggc    840
atggaatcag gagaaattca ttctgaccag atcacagctt cttcccaggc tagcaccaac    900
tggtctgcag agcgctcccg cctgaactac cctgagaatg ggtggactcc cggagaggat    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa accactgata   1200
actcgatttg tccgaatcaa gcctgcaact tgggaaactg gcatatctat gagatttgaa   1260
gtatatggtt gcnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnngacaaa   2580
actcacacat gcccaccgtg cccagcacct gaactcctgg ggggaccgtc agtcttcctc   2640
ttccccccaa acccaaggac acccctcatg atctcccgga cccctgaggt cacatgcgtg   2700
gtggtggacg tgagccacga agaccctgag gtcaagttca actggtacgt ggacggcgtg   2760
```

```
gaggtgcata atgccaagac aaagccgcgg gaggagcagt acaacagcac gtaccgtgtg   2820
gtcagcgtcc tcaccgtcct gcaccaggac tggctgaatg caaggagta caagtgcaag    2880 gtctccaaca aagccctccc agcccccatc gagaaaacca tctccaaagc caagggcag    2940 ccccgagaac acaggtgta caccctgccc ccatcccggg aggagatgac caagaaccag    3000
gtcagcctga cctgcctggt caaaggcttc tatcccagcg acatcgccgt ggagtgggag    3060
agcaatgggc agccggagaa caactacaag accacgcctc ccgtgctgga ctccgacggc    3120
tccttcttcc tctacagcaa gctcaccgtg gacaagagca ggtggcagca ggggaacgtc    3180
ttctcatgct ccgtgatgca cgaggctctg cacaaccact acacgcagaa gagcctctcc    3240
ctgtctccgg gtaaa                                                     3255
```

<210> SEQ ID NO 21
<211> LENGTH: 791
<212> TYPE: PRT
<213> ORGANISM: artificial sequence
<220> FEATURE:
<223> OTHER INFORMATION: Synthetic polypeptide

<400> SEQUENCE: 21

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270
```

-continued

```
Ser Ser Gln Ala Ser Thr Asn Trp Ser Ala Glu Arg Ser Arg Leu Asn
            275                 280                 285

Tyr Pro Glu Asn Gly Trp Thr Pro Gly Glu Asp Ser Tyr Arg Glu Trp
290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
            370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
            435                 440                 445

Gly Trp Ala Leu Pro Pro Ala Pro His Ser Tyr Ile Asn Glu Trp Leu
            450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
            515                 520                 525

Glu Leu Arg Thr Phe Pro Ala Leu Ser Thr Arg Phe Ile Arg Ile Tyr
530                 535                 540

Pro Glu Arg Ala Thr His Gly Gly Leu Gly Leu Arg Met Glu Leu Leu
545                 550                 555                 560

Gly Cys Arg Ser Asp Lys Thr His Thr Cys Pro Pro Cys Pro Ala Pro
                565                 570                 575

Glu Leu Leu Gly Gly Pro Ser Val Phe Leu Phe Pro Pro Lys Pro Lys
            580                 585                 590

Asp Thr Leu Met Ile Ser Arg Thr Pro Glu Val Thr Cys Val Val Val
            595                 600                 605

Asp Val Ser His Glu Asp Pro Glu Val Lys Phe Asn Trp Tyr Val Asp
            610                 615                 620

Gly Val Glu Val His Asn Ala Lys Thr Lys Pro Arg Glu Glu Gln Tyr
625                 630                 635                 640

Asn Ser Thr Tyr Arg Val Val Ser Val Leu Thr Val Leu His Gln Asp
                645                 650                 655

Trp Leu Asn Gly Lys Glu Tyr Lys Cys Lys Val Ser Asn Lys Ala Leu
            660                 665                 670

Pro Ala Pro Ile Glu Lys Thr Ile Ser Lys Ala Lys Gly Gln Pro Arg
            675                 680                 685

Glu Pro Gln Val Tyr Thr Leu Pro Pro Ser Arg Glu Glu Met Thr Lys
```

```
                690               695               700
Asn Gln Val Ser Leu Thr Cys Leu Val Lys Gly Phe Tyr Pro Ser Asp
705               710               715               720

Ile Ala Val Glu Trp Glu Ser Asn Gly Gln Pro Glu Asn Asn Tyr Lys
            725               730               735

Thr Thr Pro Pro Val Leu Asp Ser Asp Gly Ser Phe Phe Leu Tyr Ser
            740               745               750

Lys Leu Thr Val Asp Lys Ser Arg Trp Gln Gln Gly Asn Val Phe Ser
            755               760               765

Cys Ser Val Met His Glu Ala Leu His Asn His Tyr Thr Gln Lys Ser
            770               775               780

Leu Ser Leu Ser Pro Gly Lys
785               790

<210> SEQ ID NO 22
<211> LENGTH: 2436
<212> TYPE: DNA
<213> ORGANISM: artificial sequence
<220> FEATURE:
<223> OTHER INFORMATION: Synthetic polynucleotide

<400> SEQUENCE: 22
atggagaggg ggctgccgct cctctgcgcc gtgctcgccc tcgtcctcgc cccggccggc     60
gcttttcgca acgataaatg tggcgatact ataaaaattg aaagccccgg taccttaca    120 tctcctggtt atcctcattc ttatcaccca agtgaaaaat gcgaatggct gattcaggct    180
ccggacccat accagagaat tatgatcaac ttcaaccctc acttcgattt ggaggacaga    240
gactgcaagt atgactacgt ggaagtcttc gatggagaaa atgaaaatgg acattttagg    300
ggaaagttct gtggaaagat agcccctcct cctgttgtgt cttcagggcc atttcttttt    360
atcaaatttg tctctgacta cgaaacacat ggtgcaggat tttccatacg ttatgaactt    420
ttcaagagag gtcctgaatg ttcccagaac tacacaacac tagtggagt gataaagtcc    480 cccggattcc ctgaaaaata tcccaacagc cttgaatgca cttatattgt ctttgcgcca    540
aagatgtcag agattatcct ggaatttgaa agctttgacc tggagcctga ctcaaatcct    600 ccaggggga tgttctgtcg ctacgaccgg ctagaaatct gggatggatt ccctgatgtt    660
ggccctcaca ttgggcgtta ctgtggacag aaaacaccag tcgaatccg atcctcatcg    720 ggcattctct ccatggttt ttacaccgac agcgcgatag caaagaagg tttctcagca    780 aactacagtg tcttgcagag cagtgtctca gaagatttca atgtatgga agctctgggc    840 atggaatcag agaaattca ttctgaccag atcacagctt cttcccaggc tagcaccaac    900
tggtctgcag agcgctcccg cctgaactac cctgagaatg ggtggactcc cggagaggat    960
tcctaccgag agtggataca ggtagacttg ggccttctgc gctttgtcac ggctgtcggg   1020
acacagggcg ccatttcaaa agaaaccaag aagaaatatt atgtcaagac ttacaagatc   1080
gacgttagct ccaacgggga agactggatc accataaaag aaggaaacaa acctgttctc   1140
tttcagggaa acaccaaccc tacagatgtt gtggttgcag tattccccaa accactgata   1200
actcgatttg tccgaatcaa gcctgcaact tgggaaactg gcatatctat gagatttgaa   1260
gtatatggtt gcaagataac agattatcct tgctctggaa tgttgggtat ggtgtctgga   1320
cttatttctg actcccagat cacatcatcc aaccagggg acagaaactg gatgcctgaa   1380
aacatccgcc tggtaaccag tcgctctggc tgggcacttc acccgcacc tcattcctac   1440 atcaatgagt ggctccaaat agacctgggg gaggagaaga tcgtgagggg catcatcatt   1500
```

```
cagggtggga agcaccgaga gaacaaggtg ttcatgagga agttcaagat cgggtacagc    1560
aacaacggct cggactggaa gatgatcatg gatgacagca acgcaaggc gaagtctttt     1620 gagggcaaca acaactatga tacacctgag ctgcggactt ttccagctct ctccacgcga    1680
ttcatcagga tctaccccga gagagccact catggcggac tggggctcag aatggagctg    1740
ctgggctgta gatctgacaa aactcacaca tgcccaccgt gcccagcacc tgaactcctg    1800
gggggaccgt cagtcttcct cttccccca aaacccaagg acaccctcat gatctcccgg     1860
acccctgagg tcacatgcgt ggtggtggac gtgagccacg aagaccctga ggtcaagttc    1920
aactggtacg tggacggcgt ggaggtgcat aatgccaaga caaagccgcg ggaggagcag    1980
tacaacagca cgtaccgtgt ggtcagcgtc ctcaccgtcc tgcaccagga ctggctgaat    2040
ggcaaggagt acaagtgcaa ggtctccaac aaagccctcc cagcccccat cgagaaaacc    2100
atctccaaag ccaaagggca gccccgagaa ccacaggtgt acaccctgcc cccatcccgg    2160
gaggagatga ccaagaacca ggtcagcctg acctgcctgg tcaaaggctt ctatcccagc    2220
gacatcgccg tggagtggga gagcaatggg cagccggaga caactacaa gaccacgcct     2280 cccgtgctgg actccgacgg ctccttcttc ctctacagca agctcaccgt ggacaagagc    2340
aggtggcagc aggggaacgt cttctcatgc tccgtgatgc acgaggctct gcacaaccac    2400
tacacgcaga agagcctctc cctgtctccg ggtaaa                               2436

<210> SEQ ID NO 23
<211> LENGTH: 632
<212> TYPE: PRT
<213> ORGANISM: artificial sequence
<220> FEATURE:
<223> OTHER INFORMATION: Synthetic polypeptide

<400> SEQUENCE: 23

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190
```

```
Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
    275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
    370                 375                 380

Ile Lys Pro Ala Thr Trp Glu Thr Gly Ile Ser Met Arg Phe Glu Val
385                 390                 395                 400

Tyr Gly Cys Arg Ser Asp Lys Thr His Thr Cys Pro Pro Cys Pro Ala
                405                 410                 415

Pro Glu Leu Leu Gly Gly Pro Ser Val Phe Leu Phe Pro Pro Lys Pro
            420                 425                 430

Lys Asp Thr Leu Met Ile Ser Arg Thr Pro Glu Val Thr Cys Val Val
            435                 440                 445

Val Asp Val Ser His Glu Asp Pro Glu Val Lys Phe Asn Trp Tyr Val
450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
            515                 520                 525

Arg Glu Pro Gln Val Tyr Thr Leu Pro Pro Ser Arg Glu Glu Met Thr
    530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
    595                 600                 605

Ser Cys Ser Val Met His Glu Ala Leu His Asn His Tyr Thr Gln Lys
```

610                 615                 620
Ser Leu Ser Leu Ser Pro Gly Lys
625                 630

<210> SEQ ID NO 24
<211> LENGTH: 1962
<212> TYPE: DNA
<213> ORGANISM: artificial sequence
<220> FEATURE:
<223> OTHER INFORMATION: Synthetic polynucleotide

<400> SEQUENCE: 24

| | | | |
|---|---|---|---|
| atggagaggg | ggctgccgct | cctctgcgcc | gtgctcgccc tcgtcctcgc cccggccggc | 60 |
| gcttttcgca | acgataaatg | tggcgatact | ataaaaattg aaagccccgg gtaccttaca | 120 |
| tctcctggtt | atcctcattc | ttatcaccca | agtgaaaaat gcgaatggct gattcaggct | 180 |
| ccggacccat | accagagaat | tatgatcaac | ttcaaccctc acttcgattt ggaggacaga | 240 |
| gactgcaagt | atgactacgt | ggaagtcttc | gatggagaaa atgaaaatgg acattttagg | 300 |
| ggaaagttct | gtggaaagat | agcccctcct | cctgttgtgt cttcagggcc atttcttttt | 360 |
| atcaaatttg | tctctgacta | cgaaacacat | ggtgcaggat tttccatacg ttatgaactt | 420 |
| ttcaagagag | gtcctgaatg | ttcccagaac | tacacaacac ctagtggagt gataaagtcc | 480 |
| cccggattcc | ctgaaaaata | tcccaacagc | cttgaatgca cttatattgt ctttgcgcca | 540 |
| aagatgtcag | agattatcct | ggaatttgaa | agctttgacc tggagcctga ctcaaatcct | 600 |
| ccagggggga | tgttctgtcg | ctacgaccgg | ctagaaatct gggatggatt ccctgatgtt | 660 |
| ggccctcaca | ttgggcgtta | ctgtggacag | aaaacaccag gtcgaatccg atcctcatcg | 720 |
| ggcattctct | ccatggtttt | ttacaccgac | agcgcgatag caaaagaagg tttctcagca | 780 |
| aactacagtg | tcttgcagag | cagtgtctca | gaagatttca atgtatgga agctctgggc | 840 |
| atggaatcag | gagaaattca | ttctgaccag | atcacagctt cttcccaggc tagcaccaac | 900 |
| tggtctgcag | agcgctcccg | cctgaactac | cctgagaatg gtggactcc cggagaggat | 960 |
| tcctaccgag | agtggataca | ggtagacttg | ggccttctgc gctttgtcac ggctgtcggg | 1020 |
| acacagggcg | ccatttcaaa | agaaaccaag | aagaaatatt atgtcaagac ttacaagatc | 1080 |
| gacgttagct | ccaacgggga | agactggatc | accataaaag aaggaaacaa acctgttctc | 1140 |
| tttcagggaa | acaccaaccc | tacagatgtt | gtggttgcag tattccccaa ccactgata | 1200 |
| actcgatttg | tccgaatcaa | gcctgcaact | tgggaaactg gcatatctat gagatttgaa | 1260 |
| gtatatggtt | gcagatctga | caaaactcac | acatgcccac cgtgcccagc acctgaactc | 1320 |
| ctgggggggac | cgtcagtctt | cctcttcccc | ccaaaaccca aggacaccct catgatctcc | 1380 |
| cggacccctg | aggtcacatg | cgtggtggtg | gacgtgagcc acgaagaccc tgaggtcaag | 1440 |
| ttcaactggt | acgtggacgg | cgtggaggtg | cataatgcca agacaaagcc gcgggaggag | 1500 |
| cagtacaaca | gcacgtaccg | tgtggtcagc | gtcctcaccg tcctgcacca ggactggctg | 1560 |
| aatggcaagg | agtacaagtg | caaggtctcc | aacaaagccc tcccagcccc catcgagaaa | 1620 |
| accatctcca | aagccaaagg | gcagccccga | gaaccacagg tgtacaccct gcccccatcc | 1680 |
| cgggaggaga | tgaccaagaa | ccaggtcagc | ctgacctgcc tggtcaaagg cttctatccc | 1740 |
| agcgacatcg | ccgtggagtg | ggagagcaat | gggcagccgg agaacaacta caagaccacg | 1800 |
| cctcccgtgc | tggactccga | cggctccttc | ttcctctaca gcaagctcac cgtggacaag | 1860 |
| agcaggtggc | agcaggggaa | cgtcttctca | tgctccgtga tgcacgaggc tctgcacaac | 1920 | cactacacgc agaagagcct ctccctgtct ccgggtaaat ga                    1962

<210> SEQ ID NO 25
<211> LENGTH: 1065
<212> TYPE: PRT
<213> ORGANISM: artificial sequence
<220> FEATURE:
<223> OTHER INFORMATION: Synthetic polypeptide

<400> SEQUENCE: 25

```
Phe Arg Ser Asp Lys Cys Gly Gly Thr Ile Lys Ile Glu Asn Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Glu Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Ile Asp Gly Glu Asn Glu Gly Gly Arg Leu Trp Gly
65                  70                  75                  80

Lys Phe Cys Gly Lys Ile Ala Pro Ser Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Ile Phe Lys Arg Gly Pro Glu Cys Ser Gln
        115                 120                 125

Asn Tyr Thr Ala Pro Thr Gly Val Ile Lys Ser Pro Gly Phe Pro Glu
    130                 135                 140

Lys Tyr Pro Asn Ser Leu Glu Cys Thr Tyr Ile Ile Phe Ala Pro Lys
145                 150                 155                 160

Met Ser Glu Ile Ile Leu Glu Phe Glu Ser Phe Asp Leu Glu Gln Asp
                165                 170                 175

Ser Asn Pro Pro Gly Gly Met Phe Cys Arg Tyr Asp Arg Leu Glu Ile
            180                 185                 190

Trp Asp Gly Phe Pro Glu Val Gly Pro His Ile Gly Arg Tyr Cys Gly
        195                 200                 205

Gln Lys Thr Pro Gly Arg Ile Arg Ser Ser Ser Gly Val Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Ile Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Gly Thr Asn Trp Ser Val Glu Arg Ser Arg Leu Asn
        275                 280                 285

Tyr Pro Glu Asn Gly Trp Thr Pro Gly Glu Asp Ser Tyr Lys Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Arg Val Asp Ile Ser Ser Asn Gly Glu Asp Trp Ile Ser Leu Lys
            340                 345                 350

Glu Gly Asn Lys Ala Ile Ile Phe Gln Gly Asn Thr Asn Pro Thr Asp
```

-continued

```
            355                 360                 365
Val Val Leu Gly Val Phe Ser Lys Pro Leu Ile Thr Arg Phe Val Arg
    370                 375                 380
Ile Lys Pro Val Ser Trp Glu Thr Gly Ile Ser Met Arg Phe Glu Val
385                 390                 395                 400
Tyr Gly Cys Lys Ile Thr Asp Tyr Pro Cys Ser Gly Met Leu Gly Met
                    405                 410                 415
Val Ser Gly Leu Ile Ser Asp Ser Gln Ile Thr Ala Ser Asn Gln Ala
                420                 425                 430
Asp Arg Asn Trp Met Pro Glu Asn Ile Arg Leu Val Thr Ser Arg Thr
            435                 440                 445
Gly Trp Ala Leu Pro Pro Ser Pro His Pro Tyr Thr Asn Glu Trp Leu
        450                 455                 460
Gln Val Asp Leu Gly Asp Glu Lys Ile Val Arg Gly Val Ile Ile Gln
465                 470                 475                 480
Gly Gly Lys His Arg Glu Asn Lys Val Phe Met Arg Lys Phe Lys Ile
                    485                 490                 495
Ala Tyr Ser Asn Asn Gly Ser Asp Trp Lys Thr Ile Met Asp Asp Ser
                500                 505                 510
Lys Arg Lys Ala Lys Ser Phe Glu Gly Asn Asn Asn Tyr Asp Thr Pro
            515                 520                 525
Glu Leu Arg Thr Phe Ser Pro Leu Ser Thr Arg Phe Ile Arg Ile Tyr
        530                 535                 540
Pro Glu Arg Ala Thr His Ser Gly Leu Gly Leu Arg Met Glu Leu Leu
545                 550                 555                 560
Gly Cys Glu Val Glu Ala Pro Thr Ala Gly Pro Thr Thr Pro Asn Gly
                    565                 570                 575
Asn Pro Val Asp Glu Cys Asp Asp Gln Ala Asn Cys His Ser Gly
                580                 585                 590
Thr Gly Asp Asp Phe Gln Leu Thr Gly Gly Thr Thr Val Leu Ala Thr
            595                 600                 605
Glu Lys Pro Thr Ile Ile Asp Ser Thr Ile Gln Ser Glu Phe Pro Thr
        610                 615                 620
Tyr Gly Phe Asn Cys Glu Phe Gly Trp Gly Ser His Lys Thr Phe Cys
625                 630                 635                 640
His Trp Glu His Asp Ser His Ala Gln Leu Arg Trp Ser Val Leu Thr
                    645                 650                 655
Ser Lys Thr Gly Pro Ile Gln Asp His Thr Gly Asp Gly Asn Phe Ile
                660                 665                 670
Tyr Ser Gln Ala Asp Glu Asn Gln Lys Gly Lys Val Ala Arg Leu Val
            675                 680                 685
Ser Pro Val Val Tyr Ser Gln Ser Ser Ala His Cys Met Thr Phe Trp
        690                 695                 700
Tyr His Met Ser Gly Ser His Val Gly Thr Leu Arg Val Lys Leu Arg
705                 710                 715                 720
Tyr Gln Lys Pro Glu Glu Tyr Asp Gln Leu Val Trp Met Val Val Gly
                    725                 730                 735
His Gln Gly Asp His Trp Lys Glu Gly Arg Val Leu Leu His Lys Ser
                740                 745                 750
Leu Lys Leu Tyr Gln Val Ile Phe Glu Gly Glu Ile Gly Lys Gly Asn
            755                 760                 765
Leu Gly Gly Ile Ala Val Asp Asp Ile Ser Ile Asn Asn His Ile Ser
        770                 775                 780
```

```
Gln Glu Asp Cys Ala Lys Pro Thr Asp Leu Asp Lys Lys Asn Thr Glu
785                 790                 795                 800

Ile Lys Ile Asp Glu Thr Gly Ser Thr Pro Gly Tyr Glu Gly Glu Gly
            805                 810                 815

Glu Gly Asp Lys Asn Ile Ser Arg Lys Pro Gly Asn Val Leu Lys Thr
                820                 825                 830

Leu Asp Pro Val Ser Ser Thr Met Val Arg Ser Gly Cys Lys Pro Cys
            835                 840                 845

Ile Cys Thr Val Pro Glu Val Ser Ser Val Phe Ile Phe Pro Pro Lys
850                 855                 860

Pro Lys Asp Val Leu Thr Ile Thr Leu Thr Pro Lys Val Thr Cys Val
865                 870                 875                 880

Val Val Asp Ile Ser Lys Asp Asp Pro Glu Val Gln Phe Ser Trp Phe
                885                 890                 895

Val Asp Asp Val Glu Val His Thr Ala Gln Thr Gln Pro Arg Glu Glu
            900                 905                 910

Gln Phe Asn Ser Thr Phe Arg Ser Val Ser Glu Leu Pro Ile Met His
                915                 920                 925

Gln Asp Trp Leu Asn Gly Lys Glu Phe Lys Cys Arg Val Asn Ser Ala
930                 935                 940

Ala Phe Pro Ala Pro Ile Glu Lys Thr Ile Ser Lys Thr Lys Gly Arg
945                 950                 955                 960

Pro Lys Ala Pro Gln Val Tyr Thr Ile Pro Pro Lys Glu Gln Met
                965                 970                 975

Ala Lys Asp Lys Val Ser Leu Thr Cys Met Ile Thr Asp Phe Phe Pro
            980                 985                 990

Glu Asp Ile Thr Val Glu Trp Gln Trp Asn Gly Gln Pro Ala Glu Asn
            995                 1000                1005

Tyr Lys Asn Thr Gln Pro Ile Met Asp Thr Asp Gly Ser Tyr Phe
    1010                1015                1020

Val Tyr Ser Lys Leu Asn Val Gln Lys Ser Asn Trp Glu Ala Gly
    1025                1030                1035

Asn Thr Phe Thr Cys Ser Val Leu His Glu Gly Leu His Asn His
    1040                1045                1050

His Thr Glu Lys Ser Leu Ser His Ser Pro Gly Lys
    1055                1060                1065

<210> SEQ ID NO 26
<211> LENGTH: 3261
<212> TYPE: DNA
<213> ORGANISM: artificial sequence
<220> FEATURE:
<223> OTHER INFORMATION: Synthetic polynucleotide

<400> SEQUENCE: 26
atggagaggg ggctgccgtt gctgtgcgcc acgctcgccc ttgccctcgc cctggcgggc      60
gctttccgca gcgacaaatg tggcgggacc ataaaaatcg aaacccagg gtacctcaca      120 tctcccggtt accctcattc ttaccatcca agtgagaagt gtgaatggct aatccaagct    180
ccggaaccct accagagaat catgatcaac ttcaacccac atttcgattt ggaggacaga    240
gactgcaagt atgactacgt ggaagtaatc gatggggaga atgaaggcgg ccgcctgtgg    300
gggaagttct gtggaagat tgcaccttct cctgtggtgt cttcagggcc ctttctcttc    360
atcaaatttg tctctgacta tgagacacat ggggcagggt tttccatccg ctatgaaatc    420
```

```
ttcaagagag ggcccgaatg ttctcagaac tatacagcac ctactggagt gataaagtcc      480
cctgggttcc ctgaaaaata ccccaacagc ttggagtgca cctacatcat ctttgcacca      540
aagatgtctg agataatcct ggagtttgaa agttttgacc tggagcaaga ctcgaatcct      600 cccgaggaa tgttctgtcg ctatgaccgg ctggagatct gggatggatt ccctgaagtt      660
ggccctcaca ttgggcgtta ttgtgggcag aaaactcctg gccggatccg ctcctcttca      720
ggcgttctat ccatggtctt ttacactgac agcgcaatag caaaagaagg tttctcagcc      780
aactacagtg tgctacagag cagcatctct gaagatttta agtgtatgga ggctctgggc      840
atggaatctg gagagatcca ttctgatcag atcactgcat cttcacagta tggtaccaac      900
tggtctgtag agcgctcccg cctgaactac cctgaaaatg ggtggactcc aggagaagac      960
tcctacaagg agtggatcca ggtggacttg ggcctcctgc gattcgttac tgctgtaggg     1020
acacagggtg ccatttccaa ggaaaccaag aagaaatatt atgtcaagac ttacagagta     1080
gacatcagct ccaacggaga ggactggatc tccctgaaag agggaaataa agccattatc     1140
tttcagggaa acaccaaccc cacagatgtt gtcttaggag ttttctccaa accactgata     1200
actcgatttg tccgaatcaa acctgtatcc tgggaaactg gtatatctat gagatttgaa     1260
gtttatggct gcaagataac agattatcct tgctctggaa tgttgggcat ggtgtctgga     1320
cttatttcag actcccagat tacagcatcc aatcaagccg acaggaattg gatgccagaa     1380
aacatccgtc tggtgaccag tcgtaccggc tgggcactgc caccctcacc ccacccatac     1440
accaatgaat ggctccaagt ggacctggga gatgagaaga tagtaagagg tgtcatcatt     1500
cagggtggga agcaccgaga aaacaaggtg ttcatgagga agttcaagat cgcctatagt     1560
aacaatggct ctgactggaa aactatcatg gatgacagca agcgcaaggc taagtcgttc     1620
gaaggcaaca caactatga cacacctgag cttcggacgt tttcacctct ctccacaagg     1680
ttcatcagga tctaccctga gagagccaca cacagtgggc ttgggctgag gatggagcta     1740
ctgggctgtg aagtggaagc acctacagct ggaccaacca cacccaatgg gaacccagtg     1800
gatgagtgtg acgacgacca ggccaactgc cacagtggca caggtgatga cttccagctc     1860
acaggaggca ccactgtcct ggccacagag aagccaacca ttatagacag caccatccaa     1920
tcagagttcc cgacatacgg tttttaactgc gagtttggct ggggctctca caagacattc     1980
tgccactggg agcatgacag ccatgcacag ctcaggtgga gtgtgctgac cagcaagaca     2040
gggccgattc aggaccatac aggagatggc aacttcatct attcccaagc tgatgaaaat     2100
cagaaaggca aagtagcccg cctggtgagc cctgtggtct attcccagag ctctgcccac     2160
tgtatgacct tctggtatca catgtccggc tctcatgtgg gtacactgag ggtcaaacta     2220
cgctaccaga agccagagga atatgatcaa ctggtctgga tggtggttgg gcaccaagga     2280
gaccactgga agaaggacg tgtcttgctg cacaaatctc tgaaactata tcaggttatt     2340
tttgaaggtg aaatcggaaa aggaaaccctt ggtggaattg ctgtggatga tatcagtatt     2400
aacaaccata tttctcagga agactgtgca aaaccaacag acctagataa aaagaacaca     2460
gaaattaaaa ttgatgaaac agggagcact ccaggatatg aaggagaagg ggaaggtgac     2520
aagaacatct ccaggaagcc aggcaatgtg cttaagaccc tggatcccgt ctcgagcacc     2580
atggttagat ctggttgtaa gccttgcata tgtacagtcc cagaagtatc atctgtcttc     2640
atcttccccc caaagcccaa ggatgtgctc accattactc tgactcctaa ggtcacgtgt     2700
gttgtggtag acatcagcaa ggatgatccc gaggtccagt tcagctggtt tgtagatgat     2760
gtggaggtgc acacagctca gacgcaaccc cgggaggagc agttcaacag cactttccgc     2820
```

-continued

```
tcagtcagtg aacttcccat catgcaccag gactggctca atggcaagga gttcaaatgc    2880
agggtcaaca gtgcagcttt ccctgccccc atcgagaaaa ccatctccaa aaccaaaggc    2940
agaccgaagg ctccacaggt gtacaccatt ccacctccca aggagcagat ggccaaggat    3000
aaagtcagtc tgacctgcat gataacagac ttcttccctg aagacattac tgtggagtgg    3060
cagtggaatg ggcagccagc ggagaactac aagaacactc agcccatcat ggacacagat    3120
ggctcttact tcgtctacag caagctcaat gtgcagaaga gcaactggga ggcaggaaat    3180
actttcacct gctctgtgtt acatgagggc ctgcacaacc accatactga gaagagcctc    3240
tcccactctc ctggtaaatg a                                              3261
```

<210> SEQ ID NO 27
<211> LENGTH: 813
<212> TYPE: PRT
<213> ORGANISM: artificial sequence
<220> FEATURE:
<223> OTHER INFORMATION: Synthetic polypeptide

<400> SEQUENCE: 27

```
Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
        195                 200                 205

Asp Arg Leu Glu Ile Trp Asp Gly Phe Pro Glu Val Gly Pro His Ile
    210                 215                 220

Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
            260                 265                 270

Phe Lys Cys Met Glu Ala Leu Gly Met Glu Ser Gly Glu Ile His Ser
```

-continued

```
                275                 280                 285
Asp Gln Ile Thr Ala Ser Ser Gln Tyr Gly Thr Asn Trp Ser Val Glu
290                 295                 300
Arg Ser Arg Leu Asn Tyr Pro Glu Asn Gly Trp Thr Pro Gly Glu Asp
305                 310                 315                 320
Ser Tyr Lys Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Arg Val Asp Ile Ser Ser Asn Gly Glu Asp
                355                 360                 365
Trp Ile Ser Leu Lys Glu Gly Asn Lys Ala Ile Ile Phe Gln Gly Asn
370                 375                 380
Thr Asn Pro Thr Asp Val Val Leu Gly Val Phe Ser Lys Pro Leu Ile
385                 390                 395                 400
Thr Arg Phe Val Arg Ile Lys Pro Val Ser Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
                435                 440                 445
Ala Ser Asn Gln Ala Asp Arg Asn Trp Met Pro Glu Asn Ile Arg Leu
            450                 455                 460
Val Thr Ser Arg Thr Gly Trp Ala Leu Pro Pro Ser Pro His Pro Tyr
465                 470                 475                 480
Thr Asn Glu Trp Leu Gln Val Asp Leu Gly Asp Glu Lys Ile Val Arg
                485                 490                 495
Gly Val Ile Ile Gln Gly Gly Lys His Arg Glu Asn Lys Val Phe Met
            500                 505                 510
Arg Lys Phe Lys Ile Ala Tyr Ser Asn Asn Gly Ser Asp Trp Lys Thr
                515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Ser Pro Leu Ser Thr Arg
545                 550                 555                 560
Phe Ile Arg Ile Tyr Pro Glu Arg Ala Thr His Ser Gly Leu Gly Leu
                565                 570                 575
Arg Met Glu Leu Leu Gly Cys Val Ser Ser Thr Met Val Arg Ser Gly
            580                 585                 590
Cys Lys Pro Cys Ile Cys Thr Val Pro Glu Val Ser Ser Val Phe Ile
                595                 600                 605
Phe Pro Pro Lys Pro Lys Asp Val Leu Thr Ile Thr Leu Thr Pro Lys
            610                 615                 620
Val Thr Cys Val Val Asp Ile Ser Lys Asp Asp Pro Glu Val Gln
625                 630                 635                 640
Phe Ser Trp Phe Val Asp Asp Val Glu Val His Thr Ala Gln Thr Gln
                645                 650                 655
Pro Arg Glu Glu Gln Phe Asn Ser Thr Phe Arg Ser Val Ser Glu Leu
            660                 665                 670
Pro Ile Met His Gln Asp Trp Leu Asn Gly Lys Glu Phe Lys Cys Arg
                675                 680                 685
Val Asn Ser Ala Ala Phe Pro Ala Pro Ile Glu Lys Thr Ile Ser Lys
690                 695                 700
```

```
Thr Lys Gly Arg Pro Lys Ala Pro Gln Val Tyr Thr Ile Pro Pro Pro
705                 710                 715                 720

Lys Glu Gln Met Ala Lys Asp Lys Val Ser Leu Thr Cys Met Ile Thr
            725                 730                 735

Asp Phe Phe Pro Glu Asp Ile Thr Val Glu Trp Gln Trp Asn Gly Gln
        740                 745                 750

Pro Ala Glu Asn Tyr Lys Asn Thr Gln Pro Ile Met Asp Thr Asp Gly
    755                 760                 765

Ser Tyr Phe Val Tyr Ser Lys Leu Asn Val Gln Lys Ser Asn Trp Glu
770                 775                 780

Ala Gly Asn Thr Phe Thr Cys Ser Val Leu His Glu Gly Leu His Asn
785                 790                 795                 800

His His Thr Glu Lys Ser Leu Ser His Ser Pro Gly Lys
                805                 810

<210> SEQ ID NO 28
<211> LENGTH: 2442
<212> TYPE: DNA
<213> ORGANISM: artificial sequence
<220> FEATURE:
<223> OTHER INFORMATION: Synthetic polynucleotide

<400> SEQUENCE: 28
atggagaggg ggctgccgtt gctgtgcgcc acgctcgccc ttgccctcgc cctggcgggc      60
gctttccgca gcgacaaatg tggcgggacc ataaaaatcg aaaacccagg gtacctcaca     120
tctcccggtt accctcattc ttaccatcca agtgagaagt gtgaatggct aatccaagct     180
ccggaaccct accagagaat catgatcaac ttcaacccac atttcgattt ggaggacaga     240
gactgcaagt atgactacgt ggaagtaatc gatggggaga tgaaggcgg ccgcctgtgg     300 gggaagttct gtgggaagat tgcaccttct cctgtggtgt cttcagggcc ctttctcttc     360
atcaaatttg tctctgacta tgagacacat ggggcagggt tttccatccg ctatgaaatc     420
ttcaagagag ggcccgaatg ttctcagaac tatacagcac tactggagt gataaagtcc     480 cctgggttcc ctgaaaaata ccccaacagc ttggagtgca cctacatcat ctttgcacca     540
aagatgtctg agataatcct ggagtttgaa agttttgacc tggagcaaga ctcgaatcct     600 cccgaggaa tgttctgtcg ctatgaccgg ctggagatct gggatggatt ccctgaagtt     660
ggccctcaca ttgggcgtta ttgtgggcag aaaactcctg gccggatccg ctcctcttca     720
ggcgttctat ccatggtctt ttacactgac agcgcaatag caaaagaagg tttctcagcc     780
aactacagtg tgctacagag cagcatctct gaagatttta gtgtatgga ggctctgggc     840 atggaatctg agagatcca ttctgatcag atcactgcat cttcacagta tggtaccaac     900
tggtctgtag agcgctcccg cctgaactac cctgaaaatg gtggactcc aggagaagac     960 tcctacaagg agtggatcca ggtggacttg ggcctcctgc gattcgttac tgctgtaggg    1020
acacagggtg ccatttccaa ggaaaccaag aagaatatat gtcaagac ttacagagta     1080 gacatcagct ccaacggaga ggactggatc tccctgaaag agggaaataa agccattatc    1140
tttcagggaa acaccaaccc cacagatgtt gtcttaggag tttctccaa accactgata    1200 actcgatttg tccgaatcaa acctgtatcc tgggaaactg gtatatctat gagatttgaa    1260
gtttatggct gcaagataac agattatcct tgctctggaa tgttgggcat ggtgtctgga    1320
cttatttcag actcccagat tacagcatcc aatcaagccg acaggaattg gatgccagaa    1380
aacatccgtc tggtgaccag tcgtaccggc tgggcactgc caccctcacc ccacccatac    1440
```

```
accaatgaat ggctccaagt ggacctggga gatgagaaga tagtaagagg tgtcatcatt    1500
cagggtggga agcaccgaga aaacaaggtg ttcatgagga agttcaagat cgcctatagt    1560
aacaatggct ctgactggaa aactatcatg gatgacagca agcgcaaggc taagtcgttc    1620
gaaggcaaca caactatga cacacctgag cttcggacgt tttcacctct ctccacaagg    1680
ttcatcagga tctaccctga gagagccaca cacagtgggc ttgggctgag gatggagcta    1740
ctgggctgtg tctcgagcac catggttaga tctggttgta agccttgcat atgtacagtc    1800
ccagaagtat catctgtctt catcttcccc ccaaagccca aggatgtgct caccattact    1860
ctgactccta aggtcacgtg tgttgtggta gacatcagca aggatgatcc cgaggtccag    1920
ttcagctggt ttgtagatga tgtggaggtg cacacagctc agacgcaacc ccgggaggag    1980
cagttcaaca gcactttccg ctcagtcagt gaacttccca tcatgcacca ggactggctc    2040
aatggcaagg agttcaaatg cagggtcaac agtgcagctt ccctgccccc catcgagaaa    2100
accatctcca aaaccaaagg cagaccgaag gctccacagg tgtacaccat tccacctccc    2160
aaggagcaga tggccaagga taaagtcagt ctgacctgca tgataacaga cttcttccct    2220
gaagacatta ctgtggagtg gcagtggaat gggcagccag cggagaacta caagaacact    2280
cagcccatca tggacacaga tggctcttac ttcgtctaca gcaagctcaa tgtgcagaag    2340
agcaactggg aggcaggaaa tactttcacc tgctctgtgt tacatgaggg cctgcacaac    2400
caccatactg agaagagcct ctcccactct cctggtaaat ga                       2442
```

<210> SEQ ID NO 29
<211> LENGTH: 633
<212> TYPE: PRT
<213> ORGANISM: artificial sequence
<220> FEATURE:
<223> OTHER INFORMATION: Synthetic polypeptide

<400> SEQUENCE: 29

```
Phe Arg Ser Asp Lys Cys Gly Gly Thr Ile Lys Ile Glu Asn Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Glu Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Ile Asp Gly Glu Asn Glu Gly Gly Arg Leu Trp Gly
65                  70                  75                  80

Lys Phe Cys Gly Lys Ile Ala Pro Ser Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Ile Phe Lys Arg Gly Pro Glu Cys Ser Gln
        115                 120                 125

Asn Tyr Thr Ala Pro Thr Gly Val Ile Lys Ser Pro Gly Phe Pro Glu
    130                 135                 140

Lys Tyr Pro Asn Ser Leu Glu Cys Thr Tyr Ile Ile Phe Ala Pro Lys
145                 150                 155                 160

Met Ser Glu Ile Ile Leu Glu Phe Glu Ser Phe Asp Leu Glu Gln Asp
                165                 170                 175

Ser Asn Pro Pro Gly Gly Met Phe Cys Arg Tyr Asp Arg Leu Glu Ile
```

-continued

```
            180                 185                 190
Trp Asp Gly Phe Pro Glu Val Gly Pro His Ile Gly Arg Tyr Cys Gly
            195                 200                 205
Gln Lys Thr Pro Gly Arg Ile Arg Ser Ser Ser Gly Val Leu Ser Met
            210                 215                 220
Val Phe Tyr Thr Asp Ser Ala Ile Ala Lys Glu Gly Phe Ser Ala Asn
225                 230                 235                 240
Tyr Ser Val Leu Gln Ser Ser Ile Ser Glu Asp Phe Lys Cys Met Glu
                245                 250                 255
Ala Leu Gly Met Glu Ser Gly Glu Ile His Ser Asp Gln Ile Thr Ala
                260                 265                 270
Ser Ser Gln Tyr Gly Thr Asn Trp Ser Val Glu Arg Ser Arg Leu Asn
            275                 280                 285
Tyr Pro Glu Asn Gly Trp Thr Pro Gly Glu Asp Ser Tyr Lys Glu Trp
            290                 295                 300
Ile Gln Val Asp Leu Gly Leu Leu Arg Phe Val Thr Ala Val Gly Thr
305                 310                 315                 320
Gln Gly Ala Ile Ser Lys Glu Thr Lys Lys Lys Tyr Tyr Val Lys Thr
                325                 330                 335
Tyr Arg Val Asp Ile Ser Ser Asn Gly Glu Asp Trp Ile Ser Leu Lys
                340                 345                 350
Glu Gly Asn Lys Ala Ile Ile Phe Gln Gly Asn Thr Asn Pro Thr Asp
            355                 360                 365
Val Val Leu Gly Val Phe Ser Lys Pro Leu Ile Thr Arg Phe Val Arg
370                 375                 380
Ile Lys Pro Val Ser Trp Glu Thr Gly Ile Ser Met Arg Phe Glu Val
385                 390                 395                 400
Tyr Gly Cys Val Ser Ser Thr Met Val Arg Ser Gly Cys Lys Pro Cys
                405                 410                 415
Ile Cys Thr Val Pro Glu Val Ser Ser Val Phe Ile Phe Pro Pro Lys
            420                 425                 430
Pro Lys Asp Val Leu Thr Ile Thr Leu Thr Pro Lys Val Thr Cys Val
            435                 440                 445
Val Val Asp Ile Ser Lys Asp Asp Pro Glu Val Gln Phe Ser Trp Phe
450                 455                 460
Val Asp Asp Val Glu Val His Thr Ala Gln Thr Gln Pro Arg Glu Glu
465                 470                 475                 480
Gln Phe Asn Ser Thr Phe Arg Ser Val Ser Glu Leu Pro Ile Met His
                485                 490                 495
Gln Asp Trp Leu Asn Gly Lys Glu Phe Lys Cys Arg Val Asn Ser Ala
            500                 505                 510
Ala Phe Pro Ala Pro Ile Glu Lys Thr Ile Ser Lys Thr Lys Gly Arg
            515                 520                 525
Pro Lys Ala Pro Gln Val Tyr Thr Ile Pro Pro Lys Glu Gln Met
            530                 535                 540
Ala Lys Asp Lys Val Ser Leu Thr Cys Met Ile Thr Asp Phe Phe Pro
545                 550                 555                 560
Glu Asp Ile Thr Val Glu Trp Gln Trp Asn Gly Gln Pro Ala Glu Asn
                565                 570                 575
Tyr Lys Asn Thr Gln Pro Ile Met Asp Thr Asp Gly Ser Tyr Phe Val
                580                 585                 590
Tyr Ser Lys Leu Asn Val Gln Lys Ser Asn Trp Glu Ala Gly Asn Thr
            595                 600                 605
```

```
      Phe Thr Cys Ser Val Leu His Glu Gly Leu His Asn His His Thr Glu
          610                 615                 620

Lys Ser Leu Ser His Ser Pro Gly Lys
      625                 630

<210> SEQ ID NO 30
<211> LENGTH: 1965
<212> TYPE: DNA
<213> ORGANISM: artificial sequence
<220> FEATURE:
<223> OTHER INFORMATION: Synthetic polynucleotide

<400> SEQUENCE: 30
atggagaggg ggctgccgtt gctgtgcgcc acgctcgccc ttgccctcgc cctggcgggc      60
gctttccgca gcgacaaatg tggcgggacc ataaaaatcg aaacccagg gtacctcaca     120 tctcccggtt accctcattc ttaccatcca agtgagaagt gtgaatggct aatccaagct     180
ccggaaccct accagagaat catgatcaac ttcaacccac atttcgattt ggaggacaga     240
gactgcaagt atgactacgt ggaagtaatc gatggggaga tgaaggcgg ccgcctgtgg     300 gggaagttct gtgggaagat tgcaccttct cctgtggtgt cttcagggcc ctttctcttc     360
atcaaatttg tctctgacta tgagacacat ggggcagggt tttccatccg ctatgaaatc     420
ttcaagagag ggcccgaatg ttctcagaac tatacagcac tactggagt gataaagtcc     480 cctgggttcc ctgaaaaata ccccaacagc ttggagtgca cctacatcat ctttgcacca     540
aagatgtctg agataatcct ggagtttgaa agttttgacc tggagcaaga ctcgaatcct     600
cccggaggaa tgttctgtcg ctatgaccgg ctggagatct gggatggatt ccctgaagtt     660
ggccctcaca ttgggcgtta ttgtgggcag aaaactcctg gccggatccg ctcctcttca     720
ggcgttctat ccatggtctt ttacactgac agcgcaatag caaaagaagg tttctcagcc     780
aactacagtg tgctacagag cagcatctct gaagatttta agtgtatgga ggctctgggc     840
atggaatctg gagagatcca ttctgatcag atcactgcat cttcacagta tggtaccaac     900
tggtctgtag agcgctcccg cctgaactac cctgaaaatg ggtggactcc aggagaagac     960
tcctacaagg agtggatcca ggtggacttg ggcctcctgc gattcgttac tgctgtaggg    1020
acacagggtg ccatttccaa ggaaaccaag aagaaatatt atgtcaagac ttacagagta    1080
gacatcagct ccaacggaga ggactggatc tccctgaaag agggaaataa agccattatc    1140
tttcagggaa acaccaaccc cacagatgtt gtcttaggag ttttctccaa accactgata    1200
actcgatttg tccgaatcaa acctgtatcc tgggaaactg gtatatctat gagatttgaa    1260
gtttatggct gcgtctcgag caccatggtt agatctggtt gtaagccttg catatgtaca    1320
gtcccagaag tatcatctgt cttcatcttc ccccaaagc ccaaggatgt gctcaccatt    1380
actctgactc ctaaggtcac gtgtgttgtg gtagacatca gcaaggatga tcccgaggtc    1440
cagttcagct ggtttgtaga tgatgtggag gtgcacacag ctcagacgca accccgggag    1500
gagcagttca acagcacttt ccgctcagtc agtgaacttc ccatcatgca ccaggactgg    1560
ctcaatggca aggagttcaa atgcagggtc aacagtgcag cttttccctgc ccccatcgag    1620 aaaaccatct ccaaaaccaa aggcagaccg aaggctccac aggtgtacac cattccacct    1680
cccaaggagc agatggccaa ggataaagtc agtctgacct gcatgataac agacttcttc    1740
cctgaagaca ttactgtgga gtggcagtgg aatgggcagc cagcgagaa ctacaagaac    1800 actcagccca tcatggacac agatggctct tacttcgtct acagcaagct caatgtgcag    1860
```

```
aagagcaact gggaggcagg aaatactttc acctgctctg tgttacatga gggcctgcac   1920
aaccaccata ctgagaagag cctctcccac tctcctggta aatga                   1965
```

<210> SEQ ID NO 31
<211> LENGTH: 911
<212> TYPE: PRT
<213> ORGANISM: artificial sequence
<220> FEATURE:
<223> OTHER INFORMATION: Synthetic polypeptide

<400> SEQUENCE: 31

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350
```

```
Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
    370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Glu Val Glu Ala Pro Thr Ala
                405                 410                 415

Gly Pro Thr Thr Pro Asn Gly Asn Leu Val Asp Glu Cys Asp Asp Asp
            420                 425                 430

Gln Ala Asn Cys His Ser Gly Thr Gly Asp Asp Phe Gln Leu Thr Gly
            435                 440                 445

Gly Thr Thr Val Leu Ala Thr Glu Lys Pro Thr Val Ile Asp Ser Thr
        450                 455                 460

Ile Gln Ser Glu Phe Pro Thr Tyr Gly Phe Asn Cys Glu Phe Gly Trp
465                 470                 475                 480

Gly Ser His Lys Thr Phe Cys His Trp Glu His Asp Asn His Val Gln
                485                 490                 495

Leu Lys Trp Ser Val Leu Thr Ser Lys Thr Gly Pro Ile Gln Asp His
            500                 505                 510

Thr Gly Asp Gly Asn Phe Ile Tyr Ser Gln Ala Asp Glu Asn Gln Lys
            515                 520                 525

Gly Lys Val Ala Arg Leu Val Ser Pro Val Val Tyr Ser Gln Asn Ser
        530                 535                 540

Ala His Cys Met Thr Phe Trp Tyr His Met Ser Gly Ser His Val Gly
545                 550                 555                 560

Thr Leu Arg Val Lys Leu Arg Tyr Gln Lys Pro Glu Glu Tyr Asp Gln
                565                 570                 575

Leu Val Trp Met Ala Ile Gly His Gln Gly Asp His Trp Lys Glu Gly
            580                 585                 590

Arg Val Leu Leu His Lys Ser Leu Lys Leu Tyr Gln Val Ile Phe Glu
            595                 600                 605

Gly Glu Ile Gly Lys Gly Asn Leu Gly Gly Ile Ala Val Asp Asp Ile
        610                 615                 620

Ser Ile Asn Asn His Ile Ser Gln Glu Asp Cys Ala Lys Pro Ala Asp
625                 630                 635                 640

Leu Asp Lys Lys Asn Pro Glu Ile Lys Ile Asp Glu Thr Gly Ser Thr
                645                 650                 655

Pro Gly Tyr Glu Gly Glu Gly Glu Gly Asp Lys Asn Ile Ser Arg Lys
            660                 665                 670

Pro Gly Asn Val Leu Lys Thr Leu Asp Pro Arg Ser Asp Lys Thr His
            675                 680                 685

Thr Cys Pro Pro Cys Pro Ala Pro Glu Leu Leu Gly Gly Pro Ser Val
        690                 695                 700

Phe Leu Phe Pro Pro Lys Pro Lys Asp Thr Leu Met Ile Ser Arg Thr
705                 710                 715                 720

Pro Glu Val Thr Cys Val Val Val Asp Val Ser His Glu Asp Pro Glu
                725                 730                 735

Val Lys Phe Asn Trp Tyr Val Asp Gly Val Glu Val His Asn Ala Lys
            740                 745                 750

Thr Lys Pro Arg Glu Glu Gln Tyr Asn Ser Thr Tyr Arg Val Val Ser
            755                 760                 765
```

```
Val Leu Thr Val Leu His Gln Asp Trp Leu Asn Gly Lys Glu Tyr Lys
        770                 775                 780
Cys Lys Val Ser Asn Lys Ala Leu Pro Ala Pro Ile Glu Lys Thr Ile
785                 790                 795                 800
Ser Lys Ala Lys Gly Gln Pro Arg Glu Pro Gln Val Tyr Thr Leu Pro
                805                 810                 815
Pro Ser Arg Glu Glu Met Thr Lys Asn Gln Val Ser Leu Thr Cys Leu
            820                 825                 830
Val Lys Gly Phe Tyr Pro Ser Asp Ile Ala Val Glu Trp Glu Ser Asn
        835                 840                 845
Gly Gln Pro Glu Asn Asn Tyr Lys Thr Thr Pro Pro Val Leu Asp Ser
    850                 855                 860
Asp Gly Ser Phe Phe Leu Tyr Ser Lys Leu Thr Val Asp Lys Ser Arg
865                 870                 875                 880
Trp Gln Gln Gly Asn Val Phe Ser Cys Ser Val Met His Glu Ala Leu
                885                 890                 895
His Asn His Tyr Thr Gln Lys Ser Leu Ser Leu Ser Pro Gly Lys
            900                 905                 910

<210> SEQ ID NO 32
<211> LENGTH: 2799
<212> TYPE: DNA
<213> ORGANISM: artificial sequence
<220> FEATURE:
<223> OTHER INFORMATION: Synthetic polynucleotide

<400> SEQUENCE: 32
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac tagtggagt gataaagtcc     480 cccggattcc ctgaaaaata tcccaacagc cttaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag tcgaatccg atcctcatcg     720 ggcattctct ccatggtttt ttacaccgac agcgcgatag caaagaagg tttctcagca     780 aactacagtg tcttgcagag cagtgtctca gaagatttca atgtatgga agctctgggc     840 atggaatcag agaaattca ttctgaccag atcacagctt cttcccagta tagcaccaac     900
tggtctgcag agcgctcccg cctgaactac cctgaaatg ggtggactcc cggagaggat     960
tcctaccgag agtggataca ggtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg gcatatctat gagatttgaa    1260
```

```
gtatatggtt gcaagataac agattatcct gaagtggaag cccctacagc tggaccgacc    1320
actcccaacg ggaacttggt ggatgaatgt gatgacgacc aggccaactg ccacagtgga    1380
acaggtgatg acttccagct cacaggtggc accactgtgc tggccacaga aaagcccacg    1440
gtcatagaca gcaccataca atcagagttt ccaacatatg gttttaactg tgaatttggc    1500
tggggctctc acaagacctt ctgccactgg gaacatgaca atcacgtgca gctcaagtgg    1560
agtgtgttga ccagcaagac gggacccatt caggatcaca caggagatgg caacttcatc    1620
tattcccaag ctgacgaaaa tcagaagggc aaagtggctc gcctggtgag ccctgtggtt    1680
tattcccaga actctgccca ctgcatgacc ttctggtatc acatgtctgg gtcccacgtc    1740
ggcacactca gggtcaaact gcgctaccag aagccagagg agtacgatca gctggtctgg    1800
atggccattg acaccaagg tgaccactgg aaggaagggc gtgtcttgct ccacaagtct    1860
ctgaaacttt atcaggtgat tttcgagggc gaaatcggaa aggaaacct tggtgggatt    1920
gctgtggatg acattagtat taataaccac atttcacaag aagattgtgc aaaaccagca    1980
gacctggata aaagaacccc agaaattaaa attgatgaaa cagggagcac gccaggatac    2040
gaaggtgaag gagaaggtga caagaacatc tccaggaagc caggcaatgt gttgaagacc    2100
ttagacccca gatctgacaa aactcacaca tgcccaccgt gcccagcacc tgaactcctg    2160
gggggaccgt cagtcttcct cttccccca aaacccaagg acaccctcat gatctcccgg    2220
acccctgagg tcacatgcgt ggtggtggac gtgagccacg aagaccctga ggtcaagttc    2280
aactggtacg tggacggcgt ggaggtgcat aatgccaaga caaagccgcg ggaggagcag    2340
tacaacagca cgtaccgtgt ggtcagcgtc ctcaccgtcc tgcaccagga ctggctgaat    2400
ggcaaggagt acaagtgcaa ggtctccaac aaagccctcc cagcccccat cgagaaaacc    2460
atctccaaag ccaaagggca gccccgagaa ccacaggtgt acaccctgcc cccatcccgg    2520
gaggagatga ccaagaacca ggtcagcctg acctgcctgg tcaaaggctt ctatcccagc    2580
gacatcgccg tggagtggga gagcaatggg cagccggaga acaactacaa gaccacgcct    2640
cccgtgctgg actccgacgg ctccttcttc ctctacagca agctcaccgt ggacaagagc    2700
aggtggcagc aggggaacgt cttctcatgc tccgtgatgc acgaggctct gcacaaccac    2760
tacacgcaga agagcctctc cctgtctccg ggtaaatga                           2799
```

<210> SEQ ID NO 33
<211> LENGTH: 911
<212> TYPE: PRT
<213> ORGANISM: artificial sequence
<220> FEATURE:
<223> OTHER INFORMATION: Synthetic polypeptide

<400> SEQUENCE: 33

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Pro Val Ser Ser Gly Pro
            85                  90                  95
```

```
Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
            210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
            275                 280                 285

Tyr Pro Glu Asn Gly Trp Thr Pro Gly Glu Asp Ser Tyr Arg Glu Trp
            290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
            325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Glu Val Glu Ala Pro Thr Ala
            405                 410                 415

Gly Pro Thr Thr Pro Asn Gly Asn Leu Val Asp Glu Cys Asp Asp Asp
            420                 425                 430

Gln Ala Asn Cys His Ser Gly Thr Gly Asp Asp Phe Gln Leu Thr Gly
            435                 440                 445

Gly Thr Thr Val Leu Ala Thr Glu Lys Pro Thr Val Ile Asp Ser Thr
            450                 455                 460

Ile Gln Ser Glu Phe Pro Thr Tyr Gly Phe Asn Cys Glu Phe Gly Trp
465                 470                 475                 480

Gly Ser His Lys Thr Phe Cys His Trp Glu His Asp Asn His Val Gln
            485                 490                 495

Leu Lys Trp Ser Val Leu Thr Ser Lys Thr Gly Pro Ile Gln Asp His
            500                 505                 510
```

Thr Gly Asp Gly Asn Phe Ile Tyr Ser Gln Ala Asp Glu Asn Gln Lys
            515                 520                 525

Gly Lys Val Ala Arg Leu Val Ser Pro Val Val Tyr Ser Gln Asn Ser
530                 535                 540

Ala His Cys Met Thr Phe Trp Tyr His Met Ser Gly Ser His Val Gly
545                 550                 555                 560

Thr Leu Arg Val Lys Leu Arg Tyr Gln Lys Pro Glu Glu Tyr Asp Gln
            565                 570                 575

Leu Val Trp Met Ala Ile Gly His Gln Gly Asp His Trp Lys Glu Gly
            580                 585                 590

Arg Val Leu Leu His Lys Ser Leu Lys Leu Tyr Gln Val Ile Phe Glu
            595                 600                 605

Gly Glu Ile Gly Lys Gly Asn Leu Gly Gly Ile Ala Val Asp Asp Ile
            610                 615                 620

Ser Ile Asn Asn His Ile Ser Gln Glu Asp Cys Ala Lys Pro Ala Asp
625                 630                 635                 640

Leu Asp Lys Lys Asn Pro Glu Ile Lys Ile Asp Glu Thr Gly Ser Thr
            645                 650                 655

Pro Gly Tyr Glu Gly Glu Gly Glu Gly Asp Lys Asn Ile Ser Arg Lys
            660                 665                 670

Pro Gly Asn Val Leu Lys Thr Leu Asp Pro Arg Ser Asp Lys Thr His
            675                 680                 685

Thr Cys Pro Pro Cys Pro Ala Pro Glu Leu Leu Gly Pro Ser Val
690                 695                 700

Phe Leu Phe Pro Pro Lys Pro Lys Asp Thr Leu Met Ile Ser Arg Thr
705                 710                 715                 720

Pro Glu Val Thr Cys Val Val Val Asp Val Ser His Glu Asp Pro Glu
            725                 730                 735

Val Lys Phe Asn Trp Tyr Val Asp Gly Val Glu Val His Asn Ala Lys
            740                 745                 750

Thr Lys Pro Arg Glu Glu Gln Tyr Asn Ser Thr Tyr Arg Val Val Ser
            755                 760                 765

Val Leu Thr Val Leu His Gln Asp Trp Leu Asn Gly Lys Glu Tyr Lys
770                 775                 780

Cys Lys Val Ser Asn Lys Ala Leu Pro Ala Pro Ile Glu Lys Thr Ile
785                 790                 795                 800

Ser Lys Ala Lys Gly Gln Pro Arg Glu Pro Gln Val Tyr Thr Leu Pro
            805                 810                 815

Pro Ser Arg Glu Glu Met Thr Lys Asn Gln Val Ser Leu Thr Cys Leu
            820                 825                 830

Val Lys Gly Phe Tyr Pro Ser Asp Ile Ala Val Glu Trp Glu Ser Asn
            835                 840                 845

Gly Gln Pro Glu Asn Asn Tyr Lys Thr Thr Pro Pro Val Leu Asp Ser
850                 855                 860

Asp Gly Ser Phe Phe Leu Tyr Ser Lys Leu Thr Val Asp Lys Ser Arg
865                 870                 875                 880

Trp Gln Gln Gly Asn Val Phe Ser Cys Ser Val Met His Glu Ala Leu
            885                 890                 895

His Asn His Tyr Thr Gln Lys Ser Leu Ser Leu Ser Pro Gly Lys
            900                 905                 910

<210> SEQ ID NO 34
<211> LENGTH: 2799
<212> TYPE: DNA

<213> ORGANISM: artificial sequence
<220> FEATURE:
<223> OTHER INFORMATION: Synthetic polynucleotide

<400> SEQUENCE: 34

```
atggagaggg ggctgccgct cctctgcgcc gtgctcgccc tcgtcctcgc cccggccggc    60
gcttttcgca acgataaatg tggcgatact ataaaaattg aaagcccgg gtaccttaca    120
tctcctggtt atcctcattc ttatcaccca agtgaaaaat gcgaatggct gattcaggct   180
ccggacccat accagagaat tatgatcaac ttcaaccctc acttcgattt ggaggacaga   240
gactgcaagt atgactacgt ggaagtcttc gatggagaaa atgaaaatgg acattttagg   300
ggaaagttct gtggaaagat agcccctcct cctgttgtgt cttcagggcc atttctttt    360
atcaaatttg tctctgacta cgaaacacat ggtgcaggat tttccatacg ttatgaactt   420
ttcaagagag gtcctgaatg ttcccagaac tacacaacac ctagtggagt gataaagtcc   480
cccggattcc ctgaaaaata tcccaacagc cttgaatgca cttatattgt ctttgcgcca   540
aagatgtcag agattatcct ggaatttgaa agctttgacc tggagcctga ctcaaatcct   600
ccaggggga tgttctgtcg ctacgaccgg ctagaaatct gggatggatt ccctgatgtt    660
ggccctcaca ttgggcgtta ctgtggacag aaaacaccag tcgaatccg atcctcatcg    720
ggcattctct ccatggtttt ttacaccgac agcgcgatag caaaagaagg tttctcagca   780
aactacagtg tcttgcagag cagtgtctca gaagatttca aatgtatgga agctctgggc   840
atggaatcag gagaaattca ttctgaccag atcacagctt cttcccaggc tagcaccaac   900
tggtctgcag agcgctcccg cctgaactac cctgagaatg ggtggactcc cggagaggat   960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa ccactgata   1200
actcgatttg tccgaatcaa gcctgcaact tgggaaactg gcatatctat gagatttgaa  1260
gtatatggtt gcaagataac agattatcct gaagtggaag cccctacagc tggaccgacc  1320
actcccaacg ggaacttggt ggatgaatgt gatgacgacc aggccaactg ccacagtgga  1380
acaggtgatg acttccagct cacaggtggc accactgtgc tggccacaga aaagcccacg  1440
gtcatagaca gcaccataca atcagagttt ccaacatatg gttttaactg tgaatttggc  1500
tggggctctc acaagacctt ctgccactgg gaacatgaca atcacgtgca gctcaagtgg  1560
agtgtgttga ccagcaagac gggacccatt caggatcaca caggagatgg caacttcatc  1620
tattcccaag ctgacgaaaa tcagaagggc aaagtggctc gcctggtgag ccctgtggtt  1680
tattcccaga actctgccca ctgcatgacc ttctggtatc acatgtctgg gtcccacgtc  1740
ggcacactca gggtcaaact gcgctaccag aagccagagg agtacgatca gctggtctgg  1800
atggccattg acaccaagg tgaccactgg aaggaagggc gtgtcttgct ccacaagtct  1860
ctgaaacttt atcaggtgat tttcgagggc gaaatcggaa aggaaacct tggtgggatt  1920
gctgtggatg acattagtat taataaccac atttcacaag aagattgtgc aaaaccagca  1980
gacctggata aaagaacccc agaaattaaa attgatgaaa cagggagcac gccaggatac  2040
gaaggtgaag agaaggtgaa caagaacatc tccaggaagc caggcaatgt gttgaagacc  2100
ttagacccca gatctgacaa aactcacaca tgcccaccgt gcccagcacc tgaactcctg  2160
gggggaccgt cagtcttcct cttcccccca aaacccaagg acaccctcat gatctcccgg  2220
```

```
acccctgagg tcacatgcgt ggtggtggac gtgagccacg aagaccctga ggtcaagttc    2280
aactggtacg tggacggcgt ggaggtgcat aatgccaaga caaagccgcg ggaggagcag    2340
tacaacagca cgtaccgtgt ggtcagcgtc ctcaccgtcc tgcaccagga ctggctgaat    2400
ggcaaggagt acaagtgcaa ggtctccaac aaagccctcc cagccccat cgagaaaacc    2460 atctccaaag ccaaagggca gccccgagaa ccacaggtgt acaccctgcc cccatcccgg    2520
gaggagatga ccaagaacca ggtcagcctg acctgcctgg tcaaaggctt ctatcccagc    2580
gacatcgccg tggagtggga gagcaatggg cagccggaga caactacaa gaccacgcct    2640 cccgtgctgg actccgacgg ctccttcttc ctctacagca agctcaccgt ggacaagagc    2700
aggtggcagc aggggaacgt cttctcatgc tccgtgatgc acgaggctct gcacaaccac    2760
tacacgcaga agagcctctc cctgtctccg ggtaaatga                           2799
```

<210> SEQ ID NO 35
<211> LENGTH: 755
<212> TYPE: PRT
<213> ORGANISM: artificial sequence
<220> FEATURE:
<223> OTHER INFORMATION: Synthetic polypeptide

<400> SEQUENCE: 35

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Glu Val Glu
                245                 250                 255
```

```
Ala Pro Thr Ala Gly Pro Thr Thr Pro Asn Gly Asn Leu Val Asp Glu
            260                 265                 270

Cys Asp Asp Gln Ala Asn Cys His Ser Gly Thr Gly Asp Asp Phe
    275                 280                 285

Gln Leu Thr Gly Gly Thr Thr Val Leu Ala Thr Glu Lys Pro Thr Val
    290                 295                 300

Ile Asp Ser Thr Ile Gln Ser Glu Phe Pro Thr Tyr Gly Phe Asn Cys
305                 310                 315                 320

Glu Phe Gly Trp Gly Ser His Lys Thr Phe Cys His Trp Glu His Asp
                325                 330                 335

Asn His Val Gln Leu Lys Trp Ser Val Leu Thr Ser Lys Thr Gly Pro
            340                 345                 350

Ile Gln Asp His Thr Gly Asp Gly Asn Phe Ile Tyr Ser Gln Ala Asp
            355                 360                 365

Glu Asn Gln Lys Gly Lys Val Ala Arg Leu Val Ser Pro Val Val Tyr
            370                 375                 380

Ser Gln Asn Ser Ala His Cys Met Thr Phe Trp Tyr His Met Ser Gly
385                 390                 395                 400

Ser His Val Gly Thr Leu Arg Val Lys Leu Arg Tyr Gln Lys Pro Glu
            405                 410                 415

Glu Tyr Asp Gln Leu Val Trp Met Ala Ile Gly His Gln Gly Asp His
            420                 425                 430

Trp Lys Glu Gly Arg Val Leu Leu His Lys Ser Leu Lys Leu Tyr Gln
            435                 440                 445

Val Ile Phe Glu Gly Glu Ile Gly Lys Gly Asn Leu Gly Gly Ile Ala
    450                 455                 460

Val Asp Asp Ile Ser Ile Asn Asn His Ile Ser Gln Glu Asp Cys Ala
465                 470                 475                 480

Lys Pro Ala Asp Leu Asp Lys Lys Asn Pro Glu Ile Lys Ile Asp Glu
            485                 490                 495

Thr Gly Ser Thr Pro Gly Tyr Glu Gly Glu Gly Glu Gly Asp Lys Asn
            500                 505                 510

Ile Ser Arg Lys Pro Gly Asn Val Leu Lys Thr Leu Asp Pro Arg Ser
    515                 520                 525

Asp Lys Thr His Thr Cys Pro Pro Cys Pro Ala Pro Glu Leu Leu Gly
    530                 535                 540

Gly Pro Ser Val Phe Leu Phe Pro Pro Lys Pro Lys Asp Thr Leu Met
545                 550                 555                 560

Ile Ser Arg Thr Pro Glu Val Thr Cys Val Val Val Asp Val Ser His
            565                 570                 575

Glu Asp Pro Glu Val Lys Phe Asn Trp Tyr Val Asp Gly Val Glu Val
            580                 585                 590

His Asn Ala Lys Thr Lys Pro Arg Glu Glu Gln Tyr Asn Ser Thr Tyr
    595                 600                 605

Arg Val Val Ser Val Leu Thr Val Leu His Gln Asp Trp Leu Asn Gly
    610                 615                 620

Lys Glu Tyr Lys Cys Lys Val Ser Asn Lys Ala Leu Pro Ala Pro Ile
625                 630                 635                 640

Glu Lys Thr Ile Ser Lys Ala Lys Gly Gln Pro Arg Glu Pro Gln Val
            645                 650                 655

Tyr Thr Leu Pro Pro Ser Arg Glu Glu Met Thr Lys Asn Gln Val Ser
            660                 665                 670

Leu Thr Cys Leu Val Lys Gly Phe Tyr Pro Ser Asp Ile Ala Val Glu
```

|  |  | 675 |  |  |  | 680 |  |  |  | 685 |  |
|---|---|---|---|---|---|---|---|---|---|---|---|

Trp Glu Ser Asn Gly Gln Pro Glu Asn Asn Tyr Lys Thr Thr Pro Pro
          690                 695                 700

Val Leu Asp Ser Asp Gly Ser Phe Phe Leu Tyr Ser Lys Leu Thr Val
705             710                 715                 720

Asp Lys Ser Arg Trp Gln Gln Gly Asn Val Phe Ser Cys Ser Val Met
                725                 730                 735

His Glu Ala Leu His Asn His Tyr Thr Gln Lys Ser Leu Ser Leu Ser
            740                 745                 750

Pro Gly Lys
       755

<210> SEQ ID NO 36
<211> LENGTH: 2331
<212> TYPE: DNA
<213> ORGANISM: artificial sequence
<220> FEATURE:
<223> OTHER INFORMATION: Synthetic polynucleotide

<400> SEQUENCE: 36

```
atggagaggg ggctgccgct cctctgcgcc gtgctcgccc tcgtcctcgc cccggccggc     60
gcttttcgca acgataaatg tggcgatact ataaaaattg aaagccccgg gtaccttaca    120
tctcctggtt atcctcattc ttatcaccca agtgaaaaat gcgaatggct gattcaggct    180
ccggacccat accagagaat tatgatcaac ttcaaccctc acttcgattt ggaggacaga    240
gactgcaagt atgactacgt ggaagtcttc gatggagaaa atgaaaatgg acattttagg    300
ggaaagttct gtggaaagat agcccctcct cctgttgtgt cttcagggcc atttcttttt    360
atcaaatttg tctctgacta cgaaacacat ggtgcaggat tttccatacg ttatgaactt    420
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccagggggga tgttctgtcg ctacgaccgg ctagaaatct gggatggatt ccctgatgtt    660
ggccctcaca ttgggcgtta ctgtggacag aaaacaccag tcgaatccg atcctcatcg    720
ggcattctct ccatggtttt ttacaccgac agcgcgatag caaaagaagg tttctcagca    780
aactacagtg tcttgcagag cagtgtctca gaagatttca agaagtgga agcccctaca    840
gctggaccga ccactcccaa cgggaacttg gtggatgaat gtgatgacga ccaggccaac    900
tgccacagtg aacaggtga tgacttccag ctcacaggtg caccactgt gctggccaca    960
gaaaagccca cggtcataga cagcaccata caatcagagt tccaacata tggttttaac   1020
tgtgaatttg gctgggctc tcacaagacc ttctgccact gggaacatga caatcacgtg   1080
cagctcaagt ggagtgtgtt gaccagcaag acgggaccca ttcaggatca cacaggagat   1140
ggcaacttca tctattccca agctgacgaa atcagaaggg gcaaagtggc tcgcctggtg   1200
agccctgtgg tttattccca gaactctgcc cactgcatga ccttctggta tcacatgtct   1260
gggtcccacg tcggcacact cagggtcaaa ctgcgctacc agaagccaga ggagtacgat   1320
cagctggtct ggatggccat ggacaccaa ggtgaccact ggaaggaagg gcgtgtcttg   1380
ctccacaagt ctctgaaact ttatcaggtg attttcgagg gcgaaatcgg aaaaggaaac   1440
cttggtggga ttgctgtgga tgacattagt attaataacc acatttcaca agaagattgt   1500
gcaaaaccag cagacctgga taaaagaac ccagaaatta aaattgatga acagggagc   1560
```

```
acgccaggat acgaaggtga aggagaaggt gacaagaaca tctccaggaa gccaggcaat      1620
gtgttgaaga ccttagaccc cagatctgac aaaactcaca catgcccacc gtgcccagca      1680
cctgaactcc tggggggacc gtcagtcttc ctcttccccc caaaacccaa ggacaccctc      1740
atgatctccc ggacccctga ggtcacatgc gtggtggtgg acgtgagcca cgaagaccct      1800
gaggtcaagt tcaactggta cgtggacggc gtggaggtgc ataatgccaa gacaaagccg      1860
cgggaggagc agtacaacag cacgtaccgt gtggtcagcg tcctcaccgt cctgcaccag      1920
gactggctga atggcaagga gtacaagtgc aaggtctcca acaaagccct cccagccccc      1980
atcgagaaaa ccatctccaa agccaaaggg cagccccgag aaccacaggt gtacaccctg      2040
cccccatccc gggaggagat gaccaagaac caggtcagcc tgacctgcct ggtcaaaggc      2100
ttctatccca gcgacatcgc cgtggagtgg gagagcaatg ggcagccgga gaacaactac      2160
aagaccacgc ctcccgtgct ggactccgac ggctccttct tcctctacag caagctcacc      2220
gtggacaaga gcaggtggca gcaggggaac gtcttctcat gctccgtgat gcacgaggct      2280
ctgcacaacc actacacgca gaagagcctc tccctgtctc cgggtaaatg a               2331
```

<210> SEQ ID NO 37
<211> LENGTH: 227
<212> TYPE: PRT
<213> ORGANISM: artificial sequence
<220> FEATURE:
<223> OTHER INFORMATION: Synthetic polypeptide

<400> SEQUENCE: 37

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
```

<210> SEQ ID NO 38
<211> LENGTH: 853
<212> TYPE: PRT
<213> ORGANISM: artificial sequence
<220> FEATURE:
<223> OTHER INFORMATION: Synthetic polypeptide

<400> SEQUENCE: 38

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
```

```
                355                 360                 365
Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
                420                 425                 430

Asp Arg Asn Trp Met Pro Glu Asn Ile Arg Leu Val Thr Ser Arg Ser
                435                 440                 445

Gly Trp Ala Leu Pro Pro Ala Pro His Ser Tyr Ile Asn Glu Trp Leu
                450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
                500                 505                 510

Lys Arg Lys Ala Lys Ser Phe Glu Gly Asn Asn Asn Tyr Asp Thr Pro
                515                 520                 525

Glu Leu Arg Thr Phe Pro Ala Leu Ser Thr Arg Phe Ile Arg Ile Tyr
                530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
                580                 585                 590

Thr Gly Asp Asp Phe Gln Leu Thr Gly Gly Thr Thr Val Leu Ala Thr
                595                 600                 605

Glu Lys Pro Thr Val Ile Asp Ser Thr Ile Gln Ser Glu Phe Pro Thr
                610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
                660                 665                 670

Tyr Ser Gln Ala Asp Glu Asn Gln Lys Gly Lys Val Ala Arg Leu Val
                675                 680                 685

Ser Pro Val Val Tyr Ser Gln Asn Ser Ala His Cys Met Thr Phe Trp
                690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
                725                 730                 735

His Gln Gly Asp His Trp Lys Gly Arg Val Leu Leu His Lys Ser
                740                 745                 750

Leu Lys Leu Tyr Gln Val Ile Phe Glu Gly Glu Ile Gly Lys Gly Asn
                755                 760                 765

Leu Gly Gly Ile Ala Val Asp Asp Ile Ser Ile Asn Asn His Ile Ser
770                 775                 780
```

```
Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
            820                 825                 830

Leu Asp Pro Arg Ser Gly Ser Lys Glu Asn Leu Tyr Phe Gln Gly His
                835                 840                 845

His His His His His
        850
```

<210> SEQ ID NO 39
<211> LENGTH: 2625
<212> TYPE: DNA
<213> ORGANISM: artificial sequence
<220> FEATURE:
<223> OTHER INFORMATION: Synthetic polynucleotide

<400> SEQUENCE: 39

```
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccaggggggga tgttctgtcg ctacgaccgg ctagaaatct gggatggatt ccctgatgtt     660
ggccctcaca ttgggcgtta ctgtggacag aaaacaccag tcgaatccg atcctcatcg     720
ggcattctct ccatggtttt ttacaccgac agcgcgatag caaaagaagg tttctcagca     780
aactacagtg tcttgcagag cagtgtctca gaagatttca atgtatgga agctctgggc     840
atggaatcag gagaaattca ttctgaccag atcacagctt cttcccagta tagcaccaac     900
tggtctgcag agcgctcccg cctgaactac cctgagaatg ggtggactcc cggagaggat     960
tcctaccgag agtggataca ggtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg gcatatctat gagatttgaa    1260
gtatatggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc acccgcacc tcattcctac    1440
atcaatgagt ggctccaaat agacctgggg gaggagaaga tcgtgagggg catcatcatt    1500
cagggtggga gcaccgagaa gaacaaggtg ttcatgagga agttcaagat cgggtacagc    1560
aacaacggct cggactggaa gatgatcatg gatgacagca acgcaaggc gaagtctttt    1620
```

```
gagggcaaca acaactatga tacacctgag ctgcggactt ttccagctct ctccacgcga   1680
ttcatcagga tctaccccga gagagccact catggcggac tggggctcag aatggagctg   1740
ctgggctgtg aagtggaagc ccctacagct ggaccgacca ctcccaacgg gaacttggtg   1800
gatgaatgtg atgacgacca ggccaactgc cacagtggaa caggtgatga cttccagctc   1860
acaggtggca ccactgtgct ggccacagaa aagcccacgg tcatagacag caccatacaa   1920
tcagagtttc caacatatgg ttttaactgt gaatttggct ggggctctca caagaccttc   1980
tgccactggg aacatgacaa tcacgtgcag ctcaagtgga gtgtgttgac cagcaagacg   2040
ggacccattc aggatcacac aggagatggc aacttcatct attcccaagc tgacgaaaat   2100
cagaagggca agtggctcg cctggtgagc cctgtggttt attcccagaa ctctgcccac   2160
tgcatgacct tctggtatca catgtctggg tcccacgtcg gcacactcag ggtcaaactg   2220
cgctaccaga agccagagga gtacgatcag ctggtctgga tggccattgg acaccaaggt   2280
gaccactgga aggaagggcg tgtcttgctc cacaagtctc tgaaactta tcaggtgatt   2340 ttcgagggcg aaatcggaaa aggaaacctt ggtgggattg ctgtggatga cattagtatt   2400
aataaccaca tttcacaaga agattgtgca aaaccagcag acctggataa aaagaaccca   2460
gaaattaaaa ttgatgaaac agggagcacg ccaggatacg aaggtgaagg agaaggtgac   2520
aagaacatct ccaggaagcc aggcaatgtg ttgaagacct tagaccccag atctggatcc   2580
aaggaaaact tgtatttcca gggccatcat catcatcatc attga   2625
```

<210> SEQ ID NO 40
<211> LENGTH: 580
<212> TYPE: PRT
<213> ORGANISM: artificial sequence
<220> FEATURE:
<223> OTHER INFORMATION: Synthetic polypeptide

<400> SEQUENCE: 40

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
            85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
            165                 170                 175

Ser Asn Pro Pro Gly Gly Met Phe Cys Arg Tyr Asp Arg Leu Glu Ile
```

```
            180                 185                 190
Trp Asp Gly Phe Pro Asp Val Gly Pro His Ile Gly Arg Tyr Cys Gly
            195                 200                 205
Gln Lys Thr Pro Gly Arg Ile Arg Ser Ser Gly Ile Leu Ser Met
        210                 215                 220
Val Phe Tyr Thr Asp Ser Ala Ile Ala Lys Glu Gly Phe Ser Ala Asn
225                 230                 235                 240
Tyr Ser Val Leu Gln Ser Ser Val Ser Glu Asp Phe Lys Cys Met Glu
                245                 250                 255
Ala Leu Gly Met Glu Ser Gly Glu Ile His Ser Asp Gln Ile Thr Ala
                260                 265                 270
Ser Ser Gln Tyr Ser Thr Asn Trp Ser Ala Glu Arg Ser Arg Leu Asn
            275                 280                 285
Tyr Pro Glu Asn Gly Trp Thr Pro Gly Glu Asp Ser Tyr Arg Glu Trp
            290                 295                 300
Ile Gln Val Asp Leu Gly Leu Leu Arg Phe Val Thr Ala Val Gly Thr
305                 310                 315                 320
Gln Gly Ala Ile Ser Lys Glu Thr Lys Lys Tyr Tyr Val Lys Thr
                325                 330                 335
Tyr Lys Ile Asp Val Ser Ser Asn Gly Glu Asp Trp Ile Thr Ile Lys
                340                 345                 350
Glu Gly Asn Lys Pro Val Leu Phe Gln Gly Asn Thr Asn Pro Thr Asp
            355                 360                 365
Val Val Val Ala Val Phe Pro Lys Pro Leu Ile Thr Arg Phe Val Arg
370                 375                 380
Ile Lys Pro Ala Thr Trp Glu Thr Gly Ile Ser Met Arg Phe Glu Val
385                 390                 395                 400
Tyr Gly Cys Lys Ile Thr Asp Tyr Pro Cys Ser Gly Met Leu Gly Met
                405                 410                 415
Val Ser Gly Leu Ile Ser Asp Ser Gln Ile Thr Ser Ser Asn Gln Gly
            420                 425                 430
Asp Arg Asn Trp Met Pro Glu Asn Ile Arg Leu Val Thr Ser Arg Ser
            435                 440                 445
Gly Trp Ala Leu Pro Pro Ala Pro His Ser Tyr Ile Asn Glu Trp Leu
        450                 455                 460
Gln Ile Asp Leu Gly Glu Glu Lys Ile Val Arg Gly Ile Ile Gln
465                 470                 475                 480
Gly Gly Lys His Arg Glu Asn Lys Val Phe Met Arg Lys Phe Lys Ile
                485                 490                 495
Gly Tyr Ser Asn Asn Gly Ser Asp Trp Lys Met Ile Met Asp Asp Ser
            500                 505                 510
Lys Arg Lys Ala Lys Ser Phe Glu Gly Asn Asn Asn Tyr Asp Thr Pro
            515                 520                 525
Glu Leu Arg Thr Phe Pro Ala Leu Ser Thr Arg Phe Ile Arg Ile Tyr
        530                 535                 540
Pro Glu Arg Ala Thr His Gly Gly Leu Gly Leu Arg Met Glu Leu Leu
545                 550                 555                 560
Gly Cys Arg Ser Gly Ser Lys Glu Asn Leu Tyr Phe Gln Gly His His
                565                 570                 575
His His His His
            580

<210> SEQ ID NO 41
```

<211> LENGTH: 1806
<212> TYPE: DNA
<213> ORGANISM: artificial sequence
<220> FEATURE:
<223> OTHER INFORMATION: Synthetic polynucleotide

<400> SEQUENCE: 41

| | |
|---|---:|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acattttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccagggggga tgttctgtcg ctacgaccgg ctagaaatct gggatggatt ccctgatgtt | 660 |
| ggccctcaca ttgggcgtta ctgtggacag aaaacaccag gtcgaatccg atcctcatcg | 720 |
| ggcattctct ccatggtttt ttacaccgac agcgcgatag caaaagaagg tttctcagca | 780 |
| aactacagtg tcttgcagag cagtgtctca gaagatttca atgtatggaa agctctgggc | 840 |
| atggaatcag gagaaattca ttctgaccag atcacagctt cttcccagta tagcaccaac | 900 |
| tggtctgcag agcgctcccg cctgaactac cctgagaatg ggtggactcc cggagaggat | 960 |
| tcctaccgag agtggataca ggtagacttg ggccttctgc gctttgtcac ggctgtcggg | 1020 |
| acacagggcg ccatttcaaa agaaaccaag aagaaatatt atgtcaagac ttacaagatc | 1080 |
| gacgttagct ccaacgggga agactggatc accataaaag aaggaaacaa acctgttctc | 1140 |
| tttcagggaa acaccaaccc tacagatgtt gtggttgcag tattccccaa accactgata | 1200 |
| actcgatttg tccgaatcaa gcctgcaact tgggaaactg gcatatctat gagatttgaa | 1260 |
| gtatatggtt gcaagataac agattatcct tgctctggaa tgttgggtat ggtgtctgga | 1320 |
| cttatttctg actcccagat cacatcatcc aaccaagggg acagaaactg gatgcctgaa | 1380 |
| aacatccgcc tggtaaccag tcgctctggc tgggcacttc acccgcacc tcattcctac | 1440 |
| atcaatgagt ggctccaaat agacctgggg gaggagaaga tcgtgagggg catcatcatt | 1500 |
| cagggtggga agcaccgaga gaacaaggtg ttcatgagga agttcaagat cgggtacagc | 1560 |
| aacaacggct cggactggaa gatgatcatg gatgacagca acgcaaggc gaagtctttt | 1620 |
| gagggcaaca caactatga tacacctgag ctgcggactt ttccagctct ctccacgcga | 1680 |
| ttcatcagga tctaccccga gagagccact catggcggac tggggctcag aatggagctg | 1740 |
| ctgggctgta gatctggatc caaggaaaac ttgtatttcc agggccatca tcatcatcat | 1800 |
| cattga | 1806 |

<210> SEQ ID NO 42
<211> LENGTH: 421
<212> TYPE: PRT
<213> ORGANISM: artificial sequence
<220> FEATURE:
<223> OTHER INFORMATION: Synthetic polypeptide

<400> SEQUENCE: 42

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Arg Ser Gly Ser Lys Glu Asn Leu Tyr Phe Gln Gly His
                405                 410                 415
```

His His His His His
            420

<210> SEQ ID NO 43
<211> LENGTH: 1329
<212> TYPE: DNA
<213> ORGANISM: artificial sequence
<220> FEATURE:
<223> OTHER INFORMATION: Synthetic polynucleotide

<400> SEQUENCE: 43

| | |
|---|---|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acattttagg | 300 |
| ggaaagttct gtggaaagat agcccctcct cctgttgtgt cttcagggcc atttcttttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccaggggga tgttctgtcg ctacgaccgg ctagaaatct gggatggatt ccctgatgtt | 660 |
| ggccctcaca ttgggcgtta ctgtggacag aaaacaccag gtcgaatccg atcctcatcg | 720 |
| ggcattctct ccatggtttt ttacaccgac agcgcgatag caaaagaagg tttctcagca | 780 |
| aactacagtg tcttgcagag cagtgtctca gaagatttca aatgtatgga agctctgggc | 840 |
| atggaatcag gagaaattca ttctgaccag atcacagctt cttcccagta tagcaccaac | 900 |
| tggtctgcag agcgctcccg cctgaactac cctgagaatg ggtggactcc cggagaggat | 960 |
| tcctaccgag agtggataca ggtagacttg ggccttctgc gctttgtcac ggctgtcggg | 1020 |
| acacagggcg ccatttcaaa agaaaccaag aagaaatatt atgtcaagac ttacaagatc | 1080 |
| gacgttagct ccaacgggga agactggatc accataaaag aaggaaacaa acctgttctc | 1140 |
| tttcagggaa acaccaaccc tacagatgtt gtggttgcag tattccccaa accactgata | 1200 |
| actcgatttg tccgaatcaa gcctgcaact tgggaaactg caatatctat gagatttgaa | 1260 |
| gtatatggtt gcagatctgg atccaaggaa aacttgtatt ccagggccat catcatcat | 1320 |
| catcattga | 1329 |

<210> SEQ ID NO 44
<211> LENGTH: 262
<212> TYPE: PRT
<213> ORGANISM: artificial sequence
<220> FEATURE:
<223> OTHER INFORMATION: Synthetic polypeptide

<400> SEQUENCE: 44

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp

```
            50                  55                  60
Tyr Val Glu Val Phe Asp Gly Glu Asn Glu Asn Gly His Phe Arg Gly
 65                  70                  75                  80

Lys Phe Cys Gly Lys Ile Ala Pro Pro Val Val Ser Ser Gly Pro
                 85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
                115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190

Trp Asp Gly Phe Pro Asp Val Gly Pro His Ile Gly Arg Tyr Cys Gly
                195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Arg Ser Gly Ser Lys Glu Asn Leu Tyr Phe Gln Gly
                245                 250                 255

His His His His His His
            260

<210> SEQ ID NO 45
<211> LENGTH: 852
<212> TYPE: DNA
<213> ORGANISM: artificial sequence
<220> FEATURE:
<223> OTHER INFORMATION: Synthetic polynucleotide

<400> SEQUENCE: 45
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600 ccaggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
ggcattctct ccatggtttt ttacaccgac agcgcgatag caaaagaagg tttctcagca     780
aactacagtg tcttgagatc tggatccaag gaaaacttgt atttccaggg ccatcatcat     840
```
catcatcatt ga          852

<210> SEQ ID NO 46
<211> LENGTH: 853
<212> TYPE: PRT
<213> ORGANISM: artificial sequence
<220> FEATURE:
<223> OTHER INFORMATION: Synthetic polypeptide

<400> SEQUENCE: 46

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
```

```
            355                 360                 365
Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
                420                 425                 430

Asp Arg Asn Trp Met Pro Glu Asn Ile Arg Leu Val Thr Ser Arg Ser
                435                 440                 445

Gly Trp Ala Leu Pro Pro Ala Pro His Ser Tyr Ile Asn Glu Trp Leu
450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
                500                 505                 510

Lys Arg Lys Ala Lys Ser Phe Glu Gly Asn Asn Asn Tyr Asp Thr Pro
                515                 520                 525

Glu Leu Arg Thr Phe Pro Ala Leu Ser Thr Arg Phe Ile Arg Ile Tyr
                530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
                580                 585                 590

Thr Gly Asp Asp Phe Gln Leu Thr Gly Gly Thr Thr Val Leu Ala Thr
                595                 600                 605

Glu Lys Pro Thr Val Ile Asp Ser Thr Ile Gln Ser Glu Phe Pro Thr
                610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
                660                 665                 670

Tyr Ser Gln Ala Asp Glu Asn Gln Lys Gly Lys Val Ala Arg Leu Val
                675                 680                 685

Ser Pro Val Val Tyr Ser Gln Asn Ser Ala His Cys Met Thr Phe Trp
                690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
                725                 730                 735

His Gln Gly Asp His Trp Lys Gly Arg Val Leu Leu His Lys Ser
                740                 745                 750

Leu Lys Leu Tyr Gln Val Ile Phe Glu Gly Glu Ile Gly Lys Gly Asn
                755                 760                 765

Leu Gly Gly Ile Ala Val Asp Asp Ile Ser Ile Asn Asn His Ile Ser
                770                 775                 780
```

```
Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
            820                 825                 830

Leu Asp Pro Arg Ser Gly Ser Lys Glu Asn Leu Tyr Phe Gln Gly His
        835                 840                 845

His His His His His
    850

<210> SEQ ID NO 47
<211> LENGTH: 2625
<212> TYPE: DNA
<213> ORGANISM: artificial sequence
<220> FEATURE:
<223> OTHER INFORMATION: Synthetic polynucleotide

<400> SEQUENCE: 47
```

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaatg | tggcgatact | ataaaaattg | aaagccccgg | gtaccttaca | 120 |
| tctcctggtt | atcctcattc | ttatcaccca | agtgaaaaat | gcgaatggct | gattcaggct | 180 |
| ccggacccat | accagagaat | tatgatcaac | ttcaaccctc | acttcgattt | ggaggacaga | 240 |
| gactgcaagt | atgactacgt | ggaagtcttc | gatggagaaa | atgaaaatgg | acattttagg | 300 |
| ggaaagttct | gtggaaagat | agcccctcct | cctgttgtgt | cttcagggcc | atttcttttt | 360 |
| atcaaatttg | tctctgacta | cgaaacacat | ggtgcaggat | tttccatacg | ttatgaactt | 420 |
| ttcaagagag | gtcctgaatg | ttcccagaac | tacacaacac | ctagtggagt | gataaagtcc | 480 |
| cccggattcc | ctgaaaaata | tcccaacagc | cttgaatgca | cttatattgt | ctttgcgcca | 540 |
| aagatgtcag | agattatcct | ggaatttgaa | agctttgacc | tggagcctga | ctcaaatcct | 600 |
| ccaggggga | tgttctgtcg | ctacgaccgg | ctagaaatct | gggatggatt | ccctgatgtt | 660 |
| ggccctcaca | ttgggcgtta | ctgtggacag | aaaacaccag | gtcgaatccg | atcctcatcg | 720 |
| ggcattctct | ccatggtttt | ttacaccgac | agcgcgatag | caaagaagg | tttctcagca | 780 |
| aactacagtg | tcttgcagag | cagtgtctca | gaagatttca | atgtatgga | agctctgggc | 840 |
| atggaatcag | gagaaattca | ttctgaccag | atcacagctt | cttcccaggc | tagcaccaac | 900 |
| tggtctgcag | agcgctcccg | cctgaactac | cctgagaatg | ggtggactcc | cggagaggat | 960 |
| tcctaccgag | agtggataca | ggtagacttg | ggccttctgc | gctttgtcac | ggctgtcggg | 1020 |
| acacagggcg | ccatttcaaa | agaaaccaag | aagaaatatt | atgtcaagac | ttacaagatc | 1080 |
| gacgttagct | ccaacgggga | agactggatc | accataaaag | aaggaaacaa | acctgttctc | 1140 |
| tttcagggaa | acaccaaccc | tacagatgtt | gtggttgcag | tattccccaa | accactgata | 1200 |
| actcgatttg | tccgaatcaa | gcctgcaact | tgggaaactg | gcatatctat | gagatttgaa | 1260 |
| gtatatggtt | gcaagataac | agattatcct | tgctctggaa | tgttgggtat | ggtgtctgga | 1320 |
| cttatttctg | actcccagat | cacatcatcc | aaccaagggg | acagaaactg | gatgcctgaa | 1380 |
| aacatccgcc | tggtaaccag | tcgctctggc | tgggcacttc | acccgcacc | tcattcctac | 1440 |
| atcaatgagt | ggctccaaat | agacctgggg | gaggagaaga | tcgtgagggg | catcatcatt | 1500 |
| cagggtggga | agcaccgaga | gaacaaggtg | ttcatgagga | agttcaagat | cgggtacagc | 1560 |
| aacaacggct | cggactggaa | gatgatcatg | gatgacagca | aacgcaaggc | gaagtctttt | 1620 |

```
gagggcaaca acaactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg gaacttggtg    1800
gatgaatgtg atgacgacca ggccaactgc cacagtggaa caggtgatga cttccagctc    1860
acaggtggca ccactgtgct ggccacagaa aagcccacgg tcatagacag caccatacaa    1920
tcagagtttc caacatatgg ttttaactgt gaatttggct ggggctctca caagaccttc    1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca agtggctcg cctggtgagc cctgtggttt attcccagaa ctctgcccac    2160
tgcatgacct tctggtatca catgtctggg tcccacgtcg gcacactcag ggtcaaactg    2220
cgctaccaga agccagagga gtacgatcag ctggtctgga tggccattgg acaccaaggt    2280
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400
aataaccaca tttcacaaga agattgtgca aaaccagcag acctggataa aaagaaccca    2460
gaaattaaaa ttgatgaaac agggagcacg ccaggatacg aaggtgaagg agaaggtgac    2520
aagaacatct ccaggaagcc aggcaatgtg ttgaagacct tagacccag atctggatcc    2580 aaggaaaact tgtatttcca gggccatcat catcatcatc attga                    2625
```

<210> SEQ ID NO 48
<211> LENGTH: 580
<212> TYPE: PRT
<213> ORGANISM: artificial sequence
<220> FEATURE:
<223> OTHER INFORMATION: Synthetic polypeptide

<400> SEQUENCE: 48

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
```

```
            180                 185                 190
Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
        210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
                260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
        290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Lys Tyr Tyr Val Lys Thr
                325                 330                 335

Tyr Lys Ile Asp Val Ser Ser Asn Gly Glu Asp Trp Ile Thr Ile Lys
                340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
                420                 425                 430

Asp Arg Asn Trp Met Pro Glu Asn Ile Arg Leu Val Thr Ser Arg Ser
        435                 440                 445

Gly Trp Ala Leu Pro Pro Ala Pro His Ser Tyr Ile Asn Glu Trp Leu
        450                 455                 460

Gln Ile Asp Leu Gly Glu Glu Lys Ile Val Arg Gly Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
                500                 505                 510

Lys Arg Lys Ala Lys Ser Phe Glu Gly Asn Asn Asn Tyr Asp Thr Pro
                515                 520                 525

Glu Leu Arg Thr Phe Pro Ala Leu Ser Thr Arg Phe Ile Arg Ile Tyr
                530                 535                 540

Pro Glu Arg Ala Thr His Gly Gly Leu Gly Leu Arg Met Glu Leu Leu
545                 550                 555                 560

Gly Cys Arg Ser Gly Ser Lys Glu Asn Leu Tyr Phe Gln Gly His His
                565                 570                 575

His His His His
            580

<210> SEQ ID NO 49
```

<211> LENGTH: 1806
<212> TYPE: DNA
<213> ORGANISM: artificial sequence
<220> FEATURE:
<223> OTHER INFORMATION: Synthetic polynucleotide

<400> SEQUENCE: 49

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaatg | tggcgatact | ataaaaattg | aaagccccgg | gtaccttaca | 120 |
| tctcctggtt | atcctcattc | ttatcaccca | agtgaaaaat | gcgaatggct | gattcaggct | 180 |
| ccggacccat | accagagaat | tatgatcaac | ttcaaccctc | acttcgattt | ggaggacaga | 240 |
| gactgcaagt | atgactacgt | ggaagtcttc | gatggagaaa | atgaaaatgg | acattttagg | 300 |
| ggaaagttct | gtggaaagat | agcccctcct | cctgttgtgt | cttcagggcc | atttcttttt | 360 |
| atcaaatttg | tctctgacta | cgaaacacat | ggtgcaggat | tttccatacg | ttatgaactt | 420 |
| ttcaagagag | gtcctgaatg | ttcccagaac | tacacaacac | ctagtggagt | gataaagtcc | 480 |
| cccggattcc | ctgaaaaata | tcccaacagc | cttgaatgca | cttatattgt | ctttgcgcca | 540 |
| aagatgtcag | agattatcct | ggaatttgaa | agctttgacc | tggagcctga | ctcaaatcct | 600 |
| ccagggggga | tgttctgtcg | ctacgaccgg | ctagaaatct | gggatggatt | ccctgatgtt | 660 |
| ggccctcaca | ttgggcgtta | ctgtggacag | aaaacaccag | gtcgaatccg | atcctcatcg | 720 |
| ggcattctct | ccatggtttt | ttacaccgac | agcgcgatag | caaagaagg | tttctcagca | 780 |
| aactacagtg | tcttgcagag | cagtgtctca | gaagatttca | aatgtatgga | agctctgggc | 840 |
| atggaatcag | gagaaattca | ttctgaccag | atcacagctt | cttcccaggc | tagcaccaac | 900 |
| tggtctgcag | agcgctcccg | cctgaactac | cctgagaatg | ggtggactcc | cggagaggat | 960 |
| tcctaccgag | agtggataca | ggtagacttg | ggccttctgc | gctttgtcac | ggctgtcggg | 1020 |
| acacagggcg | ccatttcaaa | agaaaccaag | aagaaatatt | atgtcaagac | ttacaagatc | 1080 |
| gacgttagct | ccaacgggga | agactggatc | accataaaag | aaggaaacaa | acctgttctc | 1140 |
| tttcagggaa | acaccaaccc | tacagatgtt | gtggttgcag | tattccccaa | accactgata | 1200 |
| actcgatttg | tccgaatcaa | gcctgcaact | tgggaaactg | gcatatctat | gagatttgaa | 1260 |
| gtatatggtt | gcaagataac | agattatcct | tgctctggaa | tgttgggtat | ggtgtctgga | 1320 |
| cttatttctg | actcccagat | cacatcatcc | aaccaagggg | acagaaactg | gatgcctgaa | 1380 |
| aacatccgcc | tggtaaccag | tcgctctggc | tgggcacttc | cacccgcacc | tcattcctac | 1440 |
| atcaatgagt | ggctccaaat | agacctgggg | gaggagaaga | tcgtgagggg | catcatcatt | 1500 |
| cagggtggga | agcaccgaga | gaacaaggtg | ttcatgagga | agttcaagat | cgggtacagc | 1560 |
| aacaacggct | cggactggaa | gatgatcatg | gatgacagca | acgcaaggc | gaagtctttt | 1620 |
| gagggcaaca | caactatga | tacacctgag | ctgcggactt | ttccagctct | ctccacgcga | 1680 |
| ttcatcagga | tctaccccga | gagagccact | catggcggac | tggggctcag | aatggagctg | 1740 |
| ctgggctgta | gatctggatc | caaggaaaac | ttgtatttcc | agggccatca | tcatcatcat | 1800 |
| cattga | | | | | | 1806 |

<210> SEQ ID NO 50
<211> LENGTH: 421
<212> TYPE: PRT
<213> ORGANISM: artificial sequence
<220> FEATURE:
<223> OTHER INFORMATION: Synthetic polypeptide

<400> SEQUENCE: 50

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
        275                 280                 285

Tyr Pro Glu Asn Gly Trp Thr Pro Gly Glu Asp Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Arg Ser Gly Ser Lys Glu Asn Leu Tyr Phe Gln Gly His
                405                 410                 415
```

His His His His His
          420

<210> SEQ ID NO 51
<211> LENGTH: 1329
<212> TYPE: DNA
<213> ORGANISM: artificial sequence
<220> FEATURE:
<223> OTHER INFORMATION: Synthetic polynucleotide

<400> SEQUENCE: 51

```
atggagaggg ggctgccgct cctctgcgcc gtgctcgccc tcgtcctcgc cccggccggc    60
gcttttcgca acgataaatg tggcgatact ataaaaattg aaagccccgg gtaccttaca   120
tctcctggtt atcctcattc ttatcaccca agtgaaaaat gcgaatggct gattcaggct   180
ccggacccat accagagaat tatgatcaac ttcaaccctc acttcgattt ggaggacaga   240
gactgcaagt atgactacgt ggaagtcttc gatggagaaa atgaaaatgg acattttagg   300
ggaaagttct gtggaaagat agcccctcct cctgttgtgt cttcagggcc atttcttttt   360
atcaaatttg tctctgacta cgaaacacat ggtgcaggat tttccatacg ttatgaactt   420
ttcaagagag gtcctgaatg ttcccagaac tacacaacac ctagtggagt gataaagtcc   480
cccggattcc ctgaaaaata tcccaacagc cttgaatgca cttatattgt ctttgcgcca   540
aagatgtcag agattatcct ggaatttgaa agctttgacc tggagcctga ctcaaatcct   600
ccaggggga tgttctgtcg ctacgaccgg ctagaaatct gggatggatt ccctgatgtt   660
ggccctcaca ttgggcgtta ctgtggacag aaaacaccag gtcgaatccg atcctcatcg   720
ggcattctct ccatggtttt ttacaccgac agcgcgatag caaaagaagg tttctcagca   780
aactacagtg tcttgcagag cagtgtctca gaagatttca atgtatggaa gctctgggc   840
atggaatcag agaaattca ttctgaccag atcacagctt cttcccaggc tagcaccaac   900
tggtctgcag agcgctcccg cctgaactac cctgagaatg ggtggactcc cggagaggat   960
tcctaccgag agtggataca ggtagacttg ggccttctgc gctttgtcac ggctgtcggg  1020
acacagggcg ccatttcaaa agaaaccaag aagaaatatt atgtcaagac ttacaagatc  1080
gacgttagct ccaacgggga agactggatc accataaaag aaggaaacaa acctgttctc  1140
tttcagggaa acaccaaccc tacagatgtt gtggttgcag tattccccaa accactgata  1200
actcgatttg tccgaatcaa gcctgcaact tgggaaactg catatctct gagatttgaa  1260
gtatatggtt gcagatctgg atccaaggaa aacttgtatt ccagggcca tcatcatcat  1320
catcattga                                                         1329
```

<210> SEQ ID NO 52
<211> LENGTH: 700
<212> TYPE: PRT
<213> ORGANISM: artificial sequence
<220> FEATURE:
<223> OTHER INFORMATION: Synthetic polypeptide

<400> SEQUENCE: 52

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp

```
            50                  55                  60
Tyr Val Glu Val Phe Asp Gly Glu Asn Glu Asn Gly His Phe Arg Gly
 65                  70                  75                  80

Lys Phe Cys Gly Lys Ile Ala Pro Pro Val Val Ser Ser Gly Pro
                 85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
                115                 120                 125

Asn Tyr Thr Thr Pro Ser Gly Val Ile Lys Ser Pro Gly Phe Pro Glu
                130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190

Trp Asp Gly Phe Pro Asp Val Gly Pro His Ile Gly Arg Tyr Cys Gly
                195                 200                 205

Gln Lys Thr Pro Gly Arg Ile Arg Ser Ser Ser Gly Ile Leu Ser Met
210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
                260                 265                 270

Ser Ser Gln Tyr Ser Thr Asn Trp Ser Ala Glu Arg Ser Arg Leu Asn
                275                 280                 285

Tyr Pro Glu Asn Gly Trp Thr Pro Gly Glu Asp Ser Tyr Arg Glu Trp
                290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
                340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Glu Val Glu Ala Pro Thr Ala
                405                 410                 415

Gly Pro Thr Thr Pro Asn Gly Asn Leu Val Asp Glu Cys Asp Asp
                420                 425                 430

Gln Ala Asn Cys His Ser Gly Thr Gly Asp Asp Phe Gln Leu Thr Gly
                435                 440                 445

Gly Thr Thr Val Leu Ala Thr Glu Lys Pro Thr Val Ile Asp Ser Thr
                450                 455                 460

Ile Gln Ser Glu Phe Pro Thr Tyr Gly Phe Asn Cys Glu Phe Gly Trp
465                 470                 475                 480
```

```
Gly Ser His Lys Thr Phe Cys His Trp Glu His Asp Asn His Val Gln
                485                 490                 495

Leu Lys Trp Ser Val Leu Thr Ser Lys Thr Gly Pro Ile Gln Asp His
            500                 505                 510

Thr Gly Asp Gly Asn Phe Ile Tyr Ser Gln Ala Asp Glu Asn Gln Lys
        515                 520                 525

Gly Lys Val Ala Arg Leu Val Ser Pro Val Val Tyr Ser Gln Asn Ser
    530                 535                 540

Ala His Cys Met Thr Phe Trp Tyr His Met Ser Gly Ser His Val Gly
545                 550                 555                 560

Thr Leu Arg Val Lys Leu Arg Tyr Gln Lys Pro Glu Glu Tyr Asp Gln
                565                 570                 575

Leu Val Trp Met Ala Ile Gly His Gln Gly Asp His Trp Lys Glu Gly
            580                 585                 590

Arg Val Leu Leu His Lys Ser Leu Lys Leu Tyr Gln Val Ile Phe Glu
        595                 600                 605

Gly Glu Ile Gly Lys Gly Asn Leu Gly Gly Ile Ala Val Asp Asp Ile
    610                 615                 620

Ser Ile Asn Asn His Ile Ser Gln Glu Asp Cys Ala Lys Pro Ala Asp
625                 630                 635                 640

Leu Asp Lys Lys Asn Pro Glu Ile Lys Ile Asp Glu Thr Gly Ser Thr
                645                 650                 655

Pro Gly Tyr Glu Gly Glu Gly Glu Asp Lys Asn Ile Ser Arg Lys
            660                 665                 670

Pro Gly Asn Val Leu Lys Thr Leu Asp Pro Arg Ser Gly Ser Lys Glu
        675                 680                 685

Asn Leu Tyr Phe Gln Gly His His His His His
    690                 695                 700

<210> SEQ ID NO 53
<211> LENGTH: 2166
<212> TYPE: DNA
<213> ORGANISM: artificial sequence
<220> FEATURE:
<223> OTHER INFORMATION: Synthetic polynucleotide

<400> SEQUENCE: 53
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acatttaggg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600 ccaggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
ggcattctct ccatggtttt ttacaccgac agcgcgatag caaaagaagg tttctcagca     780
```

```
aactacagtg tcttgcagag cagtgtctca gaagatttca atgtatgga agctctgggc      840
atggaatcag gagaaattca ttctgaccag atcacagctt cttcccagta tagcaccaac     900
tggtctgcag agcgctcccg cctgaactac cctgagaatg ggtggactcc cggagaggat     960
tcctaccgag agtggataca ggtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg gcatatctat gagatttgaa    1260
gtatatggtt gcaagataac agattatcct gaagtggaag cccctacagc tggaccgacc    1320
actcccaacg ggaacttggt ggatgaatgt gatgacgacc aggccaactg ccacagtgga    1380
acaggtgatg acttccagct cacaggtggc accactgtgc tggccacaga aaagcccacg    1440
gtcatagaca gcaccataca atcagagttt ccaacatatg gttttaactg tgaatttggc    1500
tggggctctc acaagacctt ctgccactgg gaacatgaca atcacgtgca gctcaagtgg    1560
agtgtgttga ccagcaagac gggacccatt caggatcaca caggagatgg caacttcatc    1620
tattcccaag ctgacgaaaa tcagaagggc aaagtggctc gcctggtgag ccctgtggtt    1680
tattcccaga actctgccca ctgcatgacc ttctggtatc acatgtctgg gtcccacgtc    1740
ggcacactca gggtcaaact gcgctaccag aagccagagg agtacgatca gctggtctgg    1800
atggccattg acaccaagg tgaccactgg aaggaagggc gtgtcttgct ccacaagtct    1860
ctgaaacttt atcaggtgat tttcgagggc gaaatcggaa aaggaaacct tggtgggatt    1920
gctgtggatg acattagtat taataaccac atttcacaag aagattgtgc aaaaccagca    1980
gacctggata aaagaacccc agaaattaaa attgatgaaa cagggagcac gccaggatac    2040
gaaggtgaag gagaaggtga caagaacatc tccaggaagc caggcaatgt gttgaagacc    2100
ttagacccca gatctggatc caaggaaaac ttgtatttcc agggccatca tcatcatcat    2160
cattga                                                               2166
```

<210> SEQ ID NO 54
<211> LENGTH: 700
<212> TYPE: PRT
<213> ORGANISM: artificial sequence
<220> FEATURE:
<223> OTHER INFORMATION: Synthetic polypeptide

<400> SEQUENCE: 54

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
            85                  90                  95

Phe Leu Phe Ile Lys Phe Val Ser Asp Tyr Glu Thr His Gly Ala Gly
            100                 105                 110
```

```
Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Ala Ser Thr Asn Trp Ser Ala Glu Arg Ser Arg Leu Asn
    275                 280                 285

Tyr Pro Glu Asn Gly Trp Thr Pro Gly Glu Asp Ser Tyr Arg Glu Trp
            290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Glu Val Glu Ala Pro Thr Ala
                405                 410                 415

Gly Pro Thr Thr Pro Asn Gly Asn Leu Val Asp Glu Cys Asp Asp Asp
                420                 425                 430

Gln Ala Asn Cys His Ser Gly Thr Gly Asp Asp Phe Gln Leu Thr Gly
            435                 440                 445

Gly Thr Thr Val Leu Ala Thr Glu Lys Pro Thr Val Ile Asp Ser Thr
    450                 455                 460

Ile Gln Ser Glu Phe Pro Thr Tyr Gly Phe Asn Cys Glu Phe Gly Trp
465                 470                 475                 480

Gly Ser His Lys Thr Phe Cys His Trp Glu His Asp Asn His Val Gln
                485                 490                 495

Leu Lys Trp Ser Val Leu Thr Ser Lys Thr Gly Pro Ile Gln Asp His
                500                 505                 510

Thr Gly Asp Gly Asn Phe Ile Tyr Ser Gln Ala Asp Glu Asn Gln Lys
            515                 520                 525

Gly Lys Val Ala Arg Leu Val Ser Pro Val Val Tyr Ser Gln Asn Ser
```

Ala His Cys Met Thr Phe Trp Tyr His Met Ser Gly Ser His Val Gly
545                 550                 555                 560

Thr Leu Arg Val Lys Leu Arg Tyr Gln Lys Pro Glu Glu Tyr Asp Gln
            565                 570                 575

Leu Val Trp Met Ala Ile Gly His Gln Gly Asp His Trp Lys Glu Gly
        580                 585                 590

Arg Val Leu Leu His Lys Ser Leu Lys Leu Tyr Gln Val Ile Phe Glu
    595                 600                 605

Gly Glu Ile Gly Lys Gly Asn Leu Gly Ile Ala Val Asp Asp Ile
610                 615                 620

Ser Ile Asn Asn His Ile Ser Gln Glu Asp Cys Ala Lys Pro Ala Asp
625                 630                 635                 640

Leu Asp Lys Lys Asn Pro Glu Ile Lys Ile Asp Glu Thr Gly Ser Thr
            645                 650                 655

Pro Gly Tyr Glu Gly Glu Gly Gly Asp Lys Asn Ile Ser Arg Lys
        660                 665                 670

Pro Gly Asn Val Leu Lys Thr Leu Asp Pro Arg Ser Gly Ser Lys Glu
    675                 680                 685

Asn Leu Tyr Phe Gln Gly His His His His His His
690                 695                 700

<210> SEQ ID NO 55
<211> LENGTH: 2166
<212> TYPE: DNA
<213> ORGANISM: artificial sequence
<220> FEATURE:
<223> OTHER INFORMATION: Synthetic polynucleotide

<400> SEQUENCE: 55

| | |
|---|---:|
| atggagaggg ggctgccgct cctctgcgcc gtgctcgccc tcgtcctcgc cccggccggc | 60 |
| gcttttcgca acgataaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acattttagg | 300 |
| ggaaagttct gtggaaagat agcccctcct cctgttgtgt cttcagggcc atttctttt | 360 |
| atcaaatttg tctctgacta cgaaacacat ggtgcaggat tttccatacg ttatgaactt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccaggggga tgttctgtcg ctacgaccgg ctagaaatct gggatggatt ccctgatgtt | 660 |
| ggccctcaca ttgggcgtta ctgtggacag aaaacaccag gtcgaatccg atcctcatcg | 720 |
| ggcattctct ccatggtttt ttacaccgac agcgcgatag caaagaagg tttctcagca | 780 |
| aactacagtg tcttgcagag cagtgtctca gaagatttca atgtatgga gctctgggc | 840 |
| atggaatcag gagaaattca ttctgaccag atcacagctt cttcccaggc tagcaccaac | 900 |
| tggtctgcag agcgctcccg cctgaactac cctgagaatg gtggactcc cggagaggat | 960 |
| tcctaccgag agtggataca ggtagacttg ggccttctgc gctttgtcac ggctgtcggg | 1020 |
| acacagggcg ccatttcaaa agaaaccaag aagaaatatt atgtcaagac ttacaagatc | 1080 |
| gacgttagct ccaacgggga agactggatc accataaaag aaggaaacaa acctgttctc | 1140 |

```
tttcaggaa   acaccaaccc  tacagatgtt  gtggttgcag  tattccccaa  accactgata   1200
actcgatttg  tccgaatcaa  gcctgcaact  tgggaaactg  gcatatctat  gagatttgaa   1260
gtatatggtt  gcaagataac  agattatcct  gaagtggaag  cccctacagc  tggaccgacc   1320
actcccaacg  ggaacttggt  ggatgaatgt  gatgacgacc  aggccaactg  ccacagtgga   1380
acaggtgatg  acttccagct  cacaggtggc  accactgtgc  tggccacaga  aaagcccacg   1440
gtcatagaca  gcaccataca  atcagagttt  ccaacatatg  gttttaactg  tgaatttggc   1500
tggggctctc  acaagaccct  ctgccactgg  gaacatgaca  atcacgtgca  gctcaagtgg   1560
agtgtgttga  ccagcaagac  gggacccatt  caggatcaca  caggagatgg  caacttcatc   1620
tattcccaag  ctgacgaaaa  tcagaagggc  aaagtggctc  gcctggtgag  ccctgtggtt   1680
tattcccaga  actctgccca  ctgcatgacc  ttctggtatc  acatgtctgg  gtcccacgtc   1740
ggcacactca  gggtcaaact  gcgctaccag  aagccagagg  agtacgatca  gctggtctgg   1800
atggccattg  acaccaagg   tgaccactgg  aaggaagggc  gtgtcttgct  ccacaagtct   1860
ctgaaacttt  atcaggtgat  ttcgagggc  gaaatcggaa  aggaaacct   tggtgggatt   1920 gctgtggatg  acattagtat  taataaccac  atttcacaag  aagattgtgc  aaaaccagca   1980
gacctggata  aaagaaaccc  agaaattaaa  attgatgaaa  cagggagcac  gccaggatac   2040
gaaggtgaag  gagaaggtga  caagaacatc  tccaggaagc  caggcaatgt  gttgaagacc   2100
ttagacccca  gatctggatc  caaggaaaac  ttgtatttcc  agggccatca  tcatcatcat   2160
cattga                                                                   2166

<210> SEQ ID NO 56
<211> LENGTH: 544
<212> TYPE: PRT
<213> ORGANISM: artificial sequence
<220> FEATURE:
<223> OTHER INFORMATION: Synthetic polypeptide

<400> SEQUENCE: 56

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175
```

-continued

```
Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Glu Val Glu
                245                 250                 255

Ala Pro Thr Ala Gly Pro Thr Thr Pro Asn Gly Asn Leu Val Asp Glu
            260                 265                 270

Cys Asp Asp Gln Ala Asn Cys His Ser Gly Thr Gly Asp Asp Phe
            275                 280                 285

Gln Leu Thr Gly Gly Thr Thr Val Leu Ala Thr Glu Lys Pro Thr Val
290                 295                 300

Ile Asp Ser Thr Ile Gln Ser Glu Phe Pro Thr Tyr Gly Phe Asn Cys
305                 310                 315                 320

Glu Phe Gly Trp Gly Ser His Lys Thr Phe Cys His Trp Glu His Asp
                325                 330                 335

Asn His Val Gln Leu Lys Trp Ser Val Leu Thr Ser Lys Thr Gly Pro
            340                 345                 350

Ile Gln Asp His Thr Gly Asp Gly Asn Phe Ile Tyr Ser Gln Ala Asp
            355                 360                 365

Glu Asn Gln Lys Gly Lys Val Ala Arg Leu Val Ser Pro Val Val Tyr
370                 375                 380

Ser Gln Asn Ser Ala His Cys Met Thr Phe Trp Tyr His Met Ser Gly
385                 390                 395                 400

Ser His Val Gly Thr Leu Arg Val Lys Leu Arg Tyr Gln Lys Pro Glu
                405                 410                 415

Glu Tyr Asp Gln Leu Val Trp Met Ala Ile Gly His Gln Gly Asp His
            420                 425                 430

Trp Lys Glu Gly Arg Val Leu Leu His Lys Ser Leu Lys Leu Tyr Gln
            435                 440                 445

Val Ile Phe Glu Gly Glu Ile Gly Lys Gly Asn Leu Gly Gly Ile Ala
450                 455                 460

Val Asp Asp Ile Ser Ile Asn Asn His Ile Ser Gln Glu Asp Cys Ala
465                 470                 475                 480

Lys Pro Ala Asp Leu Asp Lys Lys Asn Pro Glu Ile Lys Ile Asp Glu
                485                 490                 495

Thr Gly Ser Thr Pro Gly Tyr Glu Gly Glu Gly Glu Gly Asp Lys Asn
            500                 505                 510

Ile Ser Arg Lys Pro Gly Asn Val Leu Lys Thr Leu Asp Pro Arg Ser
            515                 520                 525

Gly Ser Lys Glu Asn Leu Tyr Phe Gln Gly His His His His His His
530                 535                 540
```

<210> SEQ ID NO 57
<211> LENGTH: 1698
<212> TYPE: DNA
<213> ORGANISM: artificial sequence
<220> FEATURE:
<223> OTHER INFORMATION: Synthetic polynucleotide

<400> SEQUENCE: 57

```
atggagaggg ggctgccgct cctctgcgcc gtgctcgccc tcgtcctcgc cccggccggc    60
gcttttcgca acgataaatg tggcgatact ataaaaattg aaagccccgg gtaccttaca   120
tctcctggtt atcctcattc ttatcaccca agtgaaaaat gcgaatggct gattcaggct   180
ccggacccat accagagaat tatgatcaac ttcaaccctc acttcgattt ggaggacaga   240
gactgcaagt atgactacgt ggaagtcttc gatggagaaa atgaaaatgg acattttagg   300
ggaaagttct gtggaaagat agcccctcct cctgttgtgt cttcagggcc atttcttttt   360
atcaaatttg tctctgacta cgaaacacat ggtgcaggat tttccatacg ttatgaactt   420
ttcaagagag gtcctgaatg ttcccagaac tacacaacac ctagtggagt gataaagtcc   480
cccggattcc ctgaaaaata tcccaacagc cttgaatgca cttatattgt ctttgcgcca   540
aagatgtcag agattatcct ggaatttgaa agctttgacc tggagcctga ctcaaatcct   600
ccagggggga tgttctgtcg ctacgaccgg ctagaaatct gggatggatt ccctgatgtt   660
ggccctcaca ttgggcgtta ctgtggacac aaaaacaccag gtcgaatccg atcctcatcg   720
ggcattctct ccatggtttt ttacaccgac agcgcgatag caaagaaagg tttctcagca   780
aactacagtg tcttgcagag cagtgtctca gaagatttca agaagtgga agccctaca   840
gctggaccga ccactcccaa cgggaacttg gtggatgaat gtgatgacga ccaggccaac   900
tgccacagtg aacaggtga tgacttccag ctcacaggtg gcaccactgt gctggccaca   960
gaaaagccca cggtcataga cagcaccata caatcagagt ttccaacata tggttttaac  1020
tgtgaatttg ctggggctc tcacaagacc ttctgccact gggaacatga caatcacgtg  1080
cagctcaagt ggagtgtgtt gaccagcaag acgggaccca ttcaggatca cacaggagat  1140
ggcaacttca tctattccca agctgacgaa aatcagaagg gcaaagtggc tcgcctggtg  1200
agccctgtgg tttattccca gaactctgcc cactgcatga ccttctggta tcacatgtct  1260
gggtcccacg tcggcacact cagggtcaaa ctgcgctacc agaagccaga ggagtacgat  1320
cagctggtct ggatggccat ggacaccaa ggtgaccact ggaaggaagg gcgtgtcttg  1380
ctccacaagt ctctgaaact ttatcaggtg attttcgagg gcgaaatcgg aaaaggaaac  1440
cttggtggga ttgctgtgga tgacattagt attaataacc acattcaca agaagattgt  1500
gcaaaaccag cagacctgga taaaagaac ccagaaatta aaattgatga acagggagc  1560
acgccaggat acgaaggtga aggagaaggt gacaagaaca tctccaggaa gccaggcaat  1620
gtgttgaaga ccttagaccc cagatctgga tccaaggaaa acttgtatt ccagggccat  1680
catcatcatc atcattga                                                1698
```

<210> SEQ ID NO 58
<211> LENGTH: 853
<212> TYPE: PRT
<213> ORGANISM: artificial sequence
<220> FEATURE:
<223> OTHER INFORMATION: Synthetic polypeptide

<400> SEQUENCE: 58

Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp

```
                50                  55                  60
Tyr Val Glu Val Phe Asp Gly Glu Asn Glu Asn Gly His Phe Arg Gly
 65                  70                  75                  80

Lys Phe Cys Gly Lys Ile Ala Pro Pro Val Val Ser Ser Gly Pro
                 85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
                115                 120                 125

Asn Tyr Thr Thr Pro Ser Gly Val Ile Lys Ser Pro Gly Phe Pro Glu
                130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190

Trp Asp Gly Phe Pro Asp Val Gly Pro His Ile Gly Arg Tyr Cys Gly
                195                 200                 205

Gln Lys Thr Pro Gly Arg Ile Arg Ser Ser Ser Gly Ile Leu Ser Met
                210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
                260                 265                 270

Ser Ser Gln Tyr Ser Thr Asn Trp Ser Ala Glu Arg Ser Arg Leu Asn
                275                 280                 285

Tyr Pro Glu Asn Gly Trp Thr Pro Gly Glu Asp Ser Tyr Arg Glu Trp
                290                 295                 300

Ile Gln Val Asp Leu Gly Leu Leu Arg Phe Val Thr Ala Val Gly Thr
305                 310                 315                 320

Gln Gly Ala Ile Ala Lys Lys Thr Lys Lys Tyr Tyr Val Lys Thr
                325                 330                 335

Tyr Lys Ile Asp Val Ser Ser Asn Gly Glu Asp Trp Ile Thr Ile Lys
                340                 345                 350

Glu Gly Asn Lys Pro Val Leu Phe Gln Gly Asn Thr Asn Pro Thr Asp
                355                 360                 365

Val Val Val Ala Val Phe Pro Lys Pro Leu Ile Thr Arg Phe Val Arg
                370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
                420                 425                 430

Asp Arg Asn Trp Met Pro Glu Asn Ile Arg Leu Val Thr Ser Arg Ser
                435                 440                 445

Gly Trp Ala Leu Pro Pro Ala Pro His Ser Tyr Ile Asn Glu Trp Leu
                450                 455                 460

Gln Ile Asp Leu Gly Glu Glu Lys Ile Val Arg Gly Ile Ile Ile Gln
465                 470                 475                 480
```

Gly Gly Lys His Arg Glu Asn Lys Val Phe Met Arg Lys Phe Lys Ile
            485                 490                 495

Gly Tyr Ser Asn Asn Gly Ser Asp Trp Lys Met Ile Met Asp Asp Ser
        500                 505                 510

Lys Arg Lys Ala Lys Ser Phe Glu Gly Asn Asn Asn Tyr Asp Thr Pro
            515                 520                 525

Glu Leu Arg Thr Phe Pro Ala Leu Ser Thr Arg Phe Ile Arg Ile Tyr
    530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
            565                 570                 575

Asn Leu Val Asp Glu Cys Asp Asp Gln Ala Asn Cys His Ser Gly
        580                 585                 590

Thr Gly Asp Asp Phe Gln Leu Thr Gly Gly Thr Thr Val Leu Ala Thr
            595                 600                 605

Glu Lys Pro Thr Val Ile Asp Ser Thr Ile Gln Ser Glu Phe Pro Thr
    610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
            645                 650                 655

Ser Lys Thr Gly Pro Ile Gln Asp His Thr Gly Asp Gly Asn Phe Ile
        660                 665                 670

Tyr Ser Gln Ala Asp Glu Asn Gln Lys Gly Lys Val Ala Arg Leu Val
            675                 680                 685

Ser Pro Val Val Tyr Ser Gln Asn Ser Ala His Cys Met Thr Phe Trp
690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
            725                 730                 735

His Gln Gly Asp His Trp Lys Glu Gly Arg Val Leu His Lys Ser
        740                 745                 750

Leu Lys Leu Tyr Gln Val Ile Phe Glu Gly Glu Ile Gly Lys Gly Asn
            755                 760                 765

Leu Gly Gly Ile Ala Val Asp Asp Ile Ser Ile Asn Asn His Ile Ser
    770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
            805                 810                 815

Glu Gly Asp Lys Asn Ile Ser Arg Lys Pro Gly Asn Val Leu Lys Thr
        820                 825                 830

Leu Asp Pro Arg Ser Gly Ser Lys Glu Asn Leu Tyr Phe Gln Gly His
            835                 840                 845

His His His His
        850

<210> SEQ ID NO 59
<211> LENGTH: 2625
<212> TYPE: DNA
<213> ORGANISM: artificial sequence
<220> FEATURE:

<223> OTHER INFORMATION: Synthetic polynucleotide

<400> SEQUENCE: 59

```
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccaggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
ggcattctct ccatggtttt ttacaccgac agcgcgatag caaaagaagg tttctcagca     780
aactacagtg tcttgcagag cagtgtctca gaagatttca atgtatgga agctctgggc     840
atggaatcag gagaaattca ttctgaccag atcacagctt cttcccagta tagcaccaac     900
tggtctgcag agcgctcccg cctgaactac cctgagaatg ggtggactcc cggagaggat     960
tcctaccgag agtggataca ggtagacttg ggccttctgc gctttgtcac ggctgtcggg    1020
acacagggcg ccattgccaa aaagaccaag aagaaatatt atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact gggaaactg gcatatctat gagatttgaa    1260
gtatatggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca acgcaaggc gaagtctttt    1620
gagggcaaca caactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg gaacttggtg    1800
gatgaatgtg atgacgacca ggccaactgc cacagtggaa caggtgatga cttccagctc    1860
acaggtggca ccactgtgct ggccacagaa aagcccacgg tcatagacag caccataaa    1920
tcagagtttc aacatatgg ttttaactgt gaatttggct ggggctctca caagaccttc    1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca aagtggctcg cctggtgagc cctgtggttt attcccagaa ctctgcccac    2160
tgcatgacct tctggtatca catgtctggg tcccacgtcg gcacactcag ggtcaaactg    2220
cgctaccaga agccagagga gtacgatcag ctggtctgga tggccattgg acaccaaggt    2280
```

```
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400
aataaccaca tttcacaaga agattgtgca aaaccagcag acctggataa aagaaccca     2460 gaaattaaaa ttgatgaaac agggagcacg ccaggatacg aaggtgaagg agaaggtgac    2520
aagaacatct ccaggaagcc aggcaatgtg ttgaagacct tagaccccag atctggatcc    2580
aaggaaaact tgtatttcca gggccatcat catcatcatc attga                    2625
```

<210> SEQ ID NO 60
<211> LENGTH: 853
<212> TYPE: PRT
<213> ORGANISM: artificial sequence
<220> FEATURE:
<223> OTHER INFORMATION: Synthetic polypeptide

<400> SEQUENCE: 60

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
                85                  90                  95

Phe Leu Phe Ile Lys Phe Val Ser Asp Tyr Glu Thr His Gly Ala Gly
                100                 105                 110

Phe Ser Ile Arg Tyr Glu Leu Phe Lys Arg Gly Pro Glu Cys Ser Gln
            115                 120                 125

Asn Tyr Thr Thr Pro Ser Gly Val Ile Lys Ser Pro Gly Phe Pro Glu
    130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
                180                 185                 190

Trp Asp Gly Phe Pro Asp Val Gly Pro His Ile Gly Arg Tyr Cys Gly
            195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
                260                 265                 270

Ser Ser Gln Tyr Ser Thr Asn Trp Ser Ala Glu Arg Ser Arg Leu Asn
            275                 280                 285

Tyr Pro Glu Asn Gly Trp Thr Pro Gly Glu Lys Ser Tyr Arg Glu Trp
    290                 295                 300
```

```
Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Val Lys Thr
            325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
            355                 360                 365

Val Val Val Ala Val Phe Pro Lys Pro Leu Ile Thr Arg Phe Val Arg
370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
            435                 440                 445

Gly Trp Ala Leu Pro Pro Ala Pro His Ser Tyr Ile Asn Glu Trp Leu
450                 455                 460

Gln Ile Asp Leu Gly Glu Glu Lys Ile Val Arg Gly Ile Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
            515                 520                 525

Glu Leu Arg Thr Phe Pro Ala Leu Ser Thr Arg Phe Ile Arg Ile Tyr
            530                 535                 540

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
            580                 585                 590

Thr Gly Asp Asp Phe Gln Leu Thr Gly Gly Thr Thr Val Leu Ala Thr
            595                 600                 605

Glu Lys Pro Thr Val Ile Asp Ser Thr Ile Gln Ser Glu Phe Pro Thr
            610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
            660                 665                 670

Tyr Ser Gln Ala Asp Glu Asn Gln Lys Gly Lys Val Ala Arg Leu Val
            675                 680                 685

Ser Pro Val Val Tyr Ser Gln Asn Ser Ala His Cys Met Thr Phe Trp
            690                 695                 700

Tyr His Met Ser Gly Ser His Val Gly Thr Leu Arg Val Lys Leu Arg
705                 710                 715                 720
```

Tyr Gln Lys Pro Glu Glu Tyr Asp Gln Leu Val Trp Met Ala Ile Gly
            725                 730                 735

His Gln Gly Asp His Trp Lys Glu Gly Arg Val Leu Leu His Lys Ser
        740                 745                 750

Leu Lys Leu Tyr Gln Val Ile Phe Glu Gly Glu Ile Gly Lys Gly Asn
            755                 760                 765

Leu Gly Gly Ile Ala Val Asp Asp Ile Ser Ile Asn Asn His Ile Ser
        770                 775                 780

Gln Glu Asp Cys Ala Lys Pro Ala Asp Leu Lys Lys Asn Pro Glu
785                 790                 795                 800

Ile Lys Ile Asp Glu Thr Gly Ser Thr Pro Gly Tyr Glu Gly Glu Gly
            805                 810                 815

Glu Gly Asp Lys Asn Ile Ser Arg Lys Pro Gly Asn Val Leu Lys Thr
        820                 825                 830

Leu Asp Pro Arg Ser Gly Ser Lys Glu Asn Leu Tyr Phe Gln Gly His
    835                 840                 845

His His His His His
    850

<210> SEQ ID NO 61
<211> LENGTH: 2625
<212> TYPE: DNA
<213> ORGANISM: artificial sequence
<220> FEATURE:
<223> OTHER INFORMATION: Synthetic polynucleotide

<400> SEQUENCE: 61

```
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttaatgcac cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag tcgaatccga tcctcatcg     720 ggcattctct ccatggtttt ttacaccgac agcgcgatag caaagaagg tttctcagca     780 aactacagtg tcttgcagag cagtgtctca gaagatttca atgtatgga agctctgggc     840 atggaatcag agaaaattca ttctgaccag atcacagctt cttcccagta tagcaccaac     900
tggtctgcag agcgctcccg cctgaactac cctgagaatg ggtggactcc cggagagaag     960
tcctaccgag agtggataca ggtagacttg ggccttctgc gctttgtcac ggctgtcggg    1020
acacagggcg ccatttcaaa agaaccaag aagaatatat atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa ccactgata     1200 actcgatttg tccgaatcaa gcctgcaact tgggaaactg gcatatctat gagatttgaa    1260
```

```
gtatatggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca acgcaaggc gaagtctttt    1620 gagggcaaca caactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg gaacttggtg    1800
gatgaatgtg atgacgacca ggccaactgc cacagtggaa caggtgatga cttccagctc    1860
acaggtggca ccactgtgct ggccacagaa aagcccacgg tcatagacag caccatacaa    1920
tcagagtttc caacatatgg ttttaactgt gaatttggct ggggctctca caagaccttc    1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca aagtggctcg cctggtgagc cctgtggttt attcccagaa ctctgcccac    2160
tgcatgacct tctggtatca catgtctggg tcccacgtcg gcacactcag ggtcaaactg    2220
cgctaccaga agccgagga gtacgatcag ctggtctgga tggccattgg acaccaaggt    2280
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400
aataaccaca tttcacaaga agattgtgca aaaccagcag acctggataa aaagaaccca    2460
gaaattaaaa ttgatgaaac agggagcacg ccaggatacg aaggtgaagg agaaggtgac    2520
aagaacatct ccaggaagcc aggcaatgtg ttgaagacct tagaccccag atctggatcc    2580
aaggaaaact tgtatttcca gggccatcat catcatcatc attga                   2625
```

<210> SEQ ID NO 62
<211> LENGTH: 853
<212> TYPE: PRT
<213> ORGANISM: artificial sequence
<220> FEATURE:
<223> OTHER INFORMATION: Synthetic polypeptide

<400> SEQUENCE: 62

```
Phe Arg Asn Asp Lys Cys Gly Asp Thr Ile Lys Ile Glu Ser Pro Gly
1               5                   10                  15

Tyr Leu Thr Ser Pro Gly Tyr Pro His Ser Tyr His Pro Ser Glu Lys
            20                  25                  30

Cys Glu Trp Leu Ile Gln Ala Pro Asp Pro Tyr Gln Arg Ile Met Ile
        35                  40                  45

Asn Phe Asn Pro His Phe Asp Leu Glu Asp Arg Asp Cys Lys Tyr Asp
    50                  55                  60

Tyr Val Glu Val Phe Asp Gly Glu Asn Glu Asn Gly His Phe Arg Gly
65                  70                  75                  80

Lys Phe Cys Gly Lys Ile Ala Pro Pro Val Val Ser Ser Gly Pro
            85                  90                  95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser Gln
        115                 120                 125
```

```
Asn Tyr Thr Thr Pro Ser Gly Val Ile Lys Ser Pro Gly Phe Pro Glu
        130                 135                 140

Lys Tyr Pro Asn Ser Leu Glu Cys Thr Tyr Ile Val Phe Ala Pro Lys
145                 150                 155                 160

Met Ser Glu Ile Ile Leu Glu Phe Glu Ser Phe Asp Leu Glu Pro Asp
                165                 170                 175

Ser Asn Pro Pro Gly Gly Met Phe Cys Arg Tyr Asp Arg Leu Glu Ile
            180                 185                 190

Trp Asp Gly Phe Pro Asp Val Gly Pro His Ile Gly Arg Tyr Cys Gly
        195                 200                 205

Gln Lys Thr Pro Gly Arg Ile Arg Ser Ser Gly Ile Leu Ser Met
    210                 215                 220

Val Phe Tyr Thr Asp Ser Ala Ile Ala Lys Glu Gly Phe Ser Ala Asn
225                 230                 235                 240

Tyr Ser Val Leu Gln Ser Ser Val Ser Glu Asp Phe Lys Cys Met Glu
                245                 250                 255

Ala Leu Gly Met Glu Ser Gly Glu Ile His Ser Asp Gln Ile Thr Ala
            260                 265                 270

Ser Ser Gln Tyr Ser Thr Asn Trp Ser Ala Glu Arg Ser Arg Leu Asn
        275                 280                 285

Tyr Pro Glu Asn Gly Trp Thr Pro Gly Lys Lys Ser Tyr Arg Glu Trp
    290                 295                 300

Ile Gln Val Asp Leu Gly Leu Leu Arg Phe Val Thr Ala Val Gly Thr
305                 310                 315                 320

Gln Gly Ala Ile Ser Lys Glu Thr Lys Lys Tyr Tyr Val Lys Thr
                325                 330                 335

Tyr Lys Ile Asp Val Ser Ser Asn Gly Glu Asp Trp Ile Thr Ile Lys
            340                 345                 350

Glu Gly Asn Lys Pro Val Leu Phe Gln Gly Asn Thr Asn Pro Thr Asp
        355                 360                 365

Val Val Val Ala Val Phe Pro Lys Pro Leu Ile Thr Arg Phe Val Arg
    370                 375                 380

Ile Lys Pro Ala Thr Trp Glu Thr Gly Ile Ser Met Arg Phe Glu Val
385                 390                 395                 400

Tyr Gly Cys Lys Ile Thr Asp Tyr Pro Cys Ser Gly Met Leu Gly Met
                405                 410                 415

Val Ser Gly Leu Ile Ser Asp Ser Gln Ile Thr Ser Ser Asn Gln Gly
            420                 425                 430

Asp Arg Asn Trp Met Pro Glu Asn Ile Arg Leu Val Thr Ser Arg Ser
        435                 440                 445

Gly Trp Ala Leu Pro Pro Ala Pro His Ser Tyr Ile Asn Glu Trp Leu
    450                 455                 460

Gln Ile Asp Leu Gly Glu Glu Lys Ile Val Arg Gly Ile Ile Gln
465                 470                 475                 480

Gly Gly Lys His Arg Glu Asn Lys Val Phe Met Arg Lys Phe Lys Ile
                485                 490                 495

Gly Tyr Ser Asn Asn Gly Ser Asp Trp Lys Met Ile Met Asp Asp Ser
            500                 505                 510

Lys Arg Lys Ala Lys Ser Phe Glu Gly Asn Asn Asn Tyr Asp Thr Pro
        515                 520                 525

Glu Leu Arg Thr Phe Pro Ala Leu Ser Thr Arg Phe Ile Arg Ile Tyr
    530                 535                 540
```

| | | | | | | | | | | | |
|---|---|---|---|---|---|---|---|---|---|---|---|
|Pro|Glu|Arg|Ala|Thr|His|Gly|Gly|Leu|Gly|Leu|Arg|Met|Glu|Leu|Leu|
|545| | | |550| | | |555| | | |560| | | |

Pro Glu Arg Ala Thr His Gly Gly Leu Gly Leu Arg Met Glu Leu Leu
545                 550                 555                 560

Gly Cys Glu Val Glu Ala Pro Thr Ala Gly Pro Thr Thr Pro Asn Gly
                565                 570                 575

Asn Leu Val Asp Glu Cys Asp Asp Gln Ala Asn Cys His Ser Gly
            580                 585                 590

Thr Gly Asp Asp Phe Gln Leu Thr Gly Gly Thr Thr Val Leu Ala Thr
            595                 600                 605

Glu Lys Pro Thr Val Ile Asp Ser Thr Ile Gln Ser Glu Phe Pro Thr
610                 615                 620

Tyr Gly Phe Asn Cys Glu Phe Gly Trp Gly Ser His Lys Thr Phe Cys
625                 630                 635                 640

His Trp Glu His Asp Asn His Val Gln Leu Lys Trp Ser Val Leu Thr
                645                 650                 655

Ser Lys Thr Gly Pro Ile Gln Asp His Thr Gly Asp Gly Asn Phe Ile
                660                 665                 670

Tyr Ser Gln Ala Asp Glu Asn Gln Lys Gly Lys Val Ala Arg Leu Val
                675                 680                 685

Ser Pro Val Val Tyr Ser Gln Asn Ser Ala His Cys Met Thr Phe Trp
690                 695                 700

Tyr His Met Ser Gly Ser His Val Gly Thr Leu Arg Val Lys Leu Arg
705                 710                 715                 720

Tyr Gln Lys Pro Glu Glu Tyr Asp Gln Leu Val Trp Met Ala Ile Gly
                725                 730                 735

His Gln Gly Asp His Trp Lys Glu Gly Arg Val Leu Leu His Lys Ser
                740                 745                 750

Leu Lys Leu Tyr Gln Val Ile Phe Glu Gly Glu Ile Gly Lys Gly Asn
                755                 760                 765

Leu Gly Gly Ile Ala Val Asp Asp Ile Ser Ile Asn Asn His Ile Ser
770                 775                 780

Gln Glu Asp Cys Ala Lys Pro Ala Asp Leu Asp Lys Lys Asn Pro Glu
785                 790                 795                 800

Ile Lys Ile Asp Glu Thr Gly Ser Thr Pro Gly Tyr Glu Gly Glu Gly
                805                 810                 815

Glu Gly Asp Lys Asn Ile Ser Arg Lys Pro Gly Asn Val Leu Lys Thr
                820                 825                 830

Leu Asp Pro Arg Ser Gly Ser Lys Glu Asn Leu Tyr Phe Gln Gly His
                835                 840                 845

His His His His
    850

<210> SEQ ID NO 63
<211> LENGTH: 2625
<212> TYPE: DNA
<213> ORGANISM: artificial sequence
<220> FEATURE:
<223> OTHER INFORMATION: Synthetic polynucleotide

<400> SEQUENCE: 63
atggagaggg ggctgccgct cctctgcgcc gtgctcgccc tcgtcctcgc cccggccggc    60
gcttttcgca acgataaatg tggcgatact ataaaaattg aaagccccgg gtaccttaca   120
tctcctggtt atcctcattc ttatcaccca agtgaaaaat gcgaatggct gattcaggct   180
ccggacccat accagagaat tatgatcaac ttcaaccctc acttcgattt ggaggacaga   240
gactgcaagt atgactacgt ggaagtcttc gatggagaaa atgaaaatgg acattttagg   300

-continued

```
ggaaagttct gtggaaagat agccctcct cctgttgtgt cttcaggcc atttctttt      360
atcaaatttg tctctgacta cgaaacacat ggtgcaggat tttccatacg ttatgaactt    420
ttcaagagag gtcctgaatg ttcccagaac tacacaacac ctagtggagt gataaagtcc    480
cccggattcc ctgaaaaata tcccaacagc cttgaatgca cttatattgt ctttgcgcca    540
aagatgtcag agattatcct ggaatttgaa agctttgacc tggagcctga ctcaaatcct    600
ccaggggga tgttctgtcg ctacgaccgg ctagaaatct gggatggatt ccctgatgtt     660
ggccctcaca ttgggcgtta ctgtggacag aaaacaccag gtcgaatccg atcctcatcg    720
ggcattctct ccatggtttt ttacaccgac agcgcgatag caaaagaagg tttctcagca    780
aactacagtg tcttgcagag cagtgtctca gaagatttca atgtatgga gctctgggc     840
atggaatcag gagaaattca ttctgaccag atcacagctt cttcccagta tagcaccaac    900
tggtctgcag agcgctcccg cctgaactac cctgagaatg ggtggactcc cggaaagaag    960
tcctaccgag agtggataca ggtagacttg ggccttctgc gctttgtcac ggctgtcggg    1020
acacagggcg ccatttcaaa agaaaccaag aagaaatatt atgtcaagac ttacaagatc    1080
gacgttagct ccaacgggga agactggatc accataaaag aaggaaacaa acctgttctc    1140
tttcagggaa acaccaaccc tacagatgtt gtggttgcag tattccccaa accactgata    1200
actcgatttg tccgaatcaa gcctgcaact tgggaaactg gcatatctat gagatttgaa    1260
gtatatggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca aacgcaaggc gaagtctttt    1620
gagggcaaca caactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg gaacttggtg    1800
gatgaatgtg atgacgacca ggccaactgc cacagtggaa caggtgatga cttccagctc    1860
acaggtggca ccactgtgct ggccacagaa aagcccacgg tcatagacag caccatacaa    1920
tcagagtttc aacatatgg ttttaactgt gaatttggct ggggctctca caagaccttc     1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca aagtggctcg cctggtgagc cctgtggttt attcccagaa ctctgcccac    2160
tgcatgacct tctggtatca catgtctggg tcccacgtcg gcacactcag ggtcaaactg    2220
cgctaccaga agccagagga gtacgatcag ctggtctgga tggccattgg acaccaaggt    2280
gaccactgga aggaagggcg tgtcttgctc cacaagtctc tgaaacttta tcaggtgatt    2340
ttcgagggcg aaatcggaaa aggaaaacctt ggtggggattg ctgtggatga cattagtatt   2400
aataaccaca tttcacaaga agattgtgca aaaccagcag acctggataa aaagaaccca    2460
gaaattaaaa ttgatgaaac agggagcacg ccaggatacg aaggtgaagg agaaggtgac    2520
aagaacatct ccaggaagcc aggcaatgtg ttgaagacct tagacccag atctggatcc     2580
aaggaaaact tgtatttcca gggccatcat catcatcatc attga                    2625
```

<210> SEQ ID NO 64
<211> LENGTH: 771
<212> TYPE: PRT
<213> ORGANISM: human

<400> SEQUENCE: 64

| | | | | | | | | | | | | | | | |
|---|---|---|---|---|---|---|---|---|---|---|---|---|---|---|---|
| Met | Gly | Trp | Leu | Thr | Arg | Ile | Val | Cys | Leu | Phe | Trp | Gly | Val | Leu | Leu |
| 1 | | | | 5 | | | | | 10 | | | | | 15 | |
| Thr | Ala | Arg | Ala | Asn | Tyr | Gln | Asn | Gly | Lys | Asn | Asn | Val | Pro | Arg | Leu |
| | | | 20 | | | | | 25 | | | | | 30 | | |
| Lys | Leu | Ser | Tyr | Lys | Glu | Met | Leu | Glu | Ser | Asn | Asn | Val | Ile | Thr | Phe |
| | | | | 35 | | | | | 40 | | | | | 45 | |
| Asn | Gly | Leu | Ala | Asn | Ser | Ser | Ser | Tyr | His | Thr | Phe | Leu | Leu | Asp | Glu |
| | | | 50 | | | | | 55 | | | | | 60 | | |
| Glu | Arg | Ser | Arg | Leu | Tyr | Val | Gly | Ala | Lys | Asp | His | Ile | Phe | Ser | Phe |
| 65 | | | | | 70 | | | | | 75 | | | | | 80 |
| Asp | Leu | Val | Asn | Ile | Lys | Asp | Phe | Gln | Lys | Ile | Val | Trp | Pro | Val | Ser |
| | | | | 85 | | | | | 90 | | | | | 95 | |
| Tyr | Thr | Arg | Arg | Asp | Glu | Cys | Lys | Trp | Ala | Gly | Lys | Asp | Ile | Leu | Lys |
| | | | 100 | | | | | 105 | | | | | 110 | | |
| Glu | Cys | Ala | Asn | Phe | Ile | Lys | Val | Leu | Lys | Ala | Tyr | Asn | Gln | Thr | His |
| | | | | 115 | | | | | 120 | | | | | 125 | |
| Leu | Tyr | Ala | Cys | Gly | Thr | Gly | Ala | Phe | His | Pro | Ile | Cys | Thr | Tyr | Ile |
| | | | 130 | | | | | 135 | | | | | 140 | | |
| Glu | Ile | Gly | His | His | Pro | Glu | Asp | Asn | Ile | Phe | Lys | Leu | Glu | Asn | Ser |
| 145 | | | | | 150 | | | | | 155 | | | | | 160 |
| His | Phe | Glu | Asn | Gly | Arg | Gly | Lys | Ser | Pro | Tyr | Asp | Pro | Lys | Leu | Leu |
| | | | | 165 | | | | | 170 | | | | | 175 | |
| Thr | Ala | Ser | Leu | Leu | Ile | Asp | Gly | Glu | Leu | Tyr | Ser | Gly | Thr | Ala | Ala |
| | | | 180 | | | | | 185 | | | | | 190 | | |
| Asp | Phe | Met | Gly | Arg | Asp | Phe | Ala | Ile | Phe | Arg | Thr | Leu | Gly | His | His |
| | | | | 195 | | | | | 200 | | | | | 205 | |
| His | Pro | Ile | Arg | Thr | Glu | Gln | His | Asp | Ser | Arg | Trp | Leu | Asn | Asp | Pro |
| | | | 210 | | | | | 215 | | | | | 220 | | |
| Lys | Phe | Ile | Ser | Ala | His | Leu | Ile | Ser | Glu | Ser | Asp | Asn | Pro | Glu | Asp |
| 225 | | | | | 230 | | | | | 235 | | | | | 240 |
| Asp | Lys | Val | Tyr | Phe | Phe | Arg | Glu | Asn | Ala | Ile | Asp | Gly | Glu | His | |
| | | | | 245 | | | | | 250 | | | | | 255 | |
| Ser | Gly | Lys | Ala | Thr | His | Ala | Arg | Ile | Gly | Gln | Ile | Cys | Lys | Asn | Asp |
| | | | 260 | | | | | 265 | | | | | 270 | | |
| Phe | Gly | Gly | His | Arg | Ser | Leu | Val | Asn | Lys | Trp | Thr | Thr | Phe | Leu | Lys |
| | | | | 275 | | | | | 280 | | | | | 285 | |
| Ala | Arg | Leu | Ile | Cys | Ser | Val | Pro | Gly | Pro | Asn | Gly | Ile | Asp | Thr | His |
| | | | 290 | | | | | 295 | | | | | 300 | | |
| Phe | Asp | Glu | Leu | Gln | Asp | Val | Phe | Leu | Met | Asn | Phe | Lys | Asp | Pro | Lys |
| 305 | | | | | 310 | | | | | 315 | | | | | 320 |
| Asn | Pro | Val | Val | Tyr | Gly | Val | Phe | Thr | Thr | Ser | Ser | Asn | Ile | Phe | Lys |
| | | | | 325 | | | | | 330 | | | | | 335 | |
| Gly | Ser | Ala | Val | Cys | Met | Tyr | Ser | Met | Ser | Asp | Val | Arg | Arg | Val | Phe |
| | | | 340 | | | | | 345 | | | | | 350 | | |
| Leu | Gly | Pro | Tyr | Ala | His | Arg | Asp | Gly | Pro | Asn | Tyr | Gln | Trp | Val | Pro |
| | | | | 355 | | | | | 360 | | | | | 365 | |
| Tyr | Gln | Gly | Arg | Val | Pro | Tyr | Pro | Arg | Pro | Gly | Thr | Cys | Pro | Ser | Lys |
| | | | 370 | | | | | 375 | | | | | 380 | | |

```
Thr Phe Gly Gly Phe Asp Ser Thr Lys Asp Leu Pro Asp Val Ile
385                 390                 395                 400

Thr Phe Ala Arg Ser His Pro Ala Met Tyr Asn Pro Val Phe Pro Met
        405                 410                 415

Asn Asn Arg Pro Ile Val Ile Lys Thr Asp Val Asn Tyr Gln Phe Thr
            420                 425                 430

Gln Ile Val Val Asp Arg Val Asp Ala Glu Asp Gly Gln Tyr Asp Val
                435                 440                 445

Met Phe Ile Gly Thr Asp Val Gly Thr Val Leu Lys Val Val Ser Ile
450                 455                 460

Pro Lys Glu Thr Trp Tyr Asp Leu Glu Glu Val Leu Glu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
        515                 520                 525

Leu Ala Arg Asp Pro Tyr Cys Ala Trp Asp Gly Ser Ala Cys Ser Arg
530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu His His Asp Asn His His
            565                 570                 575

Gly His Ser Pro Glu Glu Arg Ile Ile Tyr Gly Val Glu Asn Ser Ser
        580                 585                 590

Thr Phe Leu Glu Cys Ser Pro Lys Ser Gln Arg Ala Leu Val Tyr Trp
    595                 600                 605

Gln Phe Gln Arg Arg Asn Glu Glu Arg Lys Glu Glu Ile Arg Val Asp
610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
            645                 650                 655

Ile Gln Thr Leu Leu Lys Val Thr Leu Glu Val Ile Asp Thr Glu His
        660                 665                 670

Leu Glu Glu Leu Leu His Lys Asp Asp Gly Asp Gly Ser Lys Thr
            675                 680                 685

Lys Glu Met Ser Asn Ser Met Thr Pro Ser Gln Lys Val Trp Tyr Arg
    690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Gln Arg
                725                 730                 735

Pro Gly His Thr Pro Gly Asn Ser Asn Lys Trp Lys His Leu Gln Glu
            740                 745                 750

Asn Lys Lys Gly Arg Asn Arg Arg Thr His Glu Phe Glu Arg Ala Pro
        755                 760                 765

Arg Ser Val
    770

<210> SEQ ID NO 65
<211> LENGTH: 609
```

<212> TYPE: PRT
<213> ORGANISM: human

<400> SEQUENCE: 65

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400
```

```
Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
        420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Gly Gly Thr Thr Val Leu
            580                 585                 590

Ala Thr Glu Lys Pro Thr Val Ile Asp Ser Thr Ile Gln Ser Gly Ile
            595                 600                 605

Lys

<210> SEQ ID NO 66
<211> LENGTH: 923
<212> TYPE: PRT
<213> ORGANISM: human

<400> SEQUENCE: 66

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160
```

-continued

```
Pro Gly Phe Pro Glu Lys Tyr Pro Asn Ser Leu Glu Cys Thr Tyr Ile
            165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
            195                 200                 205

Asp Arg Leu Glu Ile Trp Asp Gly Phe Pro Asp Val Gly Pro His Ile
            210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
            245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Ser Thr Asn Trp Ser Ala Glu
            290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
            370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
            485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
            530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
            565                 570                 575
```

Arg Met Glu Leu Leu Gly Cys Glu Val Ala Pro Thr Ala Gly Pro
                580                 585                 590

Thr Thr Pro Asn Gly Asn Leu Val Asp Glu Cys Asp Asp Gln Ala
            595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ala Met
850                 855                 860

Ser Ala Leu Gly Val Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
        915                 920

<210> SEQ ID NO 67
<211> LENGTH: 923
<212> TYPE: PRT
<213> ORGANISM: mus musculus

<400> SEQUENCE: 67

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

```
Ile Glu Asn Pro Gly Tyr Leu Thr Ser Pro Gly Tyr Pro His Ser Tyr
             35                  40                  45

His Pro Ser Glu Lys Cys Glu Trp Leu Ile Gln Ala Pro Glu Pro Tyr
 50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Ile Asp Gly Glu Asn Glu Gly
                 85                  90                  95

Gly Arg Leu Trp Gly Lys Phe Cys Gly Lys Ile Ala Pro Ser Pro Val
                100                 105                 110

Val Ser Ser Gly Pro Phe Leu Phe Ile Lys Phe Val Ser Asp Tyr Glu
                115                 120                 125

Thr His Gly Ala Gly Phe Ser Ile Arg Tyr Glu Ile Phe Lys Arg Gly
                130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
                180                 185                 190

Asp Leu Glu Gln Asp Ser Asn Pro Pro Gly Gly Met Phe Cys Arg Tyr
                195                 200                 205

Asp Arg Leu Glu Ile Trp Asp Gly Phe Pro Glu Val Gly Pro His Ile
                210                 215                 220

Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
                260                 265                 270

Phe Lys Cys Met Glu Ala Leu Gly Met Glu Ser Gly Glu Ile His Ser
                275                 280                 285

Asp Gln Ile Thr Ala Ser Ser Gln Tyr Gly Thr Asn Trp Ser Val Glu
                290                 295                 300

Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Arg Val Asp Ile Ser Ser Asn Gly Glu Asp
                355                 360                 365

Trp Ile Ser Leu Lys Glu Gly Asn Lys Ala Ile Ile Phe Gln Gly Asn
370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
                435                 440                 445
```

-continued

```
Ala Ser Asn Gln Ala Asp Arg Asn Trp Met Pro Glu Asn Ile Arg Leu
    450                 455                 460
Val Thr Ser Arg Thr Gly Trp Ala Leu Pro Pro Ser Pro His Pro Tyr
465                 470                 475                 480
Thr Asn Glu Trp Leu Gln Val Asp Leu Gly Asp Glu Lys Ile Val Arg
                485                 490                 495
Gly Val Ile Ile Gln Gly Gly Lys His Arg Glu Asn Lys Val Phe Met
                500                 505                 510
Arg Lys Phe Lys Ile Ala Tyr Ser Asn Asn Gly Ser Asp Trp Lys Thr
            515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Ser Pro Leu Ser Thr Arg
545                 550                 555                 560
Phe Ile Arg Ile Tyr Pro Glu Arg Ala Thr His Ser Gly Leu Gly Leu
                565                 570                 575
Arg Met Glu Leu Leu Gly Cys Glu Val Glu Ala Pro Thr Ala Gly Pro
            580                 585                 590
Thr Thr Pro Asn Gly Asn Pro Val Asp Glu Cys Asp Asp Gln Ala
            595                 600                 605
Asn Cys His Ser Gly Thr Gly Asp Asp Phe Gln Leu Thr Gly Gly Thr
            610                 615                 620
Thr Val Leu Ala Thr Glu Lys Pro Thr Ile Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Ser His Ala Gln Leu Arg
            660                 665                 670
Trp Ser Val Leu Thr Ser Lys Thr Gly Pro Ile Gln Asp His Thr Gly
            675                 680                 685
Asp Gly Asn Phe Ile Tyr Ser Gln Ala Asp Glu Asn Gln Lys Gly Lys
            690                 695                 700
Val Ala Arg Leu Val Ser Pro Val Val Tyr Ser Gln Ser Ser Ala His
705                 710                 715                 720
Cys Met Thr Phe Trp Tyr His Met Ser Gly Ser His Val Gly Thr Leu
                725                 730                 735
Arg Val Lys Leu Arg Tyr Gln Lys Pro Glu Glu Tyr Asp Gln Leu Val
            740                 745                 750
Trp Met Val Val Gly His Gln Gly Asp His Trp Lys Glu Gly Arg Val
            755                 760                 765
Leu Leu His Lys Ser Leu Lys Leu Tyr Gln Val Ile Phe Glu Gly Glu
770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Thr Asp Leu Asp
            805                 810                 815
Lys Lys Asn Thr Glu Ile Lys Ile Asp Glu Thr Gly Ser Thr Pro Gly
            820                 825                 830
Tyr Glu Gly Glu Gly Glu Gly Asp Lys Asn Ile Ser Arg Lys Pro Gly
            835                 840                 845
Asn Val Leu Lys Thr Leu Asp Pro Ile Leu Ile Thr Ile Ile Ala Met
850                 855                 860
Ser Ala Leu Gly Val Leu Leu Gly Ala Val Cys Gly Val Val Leu Tyr
```

```
                865                 870                 875                 880
Cys Ala Cys Trp His Asn Gly Met Ser Glu Arg Asn Leu Ser Ala Leu
                    885                 890                 895
Glu Asn Tyr Asn Phe Glu Leu Val Asp Gly Val Lys Leu Lys Lys Asp
                900                 905                 910
Lys Leu Asn Pro Gln Ser Asn Tyr Ser Glu Ala
            915                 920

<210> SEQ ID NO 68
<211> LENGTH: 923
<212> TYPE: PRT
<213> ORGANISM: ratus norvegicus

<400> SEQUENCE: 68

Met Glu Arg Gly Leu Pro Leu Leu Cys Ala Thr Leu Ala Leu Ala Leu
1               5                   10                  15
Ala Leu Ala Gly Ala Phe Arg Ser Asp Lys Cys Gly Gly Thr Ile Lys
                20                  25                  30
Ile Glu Asn Pro Gly Tyr Leu Thr Ser Pro Gly Tyr Pro His Ser Tyr
                35                  40                  45
His Pro Ser Glu Lys Cys Glu Trp Leu Ile Gln Ala Pro Glu Pro Tyr
        50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Ile Asp Gly Glu Asn Glu Gly
                85                  90                  95
Gly Arg Leu Trp Gly Lys Phe Cys Gly Lys Ile Ala Pro Ser Pro Val
                100                 105                 110
Val Ser Ser Gly Pro Phe Leu Phe Ile Lys Phe Val Ser Asp Tyr Glu
            115                 120                 125
Thr His Gly Ala Gly Phe Ser Ile Arg Tyr Glu Ile Phe Lys Arg Gly
    130                 135                 140
Pro Glu Cys Ser Gln Asn Tyr Thr Ala Pro Thr Gly Val Ile Lys Ser
145                 150                 155                 160
Pro Gly Phe Pro Glu Lys Tyr Pro Asn Ser Leu Glu Cys Thr Tyr Ile
                165                 170                 175
Ile Phe Ala Pro Lys Met Ser Glu Ile Ile Leu Glu Phe Glu Ser Phe
                180                 185                 190
Asp Leu Glu Gln Asp Ser Asn Pro Pro Gly Gly Val Phe Cys Arg Tyr
            195                 200                 205
Asp Arg Leu Glu Ile Trp Asp Gly Phe Pro Glu Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
                260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Gly Thr Asn Trp Ser Val Glu
    290                 295                 300
Arg Ser Arg Leu Asn Tyr Pro Glu Asn Gly Trp Thr Pro Gly Glu Asp
305                 310                 315                 320
```

```
Ser Tyr Arg Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys
    340                 345                 350

Tyr Tyr Val Lys Thr Tyr Arg Val Asp Ile Ser Ser Asn Gly Glu Asp
            355                 360                 365

Trp Ile Thr Leu Lys Glu Gly Asn Lys Ala Ile Ile Phe Gln Gly Asn
370                 375                 380

Thr Asn Pro Thr Asp Val Val Phe Gly Val Phe Pro Lys Pro Leu Ile
385                 390                 395                 400

Thr Arg Phe Val Arg Ile Lys Pro Ala Ser Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
                435                 440                 445

Ala Ser Asn Gln Gly Asp Arg Asn Trp Met Pro Glu Asn Ile Arg Leu
    450                 455                 460

Val Thr Ser Arg Thr Gly Trp Ala Leu Pro Pro Ser Pro His Pro Tyr
465                 470                 475                 480

Ile Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
                500                 505                 510

Arg Lys Phe Lys Ile Ala Tyr Ser Asn Asn Gly Ser Asp Trp Lys Met
    515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Ala Phe Thr Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Val Pro Thr Ala Gly Pro
        580                 585                 590

Thr Thr Pro Asn Gly Asn Pro Val Asp Glu Cys Asp Asp Gln Ala
    595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
                660                 665                 670

Trp Arg Val Leu Thr Ser Lys Thr Gly Pro Ile Gln Asp His Thr Gly
                675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu His Tyr Gln Lys Pro Glu Glu Tyr Asp Gln Leu Val
```

```
                740                 745                 750
Trp Met Val Val Gly His Gln Gly Asp His Trp Lys Glu Gly Arg Val
            755                 760                 765

Leu Leu His Lys Ser Leu Lys Leu Tyr Gln Val Ile Phe Glu Gly Glu
        770                 775                 780

Ile Gly Lys Gly Asn Leu Gly Gly Ile Ala Val Asp Asp Ile Ser Ile
785                 790                 795                 800

Asn Asn His Ile Pro Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Glu Glu Gly Lys Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
                900                 905                 910

Lys Leu Asn Pro Gln Ser Asn Tyr Ser Glu Ala
            915                 920

<210> SEQ ID NO 69
<211> LENGTH: 923
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
```

```
<221> NAME/KEY: misc_feature
<222> LOCATION: (98)..(100)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (303)..(303)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (359)..(360)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (371)..(372)
<223> OTHER INFORMATION: Xaa can be any naturally occurring amino acid
<220> FEATURE:
<221> NAME/KEY: misc_feature
<222> LOCATION: (378)..(380)
<223> OTHER INFORMATION: Xaa can be any naturally occurring amino acid
<220> FEATURE:
<221> NAME/KEY: misc_feature
<222> LOCATION: (392)..(393)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
```

```
<220> FEATURE:
<221> NAME/KEY: misc_feature
<222> LOCATION: (409)..(410)
<223> OTHER INFORMATION: Xaa can be any naturally occurring amino acid
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: misc_feature
<222> LOCATION: (453)..(453)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (498)..(498)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (528)..(528)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (555)..(556)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: misc_feature
<222> LOCATION: (587)..(587)
<223> OTHER INFORMATION: Xaa can be any naturally occurring amino acid
<220> FEATURE:
<221> NAME/KEY: misc_feature
<222> LOCATION: (599)..(599)
<223> OTHER INFORMATION: Xaa can be any naturally occurring amino acid
<220> FEATURE:
<221> NAME/KEY: misc_feature
<222> LOCATION: (634)..(634)
<223> OTHER INFORMATION: Xaa can be any naturally occurring amino acid
<220> FEATURE:
<221> NAME/KEY: misc_feature
<222> LOCATION: (667)..(667)
<223> OTHER INFORMATION: Xaa can be any naturally occurring amino acid
<220> FEATURE:
<221> NAME/KEY: misc_feature
<222> LOCATION: (669)..(669)
```

-continued

```
<223> OTHER INFORMATION: Xaa can be any naturally occurring amino acid
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: misc_feature
<222> LOCATION: (674)..(674)
<223> OTHER INFORMATION: Xaa can be any naturally occurring amino acid
<220> FEATURE:
<221> NAME/KEY: misc_feature
<222> LOCATION: (717)..(717)
<223> OTHER INFORMATION: Xaa can be any naturally occurring amino acid
<220> FEATURE:
<221> NAME/KEY: misc_feature
<222> LOCATION: (741)..(741)
<223> OTHER INFORMATION: Xaa can be any naturally occurring amino acid
<220> FEATURE:
<221> NAME/KEY: misc_feature
<222> LOCATION: (755)..(756)
<223> OTHER INFORMATION: Xaa can be any naturally occurring amino acid
<220> FEATURE:
<221> NAME/KEY: misc_feature
<222> LOCATION: (805)..(805)
<223> OTHER INFORMATION: Xaa can be any naturally occurring amino acid
<220> FEATURE:
<221> NAME/KEY: misc_feature
<222> LOCATION: (812)..(812)
<223> OTHER INFORMATION: Xaa can be any naturally occurring amino acid
<220> FEATURE:
<221> NAME/KEY: misc_feature
<222> LOCATION: (819)..(820)
<223> OTHER INFORMATION: Xaa can be any naturally occurring amino acid
<220> FEATURE:
<221> NAME/KEY: misc_feature
<222> LOCATION: (835)..(835)
<223> OTHER INFORMATION: Xaa can be any naturally occurring amino acid
<220> FEATURE:
<221> NAME/KEY: misc_feature
<222> LOCATION: (838)..(838)
<223> OTHER INFORMATION: Xaa can be any naturally occurring amino acid
<220> FEATURE:
<221> NAME/KEY: misc_feature
<222> LOCATION: (916)..(916)
<223> OTHER INFORMATION: Xaa can be any naturally occurring amino acid
<220> FEATURE:
<221> NAME/KEY: misc_feature
<222> LOCATION: (919)..(919)
<223> OTHER INFORMATION: Xaa can be any naturally occurring amino acid

<400> SEQUENCE: 69

Met Glu Arg Gly Leu Pro Leu Leu Cys Ala Xaa Leu Ala Leu Xaa Leu
1               5                   10                  15

Ala Xaa Ala Gly Ala Phe Arg Xaa Asp Lys Cys Gly Xaa Thr Ile Lys
            20                  25                  30

Ile Glu Xaa Pro Gly Tyr Leu Thr Ser Pro Gly Tyr Pro His Ser Tyr
        35                  40                  45

His Pro Ser Glu Lys Cys Glu Trp Leu Ile Gln Ala Pro Xaa Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Xaa Asp Gly Glu Asn Glu Xaa
                85                  90                  95

Gly Xaa Xaa Xaa Gly Lys Phe Cys Gly Lys Ile Ala Pro Xaa Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Xaa Phe Lys Arg Gly
    130                 135                 140
```

-continued

```
Pro Glu Cys Ser Gln Asn Tyr Thr Xaa Pro Xaa Gly Val Ile Lys Ser
145                 150                 155                 160
Pro Gly Phe Pro Glu Lys Tyr Pro Asn Ser Leu Glu Cys Thr Tyr Ile
                165                 170                 175
Xaa Phe Ala Pro Lys Met Ser Glu Ile Ile Leu Glu Phe Glu Ser Phe
            180                 185                 190
Asp Leu Glu Xaa Asp Ser Asn Pro Pro Gly Gly Xaa Phe Cys Arg Tyr
        195                 200                 205
Asp Arg Leu Glu Ile Trp Asp Gly Phe Pro Xaa Val Gly Pro His Ile
    210                 215                 220
Gly Arg Tyr Cys Gly Gln Lys Thr Pro Gly Arg Ile Arg Ser Ser Ser
225                 230                 235                 240
Gly Xaa Leu Ser Met Val Phe Tyr Thr Asp Ser Ala Ile Ala Lys Glu
                245                 250                 255
Gly Phe Ser Ala Asn Tyr Ser Val Leu Gln Ser Ser Xaa Ser Glu Asp
            260                 265                 270
Phe Lys Cys Met Glu Ala Leu Gly Met Glu Ser Gly Glu Ile His Ser
        275                 280                 285
Asp Gln Ile Thr Ala Ser Ser Gln Tyr Xaa Thr Asn Trp Ser Xaa Glu
    290                 295                 300
Arg Ser Arg Leu Asn Tyr Pro Glu Asn Gly Trp Thr Pro Gly Glu Asp
305                 310                 315                 320
Ser Tyr Xaa Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Xaa Xaa Asp Xaa Ser Ser Asn Gly Glu Asp
        355                 360                 365
Trp Ile Xaa Xaa Lys Glu Gly Asn Lys Xaa Xaa Phe Gln Gly Asn
    370                 375                 380
Thr Asn Pro Thr Asp Val Val Xaa Xaa Val Phe Xaa Lys Pro Leu Ile
385                 390                 395                 400
Thr Arg Phe Val Arg Ile Lys Pro Xaa Xaa Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
        435                 440                 445
Xaa Ser Asn Gln Xaa Asp Arg Asn Trp Met Pro Glu Asn Ile Arg Leu
    450                 455                 460
Val Thr Ser Arg Xaa Gly Trp Ala Leu Pro Pro Xaa Pro His Xaa Tyr
465                 470                 475                 480
Xaa Asn Glu Trp Leu Gln Xaa Asp Leu Gly Xaa Glu Lys Ile Val Arg
                485                 490                 495
Gly Xaa Ile Ile Gln Gly Gly Lys His Arg Glu Asn Lys Val Phe Met
            500                 505                 510
Arg Lys Phe Lys Ile Xaa Tyr Ser Asn Asn Gly Ser Asp Trp Lys Xaa
        515                 520                 525
Ile Met Asp Asp Ser Lys Arg Lys Ala Lys Ser Phe Glu Gly Asn Asn
    530                 535                 540
Asn Tyr Asp Thr Pro Glu Leu Arg Xaa Phe Xaa Xaa Leu Ser Thr Arg
545                 550                 555                 560
Phe Ile Arg Ile Tyr Pro Glu Arg Ala Thr His Xaa Gly Leu Gly Leu
```

```
                    565                 570                 575
Arg Met Glu Leu Leu Gly Cys Glu Val Glu Xaa Pro Thr Ala Gly Pro
            580                 585                 590

Thr Thr Pro Asn Gly Asn Xaa Val Asp Glu Cys Asp Asp Gln Ala
        595                 600             605

Asn Cys His Ser Gly Thr Gly Asp Asp Phe Gln Leu Thr Gly Gly Thr
        610                 615                 620

Thr Val Leu Ala Thr Glu Lys Pro Thr Xaa Ile Asp Ser Thr Ile Gln
625                 630                 635                 640

Ser Glu Phe Pro Thr Tyr Gly Phe Asn Cys Glu Phe Gly Trp Gly Ser
                    645                 650                 655

His Lys Thr Phe Cys His Trp Glu His Asp Xaa His Xaa Gln Leu Xaa
                660                 665                 670

Trp Xaa Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Xaa Ser Ala His
705                 710                 715                 720

Cys Met Thr Phe Trp Tyr His Met Ser Gly Ser His Val Gly Thr Leu
                    725                 730                 735

Arg Val Lys Leu Xaa Tyr Gln Lys Pro Glu Glu Tyr Asp Gln Leu Val
                740                 745                 750

Trp Met Xaa Xaa Gly His Gln Gly Asp His Trp Lys Glu Gly Arg Val
            755                 760                 765

Leu Leu His Lys Ser Leu Lys Leu Tyr Gln Val Ile Phe Glu Gly Glu
770                 775                 780

Ile Gly Lys Gly Asn Leu Gly Gly Ile Ala Val Asp Asp Ile Ser Ile
785                 790                 795                 800

Asn Asn His Ile Xaa Gln Glu Asp Cys Ala Lys Xaa Asp Leu Asp Lys
                    805                 810                 815

Lys Asn Xaa Xaa Glu Ile Lys Ile Asp Glu Thr Gly Ser Thr Pro Gly
            820                 825                 830

Tyr Glu Xaa Glu Gly Xaa Gly Asp Lys Asn Ile Ser Arg Lys Pro Gly
        835                 840                 845

Asn Val Leu Lys Thr Leu Asp Pro Ile Leu Ile Thr Ile Ala Met
        850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                    885                 890                 895

Glu Asn Tyr Asn Phe Glu Leu Val Asp Gly Val Lys Leu Lys Lys Asp
                900                 905                 910

Lys Leu Asn Xaa Gln Ser Xaa Tyr Ser Glu Ala
            915                 920

<210> SEQ ID NO 70
<211> LENGTH: 21
<212> TYPE: PRT
<213> ORGANISM: human

<400> SEQUENCE: 70

Met Glu Arg Gly Leu Pro Leu Leu Cys Ala Val Leu Ala Leu Val Leu
1               5                   10                  15
```

Ala Pro Ala Gly Ala
            20

<210> SEQ ID NO 71
<211> LENGTH: 115
<212> TYPE: PRT
<213> ORGANISM: human

<400> SEQUENCE: 71

Cys Gly Asp Thr Ile Lys Ile Glu Ser Pro Gly Tyr Leu Thr Ser Pro
1               5                   10                  15

Gly Tyr Pro His Ser Tyr His Pro Ser Glu Lys Cys Glu Trp Leu Ile
            20                  25                  30

Gln Ala Pro Asp Pro Tyr Gln Arg Ile Met Ile Asn Phe Asn Pro His
        35                  40                  45

Phe Asp Leu Glu Asp Arg Asp Cys Lys Tyr Asp Tyr Val Glu Val Phe
    50                  55                  60

Asp Gly Glu Asn Glu Asn Gly His Phe Arg Gly Lys Phe Cys Gly Lys
65                  70                  75                  80

Ile Ala Pro Pro Pro Val Val Ser Ser Gly Pro Phe Leu Phe Ile Lys
                85                  90                  95

Phe Val Ser Asp Tyr Glu Thr His Gly Ala Gly Phe Ser Ile Arg Tyr
            100                 105                 110

Glu Leu Phe
        115

<210> SEQ ID NO 72
<211> LENGTH: 119
<212> TYPE: PRT
<213> ORGANISM: human

<400> SEQUENCE: 72

Cys Ser Gln Asn Tyr Thr Thr Pro Ser Gly Val Ile Lys Ser Pro Gly
1               5                   10                  15

Phe Pro Glu Lys Tyr Pro Asn Ser Leu Glu Cys Thr Tyr Ile Val Phe
            20                  25                  30

Ala Pro Lys Met Ser Glu Ile Ile Leu Glu Phe Glu Ser Phe Asp Leu
        35                  40                  45

Glu Pro Asp Ser Asn Pro Pro Gly Gly Met Phe Cys Arg Tyr Asp Arg
    50                  55                  60

Leu Glu Ile Trp Asp Gly Phe Pro Asp Val Gly Pro His Ile Gly Arg
65                  70                  75                  80

Tyr Cys Gly Gln Lys Thr Pro Gly Arg Ile Arg Ser Ser Ser Gly Ile
                85                  90                  95

Leu Ser Met Val Phe Tyr Thr Asp Ser Ala Ile Ala Lys Glu Gly Phe
            100                 105                 110

Ser Ala Asn Tyr Ser Val Leu
        115

<210> SEQ ID NO 73
<211> LENGTH: 150
<212> TYPE: PRT
<213> ORGANISM: human

<400> SEQUENCE: 73

Cys Met Glu Ala Leu Gly Met Glu Ser Gly Glu Ile His Ser Asp Gln
1               5                   10                  15

Ile Thr Ala Ser Ser Gln Tyr Ser Thr Asn Trp Ser Ala Glu Arg Ser

```
            20                  25                  30
Arg Leu Asn Tyr Pro Glu Asn Gly Trp Thr Pro Gly Glu Asp Ser Tyr
            35                  40                  45

Arg Glu Trp Ile Gln Val Asp Leu Gly Leu Leu Arg Phe Val Thr Ala
    50                  55                  60

Val Gly Thr Gln Gly Ala Ile Ser Lys Glu Thr Lys Lys Lys Tyr Tyr
65                  70                  75                  80

Val Lys Thr Tyr Lys Ile Asp Val Ser Ser Asn Gly Glu Asp Trp Ile
                85                  90                  95

Thr Ile Lys Glu Gly Asn Lys Pro Val Leu Phe Gln Gly Asn Thr Asn
            100                 105                 110

Pro Thr Asp Val Val Val Ala Val Phe Pro Lys Pro Leu Ile Thr Arg
        115                 120                 125

Phe Val Arg Ile Lys Pro Ala Thr Trp Glu Thr Gly Ile Ser Met Arg
    130                 135                 140

Phe Glu Val Tyr Gly Cys
145                 150

<210> SEQ ID NO 74
<211> LENGTH: 153
<212> TYPE: PRT
<213> ORGANISM: human

<400> SEQUENCE: 74

Cys Ser Gly Met Leu Gly Met Val Ser Gly Leu Ile Ser Asp Ser Gln
1               5                   10                  15

Ile Thr Ser Ser Asn Gln Gly Asp Arg Asn Trp Met Pro Glu Asn Ile
            20                  25                  30

Arg Leu Val Thr Ser Arg Ser Gly Trp Ala Leu Pro Pro Ala Pro His
            35                  40                  45

Ser Tyr Ile Asn Glu Trp Leu Gln Ile Asp Leu Gly Glu Glu Lys Ile
    50                  55                  60

Val Arg Gly Ile Ile Ile Gln Gly Gly Lys His Arg Glu Asn Lys Val
65                  70                  75                  80

Phe Met Arg Lys Phe Lys Ile Gly Tyr Ser Asn Asn Gly Ser Asp Trp
                85                  90                  95

Lys Met Ile Met Asp Asp Ser Lys Arg Lys Ala Lys Ser Phe Glu Gly
            100                 105                 110

Asn Asn Asn Tyr Asp Thr Pro Glu Leu Arg Thr Phe Pro Ala Leu Ser
        115                 120                 125

Thr Arg Phe Ile Arg Ile Tyr Pro Glu Arg Ala Thr His Gly Gly Leu
    130                 135                 140

Gly Leu Arg Met Glu Leu Leu Gly Cys
145                 150

<210> SEQ ID NO 75
<211> LENGTH: 167
<212> TYPE: PRT
<213> ORGANISM: human

<400> SEQUENCE: 75

Thr Tyr Gly Phe Asn Cys Glu Phe Gly Trp Gly Ser His Lys Thr Phe
1               5                   10                  15

Cys His Trp Glu His Asp Asn His Val Gln Leu Lys Trp Ser Val Leu
            20                  25                  30

Thr Ser Lys Thr Gly Pro Ile Gln Asp His Thr Gly Asp Gly Asn Phe
```

```
                35                  40                  45
Ile Tyr Ser Gln Ala Asp Glu Asn Gln Lys Gly Lys Val Ala Arg Leu
 50                  55                  60

Val Ser Pro Val Val Tyr Ser Gln Asn Ser Ala His Cys Met Thr Phe
 65                  70                  75                  80

Trp Tyr His Met Ser Gly Ser His Val Gly Thr Leu Arg Val Lys Leu
                 85                  90                  95

Arg Tyr Gln Lys Pro Glu Glu Tyr Asp Gln Leu Val Trp Met Ala Ile
                100                 105                 110

Gly His Gln Gly Asp His Trp Lys Glu Gly Arg Val Leu Leu His Lys
                115                 120                 125

Ser Leu Lys Leu Tyr Gln Val Ile Phe Glu Gly Glu Ile Gly Lys Gly
130                 135                 140

Asn Leu Gly Gly Ile Ala Val Asp Asp Ile Ser Ile Asn Asn His Ile
145                 150                 155                 160

Ser Gln Glu Asp Cys Ala Lys
                165

<210> SEQ ID NO 76
<211> LENGTH: 10
<212> TYPE: PRT
<213> ORGANISM: artificial sequence
<220> FEATURE:
<223> OTHER INFORMATION: Synthetic polypeptide

<400> SEQUENCE: 76

Gly Ser Lys Glu Asn Leu Tyr Phe Gln Gly
 1               5                  10

<210> SEQ ID NO 77
<211> LENGTH: 40
<212> TYPE: PRT
<213> ORGANISM: human

<400> SEQUENCE: 77

Trp His Asn Gly Met Ser Glu Arg Asn Leu Ser Ala Leu Glu Asn Tyr
 1               5                  10                  15

Asn Phe Glu Leu Val Asp Gly Val Lys Leu Lys Lys Asp Lys Leu Asn
                20                  25                  30

Thr Gln Ser Thr Tyr Ser Glu Ala
                35                  40

<210> SEQ ID NO 78
<211> LENGTH: 127
<212> TYPE: PRT
<213> ORGANISM: human

<400> SEQUENCE: 78

Phe Arg Asn Asp Lys Cys Gly Asp Thr Ile Lys Ile Glu Ser Pro Gly
 1               5                  10                  15

Tyr Leu Thr Ser Pro Gly Tyr Pro His Ser Tyr His Pro Ser Glu Lys
                20                  25                  30

Cys Glu Trp Leu Ile Gln Ala Pro Asp Pro Tyr Gln Arg Ile Met Ile
                35                  40                  45

Asn Phe Asn Pro His Phe Asp Leu Glu Asp Arg Asp Cys Lys Tyr Asp
 50                  55                  60

Tyr Val Glu Val Phe Asp Gly Glu Asn Glu Asn Gly His Phe Arg Gly
 65                  70                  75                  80
```

```
Lys Phe Cys Gly Lys Ile Ala Pro Pro Val Ser Ser Gly Pro
                85                  90              95

Phe Leu Phe Ile Lys Phe Val Ser Asp Tyr Glu Thr His Gly Ala Gly
            100                 105                 110

Phe Ser Ile Arg Tyr Glu Leu Phe Lys Arg Gly Pro Glu Cys Ser
            115                 120                 125
```

<210> SEQ ID NO 79
<211> LENGTH: 127
<212> TYPE: PRT
<213> ORGANISM: human

<400> SEQUENCE: 79

```
Gln Asn Tyr Thr Thr Pro Ser Gly Val Ile Lys Ser Pro Gly Phe Pro
1               5                   10                  15

Glu Lys Tyr Pro Asn Ser Leu Glu Cys Thr Tyr Ile Val Phe Ala Pro
            20                  25                  30

Lys Met Ser Glu Ile Ile Leu Glu Phe Glu Ser Phe Asp Leu Glu Pro
            35                  40                  45

Asp Ser Asn Pro Pro Gly Gly Met Phe Cys Arg Tyr Asp Arg Leu Glu
50              55                  60

Ile Trp Asp Gly Phe Pro Asp Val Gly Pro His Ile Gly Arg Tyr Cys
65              70                  75                  80

Gly Gln Lys Thr Pro Gly Arg Ile Arg Ser Ser Ser Gly Ile Leu Ser
            85                  90                  95

Met Val Phe Tyr Thr Asp Ser Ala Ile Ala Lys Glu Gly Phe Ser Ala
            100                 105                 110

Asn Tyr Ser Val Leu Gln Ser Ser Val Ser Glu Asp Phe Lys Cys
            115                 120                 125
```

<210> SEQ ID NO 80
<211> LENGTH: 153
<212> TYPE: PRT
<213> ORGANISM: human

<400> SEQUENCE: 80

```
Met Glu Ala Leu Gly Met Glu Ser Gly Glu Ile His Ser Asp Gln Ile
1               5                   10                  15

Thr Ala Ser Ser Gln Tyr Ser Thr Asn Trp Ser Ala Glu Arg Ser Arg
            20                  25                  30

Leu Asn Tyr Pro Glu Asn Gly Trp Thr Pro Gly Glu Asp Ser Tyr Arg
            35                  40                  45

Glu Trp Ile Gln Val Asp Leu Gly Leu Leu Arg Phe Val Thr Ala Val
50              55                  60

Gly Thr Gln Gly Ala Ile Ser Lys Glu Thr Lys Lys Lys Tyr Tyr Val
65              70                  75                  80

Lys Thr Tyr Lys Ile Asp Val Ser Ser Asn Gly Glu Asp Trp Ile Thr
            85                  90                  95

Ile Lys Glu Gly Asn Lys Pro Val Leu Phe Gln Gly Asn Thr Asn Pro
            100                 105                 110

Thr Asp Val Val Val Ala Val Phe Pro Lys Pro Leu Ile Thr Arg Phe
            115                 120                 125

Val Arg Ile Lys Pro Ala Thr Trp Glu Thr Gly Ile Ser Met Arg Phe
130             135                 140

Glu Val Tyr Gly Cys Lys Ile Thr Asp
145                 150
```

<210> SEQ ID NO 81
<211> LENGTH: 161
<212> TYPE: PRT
<213> ORGANISM: human

<400> SEQUENCE: 81

```
Tyr Pro Cys Ser Gly Met Leu Gly Met Val Ser Gly Leu Ile Ser Asp
1               5                   10                  15

Ser Gln Ile Thr Ser Ser Asn Gln Gly Asp Arg Asn Trp Met Pro Glu
            20                  25                  30

Asn Ile Arg Leu Val Thr Ser Arg Ser Gly Trp Ala Leu Pro Pro Ala
        35                  40                  45

Pro His Ser Tyr Ile Asn Glu Trp Leu Gln Ile Asp Leu Gly Glu Glu
    50                  55                  60

Lys Ile Val Arg Gly Ile Ile Gln Gly Gly Lys His Arg Glu Asn
65                  70                  75                  80

Lys Val Phe Met Arg Lys Phe Lys Ile Gly Tyr Ser Asn Asn Gly Ser
                85                  90                  95

Asp Trp Lys Met Ile Met Asp Asp Ser Lys Arg Lys Ala Lys Ser Phe
            100                 105                 110

Glu Gly Asn Asn Asn Tyr Asp Thr Pro Glu Leu Arg Thr Phe Pro Ala
        115                 120                 125

Leu Ser Thr Arg Phe Ile Arg Ile Tyr Pro Glu Arg Ala Thr His Gly
    130                 135                 140

Gly Leu Gly Leu Arg Met Glu Leu Leu Gly Cys Glu Val Glu Ala Pro
145                 150                 155                 160

Thr
```

<210> SEQ ID NO 82
<211> LENGTH: 270
<212> TYPE: PRT
<213> ORGANISM: human

<400> SEQUENCE: 82

```
Ala Gly Pro Thr Thr Pro Asn Gly Asn Leu Val Asp Glu Cys Asp Asp
1               5                   10                  15

Asp Gln Ala Asn Cys His Ser Gly Thr Gly Asp Asp Phe Gln Leu Thr
            20                  25                  30

Gly Gly Thr Thr Val Leu Ala Thr Glu Lys Pro Thr Val Ile Asp Ser
        35                  40                  45

Thr Ile Gln Ser Glu Phe Pro Thr Tyr Gly Phe Asn Cys Glu Phe Gly
    50                  55                  60

Trp Gly Ser His Lys Thr Phe Cys His Trp Glu His Asp Asn His Val
65                  70                  75                  80

Gln Leu Lys Trp Ser Val Leu Thr Ser Lys Thr Gly Pro Ile Gln Asp
                85                  90                  95

His Thr Gly Asp Gly Asn Phe Ile Tyr Ser Gln Ala Asp Glu Asn Gln
            100                 105                 110

Lys Gly Lys Val Ala Arg Leu Val Ser Pro Val Val Tyr Ser Gln Asn
        115                 120                 125

Ser Ala His Cys Met Thr Phe Trp Tyr His Met Ser Gly Ser His Val
    130                 135                 140

Gly Thr Leu Arg Val Lys Leu Arg Tyr Gln Lys Pro Glu Glu Tyr Asp
145                 150                 155                 160

Gln Leu Val Trp Met Ala Ile Gly His Gln Gly Asp His Trp Lys Glu
```

```
                        165                 170                 175
Gly Arg Val Leu Leu His Lys Ser Leu Lys Leu Tyr Gln Val Ile Phe
                180                 185                 190
Glu Gly Glu Ile Gly Lys Gly Asn Leu Gly Gly Ile Ala Val Asp Asp
            195                 200                 205
Ile Ser Ile Asn Asn His Ile Ser Gln Glu Asp Cys Ala Lys Pro Ala
210                 215                 220
Asp Leu Asp Lys Asn Pro Glu Ile Lys Ile Asp Glu Thr Gly Ser
225                 230                 235                 240
Thr Pro Gly Tyr Glu Gly Glu Gly Asp Lys Asn Ile Ser Arg
                245                 250                 255
Lys Pro Gly Asn Val Leu Lys Thr Leu Asp Pro Ile Leu Ile
                260                 265                 270

<210> SEQ ID NO 83
<211> LENGTH: 834
<212> TYPE: PRT
<213> ORGANISM: artificial sequence
<220> FEATURE:
<223> OTHER INFORMATION: Synthetic polypeptide

<400> SEQUENCE: 83

Arg Asn Asp Lys Cys Gly Asp Thr Ile Lys Ile Glu Ser Pro Gly Tyr
1               5                   10                  15
Leu Thr Ser Pro Gly Tyr Pro His Ser Tyr His Pro Ser Glu Lys Cys
                20                  25                  30
Glu Trp Leu Ile Gln Ala Pro Asp Pro Tyr Gln Arg Ile Met Ile Asn
            35                  40                  45
Phe Asn Pro His Phe Asp Leu Glu Asp Arg Asp Cys Lys Tyr Asp Tyr
50                  55                  60
Val Glu Val Phe Asp Gly Glu Asn Glu Asn Gly His Phe Arg Gly Lys
65                  70                  75                  80
Phe Cys Gly Lys Ile Ala Pro Pro Val Val Ser Ser Gly Pro Phe
                85                  90                  95
Leu Phe Ile Lys Phe Val Ser Asp Tyr Glu Thr His Gly Ala Gly Phe
                100                 105                 110
Ser Ile Arg Tyr Glu Leu Phe Lys Arg Gly Pro Glu Cys Ser Gln Asn
            115                 120                 125
Tyr Thr Thr Pro Ser Gly Val Ile Lys Ser Pro Gly Phe Pro Glu Lys
        130                 135                 140
Tyr Pro Asn Ser Leu Glu Cys Thr Tyr Ile Val Phe Ala Pro Lys Met
145                 150                 155                 160
Ser Glu Ile Ile Leu Glu Phe Glu Ser Phe Asp Leu Glu Pro Asp Ser
                165                 170                 175
Asn Pro Pro Gly Gly Met Phe Cys Arg Tyr Asp Arg Leu Glu Ile Trp
                180                 185                 190
Asp Gly Phe Pro Asp Val Gly Pro His Ile Gly Arg Tyr Cys Gly Gln
            195                 200                 205
Lys Thr Pro Gly Arg Ile Arg Ser Ser Ser Gly Ile Leu Ser Met Val
        210                 215                 220
Phe Tyr Thr Asp Ser Ala Ile Ala Lys Glu Gly Phe Ser Ala Asn Tyr
225                 230                 235                 240
Ser Val Leu Gln Ser Ser Val Ser Glu Asp Phe Lys Cys Met Glu Ala
                245                 250                 255
Leu Gly Met Glu Ser Gly Glu Ile His Ser Asp Gln Ile Thr Ala Ser
```

-continued

```
                260                 265                 270
Ser Gln Tyr Ser Thr Asn Trp Ser Ala Glu Arg Ser Arg Leu Asn Tyr
            275                 280                 285
Pro Glu Asn Gly Trp Thr Pro Gly Glu Asp Ser Tyr Arg Glu Trp Ile
        290                 295                 300
Gln Val Asp Leu Gly Leu Leu Arg Phe Val Thr Ala Val Gly Thr Gln
305                 310                 315                 320
Gly Ala Ile Ser Lys Glu Thr Lys Lys Tyr Tyr Val Lys Thr Tyr
                325                 330                 335
Lys Ile Asp Val Ser Ser Asn Gly Glu Asp Trp Ile Thr Ile Lys Glu
                340                 345                 350
Gly Asn Lys Pro Val Leu Phe Gln Gly Asn Thr Asn Pro Thr Asp Val
            355                 360                 365
Val Val Ala Val Phe Pro Lys Pro Leu Ile Thr Arg Phe Val Arg Ile
        370                 375                 380
Lys Pro Ala Thr Trp Glu Thr Gly Ile Ser Met Arg Phe Glu Val Tyr
385                 390                 395                 400
Gly Cys Lys Ile Thr Asp Tyr Pro Cys Ser Gly Met Leu Gly Met Val
                405                 410                 415
Ser Gly Leu Ile Ser Asp Ser Gln Ile Thr Ser Ser Asn Gln Gly Asp
                420                 425                 430
Arg Asn Trp Met Pro Glu Asn Ile Arg Leu Val Thr Ser Arg Ser Gly
            435                 440                 445
Trp Ala Leu Pro Pro Ala Pro His Ser Tyr Ile Asn Glu Trp Leu Gln
        450                 455                 460
Ile Asp Leu Gly Glu Glu Lys Ile Val Arg Gly Ile Ile Gln Gly
465                 470                 475                 480
Gly Lys His Arg Glu Asn Lys Val Phe Met Arg Lys Phe Lys Ile Gly
                485                 490                 495
Tyr Ser Asn Asn Gly Ser Asp Trp Lys Met Ile Met Asp Asp Ser Lys
                500                 505                 510
Arg Lys Ala Lys Ser Phe Glu Gly Asn Asn Asn Tyr Asp Thr Pro Glu
            515                 520                 525
Leu Arg Thr Phe Pro Ala Leu Ser Thr Arg Phe Ile Arg Ile Tyr Pro
        530                 535                 540
Glu Arg Ala Thr His Gly Gly Leu Gly Leu Arg Met Glu Leu Leu Gly
545                 550                 555                 560
Cys Glu Val Glu Ala Pro Thr Ala Gly Pro Thr Thr Pro Asn Gly Asn
                565                 570                 575
Leu Val Asp Glu Cys Asp Asp Gln Ala Asn Cys His Ser Gly Thr
            580                 585                 590
Gly Asp Asp Phe Gln Leu Thr Gly Thr Thr Val Leu Ala Thr Glu
        595                 600                 605
Lys Pro Thr Val Ile Asp Ser Thr Ile Gln Ser Glu Phe Pro Thr Tyr
        610                 615                 620
Gly Phe Asn Cys Glu Phe Gly Trp Gly Ser His Lys Thr Phe Cys His
625                 630                 635                 640
Trp Glu His Asp Asn His Val Gln Leu Lys Trp Ser Val Leu Thr Ser
                645                 650                 655
Lys Thr Gly Pro Ile Gln Asp His Thr Gly Asp Gly Asn Phe Ile Tyr
            660                 665                 670
Ser Gln Ala Asp Glu Asn Gln Lys Gly Lys Val Ala Arg Leu Val Ser
            675                 680                 685
```

```
Pro Val Tyr Ser Gln Asn Ser Ala His Cys Met Thr Phe Trp Tyr
    690                 695                 700

His Met Ser Gly Ser His Val Gly Thr Leu Arg Val Lys Leu Arg Tyr
705                 710                 715                 720

Gln Lys Pro Glu Glu Tyr Asp Gln Leu Val Trp Met Ala Ile Gly His
                725                 730                 735

Gln Gly Asp His Trp Lys Glu Gly Arg Val Leu Leu His Lys Ser Leu
            740                 745                 750

Lys Leu Tyr Gln Val Ile Phe Glu Gly Glu Ile Gly Lys Gly Asn Leu
        755                 760                 765

Gly Gly Ile Ala Val Asp Asp Ile Ser Ile Asn Asn His Ile Ser Gln
    770                 775                 780

Glu Asp Cys Ala Lys Pro Ala Asp Leu Asp Lys Lys Asn Pro Glu Ile
785                 790                 795                 800

Lys Ile Asp Glu Thr Gly Ser Thr Pro Gly Tyr Glu Gly Glu Gly Glu
                805                 810                 815

Gly Asp Lys Asn Ile Ser Arg Lys Pro Gly Asn Val Leu Lys Thr Leu
            820                 825                 830

Asp Pro

<210> SEQ ID NO 84
<211> LENGTH: 2571
<212> TYPE: DNA
<213> ORGANISM: artificial sequence
<220> FEATURE:
<223> OTHER INFORMATION: Synthetic polynucleotide

<400> SEQUENCE: 84
atggagaggg ggctgccgct cctctgcgcc gtgctcgccc tcgtcctcgc cccggccggc      60
gcttttcgca acgataaatg tggcgatact ataaaaattg aaagccccgg gtaccttaca     120
tctcctggtt atcctcattc ttatcaccca agtgaaaaat gcgaatggct gattcaggct     180
ccggacccat accagagaat tatgatcaac ttcaaccctc acttcgattt ggaggacaga     240
gactgcaagt atgactacgt ggaagtcttc gatggagaaa atgaaaatgg acattttagg     300
ggaaagttct gtggaaagat agcccctcct cctgttgtgt cttcagggcc atttcttttt     360
atcaaatttg tctctgacta cgaaacacat ggtgcaggat tttccatacg ttatgaactt     420
ttcaagagag gtcctgaatg ttcccagaac tacacaacac ctagtggagt gataaagtcc     480
cccggattcc ctgaaaaata tcccaacagc cttgaatgca cttatattgt ctttgcgcca     540
aagatgtcag agattatcct ggaatttgaa agctttgacc tggagcctga ctcaaatcct     600
ccagggggga tgttctgtcg ctacgaccgg ctagaaatct gggatggatt ccctgatgtt     660
ggccctcaca ttgggcgtta ctgtggacag aaaacaccag gtcgaatccg atcctcatcg     720
ggcattctct ccatggtttt ttacaccgac agcgcgatag caaaagaagg tttctcagca     780
aactacagtg tcttgcagag cagtgtctca gaagatttca atgtatgga agctctgggc     840 atggaatcag gagaaattca ttctgaccag atcacagctt cttcccagta tagcaccaac     900
tggtctgcag agcgctcccg cctgaactac cctgagaatg gtggactcc cggagaggat      960 tcctaccgag agtggataca ggtagacttg ggccttctgc gctttgtcac ggctgtcggg    1020
acacagggcg ccatttcaaa agaaaccaag aagaatatt atgtcaagac ttacaagatc     1080
gacgttagct ccaacgggga agactggatc accataaaag aaggaaacaa acctgttctc    1140
tttcagggaa acaccaaccc tacagatgtt gtggttgcag tattccccaa accactgata    1200
```

```
actcgatttg tccgaatcaa gcctgcaact tgggaaactg gcatatctat gagatttgaa    1260
gtatatggtt gcaagataac agattatcct tgctctggaa tgttgggtat ggtgtctgga    1320
cttatttctg actcccagat cacatcatcc aaccaagggg acagaaactg gatgcctgaa    1380
aacatccgcc tggtaaccag tcgctctggc tgggcacttc cacccgcacc tcattcctac    1440
atcaatgagt ggctccaaat agacctgggg gaggagaaga tcgtgagggg catcatcatt    1500
cagggtggga agcaccgaga gaacaaggtg ttcatgagga agttcaagat cgggtacagc    1560
aacaacggct cggactggaa gatgatcatg gatgacagca acgcaaggc gaagtctttt    1620 gagggcaaca caactatga tacacctgag ctgcggactt ttccagctct ctccacgcga    1680
ttcatcagga tctaccccga gagagccact catggcggac tggggctcag aatggagctg    1740
ctgggctgtg aagtggaagc ccctacagct ggaccgacca ctcccaacgg gaacttggtg    1800
gatgaatgtg atgacgacca ggccaactgc cacagtggaa caggtgatga cttccagctc    1860
acaggtggca ccactgtgct ggccacagaa aagcccacgg tcatagacag caccatacaa    1920
tcagagtttc caacatatgg ttttaactgt gaatttggct ggggctctca caagaccttc    1980
tgccactggg aacatgacaa tcacgtgcag ctcaagtgga gtgtgttgac cagcaagacg    2040
ggacccattc aggatcacac aggagatggc aacttcatct attcccaagc tgacgaaaat    2100
cagaagggca agtggctcg cctggtgagc cctgtggttt attcccagaa ctctgcccac    2160
tgcatgacct tctggtatca catgtctggg tcccacgtcg gcacactcag ggtcaaactg    2220
cgctaccaga agccagagga gtacgatcag ctggtctgga tggccattgg acaccaaggt    2280
gaccactgga aggaagggcg tgtcttgctc cacaagtctc tgaaacttta tcaggtgatt    2340
ttcgagggcg aaatcggaaa aggaaacctt ggtgggattg ctgtggatga cattagtatt    2400 ataaccaca tttcacaaga agattgtgca aaaccagcag acctggataa aaagaaccca    2460
gaaattaaaa ttgatgaaac agggagcacg ccaggatacg aaggtgaagg agaaggtgac    2520
aagaacatct ccaggaagcc aggcaatgtg ttgaagacct tagacccctg a             2571
```

<210> SEQ ID NO 85
<211> LENGTH: 22
<212> TYPE: DNA
<213> ORGANISM: artificial sequence
<220> FEATURE:
<223> OTHER INFORMATION: Synthetic oligonucleotide

<400> SEQUENCE: 85
gacggccagg tcatcactat tg                                              22

<210> SEQ ID NO 86
<211> LENGTH: 22
<212> TYPE: DNA
<213> ORGANISM: artificial sequence
<220> FEATURE:
<223> OTHER INFORMATION: Synthetic oligonucleotide

<400> SEQUENCE: 86
ccacaggatt ccatacccaa ga                                              22

<210> SEQ ID NO 87
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 87
gctcctgctc cgtagcctgc                                           20

<210> SEQ ID NO 88
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 88
tcggcgttgc tttcggtccc                                           20

<210> SEQ ID NO 89
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 89
gccctgagtc aagaggacag                                           20

<210> SEQ ID NO 90
<211> LENGTH: 20
<212> TYPE: DNA
<213> ORGANISM: artificial sequence
<220> FEATURE:
<223> OTHER INFORMATION: Synthetic oligonucleotide

<400> SEQUENCE: 90
ctcctaggcc cctcagaagt                                           20

<210> SEQ ID NO 91
<211> LENGTH: 23
<212> TYPE: DNA
<213> ORGANISM: artificial sequence
<220> FEATURE:
<223> OTHER INFORMATION: Synthetic oligonucleotide

<400> SEQUENCE: 91
ccctcacact cagatcatct tct                                       23

<210> SEQ ID NO 92
<211> LENGTH: 19
<212> TYPE: DNA
<213> ORGANISM: artificial sequence
<220> FEATURE:
<223> OTHER INFORMATION: Synthetic oligonucleotide

<400> SEQUENCE: 92
gctacgacgt gggctacag                                            19

<210> SEQ ID NO 93
<211> LENGTH: 21
<212> TYPE: DNA
<213> ORGANISM: artificial sequence
<220> FEATURE:
<223> OTHER INFORMATION: Synthetic polynucleotide

<400> SEQUENCE: 93
ctggtacatc aggacctcac a                                         21

<210> SEQ ID NO 94
<211> LENGTH: 20

```
<212> TYPE: DNA
<213> ORGANISM: artificial sequence
<220> FEATURE:
<223> OTHER INFORMATION: Synthetic oligonucleotide

<400> SEQUENCE: 94
gagctcctta acatgccctg                                                    20

<210> SEQ ID NO 95
<211> LENGTH: 25
<212> TYPE: DNA
<213> ORGANISM: artificial sequence
<220> FEATURE:
<223> OTHER INFORMATION: Synthetic oligonucleotide

<400> SEQUENCE: 95
agacaaagcc agagtccttc agaga                                              25

<210> SEQ ID NO 96
<211> LENGTH: 23
<212> TYPE: DNA
<213> ORGANISM: artificial sequence
<220> FEATURE:
<223> OTHER INFORMATION: Synthetic oligonucleotide

<400> SEQUENCE: 96
gccactcctt ctgtgactcg agc                                                23

<210> SEQ ID NO 97
<211> LENGTH: 40
<212> TYPE: PRT
<213> ORGANISM: human

<400> SEQUENCE: 97

Trp His Asn Gly Met Ser Glu Arg Asn Leu Ser Ala Leu Glu Asn Tyr
1               5                  10                  15

Asn Phe Glu Leu Val Asp Gly Val Lys Leu Lys Lys Asp Lys Leu Asn
            20                  25                  30

Thr Gln Ser Thr Tyr Ser Glu Ala
        35                  40

<210> SEQ ID NO 98
<211> LENGTH: 64
<212> TYPE: PRT
<213> ORGANISM: human

<400> SEQUENCE: 98

Thr Ile Ile Ala Met Ser Ala Leu Gly Val Leu Leu Gly Ala Val Cys
1               5                  10                  15

Gly Val Val Leu Tyr Cys Ala Cys Trp His Asn Gly Met Ser Glu Arg
            20                  25                  30

Asn Leu Ser Ala Leu Glu Asn Tyr Asn Phe Glu Leu Val Asp Gly Val
        35                  40                  45

Lys Leu Lys Lys Asp Lys Leu Asn Thr Gln Ser Thr Tyr Ser Glu Ala
    50                  55                  60

<210> SEQ ID NO 99
<211> LENGTH: 19
<212> TYPE: PRT
<213> ORGANISM: human

<400> SEQUENCE: 99

Val Leu Ala Thr Glu Lys Pro Thr Val Ile Asp Ser Thr Ile Gln Ser
```

1               5               10              15

Gly Ile Lys

<210> SEQ ID NO 100
<211> LENGTH: 856
<212> TYPE: PRT
<213> ORGANISM: Artificial sequence
<220> FEATURE:
<223> OTHER INFORMATION: Synthetic polynucleotide

<400> SEQUENCE: 100

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

```
Tyr Tyr Val Lys Thr Lys Ile Asp Val Ser Ser Asn Gly Glu Asp
            355                 360                 365

Trp Ile Thr Ile Lys Glu Gly Asn Lys Pro Val Leu Phe Gln Gly Asn
        370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
            450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Asp Gln Ala
            595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
                740                 745                 750

Trp Met Ala Ile Gly His Gln Gly Asp His Trp Lys Glu Gly Arg Val
            755                 760                 765
```

```
Leu Leu His Lys Ser Leu Lys Leu Tyr Gln Val Ile Phe Glu Gly Glu
    770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Ala Asp Leu Asp
            805                 810                 815
Lys Lys Asn Pro Glu Ile Lys Ile Asp Glu Thr Gly Ser Thr Pro Gly
        820                 825                 830
Tyr Glu Gly Glu Gly Gly Asp Lys Asn Ile Ser Arg Lys Pro Gly
    835                 840                 845
Asn Val Leu Lys Thr Leu Asp Pro
    850                 855

<210> SEQ ID NO 101
<211> LENGTH: 856
<212> TYPE: PRT
<213> ORGANISM: Artificial sequence
<220> FEATURE:
<223> OTHER INFORMATION: Synthetic polynucleotide

<400> SEQUENCE: 101

Met Glu Arg Gly Leu Pro Leu Leu Cys Ala Val Leu Ala Leu Val Leu
1               5                   10                  15
Ala Pro Ala Gly Ala Phe Arg Asn Asp Lys Cys Gly Asp Thr Ile Lys
            20                  25                  30
Ile Glu Ser Pro Gly Tyr Leu Thr Ser Pro Gly Tyr Pro His Ser Tyr
        35                  40                  45
His Pro Ser Glu Lys Cys Glu Trp Leu Ile Gln Ala Pro Asp Pro Tyr
    50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Phe Asp Gly Glu Asn Glu Asn
                85                  90                  95
Gly His Phe Arg Gly Lys Phe Cys Gly Lys Ile Ala Pro Pro Pro Val
            100                 105                 110
Val Ser Ser Gly Pro Phe Leu Phe Ile Lys Phe Val Ser Asp Tyr Glu
        115                 120                 125
Thr His Gly Ala Gly Phe Ser Ile Arg Tyr Glu Leu Phe Lys Arg Gly
    130                 135                 140
Pro Glu Cys Ser Gln Asn Tyr Thr Thr Pro Ser Gly Val Ile Lys Ser
145                 150                 155                 160
Pro Gly Phe Pro Glu Lys Tyr Pro Asn Ser Leu Glu Cys Thr Tyr Ile
                165                 170                 175
Val Phe Ala Pro Lys Met Ser Glu Ile Ile Leu Glu Phe Glu Ser Phe
            180                 185                 190
Asp Leu Glu Pro Asp Ser Asn Pro Pro Gly Gly Met Phe Cys Arg Tyr
        195                 200                 205
Asp Arg Leu Glu Ile Trp Asp Gly Phe Pro Asp Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
            260                 265                 270
```

```
Phe Lys Cys Met Glu Ala Leu Gly Met Glu Ser Gly Glu Ile His Ser
        275                 280                 285

Asp Gln Ile Thr Ala Ser Ser Gln Ala Ser Thr Asn Trp Ser Ala Glu
290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
            595                 600                 605

Asn Cys His Ser Gly Thr Gly Asp Asp Phe Gln Leu Thr Gly Gly Thr
610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
```

```
                690             695             700
Val Ala Arg Leu Val Ser Pro Val Val Tyr Ser Gln Asn Ser Ala His
705                     710                     715                     720

Cys Met Thr Phe Trp Tyr His Met Ser Gly Ser His Val Gly Thr Leu
                    725                     730                     735

Arg Val Lys Leu Arg Tyr Gln Lys Pro Glu Glu Tyr Asp Gln Leu Val
                    740                     745                     750

Trp Met Ala Ile Gly His Gln Gly Asp His Trp Lys Glu Gly Arg Val
                    755                     760                     765

Leu Leu His Lys Ser Leu Lys Leu Tyr Gln Val Ile Phe Glu Gly Glu
            770                     775                     780

Ile Gly Lys Gly Asn Leu Gly Gly Ile Ala Val Asp Asp Ile Ser Ile
785                     790                     795                     800

Asn Asn His Ile Ser Gln Glu Asp Cys Ala Lys Pro Ala Asp Leu Asp
                    805                     810                     815

Lys Lys Asn Pro Glu Ile Lys Ile Asp Glu Thr Gly Ser Thr Pro Gly
                    820                     825                     830

Tyr Glu Gly Glu Gly Glu Asp Lys Asn Ile Ser Arg Lys Pro Gly
            835                     840                     845

Asn Val Leu Lys Thr Leu Asp Pro
        850                     855

<210> SEQ ID NO 102
<211> LENGTH: 856
<212> TYPE: PRT
<213> ORGANISM: Artificial sequence
<220> FEATURE:
<223> OTHER INFORMATION: Synthetic polynucleotide

<400> SEQUENCE: 102

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
```

-continued

```
            195                 200                 205
Asp Arg Leu Glu Ile Trp Asp Gly Phe Pro Asp Val Gly Pro His Ile
210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
                260                 265                 270
Phe Lys Cys Met Glu Ala Leu Gly Met Glu Ser Gly Glu Ile His Ser
                275                 280                 285
Asp Gln Ile Thr Ala Ser Ser Gln Tyr Ser Thr Asn Trp Ser Ala Glu
290                 295                 300
Arg Ser Arg Leu Asn Tyr Pro Glu Asn Gly Trp Thr Pro Gly Lys Lys
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
                340                 345                 350
Tyr Tyr Val Lys Thr Tyr Lys Ile Asp Val Ser Ser Asn Gly Glu Asp
                355                 360                 365
Trp Ile Thr Ile Lys Glu Gly Asn Lys Pro Val Leu Phe Gln Gly Asn
370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
                435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
                500                 505                 510
Arg Lys Phe Lys Ile Gly Tyr Ser Asn Asn Gly Ser Asp Trp Lys Met
                515                 520                 525
Ile Met Asp Asp Ser Lys Arg Lys Ala Lys Ser Phe Glu Gly Asn Asn
                530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
                580                 585                 590
Thr Thr Pro Asn Gly Asn Leu Val Asp Glu Cys Asp Asp Gln Ala
                595                 600                 605
Asn Cys His Ser Gly Thr Gly Asp Asp Phe Gln Leu Thr Gly Gly Thr
                610                 615                 620
```

```
Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
            645                 650                 655

His Lys Thr Phe Cys His Trp Glu His Asp Asn His Val Gln Leu Lys
        660                 665                 670

Trp Ser Val Leu Thr Ser Lys Thr Gly Pro Ile Gln Asp His Thr Gly
    675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro
    850                 855

<210> SEQ ID NO 103
<211> LENGTH: 856
<212> TYPE: PRT
<213> ORGANISM: Artificial sequence
<220> FEATURE:
<223> OTHER INFORMATION: Synthetic polynucleotide

<400> SEQUENCE: 103

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125
```

```
Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Gly Gly Met Phe Cys Arg Tyr
        195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ala Lys Lys Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
530                 535                 540
```

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
                660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro
850                 855

<210> SEQ ID NO 104
<211> LENGTH: 856
<212> TYPE: PRT
<213> ORGANISM: Artificial sequence
<220> FEATURE:
<223> OTHER INFORMATION: Synthetic polynucleotide

<400> SEQUENCE: 104

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

```
His Pro Ser Glu Lys Cys Glu Trp Leu Ile Gln Ala Pro Asp Pro Tyr
    50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Phe Asp Gly Glu Asn Glu Asn
                85                  90                  95
Gly His Phe Arg Gly Lys Phe Cys Gly Lys Ile Ala Pro Pro Pro Val
            100                 105                 110
Val Ser Ser Gly Pro Phe Leu Phe Ile Lys Phe Val Ser Asp Tyr Glu
            115                 120                 125
Thr His Gly Ala Gly Phe Ser Ile Arg Tyr Glu Leu Phe Lys Arg Gly
            130                 135                 140
Pro Glu Cys Ser Gln Asn Tyr Thr Thr Pro Ser Gly Val Ile Lys Ser
145                 150                 155                 160
Pro Gly Phe Pro Glu Lys Tyr Pro Asn Ser Leu Glu Cys Thr Tyr Ile
                165                 170                 175
Val Phe Ala Pro Lys Met Ser Glu Ile Ile Leu Glu Phe Glu Ser Phe
            180                 185                 190
Asp Leu Glu Pro Asp Ser Asn Pro Pro Gly Gly Met Phe Cys Arg Tyr
            195                 200                 205
Asp Arg Leu Glu Ile Trp Asp Gly Phe Pro Asp Val Gly Pro His Ile
            210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
            260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Ser Thr Asn Trp Ser Ala Glu
            290                 295                 300
Arg Ser Arg Leu Asn Tyr Pro Glu Asn Gly Trp Thr Pro Gly Glu Lys
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Lys Ile Asp Val Ser Ser Asn Gly Glu Asp
            355                 360                 365
Trp Ile Thr Ile Lys Glu Gly Asn Lys Pro Val Leu Phe Gln Gly Asn
            370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
            435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
```

```
              465                 470                 475                 480
        Ile Asn Glu Trp Leu Gln Ile Asp Leu Gly Glu Glu Lys Ile Val Arg
                        485                 490                 495
        Gly Ile Ile Ile Gln Gly Gly Lys His Arg Glu Asn Lys Val Phe Met
                        500                 505                 510
        Arg Lys Phe Lys Ile Gly Tyr Ser Asn Asn Gly Ser Asp Trp Lys Met
                        515                 520                 525
        Ile Met Asp Asp Ser Lys Arg Lys Ala Lys Ser Phe Glu Gly Asn Asn
                        530                 535                 540
        Asn Tyr Asp Thr Pro Glu Leu Arg Thr Phe Pro Ala Leu Ser Thr Arg
        545                 550                 555                 560
        Phe Ile Arg Ile Tyr Pro Glu Arg Ala Thr His Gly Gly Leu Gly Leu
                        565                 570                 575
        Arg Met Glu Leu Leu Gly Cys Glu Val Glu Ala Pro Thr Ala Gly Pro
                        580                 585                 590
        Thr Thr Pro Asn Gly Asn Leu Val Asp Glu Cys Asp Asp Gln Ala
                        595                 600                 605
        Asn Cys His Ser Gly Thr Gly Asp Asp Phe Gln Leu Thr Gly Gly Thr
                        610                 615                 620
        Thr Val Leu Ala Thr Glu Lys Pro Thr Val Ile Asp Ser Thr Ile Gln
        625                 630                 635                 640
        Ser Glu Phe Pro Thr Tyr Gly Phe Asn Cys Glu Phe Gly Trp Gly Ser
                        645                 650                 655
        His Lys Thr Phe Cys His Trp Glu His Asp Asn His Val Gln Leu Lys
                        660                 665                 670
        Trp Ser Val Leu Thr Ser Lys Thr Gly Pro Ile Gln Asp His Thr Gly
                        675                 680                 685
        Asp Gly Asn Phe Ile Tyr Ser Gln Ala Asp Glu Asn Gln Lys Gly Lys
                        690                 695                 700
        Val Ala Arg Leu Val Ser Pro Val Val Tyr Ser Gln Asn Ser Ala His
        705                 710                 715                 720
        Cys Met Thr Phe Trp Tyr His Met Ser Gly Ser His Val Gly Thr Leu
                        725                 730                 735
        Arg Val Lys Leu Arg Tyr Gln Lys Pro Glu Glu Tyr Asp Gln Leu Val
                        740                 745                 750
        Trp Met Ala Ile Gly His Gln Gly Asp His Trp Lys Glu Gly Arg Val
                        755                 760                 765
        Leu Leu His Lys Ser Leu Lys Leu Tyr Gln Val Ile Phe Glu Gly Glu
                        770                 775                 780
        Ile Gly Lys Gly Asn Leu Gly Gly Ile Ala Val Asp Asp Ile Ser Ile
        785                 790                 795                 800
        Asn Asn His Ile Ser Gln Glu Asp Cys Ala Lys Pro Ala Asp Leu Asp
                        805                 810                 815
        Lys Lys Asn Pro Glu Ile Lys Ile Asp Glu Thr Gly Ser Thr Pro Gly
                        820                 825                 830
        Tyr Glu Gly Glu Gly Glu Gly Asp Lys Asn Ile Ser Arg Lys Pro Gly
                        835                 840                 845
        Asn Val Leu Lys Thr Leu Asp Pro
        850                 855

<210> SEQ ID NO 105
<211> LENGTH: 583
<212> TYPE: PRT
<213> ORGANISM: Artificial sequence
```

<220> FEATURE:
<223> OTHER INFORMATION: Synthetic polynucleotide

<400> SEQUENCE: 105

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400
```

Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
            485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
            565                 570                 575

Arg Met Glu Leu Leu Gly Cys
            580

<210> SEQ ID NO 106
<211> LENGTH: 583
<212> TYPE: PRT
<213> ORGANISM: Artificial sequence
<220> FEATURE:
<223> OTHER INFORMATION: Synthetic polynucleotide

<400> SEQUENCE: 106

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
            130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

```
Val Phe Ala Pro Lys Met Ser Glu Ile Ile Leu Glu Phe Glu Ser Phe
            180                 185                 190

Asp Leu Glu Pro Asp Ser Asn Pro Gly Gly Met Phe Cys Arg Tyr
            195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
                260                 265                 270

Phe Lys Cys Met Glu Ala Leu Gly Met Glu Ser Gly Glu Ile His Ser
            275                 280                 285

Asp Gln Ile Thr Ala Ser Ser Gln Ala Ser Thr Asn Trp Ser Ala Glu
            290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Lys Ile Asp Val Ser Ser Asn Gly Glu Asp
                355                 360                 365

Trp Ile Thr Ile Lys Glu Gly Asn Lys Pro Val Leu Phe Gln Gly Asn
            370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
            530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys
            580
```

```
<210> SEQ ID NO 107
<211> LENGTH: 424
<212> TYPE: PRT
<213> ORGANISM: Artificial sequence
<220> FEATURE:
<223> OTHER INFORMATION: Synthetic polynucleotide

<400> SEQUENCE: 107

Met Glu Arg Gly Leu Pro Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365
```

```
Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys
            420

<210> SEQ ID NO 108
<211> LENGTH: 424
<212> TYPE: PRT
<213> ORGANISM: Artificial sequence
<220> FEATURE:
<223> OTHER INFORMATION: Synthetic polynucleotide

<400> SEQUENCE: 108

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Ala Ser Thr Asn Trp Ser Ala Glu
    290                 295                 300
```

```
Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys
                420

<210> SEQ ID NO 109
<211> LENGTH: 265
<212> TYPE: PRT
<213> ORGANISM: Artificial sequence
<220> FEATURE:
<223> OTHER INFORMATION: Synthetic polynucleotide

<400> SEQUENCE: 109

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240
```

Gly Ile Leu Ser Met Val Phe Tyr Thr Asp Ser Ala Ile Ala Lys Glu
            245                 250                 255

Gly Phe Ser Ala Asn Tyr Ser Val Leu
        260                 265

<210> SEQ ID NO 110
<211> LENGTH: 642
<212> TYPE: PRT
<213> ORGANISM: Artificial sequence
<220> FEATURE:
<223> OTHER INFORMATION: Synthetic polynucleotide

<400> SEQUENCE: 110

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

```
Thr Ala Val Gly Thr Gln Gly Ala Ile Ser Lys Glu Thr Lys Lys
                340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
        370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Glu Val
            420                 425                 430

Glu Ala Pro Thr Ala Gly Pro Thr Thr Pro Asn Gly Asn Leu Val Asp
        435                 440                 445

Glu Cys Asp Asp Asp Gln Ala Asn Cys His Ser Gly Thr Gly Asp Asp
    450                 455                 460

Phe Gln Leu Thr Gly Gly Thr Thr Val Leu Ala Thr Glu Lys Pro Thr
465                 470                 475                 480

Val Ile Asp Ser Thr Ile Gln Ser Glu Phe Pro Thr Tyr Gly Phe Asn
                485                 490                 495

Cys Glu Phe Gly Trp Gly Ser His Lys Thr Phe Cys His Trp Glu His
            500                 505                 510

Asp Asn His Val Gln Leu Lys Trp Ser Val Leu Thr Ser Lys Thr Gly
        515                 520                 525

Pro Ile Gln Asp His Thr Gly Asp Gly Asn Phe Ile Tyr Ser Gln Ala
    530                 535                 540

Asp Glu Asn Gln Lys Gly Lys Val Ala Arg Leu Val Ser Pro Val Val
545                 550                 555                 560

Tyr Ser Gln Asn Ser Ala His Cys Met Thr Phe Trp Tyr His Met Ser
                565                 570                 575

Gly Ser His Val Gly Thr Leu Arg Val Lys Leu Arg Tyr Gln Lys Pro
            580                 585                 590

Glu Glu Tyr Asp Gln Leu Val Trp Met Ala Ile Gly His Gln Gly Asp
        595                 600                 605

His Trp Lys Glu Gly Arg Val Leu His Lys Ser Leu Lys Leu Tyr
    610                 615                 620

Gln Val Ile Phe Glu Gly Ile Gly Lys Gly Asn Leu Gly Gly Ile
625                 630                 635                 640

Ala Val

<210> SEQ ID NO 111
<211> LENGTH: 703
<212> TYPE: PRT
<213> ORGANISM: Artificial sequence
<220> FEATURE:
<223> OTHER INFORMATION: Synthetic polynucleotide

<400> SEQUENCE: 111

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
```

-continued

```
                50                  55                  60
Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Leu Phe Lys Arg Gly
            130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
            165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
            195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
            245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Ile His Ser
            275                 280                 285

Asp Gln Ile Thr Ala Ser Ser Gln Ala Ser Thr Asn Trp Ser Ala Glu
            290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
            325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Glu Val
            420                 425                 430

Glu Ala Pro Thr Ala Gly Pro Thr Thr Pro Asn Gly Asn Leu Val Asp
            435                 440                 445

Glu Cys Asp Asp Asp Gln Ala Asn Cys His Ser Gly Thr Gly Asp Asp
450                 455                 460

Phe Gln Leu Thr Gly Gly Thr Thr Val Leu Ala Thr Glu Lys Pro Thr
465                 470                 475                 480
```

Val Ile Asp Ser Thr Ile Gln Ser Glu Phe Pro Thr Tyr Gly Phe Asn
            485                 490                 495

Cys Glu Phe Gly Trp Gly Ser His Lys Thr Phe Cys His Trp Glu His
            500                 505                 510

Asp Asn His Val Gln Leu Lys Trp Ser Val Leu Thr Ser Lys Thr Gly
            515                 520                 525

Pro Ile Gln Asp His Thr Gly Asp Gly Asn Phe Ile Tyr Ser Gln Ala
            530                 535                 540

Asp Glu Asn Gln Lys Gly Lys Val Ala Arg Leu Val Ser Pro Val Val
545                 550                 555                 560

Tyr Ser Gln Asn Ser Ala His Cys Met Thr Phe Trp Tyr His Met Ser
            565                 570                 575

Gly Ser His Val Gly Thr Leu Arg Val Lys Leu Arg Tyr Gln Lys Pro
            580                 585                 590

Glu Glu Tyr Asp Gln Leu Val Trp Met Ala Ile Gly His Gln Gly Asp
            595                 600                 605

His Trp Lys Glu Gly Arg Val Leu Leu His Lys Ser Leu Lys Leu Tyr
            610                 615                 620

Gln Val Ile Phe Glu Gly Glu Ile Gly Lys Gly Asn Leu Gly Gly Ile
625                 630                 635                 640

Ala Val Asp Asp Ile Ser Ile Asn Asn His Ile Ser Gln Glu Asp Cys
            645                 650                 655

Ala Lys Pro Ala Asp Leu Asp Lys Lys Asn Pro Glu Ile Lys Ile Asp
            660                 665                 670

Glu Thr Gly Ser Thr Pro Gly Tyr Glu Gly Gly Gly Gly Asp Lys
            675                 680                 685

Asn Ile Ser Arg Lys Pro Gly Asn Val Leu Lys Thr Leu Asp Pro
            690                 695                 700

<210> SEQ ID NO 112
<211> LENGTH: 547
<212> TYPE: PRT
<213> ORGANISM: Artificial sequence
<220> FEATURE:
<223> OTHER INFORMATION: Synthetic polynucleotide

<400> SEQUENCE: 112

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
            85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Leu Phe Lys Arg Gly
            130                 135                 140

```
Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
            165                 170                 175

Val Phe Ala Pro Lys Met Ser Glu Ile Ile Leu Glu Phe Glu Ser Phe
        180                 185                 190

Asp Leu Glu Pro Asp Ser Asn Pro Pro Gly Met Phe Cys Arg Tyr
    195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Glu Val Glu Ala Pro Thr Ala Gly Pro Thr Thr Pro Asn Gly
        275                 280                 285

Asn Leu Val Asp Glu Cys Asp Asp Gln Ala Asn Cys His Ser Gly
    290                 295                 300

Thr Gly Asp Asp Phe Gln Leu Thr Gly Gly Thr Thr Val Leu Ala Thr
305                 310                 315                 320

Glu Lys Pro Thr Val Ile Asp Ser Thr Ile Gln Ser Glu Phe Pro Thr
            325                 330                 335

Tyr Gly Phe Asn Cys Glu Phe Gly Trp Gly Ser His Lys Thr Phe Cys
        340                 345                 350

His Trp Glu His Asp Asn His Val Gln Leu Lys Trp Ser Val Leu Thr
    355                 360                 365

Ser Lys Thr Gly Pro Ile Gln Asp His Thr Gly Asp Gly Asn Phe Ile
370                 375                 380

Tyr Ser Gln Ala Asp Glu Asn Gln Lys Gly Lys Val Ala Arg Leu Val
385                 390                 395                 400

Ser Pro Val Val Tyr Ser Gln Asn Ser Ala His Cys Met Thr Phe Trp
            405                 410                 415

Tyr His Met Ser Gly Ser His Val Gly Thr Leu Arg Val Lys Leu Arg
        420                 425                 430

Tyr Gln Lys Pro Glu Glu Tyr Asp Gln Leu Val Trp Met Ala Ile Gly
        435                 440                 445

His Gln Gly Asp His Trp Lys Glu Gly Arg Val Leu Leu His Lys Ser
    450                 455                 460

Leu Lys Leu Tyr Gln Val Ile Phe Glu Gly Glu Ile Gly Lys Gly Asn
465                 470                 475                 480

Leu Gly Gly Ile Ala Val Asp Asp Ile Ser Ile Asn Asn His Ile Ser
            485                 490                 495

Gln Glu Asp Cys Ala Lys Pro Ala Asp Leu Asp Lys Lys Asn Pro Glu
        500                 505                 510

Ile Lys Ile Asp Glu Thr Gly Ser Thr Pro Gly Tyr Glu Gly Glu Gly
        515                 520                 525

Glu Gly Asp Lys Asn Ile Ser Arg Lys Pro Gly Asn Val Leu Lys Thr
    530                 535                 540

Leu Asp Pro
545
```

<210> SEQ ID NO 113
<211> LENGTH: 703
<212> TYPE: PRT
<213> ORGANISM: artificial sequence
<220> FEATURE:
<223> OTHER INFORMATION: Synthetic polypeptide

<400> SEQUENCE: 113

```
Met Glu Arg Gly Leu Pro Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365
```

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                    405                 410                 415

Met Arg Phe Glu Val Tyr Gly Cys Lys Ile Thr Asp Tyr Pro Glu Val
                420                 425                 430

Glu Ala Pro Thr Ala Gly Pro Thr Pro Asn Gly Asn Leu Val Asp
            435                 440                 445

Glu Cys Asp Asp Gln Ala Asn Cys His Ser Gly Thr Gly Asp Asp
450                 455                 460

Phe Gln Leu Thr Gly Gly Thr Thr Val Leu Ala Thr Glu Lys Pro Thr
465                 470                 475                 480

Val Ile Asp Ser Thr Ile Gln Ser Glu Phe Pro Thr Tyr Gly Phe Asn
                485                 490                 495

Cys Glu Phe Gly Trp Gly Ser His Lys Thr Phe Cys His Trp Glu His
                500                 505                 510

Asp Asn His Val Gln Leu Lys Trp Ser Val Leu Thr Ser Lys Thr Gly
                515                 520                 525

Pro Ile Gln Asp His Thr Gly Asp Gly Asn Phe Ile Tyr Ser Gln Ala
            530                 535                 540

Asp Glu Asn Gln Lys Gly Lys Val Ala Arg Leu Val Ser Pro Val Val
545                 550                 555                 560

Tyr Ser Gln Asn Ser Ala His Cys Met Thr Phe Trp Tyr His Met Ser
                565                 570                 575

Gly Ser His Val Gly Thr Leu Arg Val Lys Leu Arg Tyr Gln Lys Pro
            580                 585                 590

Glu Glu Tyr Asp Gln Leu Val Trp Met Ala Ile Gly His Gln Gly Asp
                595                 600                 605

His Trp Lys Glu Gly Arg Val Leu Leu His Lys Ser Leu Lys Leu Tyr
    610                 615                 620

Gln Val Ile Phe Glu Gly Glu Ile Gly Lys Gly Asn Leu Gly Gly Ile
625                 630                 635                 640

Ala Val Asp Asp Ile Ser Ile Asn Asn His Ile Ser Gln Glu Asp Cys
                645                 650                 655

Ala Lys Pro Ala Asp Leu Asp Lys Lys Asn Pro Glu Ile Lys Ile Asp
                660                 665                 670

Glu Thr Gly Ser Thr Pro Gly Tyr Glu Gly Glu Gly Glu Gly Asp Lys
            675                 680                 685

Asn Ile Ser Arg Lys Pro Gly Asn Val Leu Lys Thr Leu Asp Pro
    690                 695                 700

<210> SEQ ID NO 114
<211> LENGTH: 1085
<212> TYPE: PRT
<213> ORGANISM: artificial sequence
<220> FEATURE:
<223> OTHER INFORMATION: Synthetic polypeptide

<400> SEQUENCE: 114

Met Glu Arg Gly Leu Pro Leu Leu Cys Ala Val Leu Ala Leu Val Leu
1               5                   10                  15

Ala Pro Gly Ala Phe Arg Asn Asp Lys Cys Gly Asp Thr Ile Lys
                20                  25                  30

-continued

```
Ile Glu Ser Pro Gly Tyr Leu Thr Ser Pro Gly Tyr Pro His Ser Tyr
         35                  40                  45

His Pro Ser Glu Lys Cys Glu Trp Leu Ile Gln Ala Pro Asp Pro Tyr
 50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
             115                 120                 125

Thr His Gly Ala Gly Phe Ser Ile Arg Tyr Glu Leu Phe Lys Arg Gly
         130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
             180                 185                 190

Asp Leu Glu Pro Asp Ser Asn Pro Pro Gly Gly Met Phe Cys Arg Tyr
         195                 200                 205

Asp Arg Leu Glu Ile Trp Asp Gly Phe Pro Asp Val Gly Pro His Ile
         210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
             260                 265                 270

Phe Lys Cys Met Glu Ala Leu Gly Met Glu Ser Gly Glu Ile His Ser
         275                 280                 285

Asp Gln Ile Thr Ala Ser Ser Gln Tyr Ser Thr Asn Trp Ser Ala Glu
         290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
             340                 345                 350

Tyr Tyr Val Lys Thr Tyr Lys Ile Asp Val Ser Ser Asn Gly Glu Asp
         355                 360                 365

Trp Ile Thr Ile Lys Glu Gly Asn Lys Pro Val Leu Phe Gln Gly Asn
 370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
             420                 425                 430

Gly Met Leu Gly Met Val Ser Gly Leu Ile Ser Asp Ser Gln Ile Thr
         435                 440                 445

Ser Ser Asn Gln Gly Asp Arg Asn Trp Met Pro Glu Asn Ile Arg Leu
```

```
              450                 455                 460
Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Arg Ser Asp Lys Thr His Thr Cys
        850                 855                 860

Pro Pro Cys Pro Ala Pro Glu Leu Leu Gly Gly Pro Ser Val Phe Leu
865                 870                 875                 880
```

-continued

```
Phe Pro Pro Lys Pro Lys Asp Thr Leu Met Ile Ser Arg Thr Pro Glu
                885                 890                 895
Val Thr Cys Val Val Asp Val Ser His Glu Asp Pro Glu Val Lys
            900                 905                 910
Phe Asn Trp Tyr Val Asp Gly Val Glu Val His Asn Ala Lys Thr Lys
        915                 920                 925
Pro Arg Glu Glu Gln Tyr Asn Ser Thr Tyr Arg Val Val Ser Val Leu
    930                 935                 940
Thr Val Leu His Gln Asp Trp Leu Asn Gly Lys Glu Tyr Lys Cys Lys
945                 950                 955                 960
Val Ser Asn Lys Ala Leu Pro Ala Pro Ile Glu Lys Thr Ile Ser Lys
                965                 970                 975
Ala Lys Gly Gln Pro Arg Glu Pro Gln Val Tyr Thr Leu Pro Pro Ser
            980                 985                 990
Arg Glu Glu Met Thr Lys Asn Gln  Val Ser Leu Thr Cys  Leu Val Lys
        995                 1000                1005
Gly Phe  Tyr Pro Ser Asp Ile  Ala Val Glu Trp Glu  Ser Asn Gly
    1010                1015                1020
Gln Pro  Glu Asn Asn Tyr Lys  Thr Thr Pro Pro Val  Leu Asp Ser
    1025                1030                1035
Asp Gly  Ser Phe Phe Leu Tyr  Ser Lys Leu Thr Val  Asp Lys Ser
    1040                1045                1050
Arg Trp  Gln Gln Gly Asn Val  Phe Ser Cys Ser Val  Met His Glu
    1055                1060                1065
Ala Leu  His Asn His Tyr Thr  Gln Lys Ser Leu Ser  Leu Ser Pro
    1070                1075                1080
Gly Lys
    1085

<210> SEQ ID NO 115
<211> LENGTH: 1085
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (584)..(858)
<223> OTHER INFORMATION: Xaa can be any naturally occurring amino acid

<400> SEQUENCE: 115

Met Glu Arg Gly Leu Pro Leu Leu Cys Ala Val Leu Ala Leu Val Leu
1               5                   10                  15
Ala Pro Ala Gly Ala Phe Arg Asn Asp Lys Cys Gly Asp Thr Ile Lys
            20                  25                  30
Ile Glu Ser Pro Gly Tyr Leu Thr Ser Pro Gly Tyr Pro His Ser Tyr
        35                  40                  45
His Pro Ser Glu Lys Cys Glu Trp Leu Ile Gln Ala Pro Asp Pro Tyr
    50                  55                  60
Gln Arg Ile Met Ile Asn Phe Asn Pro His Phe Asp Leu Glu Asp Arg
65                  70                  75                  80
Asp Cys Lys Tyr Asp Tyr Val Glu Val Phe Asp Gly Glu Asn Glu Asn
                85                  90                  95
Gly His Phe Arg Gly Lys Phe Cys Gly Lys Ile Ala Pro Pro Val
            100                 105                 110
Val Ser Ser Gly Pro Phe Leu Phe Ile Lys Phe Val Ser Asp Tyr Glu
```

-continued

```
            115                 120                 125
Thr His Gly Ala Gly Phe Ser Ile Arg Tyr Glu Leu Phe Lys Arg Gly
130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
                180                 185                 190

Asp Leu Glu Pro Asp Ser Asn Pro Pro Gly Gly Met Phe Cys Arg Tyr
                195                 200                 205

Asp Arg Leu Glu Ile Trp Asp Gly Phe Pro Asp Val Gly Pro His Ile
                210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
                260                 265                 270

Phe Lys Cys Met Glu Ala Leu Gly Met Glu Ser Gly Glu Ile His Ser
                275                 280                 285

Asp Gln Ile Thr Ala Ser Ser Gln Tyr Ser Thr Asn Trp Ser Ala Glu
290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Lys Ile Asp Val Ser Ser Asn Gly Glu Asp
                355                 360                 365

Trp Ile Thr Ile Lys Glu Gly Asn Lys Pro Val Leu Phe Gln Gly Asn
                370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
                435                 440                 445

Ser Ser Asn Gln Gly Asp Arg Asn Trp Met Pro Glu Asn Ile Arg Leu
                450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
                515                 520                 525

Ile Met Asp Asp Ser Lys Arg Lys Ala Lys Ser Phe Glu Gly Asn Asn
530                 535                 540
```

```
Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
            565                 570                 575

Arg Met Glu Leu Leu Gly Cys Xaa Xaa Xaa Xaa Xaa Xaa Xaa Xaa
        580                 585                 590

Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa
        610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa
        690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa
            835                 840                 845

Xaa Xaa Xaa Xaa Xaa Xaa Xaa Xaa Xaa Asp Lys Thr His Thr Cys
        850                 855                 860

Pro Pro Cys Pro Ala Pro Glu Leu Leu Gly Gly Pro Ser Val Phe Leu
865                 870                 875                 880

Phe Pro Pro Lys Pro Lys Asp Thr Leu Met Ile Ser Arg Thr Pro Glu
                885                 890                 895

Val Thr Cys Val Val Val Asp Val Ser His Glu Asp Pro Glu Val Lys
            900                 905                 910

Phe Asn Trp Tyr Val Asp Gly Val Glu Val His Asn Ala Lys Thr Lys
            915                 920                 925

Pro Arg Glu Glu Gln Tyr Asn Ser Thr Tyr Arg Val Val Ser Val Leu
        930                 935                 940

Thr Val Leu His Gln Asp Trp Leu Asn Gly Lys Glu Tyr Lys Cys Lys
945                 950                 955                 960
```

Val Ser Asn Lys Ala Leu Pro Ala Pro Ile Glu Lys Thr Ile Ser Lys
            965                 970                 975

Ala Lys Gly Gln Pro Arg Glu Pro Gln Val Tyr Thr Leu Pro Pro Ser
        980                 985                 990

Arg Glu Glu Met Thr Lys Asn Gln Val Ser Leu Thr Cys Leu Val Lys
        995                 1000                1005

Gly Phe Tyr Pro Ser Asp Ile Ala Val Glu Trp Glu Ser Asn Gly
    1010                1015                1020

Gln Pro Glu Asn Asn Tyr Lys Thr Thr Pro Pro Val Leu Asp Ser
    1025                1030                1035

Asp Gly Ser Phe Phe Leu Tyr Ser Lys Leu Thr Val Asp Lys Ser
    1040                1045                1050

Arg Trp Gln Gln Gly Asn Val Phe Ser Cys Ser Val Met His Glu
    1055                1060                1065

Ala Leu His Asn His Tyr Thr Gln Lys Ser Leu Ser Leu Ser Pro
    1070                1075                1080

Gly Lys
    1085

<210> SEQ ID NO 116
<211> LENGTH: 1085
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (425)..(858)
<223> OTHER INFORMATION: Xaa can be any naturally occurring amino acid

<400> SEQUENCE: 116

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

```
Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
                260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Ser Thr Asn Trp Ser Ala Glu
        290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Lys Ile Asp Val Ser Ser Asn Gly Glu Asp
                355                 360                 365

Trp Ile Thr Ile Lys Glu Gly Asn Lys Pro Val Leu Phe Gln Gly Asn
370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
                500                 505                 510

Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa
530                 535                 540

Xaa Xaa Xaa Xaa Xaa Xaa Xaa Xaa Xaa Xaa Xaa Xaa Xaa Xaa Xaa Xaa
545             550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa
    610                 615                 620
```

```
Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa
            725                 730                 735

Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa
            770                 775                 780

Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa
            835                 840                 845

Xaa Xaa Xaa Xaa Xaa Xaa Xaa Xaa Xaa Asp Lys Thr His Thr Cys
850                 855                 860

Pro Pro Cys Pro Ala Pro Glu Leu Leu Gly Gly Pro Ser Val Phe Leu
865                 870                 875                 880

Phe Pro Pro Lys Pro Lys Asp Thr Leu Met Ile Ser Arg Thr Pro Glu
            885                 890                 895

Val Thr Cys Val Val Val Asp Val Ser His Glu Asp Pro Glu Val Lys
            900                 905                 910

Phe Asn Trp Tyr Val Asp Gly Val Glu Val His Asn Ala Lys Thr Lys
            915                 920                 925

Pro Arg Glu Glu Gln Tyr Asn Ser Thr Tyr Arg Val Val Ser Val Leu
930                 935                 940

Thr Val Leu His Gln Asp Trp Leu Asn Gly Lys Glu Tyr Lys Cys Lys
945                 950                 955                 960

Val Ser Asn Lys Ala Leu Pro Ala Pro Ile Glu Lys Thr Ile Ser Lys
            965                 970                 975

Ala Lys Gly Gln Pro Arg Glu Pro Gln Val Tyr Thr Leu Pro Pro Ser
            980                 985                 990

Arg Glu Glu Met Thr Lys Asn Gln Val Ser Leu Thr Cys Leu Val Lys
            995                 1000                1005

Gly Phe Tyr Pro Ser Asp Ile Ala Val Glu Trp Glu Ser Asn Gly
            1010                1015                1020

Gln Pro Glu Asn Asn Tyr Lys Thr Thr Pro Pro Val Leu Asp Ser
            1025                1030                1035

Asp Gly Ser Phe Phe Leu Tyr Ser Lys Leu Thr Val Asp Lys Ser
```

-continued

```
                1040                1045                1050

Arg Trp Gln Gln Gly Asn Val Phe Ser Cys Ser Val Met His Glu
        1055                1060                1065

Ala Leu His Asn His Tyr Thr Gln Lys Ser Leu Ser Leu Ser Pro
    1070                1075                1080

Gly Lys
    1085

<210> SEQ ID NO 117
<211> LENGTH: 1085
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (266)..(858)
<223> OTHER INFORMATION: Xaa can be any naturally occurring amino acid

<400> SEQUENCE: 117

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285
```

-continued

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
    355                 360                 365

Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Xaa
    515                 520                 525

Xaa Xaa Xaa Xaa Xaa Xaa Xaa Xaa Xaa Xaa Xaa Xaa Xaa Xaa Xaa
530                 535                 540

Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
        580                 585                 590

Xaa Xaa Xaa Xaa Xaa Xaa Xaa Xaa Xaa Xaa Xaa Xaa Xaa Xaa Xaa
    595                 600                 605

Xaa Xaa Xaa Xaa Xaa Xaa Xaa Xaa Xaa Xaa Xaa Xaa Xaa Xaa Xaa
610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
        660                 665                 670

Xaa Xaa Xaa Xaa Xaa Xaa Xaa Xaa Xaa Xaa Xaa Xaa Xaa Xaa Xaa
    675                 680                 685

Xaa Xaa Xaa Xaa Xaa Xaa Xaa Xaa Xaa Xaa Xaa Xaa Xaa Xaa Xaa
690                 695                 700

Xaa Xaa Xaa Xaa Xaa Xaa Xaa Xaa Xaa Xaa Xaa Xaa Xaa Xaa Xaa

```
            705                 710                 715                 720
Xaa Xaa Xaa Xaa Xaa Xaa Xaa Xaa Xaa Xaa Xaa Xaa Xaa Xaa Xaa
                725                 730                 735
Xaa Xaa Xaa Xaa Xaa Xaa Xaa Xaa Xaa Xaa Xaa Xaa Xaa Xaa Xaa
                740                 745                 750
Xaa Xaa Xaa Xaa Xaa Xaa Xaa Xaa Xaa Xaa Xaa Xaa Xaa Xaa Xaa
                755                 760                 765
Xaa Xaa Xaa Xaa Xaa Xaa Xaa Xaa Xaa Xaa Xaa Xaa Xaa Xaa Xaa
                770                 775                 780
Xaa Xaa Xaa Xaa Xaa Xaa Xaa Xaa Xaa Xaa Xaa Xaa Xaa Xaa Xaa
785                 790                 795                 800
Xaa Xaa Xaa Xaa Xaa Xaa Xaa Xaa Xaa Xaa Xaa Xaa Xaa Xaa Xaa
                805                 810                 815
Xaa Xaa Xaa Xaa Xaa Xaa Xaa Xaa Xaa Xaa Xaa Xaa Xaa Xaa Xaa
                820                 825                 830
Xaa Xaa Xaa Xaa Xaa Xaa Xaa Xaa Xaa Xaa Xaa Xaa Xaa Xaa Xaa
                835                 840                 845
Xaa Xaa Xaa Xaa Xaa Xaa Xaa Xaa Xaa Asp Lys Thr His Thr Cys
850                 855                 860
Pro Pro Cys Pro Ala Pro Glu Leu Leu Gly Gly Pro Ser Val Phe Leu
865                 870                 875                 880
Phe Pro Pro Lys Pro Lys Asp Thr Leu Met Ile Ser Arg Thr Pro Glu
                885                 890                 895
Val Thr Cys Val Val Val Asp Val Ser His Glu Asp Pro Glu Val Lys
                900                 905                 910
Phe Asn Trp Tyr Val Asp Gly Val Glu Val His Asn Ala Lys Thr Lys
                915                 920                 925
Pro Arg Glu Glu Gln Tyr Asn Ser Thr Tyr Arg Val Val Ser Val Leu
                930                 935                 940
Thr Val Leu His Gln Asp Trp Leu Asn Gly Lys Glu Tyr Lys Cys Lys
945                 950                 955                 960
Val Ser Asn Lys Ala Leu Pro Ala Pro Ile Glu Lys Thr Ile Ser Lys
                965                 970                 975
Ala Lys Gly Gln Pro Arg Glu Pro Gln Val Tyr Thr Leu Pro Pro Ser
                980                 985                 990
Arg Glu Glu Met Thr Lys Asn Gln Val Ser Leu Thr Cys Leu Val Lys
                995                1000                1005
Gly Phe Tyr Pro Ser Asp Ile Ala Val Glu Trp Glu Ser Asn Gly
            1010                1015                1020
Gln Pro Glu Asn Asn Tyr Lys Thr Thr Pro Pro Val Leu Asp Ser
            1025                1030                1035
Asp Gly Ser Phe Phe Leu Tyr Ser Lys Leu Thr Val Asp Lys Ser
            1040                1045                1050
Arg Trp Gln Gln Gly Asn Val Phe Ser Cys Ser Val Met His Glu
            1055                1060                1065
Ala Leu His Asn His Tyr Thr Gln Lys Ser Leu Ser Leu Ser Pro
            1070                1075                1080
Gly Lys
    1085

<210> SEQ ID NO 118
<211> LENGTH: 812
<212> TYPE: PRT
<213> ORGANISM: artificial sequence
```

```
<220> FEATURE:
<223> OTHER INFORMATION: Synthetic polypeptide

<400> SEQUENCE: 118

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400
```

```
Thr Arg Phe Val Arg Ile Lys Pro Ala Thr Trp Glu Thr Gly Ile Ser
            405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
        450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
                    500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
            530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Arg Ser Asp Lys Thr His Thr Cys Pro
            580                 585                 590

Pro Cys Pro Ala Pro Glu Leu Leu Gly Gly Pro Ser Val Phe Leu Phe
            595                 600                 605

Pro Pro Lys Pro Lys Asp Thr Leu Met Ile Ser Arg Thr Pro Glu Val
            610                 615                 620

Thr Cys Val Val Val Asp Val Ser His Glu Asp Pro Glu Val Lys Phe
625                 630                 635                 640

Asn Trp Tyr Val Asp Gly Val Glu Val His Asn Ala Lys Thr Lys Pro
                645                 650                 655

Arg Glu Glu Gln Tyr Asn Ser Thr Tyr Arg Val Val Ser Val Leu Thr
            660                 665                 670

Val Leu His Gln Asp Trp Leu Asn Gly Lys Glu Tyr Lys Cys Lys Val
            675                 680                 685

Ser Asn Lys Ala Leu Pro Ala Pro Ile Glu Lys Thr Ile Ser Lys Ala
        690                 695                 700

Lys Gly Gln Pro Arg Glu Pro Gln Val Tyr Thr Leu Pro Pro Ser Arg
705                 710                 715                 720

Glu Glu Met Thr Lys Asn Gln Val Ser Leu Thr Cys Leu Val Lys Gly
                725                 730                 735

Phe Tyr Pro Ser Asp Ile Ala Val Glu Trp Glu Ser Asn Gly Gln Pro
            740                 745                 750

Glu Asn Asn Tyr Lys Thr Thr Pro Pro Val Leu Asp Ser Asp Gly Ser
        755                 760                 765

Phe Phe Leu Tyr Ser Lys Leu Thr Val Asp Lys Ser Arg Trp Gln Gln
770                 775                 780

Gly Asn Val Phe Ser Cys Ser Val Met His Glu Ala Leu His Asn His
785                 790                 795                 800

Tyr Thr Gln Lys Ser Leu Ser Leu Ser Pro Gly Lys
                805                 810
```

-continued

```
<210> SEQ ID NO 119
<211> LENGTH: 653
<212> TYPE: PRT
<213> ORGANISM: artificial sequence
<220> FEATURE:
<223> OTHER INFORMATION: Synthetic polypeptide

<400> SEQUENCE: 119

Met Glu Arg Gly Leu Pro Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365
```

```
Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Arg Ser Asp Lys Thr His Thr Cys
                420                 425                 430

Pro Pro Cys Pro Ala Pro Glu Leu Gly Gly Pro Ser Val Phe Leu
                435                 440                 445

Phe Pro Pro Lys Pro Lys Asp Thr Leu Met Ile Ser Arg Thr Pro Glu
450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Asn Ser Thr Tyr Arg Val Val Ser Val Leu
                500                 505                 510

Thr Val Leu His Gln Asp Trp Leu Asn Gly Lys Glu Tyr Lys Cys Lys
                515                 520                 525

Val Ser Asn Lys Ala Leu Pro Ala Pro Ile Glu Lys Thr Ile Ser Lys
530                 535                 540

Ala Lys Gly Gln Pro Arg Glu Pro Gln Val Tyr Thr Leu Pro Pro Ser
545                 550                 555                 560

Arg Glu Glu Met Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
                580                 585                 590

Pro Glu Asn Asn Tyr Lys Thr Thr Pro Pro Val Leu Asp Ser Asp Gly
                595                 600                 605

Ser Phe Phe Leu Tyr Ser Lys Leu Thr Val Asp Lys Ser Arg Trp Gln
                610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys
                645                 650

<210> SEQ ID NO 120
<211> LENGTH: 494
<212> TYPE: PRT
<213> ORGANISM: artificial sequence
<220> FEATURE:
<223> OTHER INFORMATION: Synthetic polypeptide

<400> SEQUENCE: 120

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
                35                  40                  45

His Pro Ser Glu Lys Cys Glu Trp Leu Ile Gln Ala Pro Asp Pro Tyr
                50                  55                  60

Gln Arg Ile Met Ile Asn Phe Asn Pro His Phe Asp Leu Glu Asp Arg
65                  70                  75                  80
```

```
Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Arg Ser Asp Lys Thr His Thr
            260                 265                 270

Cys Pro Pro Cys Pro Ala Pro Glu Leu Leu Gly Gly Pro Ser Val Phe
    275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490
```

<210> SEQ ID NO 121
<211> LENGTH: 1085
<212> TYPE: PRT
<213> ORGANISM: artificial sequence
<220> FEATURE:
<223> OTHER INFORMATION: Synthetic polypeptide

<400> SEQUENCE: 121

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Ala Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
```

```
            370                 375                 380
Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
            610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
        770                 775                 780

Ile Gly Lys Gly Asn Leu Gly Gly Ile Ala Val Asp Asp Ile Ser Ile
785                 790                 795                 800
```

```
Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Arg Ser Asp Lys Thr His Thr Cys
    850                 855                 860

Pro Pro Cys Pro Ala Pro Glu Leu Leu Gly Gly Pro Ser Val Phe Leu
865                 870                 875                 880

Phe Pro Pro Lys Pro Lys Asp Thr Leu Met Ile Ser Arg Thr Pro Glu
            885                 890                 895

Val Thr Cys Val Val Val Asp Val Ser His Glu Asp Pro Glu Val Lys
        900                 905                 910

Phe Asn Trp Tyr Val Asp Gly Val Glu Val His Asn Ala Lys Thr Lys
    915                 920                 925

Pro Arg Glu Glu Gln Tyr Asn Ser Thr Tyr Arg Val Val Ser Val Leu
930                 935                 940

Thr Val Leu His Gln Asp Trp Leu Asn Gly Lys Glu Tyr Lys Cys Lys
945                 950                 955                 960

Val Ser Asn Lys Ala Leu Pro Ala Pro Ile Glu Lys Thr Ile Ser Lys
            965                 970                 975

Ala Lys Gly Gln Pro Arg Glu Pro Gln Val Tyr Thr Leu Pro Pro Ser
        980                 985                 990

Arg Glu Glu Met Thr Lys Asn Gln Val Ser Leu Thr Cys Leu Val Lys
    995                 1000                1005

Gly Phe Tyr Pro Ser Asp Ile Ala Val Glu Trp Glu Ser Asn Gly
    1010                1015                1020

Gln Pro Glu Asn Asn Tyr Lys Thr Thr Pro Pro Val Leu Asp Ser
    1025                1030                1035

Asp Gly Ser Phe Phe Leu Tyr Ser Lys Leu Thr Val Asp Lys Ser
    1040                1045                1050

Arg Trp Gln Gln Gly Asn Val Phe Ser Cys Ser Val Met His Glu
    1055                1060                1065

Ala Leu His Asn His Tyr Thr Gln Lys Ser Leu Ser Leu Ser Pro
    1070                1075                1080

Gly Lys
    1085

<210> SEQ ID NO 122
<211> LENGTH: 1085
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (584)..(858)
<223> OTHER INFORMATION: Xaa can be any naturally occurring amino acid

<400> SEQUENCE: 122

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
```

```
                35                  40                  45
His Pro Ser Glu Lys Cys Glu Trp Leu Ile Gln Ala Pro Asp Pro Tyr
 50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Ala Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
    450                 455                 460
```

-continued

```
Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
            485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
        530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa
        660                 665                 670

Xaa Xaa Xaa Xaa Xaa Xaa Xaa Xaa Xaa Xaa Xaa Xaa Xaa
    675                 680                 685

Xaa Xaa Xaa Xaa Xaa Xaa Xaa Xaa Xaa Xaa Xaa Xaa Xaa
690                 695                 700

Xaa Xaa Xaa Xaa Xaa Xaa Xaa Xaa Xaa Xaa Xaa Xaa Xaa Xaa Xaa
705             710             715             720

Xaa Xaa Xaa Xaa Xaa Xaa Xaa Xaa Xaa Xaa Xaa Xaa Xaa
        725                 730                 735

Xaa Xaa Xaa Xaa Xaa Xaa Xaa Xaa Xaa Xaa Xaa Xaa Xaa
    740                 745                 750

Xaa Xaa Xaa Xaa Xaa Xaa Xaa Xaa Xaa Xaa Xaa Xaa Xaa
755                 760                 765

Xaa Xaa Xaa Xaa Xaa Xaa Xaa Xaa Xaa Xaa Xaa Xaa Xaa
        770                 775                 780

Xaa Xaa Xaa Xaa Xaa Xaa Xaa Xaa Xaa Xaa Xaa Xaa Xaa
785             790                 795                 800

Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa
        820                 825                 830

Xaa Xaa Xaa Xaa Xaa Xaa Xaa Xaa Xaa Xaa Xaa Xaa Xaa
    835                 840                 845

Xaa Xaa Xaa Xaa Xaa Xaa Xaa Xaa Xaa Xaa Asp Lys Thr His Thr Cys
            850                 855                 860

Pro Pro Cys Pro Ala Pro Glu Leu Leu Gly Gly Pro Ser Val Phe Leu
865                 870                 875                 880
```

```
Phe Pro Pro Lys Pro Lys Asp Thr Leu Met Ile Ser Arg Thr Pro Glu
            885                 890                 895

Val Thr Cys Val Val Asp Val Ser His Glu Asp Pro Glu Val Lys
        900                 905                 910

Phe Asn Trp Tyr Val Asp Gly Val Glu Val His Asn Ala Lys Thr Lys
            915                 920                 925

Pro Arg Glu Glu Gln Tyr Asn Ser Thr Tyr Arg Val Val Ser Val Leu
        930                 935                 940

Thr Val Leu His Gln Asp Trp Leu Asn Gly Lys Glu Tyr Lys Cys Lys
945                 950                 955                 960

Val Ser Asn Lys Ala Leu Pro Ala Pro Ile Glu Lys Thr Ile Ser Lys
            965                 970                 975

Ala Lys Gly Gln Pro Arg Glu Pro Gln Val Tyr Thr Leu Pro Pro Ser
        980                 985                 990

Arg Glu Glu Met Thr Lys Asn Gln Val Ser Leu Thr Cys Leu Val Lys
            995                 1000                1005

Gly Phe Tyr Pro Ser Asp Ile Ala Val Glu Trp Glu Ser Asn Gly
    1010                1015                1020

Gln Pro Glu Asn Asn Tyr Lys Thr Thr Pro Pro Val Leu Asp Ser
    1025                1030                1035

Asp Gly Ser Phe Phe Leu Tyr Ser Lys Leu Thr Val Asp Lys Ser
    1040                1045                1050

Arg Trp Gln Gln Gly Asn Val Phe Ser Cys Ser Val Met His Glu
    1055                1060                1065

Ala Leu His Asn His Tyr Thr Gln Lys Ser Leu Ser Leu Ser Pro
    1070                1075                1080

Gly Lys
    1085

<210> SEQ ID NO 123
<211> LENGTH: 1085
<212> TYPE: PRT
<213> ORGANISM: artificial sequence
<220> FEATURE:
<223> OTHER INFORMATION: Synthetic polypeptide
<220> FEATURE:
<221> NAME/KEY: misc_feature
<222> LOCATION: (425)..(858)
<223> OTHER INFORMATION: Xaa can be any naturally occurring amino acid

<400> SEQUENCE: 123

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
            85                  90                  95

Gly His Phe Arg Gly Lys Phe Cys Gly Lys Ile Ala Pro Pro Pro Val
        100                 105                 110

Val Ser Ser Gly Pro Phe Leu Phe Ile Lys Phe Val Ser Asp Tyr Glu
    115                 120                 125
```

```
Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Ala Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa
    530                 535                 540
```

-continued

```
Xaa Xaa Xaa Xaa Xaa Xaa Xaa Xaa Xaa Xaa Xaa Xaa Xaa Xaa Xaa Xaa
545                 550                 555                 560
Xaa Xaa Xaa Xaa Xaa Xaa Xaa Xaa Xaa Xaa Xaa Xaa Xaa Xaa Xaa
            565                 570                 575
Xaa Xaa Xaa Xaa Xaa Xaa Xaa Xaa Xaa Xaa Xaa Xaa Xaa Xaa Xaa
            580                 585                 590
Xaa Xaa Xaa Xaa Xaa Xaa Xaa Xaa Xaa Xaa Xaa Xaa Xaa Xaa Xaa
            595                 600                 605
Xaa Xaa Xaa Xaa Xaa Xaa Xaa Xaa Xaa Xaa Xaa Xaa Xaa Xaa Xaa
            610                 615                 620
Xaa Xaa Xaa Xaa Xaa Xaa Xaa Xaa Xaa Xaa Xaa Xaa Xaa Xaa Xaa Xaa
625                 630                 635                 640
Xaa Xaa Xaa Xaa Xaa Xaa Xaa Xaa Xaa Xaa Xaa Xaa Xaa Xaa Xaa
            645                 650                 655
Xaa Xaa Xaa Xaa Xaa Xaa Xaa Xaa Xaa Xaa Xaa Xaa Xaa Xaa Xaa
            660                 665                 670
Xaa Xaa Xaa Xaa Xaa Xaa Xaa Xaa Xaa Xaa Xaa Xaa Xaa Xaa Xaa
            675                 680                 685
Xaa Xaa Xaa Xaa Xaa Xaa Xaa Xaa Xaa Xaa Xaa Xaa Xaa Xaa Xaa
            690                 695                 700
Xaa Xaa Xaa Xaa Xaa Xaa Xaa Xaa Xaa Xaa Xaa Xaa Xaa Xaa Xaa Xaa
705                 710                 715                 720
Xaa Xaa Xaa Xaa Xaa Xaa Xaa Xaa Xaa Xaa Xaa Xaa Xaa Xaa Xaa
            725                 730                 735
Xaa Xaa Xaa Xaa Xaa Xaa Xaa Xaa Xaa Xaa Xaa Xaa Xaa Xaa Xaa
            740                 745                 750
Xaa Xaa Xaa Xaa Xaa Xaa Xaa Xaa Xaa Xaa Xaa Xaa Xaa Xaa Xaa
            755                 760                 765
Xaa Xaa Xaa Xaa Xaa Xaa Xaa Xaa Xaa Xaa Xaa Xaa Xaa Xaa Xaa
            770                 775                 780
Xaa Xaa Xaa Xaa Xaa Xaa Xaa Xaa Xaa Xaa Xaa Xaa Xaa Xaa Xaa Xaa
785                 790                 795                 800
Xaa Xaa Xaa Xaa Xaa Xaa Xaa Xaa Xaa Xaa Xaa Xaa Xaa Xaa Xaa
            805                 810                 815
Xaa Xaa Xaa Xaa Xaa Xaa Xaa Xaa Xaa Xaa Xaa Xaa Xaa Xaa Xaa
            820                 825                 830
Xaa Xaa Xaa Xaa Xaa Xaa Xaa Xaa Xaa Xaa Xaa Xaa Xaa Xaa Xaa
            835                 840                 845
Xaa Xaa Xaa Xaa Xaa Xaa Xaa Xaa Xaa Asp Lys Thr His Thr Cys
850                 855                 860
Pro Pro Cys Pro Ala Pro Glu Leu Leu Gly Gly Pro Ser Val Phe Leu
865                 870                 875                 880
Phe Pro Pro Lys Pro Lys Asp Thr Leu Met Ile Ser Arg Thr Pro Glu
                885                 890                 895
Val Thr Cys Val Val Val Asp Val Ser His Glu Asp Pro Glu Val Lys
            900                 905                 910
Phe Asn Trp Tyr Val Asp Gly Val Glu Val His Asn Ala Lys Thr Lys
        915                 920                 925
Pro Arg Glu Glu Gln Tyr Asn Ser Thr Tyr Arg Val Val Ser Val Leu
    930                 935                 940
Thr Val Leu His Gln Asp Trp Leu Asn Gly Lys Glu Tyr Lys Cys Lys
945                 950                 955                 960
Val Ser Asn Lys Ala Leu Pro Ala Pro Ile Glu Lys Thr Ile Ser Lys
```

```
                        965                 970                 975
Ala Lys Gly Gln Pro Arg Glu Pro Gln Val Tyr Thr Leu Pro Pro Ser
                980                 985                 990

Arg Glu Glu Met Thr Lys Asn Gln Val Ser Leu Thr Cys Leu Val Lys
            995                1000                1005

Gly Phe Tyr Pro Ser Asp Ile Ala Val Glu Trp Glu Ser Asn Gly
   1010                1015                1020

Gln Pro Glu Asn Asn Tyr Lys Thr Thr Pro Pro Val Leu Asp Ser
   1025                1030                1035

Asp Gly Ser Phe Phe Leu Tyr Ser Lys Leu Thr Val Asp Lys Ser
   1040                1045                1050

Arg Trp Gln Gln Gly Asn Val Phe Ser Cys Ser Val Met His Glu
   1055                1060                1065

Ala Leu His Asn His Tyr Thr Gln Lys Ser Leu Ser Leu Ser Pro
   1070                1075                1080

Gly Lys
   1085

<210> SEQ ID NO 124
<211> LENGTH: 812
<212> TYPE: PRT
<213> ORGANISM: artificial sequence
<220> FEATURE:
<223> OTHER INFORMATION: Synthetic polypeptide

<400> SEQUENCE: 124

Met Glu Arg Gly Leu Pro Leu Leu Cys Ala Val Leu Ala Leu Val Leu
1               5                  10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
```

```
                    225                 230                 235                 240

Gly Ile Leu Ser Met Val Phe Tyr Thr Asp Ser Ala Ile Ala Lys Glu
                        245                 250                 255

Gly Phe Ser Ala Asn Tyr Ser Val Leu Gln Ser Ser Val Ser Glu Asp
                        260                 265                 270

Phe Lys Cys Met Glu Ala Leu Gly Met Glu Ser Gly Glu Ile His Ser
                        275                 280                 285

Asp Gln Ile Thr Ala Ser Ser Gln Ala Ser Thr Asn Trp Ser Ala Glu
                        290                 295                 300

Arg Ser Arg Leu Asn Tyr Pro Glu Asn Gly Trp Thr Pro Gly Glu Asp
        305                 310                 315                 320

Ser Tyr Arg Glu Trp Ile Gln Val Asp Leu Gly Leu Leu Arg Phe Val
                        325                 330                 335

Thr Ala Val Gly Thr Gln Gly Ala Ile Ser Lys Glu Thr Lys Lys Lys
                        340                 345                 350

Tyr Tyr Val Lys Thr Tyr Lys Ile Asp Val Ser Ser Asn Gly Glu Asp
                        355                 360                 365

Trp Ile Thr Ile Lys Glu Gly Asn Lys Pro Val Leu Phe Gln Gly Asn
                        370                 375                 380

Thr Asn Pro Thr Asp Val Val Val Ala Val Phe Pro Lys Pro Leu Ile
        385                 390                 395                 400

Thr Arg Phe Val Arg Ile Lys Pro Ala Thr Trp Glu Thr Gly Ile Ser
                        405                 410                 415

Met Arg Phe Glu Val Tyr Gly Cys Lys Ile Thr Asp Tyr Pro Cys Ser
                        420                 425                 430

Gly Met Leu Gly Met Val Ser Gly Leu Ile Ser Asp Ser Gln Ile Thr
                        435                 440                 445

Ser Ser Asn Gln Gly Asp Arg Asn Trp Met Pro Glu Asn Ile Arg Leu
                        450                 455                 460

Val Thr Ser Arg Ser Gly Trp Ala Leu Pro Pro Ala Pro His Ser Tyr
        465                 470                 475                 480

Ile Asn Glu Trp Leu Gln Ile Asp Leu Gly Glu Glu Lys Ile Val Arg
                        485                 490                 495

Gly Ile Ile Ile Gln Gly Gly Lys His Arg Glu Asn Lys Val Phe Met
                        500                 505                 510

Arg Lys Phe Lys Ile Gly Tyr Ser Asn Asn Gly Ser Asp Trp Lys Met
                        515                 520                 525

Ile Met Asp Asp Ser Lys Arg Lys Ala Lys Ser Phe Glu Gly Asn Asn
        530                 535                 540

Asn Tyr Asp Thr Pro Glu Leu Arg Thr Phe Pro Ala Leu Ser Thr Arg
        545                 550                 555                 560

Phe Ile Arg Ile Tyr Pro Glu Arg Ala Thr His Gly Gly Leu Gly Leu
                        565                 570                 575

Arg Met Glu Leu Leu Gly Cys Arg Ser Asp Lys Thr His Thr Cys Pro
                        580                 585                 590

Pro Cys Pro Ala Pro Glu Leu Leu Gly Gly Pro Ser Val Phe Leu Phe
                        595                 600                 605

Pro Pro Lys Pro Lys Asp Thr Leu Met Ile Ser Arg Thr Pro Glu Val
                        610                 615                 620

Thr Cys Val Val Val Asp Val Ser His Glu Asp Pro Glu Val Lys Phe
        625                 630                 635                 640

Asn Trp Tyr Val Asp Gly Val Glu Val His Asn Ala Lys Thr Lys Pro
                        645                 650                 655
```

Arg Glu Glu Gln Tyr Asn Ser Thr Tyr Arg Val Val Ser Val Leu Thr
              660                 665                 670

Val Leu His Gln Asp Trp Leu Asn Gly Lys Glu Tyr Lys Cys Lys Val
        675                 680                 685

Ser Asn Lys Ala Leu Pro Ala Pro Ile Glu Lys Thr Ile Ser Lys Ala
690                 695                 700

Lys Gly Gln Pro Arg Glu Pro Gln Val Tyr Thr Leu Pro Pro Ser Arg
705                 710                 715                 720

Glu Glu Met Thr Lys Asn Gln Val Ser Leu Thr Cys Leu Val Lys Gly
                725                 730                 735

Phe Tyr Pro Ser Asp Ile Ala Val Glu Trp Glu Ser Asn Gly Gln Pro
                740                 745                 750

Glu Asn Asn Tyr Lys Thr Thr Pro Pro Val Leu Asp Ser Asp Gly Ser
                755                 760                 765

Phe Phe Leu Tyr Ser Lys Leu Thr Val Asp Lys Ser Arg Trp Gln Gln
                770                 775                 780

Gly Asn Val Phe Ser Cys Ser Val Met His Glu Ala Leu His Asn His
785                 790                 795                 800

Tyr Thr Gln Lys Ser Leu Ser Leu Ser Pro Gly Lys
                805                 810

<210> SEQ ID NO 125
<211> LENGTH: 653
<212> TYPE: PRT
<213> ORGANISM: artificial sequence
<220> FEATURE:
<223> OTHER INFORMATION: Synthetic polypeptide

<400> SEQUENCE: 125

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
                35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Leu Phe Lys Arg Gly
        130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
                180                 185                 190

Asp Leu Glu Pro Asp Ser Asn Pro Pro Gly Gly Met Phe Cys Arg Tyr
                195                 200                 205

```
Asp Arg Leu Glu Ile Trp Asp Gly Phe Pro Asp Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
                260                 265                 270
Phe Lys Cys Met Glu Ala Leu Gly Met Glu Ser Gly Glu Ile His Ser
            275                 280                 285
Asp Gln Ile Thr Ala Ser Ser Gln Ala Ser Thr Asn Trp Ser Ala Glu
        290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
                340                 345                 350
Tyr Tyr Val Lys Thr Tyr Lys Ile Asp Val Ser Ser Asn Gly Glu Asp
            355                 360                 365
Trp Ile Thr Ile Lys Glu Gly Asn Lys Pro Val Leu Phe Gln Gly Asn
        370                 375                 380
Thr Asn Pro Thr Asp Val Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Arg Ser Asp Lys Thr His Thr Cys
                420                 425                 430
Pro Pro Cys Pro Ala Pro Glu Leu Leu Gly Gly Pro Ser Val Phe Leu
            435                 440                 445
Phe Pro Pro Lys Pro Lys Asp Thr Leu Met Ile Ser Arg Thr Pro Glu
        450                 455                 460
Val Thr Cys Val Val Val Asp Val Ser His Glu Asp Pro Glu Val Lys
465                 470                 475                 480
Phe Asn Trp Tyr Val Asp Gly Val Glu Val His Asn Ala Lys Thr Lys
                485                 490                 495
Pro Arg Glu Glu Gln Tyr Asn Ser Thr Tyr Arg Val Val Ser Val Leu
                500                 505                 510
Thr Val Leu His Gln Asp Trp Leu Asn Gly Lys Glu Tyr Lys Cys Lys
            515                 520                 525
Val Ser Asn Lys Ala Leu Pro Ala Pro Ile Glu Lys Thr Ile Ser Lys
        530                 535                 540
Ala Lys Gly Gln Pro Arg Glu Pro Gln Val Tyr Thr Leu Pro Pro Ser
545                 550                 555                 560
Arg Glu Glu Met Thr Lys Asn Gln Val Ser Leu Thr Cys Leu Val Lys
                565                 570                 575
Gly Phe Tyr Pro Ser Asp Ile Ala Val Glu Trp Glu Ser Asn Gly Gln
                580                 585                 590
Pro Glu Asn Asn Tyr Lys Thr Thr Pro Pro Val Leu Asp Ser Asp Gly
            595                 600                 605
Ser Phe Phe Leu Tyr Ser Lys Leu Thr Val Asp Lys Ser Arg Trp Gln
        610                 615                 620
```

```
Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys
            645                 650

<210> SEQ ID NO 126
<211> LENGTH: 1086
<212> TYPE: PRT
<213> ORGANISM: artificial sequence
<220> FEATURE:
<223> OTHER INFORMATION: Synthetic polypeptide

<400> SEQUENCE: 126

Met Glu Arg Gly Leu Pro Leu Leu Cys Ala Val Leu Ala Leu Val Leu
1               5                   10                  15

Ala Pro Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
        195                 200                 205

Asp Arg Leu Glu Ile Trp Asp Gly Phe Pro Glu Val Gly Pro His Ile
210                 215                 220

Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Gly Thr Asn Trp Ser Val Glu
290                 295                 300

Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
                325                 330                 335
```

```
Thr Ala Val Gly Thr Gln Gly Ala Ile Ser Lys Glu Thr Lys Lys
                340                 345                 350

Tyr Tyr Val Lys Thr Tyr Arg Val Asp Ile Ser Ser Asn Gly Glu Asp
            355                 360                 365

Trp Ile Ser Leu Lys Glu Gly Asn Lys Ala Ile Ile Phe Gln Gly Asn
        370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
            435                 440                 445

Ala Ser Asn Gln Ala Asp Arg Asn Trp Met Pro Glu Asn Ile Arg Leu
        450                 455                 460

Val Thr Ser Arg Thr Gly Trp Ala Leu Pro Pro Ser Pro His Pro Tyr
465                 470                 475                 480

Thr Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val Asp Glu Cys Asp Asp Asp Gln Ala
        595                 600                 605

Asn Cys His Ser Gly Thr Gly Asp Asp Phe Gln Leu Thr Gly Gly Thr
610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
```

```
                755                 760                 765
Leu Leu His Lys Ser Leu Lys Leu Tyr Gln Val Ile Phe Glu Gly Glu
        770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Thr Asp Leu Asp
                805                 810                 815
Lys Lys Asn Thr Glu Ile Lys Ile Asp Glu Thr Gly Ser Thr Pro Gly
        820                 825                 830
Tyr Glu Gly Glu Gly Glu Gly Asp Lys Asn Ile Ser Arg Lys Pro Gly
                835                 840                 845
Asn Val Leu Lys Thr Leu Asp Pro Val Ser Ser Thr Met Val Arg Ser
850                 855                 860
Gly Cys Lys Pro Cys Ile Cys Thr Val Pro Glu Val Ser Ser Val Phe
865                 870                 875                 880
Ile Phe Pro Pro Lys Pro Lys Asp Val Leu Thr Ile Thr Leu Thr Pro
                885                 890                 895
Lys Val Thr Cys Val Val Val Asp Ile Ser Lys Asp Asp Pro Glu Val
        900                 905                 910
Gln Phe Ser Trp Phe Val Asp Asp Val Glu Val His Thr Ala Gln Thr
                915                 920                 925
Gln Pro Arg Glu Glu Gln Phe Asn Ser Thr Phe Arg Ser Val Ser Glu
        930                 935                 940
Leu Pro Ile Met His Gln Asp Trp Leu Asn Gly Lys Glu Phe Lys Cys
945                 950                 955                 960
Arg Val Asn Ser Ala Ala Phe Pro Ala Pro Ile Glu Lys Thr Ile Ser
                965                 970                 975
Lys Thr Lys Gly Arg Pro Lys Ala Pro Gln Val Tyr Thr Ile Pro Pro
        980                 985                 990
Pro Lys Glu Gln Met Ala Lys Asp Lys Val Ser Leu Thr Cys Met Ile
                995                 1000                1005
Thr Asp Phe Phe Pro Glu Asp Ile Thr Val Glu Trp Gln Trp Asn
        1010                1015                1020
Gly Gln Pro Ala Glu Asn Tyr Lys Asn Thr Gln Pro Ile Met Asp
        1025                1030                1035
Thr Asp Gly Ser Tyr Phe Val Tyr Ser Lys Leu Asn Val Gln Lys
        1040                1045                1050
Ser Asn Trp Glu Ala Gly Asn Thr Phe Thr Cys Ser Val Leu His
        1055                1060                1065
Glu Gly Leu His Asn His His Thr Glu Lys Ser Leu Ser His Ser
        1070                1075                1080
Pro Gly Lys
        1085

<210> SEQ ID NO 127
<211> LENGTH: 813
<212> TYPE: PRT
<213> ORGANISM: artificial sequence
<220> FEATURE:
<223> OTHER INFORMATION: Synthetic polypeptide

<400> SEQUENCE: 127

Met Glu Arg Gly Leu Pro Leu Leu Cys Ala Val Leu Ala Leu Val Leu
1               5                   10                  15

Ala Pro Ala Gly Ala Phe Arg Ser Asp Lys Cys Gly Gly Thr Ile Lys
```

```
                20                  25                  30
Ile Glu Asn Pro Gly Tyr Leu Thr Ser Pro Gly Tyr Pro His Ser Tyr
            35                  40                  45
His Pro Ser Glu Lys Cys Glu Trp Leu Ile Gln Ala Pro Glu Pro Tyr
50                      55                  60
Gln Arg Ile Met Ile Asn Phe Asn Pro His Phe Asp Leu Glu Asp Arg
65                      70                  75                  80
Asp Cys Lys Tyr Asp Tyr Val Glu Val Ile Asp Gly Glu Asn Glu Gly
                    85                  90                  95
Gly Arg Leu Trp Gly Lys Phe Cys Gly Lys Ile Ala Pro Ser Pro Val
                100                 105                 110
Val Ser Ser Gly Pro Phe Leu Phe Ile Lys Phe Val Ser Asp Tyr Glu
            115                 120                 125
Thr His Gly Ala Gly Phe Ser Ile Arg Tyr Glu Ile Phe Lys Arg Gly
            130                 135                 140
Pro Glu Cys Ser Gln Asn Tyr Thr Ala Pro Thr Gly Val Ile Lys Ser
145                 150                 155                 160
Pro Gly Phe Pro Glu Lys Tyr Pro Asn Ser Leu Glu Cys Thr Tyr Ile
                165                 170                 175
Ile Phe Ala Pro Lys Met Ser Glu Ile Ile Leu Glu Phe Glu Ser Phe
                180                 185                 190
Asp Leu Glu Gln Asp Ser Asn Pro Pro Gly Gly Met Phe Cys Arg Tyr
            195                 200                 205
Asp Arg Leu Glu Ile Trp Asp Gly Phe Pro Glu Val Gly Pro His Ile
            210                 215                 220
Gly Arg Tyr Cys Gly Gln Lys Thr Pro Gly Arg Ile Arg Ser Ser Ser
225                 230                 235                 240
Gly Val Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
                260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Gly Thr Asn Trp Ser Val Glu
            290                 295                 300
Arg Ser Arg Leu Asn Tyr Pro Glu Asn Gly Trp Thr Pro Gly Glu Asp
305                 310                 315                 320
Ser Tyr Lys Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Arg Val Asp Ile Ser Ser Asn Gly Glu Asp
            355                 360                 365
Trp Ile Ser Leu Lys Glu Gly Asn Lys Ala Ile Ile Phe Gln Gly Asn
            370                 375                 380
Thr Asn Pro Thr Asp Val Val Leu Gly Val Phe Ser Lys Pro Leu Ile
385                 390                 395                 400
Thr Arg Phe Val Arg Ile Lys Pro Val Ser Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
            435                 440                 445
```

Ala Ser Asn Gln Ala Asp Arg Asn Trp Met Pro Glu Asn Ile Arg Leu
    450                 455                 460

Val Thr Ser Arg Thr Gly Trp Ala Leu Pro Pro Ser Pro His Pro Tyr
465                 470                 475                 480

Thr Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Val Ser Ser Thr Met Val Arg Ser Gly
            580                 585                 590

Cys Lys Pro Cys Ile Cys Thr Val Pro Glu Val Ser Ser Val Phe Ile
        595                 600                 605

Phe Pro Pro Lys Pro Lys Asp Val Leu Thr Ile Thr Leu Thr Pro Lys
    610                 615                 620

Val Thr Cys Val Val Val Asp Ile Ser Lys Asp Asp Pro Glu Val Gln
625                 630                 635                 640

Phe Ser Trp Phe Val Asp Asp Val Glu Val His Thr Ala Gln Thr Gln
                645                 650                 655

Pro Arg Glu Glu Gln Phe Asn Ser Thr Phe Arg Ser Val Ser Glu Leu
            660                 665                 670

Pro Ile Met His Gln Asp Trp Leu Asn Gly Lys Glu Phe Lys Cys Arg
        675                 680                 685

Val Asn Ser Ala Ala Phe Pro Ala Pro Ile Glu Lys Thr Ile Ser Lys
    690                 695                 700

Thr Lys Gly Arg Pro Lys Ala Pro Gln Val Tyr Thr Ile Pro Pro Pro
705                 710                 715                 720

Lys Glu Gln Met Ala Lys Asp Lys Val Ser Leu Thr Cys Met Ile Thr
                725                 730                 735

Asp Phe Phe Pro Glu Asp Ile Thr Val Glu Trp Gln Trp Asn Gly Gln
            740                 745                 750

Pro Ala Glu Asn Tyr Lys Asn Thr Gln Pro Ile Met Asp Thr Asp Gly
        755                 760                 765

Ser Tyr Phe Val Tyr Ser Lys Leu Asn Val Gln Lys Ser Asn Trp Glu
    770                 775                 780

Ala Gly Asn Thr Phe Thr Cys Ser Val Leu His Glu Gly Leu His Asn
785                 790                 795                 800

His His Thr Glu Lys Ser Leu Ser His Ser Pro Gly Lys
                805                 810

<210> SEQ ID NO 128
<211> LENGTH: 654
<212> TYPE: PRT
<213> ORGANISM: artificial sequence
<220> FEATURE:
<223> OTHER INFORMATION: Synthetic polypeptide

<400> SEQUENCE: 128

-continued

```
Met Glu Arg Gly Leu Pro Leu Leu Cys Ala Val Leu Ala Leu Val Leu
1               5                   10                  15

Ala Pro Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
                100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
                180                 185                 190

Asp Leu Glu Gln Asp Ser Asn Pro Pro Gly Gly Met Phe Cys Arg Tyr
            195                 200                 205

Asp Arg Leu Glu Ile Trp Asp Gly Phe Pro Glu Val Gly Pro His Ile
            210                 215                 220

Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Gly Thr Asn Trp Ser Val Glu
        290                 295                 300

Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Arg Val Asp Ile Ser Ser Asn Gly Glu Asp
        355                 360                 365

Trp Ile Ser Leu Lys Glu Gly Asn Lys Ala Ile Ile Phe Gln Gly Asn
    370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415
```

-continued

```
Met Arg Phe Glu Val Tyr Gly Cys Val Ser Ser Thr Met Val Arg Ser
            420             425                 430

Gly Cys Lys Pro Cys Ile Cys Thr Val Pro Glu Val Ser Ser Val Phe
            435             440                 445

Ile Phe Pro Pro Lys Pro Lys Asp Val Leu Thr Ile Thr Leu Thr Pro
    450             455             460

Lys Val Thr Cys Val Val Val Asp Ile Ser Lys Asp Asp Pro Glu Val
465             470             475             480

Gln Phe Ser Trp Phe Val Asp Asp Val Glu Val His Thr Ala Gln Thr
                485             490             495

Gln Pro Arg Glu Glu Gln Phe Asn Ser Thr Phe Arg Ser Val Ser Glu
            500             505             510

Leu Pro Ile Met His Gln Asp Trp Leu Asn Gly Lys Glu Phe Lys Cys
            515             520             525

Arg Val Asn Ser Ala Ala Phe Pro Ala Pro Ile Glu Lys Thr Ile Ser
    530             535             540

Lys Thr Lys Gly Arg Pro Lys Ala Pro Gln Val Tyr Thr Ile Pro Pro
545             550             555             560

Pro Lys Glu Gln Met Ala Lys Asp Lys Val Ser Leu Thr Cys Met Ile
                565             570             575

Thr Asp Phe Phe Pro Glu Asp Ile Thr Val Glu Trp Gln Trp Asn Gly
            580             585             590

Gln Pro Ala Glu Asn Tyr Lys Asn Thr Gln Pro Ile Met Asp Thr Asp
            595             600             605

Gly Ser Tyr Phe Val Tyr Ser Lys Leu Asn Val Gln Lys Ser Asn Trp
    610             615             620

Glu Ala Gly Asn Thr Phe Thr Cys Ser Val Leu His Glu Gly Leu His
625             630             635             640

Asn His His Thr Glu Lys Ser Leu Ser His Ser Pro Gly Lys
                645             650
```